US012686665B2

(12) United States Patent
Kim et al.

(10) Patent No.: US 12,686,665 B2
(45) Date of Patent: Jul. 21, 2026

(54) BICYCLIC FUSED RING DERIVATIVE OR SALT THEREOF AND PHARMACEUTICAL COMPOSITION COMPRISING SAME

(71) Applicant: YUHAN CORPORATION, Seoul (KR)

(72) Inventors: Eun-Kyung Kim, Seongnam-si (KR); Cheol-Hee Lim, Suwon-si (KR); Kang-Yo Lee, Seoul (KR); Hyun-Ho Choi, Yongin-si (KR)

(73) Assignee: YUHAN CORPORATION, Seoul (KR)

( * ) Notice: Subject to any disclaimer, the term of this patent is extended or adjusted under 35 U.S.C. 154(b) by 321 days.

(21) Appl. No.: 18/696,807

(22) PCT Filed: Sep. 29, 2022

(86) PCT No.: PCT/KR2022/014656
§ 371 (c)(1),
(2) Date: Mar. 28, 2024

(87) PCT Pub. No.: WO2023/055124
PCT Pub. Date: Apr. 6, 2023

(65) Prior Publication Data

US 2025/0066308 A1 Feb. 27, 2025

(30) Foreign Application Priority Data

Oct. 1, 2021 (KR) ........................ 10-2021-0130916

(51) Int. Cl.

| | |
|---|---|
| ***C07D 235/14*** | (2006.01) |
| ***A61K 31/4184*** | (2006.01) |
| ***A61K 31/4192*** | (2006.01) |
| ***A61K 31/4439*** | (2006.01) |
| ***A61K 31/454*** | (2006.01) |
| ***A61K 31/496*** | (2006.01) |
| ***A61K 31/506*** | (2006.01) |
| ***A61K 31/52*** | (2006.01) |
| ***A61K 31/5377*** | (2006.01) |
| ***A61K 31/675*** | (2006.01) |
| ***C07D 249/18*** | (2006.01) |
| ***C07D 403/10*** | (2006.01) |
| ***C07D 403/12*** | (2006.01) |
| ***C07D 487/04*** | (2006.01) |
| ***C07F 9/6506*** | (2006.01) |
| ***C07F 9/6518*** | (2006.01) |

(52) U.S. Cl.
CPC ........ *C07D 235/14* (2013.01); *A61K 31/4184* (2013.01); *A61K 31/4192* (2013.01); *A61K 31/4439* (2013.01); *A61K 31/454* (2013.01); *A61K 31/496* (2013.01); *A61K 31/506* (2013.01); *A61K 31/52* (2013.01); *A61K 31/5377* (2013.01); *A61K 31/675* (2013.01); *C07D 249/18* (2013.01); *C07D 403/10* (2013.01); *C07D 403/12* (2013.01); *C07D 487/04* (2013.01); *C07F 9/65068* (2013.01); *C07F 9/65188* (2013.01)

(58) Field of Classification Search
CPC .. C07D 235/14; C07D 249/18; C07D 403/10; C07D 403/12; C07D 487/04; A61K 31/4184; A61K 31/4192; A61K 31/4439; A61K 31/454; A61K 31/496; A61K 31/506; A61K 31/52; A61K 31/5377; A61K 31/675; C07F 9/65068; C07F 9/65188
See application file for complete search history.

(56) References Cited

U.S. PATENT DOCUMENTS

| | | | | |
|---|---|---|---|---|
| 8,293,736 | B2 * | 10/2012 | Li ............................ | A61P 5/00 544/118 |
| 9,227,967 | B2 | 1/2016 | Evans et al. | |
| 10,717,733 | B2 | 7/2020 | Findlay et al. | |
| 10,717,734 | B2 | 7/2020 | Findlay et al. | |
| 10,981,917 | B2 | 4/2021 | Lee et al. | |
| 11,098,045 | B2 | 8/2021 | Findlay et al. | |

(Continued)

FOREIGN PATENT DOCUMENTS

| | | | |
|---|---|---|---|
| KR | 10-2018-0091770 | A | 8/2018 |
| KR | 10-2018-0134849 | A | 12/2018 |
| WO | 2011/113798 | A2 | 9/2011 |

OTHER PUBLICATIONS

Findlay et al., "Identification and Optimization of Mechanism-Based Fluoroallylamine Inhibitors of Lysyl Oxidase-like ⅔", J. Med. Chem., 2019, vol. 62, pp. 9874-9889.
Aumiller et al., "Comparative analysis of lysyl oxidase (like) family members in pulmonary fibrosis", Nature: Scientific Reports, vol. 7, No. 149, 13 pages, 2017.
Barker et al., "The rationale for targeting the LOX family in cancer", Nature: Reviews, vol. 12, pp. 540-552, 2012.
Barry-Hamilton et al., "Allosteric inhibition of lysyl oxidase-like-2 impedes the development of a pathologic microenvironment", Nature Medicine, vol. 16, No. 9, pp. 1009-1017, 2010.

(Continued)

*Primary Examiner* — D Margaret M Seaman
(74) *Attorney, Agent, or Firm* — Vorys, Sater, Seymour and Pease LLP; Mih Suhn Koh

(57) ABSTRACT

Provided are a bicyclic fused ring, such as for example, benzo[d]imidazole, benzo[d][1,2,3]triazole, or 8-oxo-8,9-dihydro-7H-purine derivative, or pharmaceutically acceptable salt thereof, a process for the preparation thereof, a pharmaceutical composition comprising the same and a use thereof, wherein the bicyclic fused ring derivative or pharmaceutically acceptable salt thereof has an inhibitory activity against the lysyl oxidase family and can be usefully applied for preventing or treating various diseases associated with the lysyl oxidase family, such as idiopathic pulmonary fibrosis (IPF), non-alcoholic steatohepatitis (NASH), chronic kidney disease (CKD), or liver cirrhosis.

10 Claims, No Drawings

(56) References Cited

U.S. PATENT DOCUMENTS

| | | | | |
|---|---|---|---|---|
| 2008/0233127 | A1* | 9/2008 | Bursavich | A61P 29/00 544/122 |
| 2008/0293936 | A1 | 11/2008 | Burchardt | |
| 2013/0102587 | A1 | 4/2013 | Evans et al. | |
| 2019/0040007 | A1 | 2/2019 | Findlay et al. | |
| 2019/0119269 | A1 | 4/2019 | Findlay et al. | |
| 2019/0359617 | A1 | 11/2019 | Lee et al. | |
| 2020/0317666 | A1 | 10/2020 | Findlay et al. | |

OTHER PUBLICATIONS

Ikenaga et al., "Selective targeting of lysyl oxidase-like 2 (LOXL2) suppresses hepatic fibrosis progression and accelerates its reversal", Gut, vol. 66, pp. 1697-1708, 2017.

Iwasaki et al., "Molecular Mechanism Responsible for Fibronectin-controlled Alterations in Matrix Stiffness in Advanced Chronic Liver Fibrogenesis", Journal of Biological Chemistry, vol. 291, No. 1, pp. 72-88, 2016.

Kim, "Treatment Options in Non-alcoholic Fatty Liver Disease", Korean J Gastroenterol, vol. 69, No. 6, pp. 353-358, 2017.

Liu et al., "Lysyl oxidase activity contributes to collagen stabilization during liver fibrosis progression and limits spontaneous fibrosis reversal in mice", The Faseb Journal, vol. 30, 11 pages, 2015.

Murawaki et al., "Serum Lysyl Oxidase Activity in Chronic Liver Disease in Comparison with Serum Levels of Prolyl Hydroxylase and Laminin", Hepatology, vol. 14, No. 6, pp. 1167-1173, 1991.

Nguyen et al., "Lysyl oxidase inhibitors attenuate cyclosporin A-induced nephropathy in mouse", Nature: Scientific Reports, vol. 11, 12437, 12 pages, 2021.

Puente et al., "LOXL2—A New Target in Antifibrogenic Therapy?", Int. J. Mol. Sci., vol. 20, 12 pages, 2019.

Rowbottom et al., "Identification of 4-(Aminomethyl)-6-(trifluoromethyl)-2-(phenoxy)pyridine Derivatives as Potent, Selective, and Orally Efficacious Inhibitors of the Copper-Dependent Amine Oxidase, Lysyl Oxidase-Like 2 (LOXL2)", J. Med. Chem., vol. 60, pp. 4403-4423, 2017.

Schilter et al., "The lysyl oxidase like 2/3 enzymatic inhibitor, PXS-5153A, reduces crosslinks and ameliorates fibrosis", J Cell Mol Med., vol. 23, pp. 1759-1770, 2019.

Shen et al., "Selective Synthesis and Application to the Synthesis of (E)-Fluorovinyl Nucleotides", Nucleosides, Nucleotides, and Nucleic Acids, vol. 27, pp. 213-223, 2008.

Siegel et al., "Biochemical and immunochemical study of lysyl oxidase in experimental hepatic fibrosis in the rat", Proc. Natl. Acad. Sci. USA, vol. 75, No. 6, pp. 2945-2949, 1978.

Sivakumar et al., "Upregulation of lysyl oxidase and MMPs during cardiac remodeling in human dilated cardiomyopathy", Mol Cell Biochem, vol. 307, pp. 159-167, 2008.

Torres et al., "LOXL2 Is Highly Expressed in Cancer-Associated Fibroblasts and Associates to Poor Colon Cancer Survival", Clin Cancer Res, vol. 21, No. 21, pp. 4892-4902, 2015.

Vadasz et al., "Abnormal deposition of collagen around hepatocytes in Wilson's disease is associated with hepatocyte specific expression of lysyl oxidase and lysyl oxidase like protein-2", Journal of Hepatology, vol. 43, pp. 499-507, 2005.

Vallet et al., "Lysyl oxidases: from enzyme activity to extracellular matrix cross-links", Essays in Biochemistry, vol. 63, pp. 349-364, 2019.

Van Bergen et al., "The Role of LOX and LOXL2 in Scar Formation After Glaucoma Surgery", Invest Ophthalmol Vis Sci., vol. 54, pp. 5788-5796, 2013.

Yang et al., "Targeting LOXL2 for cardiac interstitial fibrosis and heart failure treatment", Nature Communications, vol. 7, 13710, 15 pages, 2016.

Yao et al., "Pan-Lysyl Oxidase Inhibitor PXS-5505 Ameliorates Multiple-Organ Fibrosis by Inhibiting Collagen Crosslinks in Rodent Models of Systemic Sclerosis", Int. J. Mol. Sci., vol. 23, 5533, 20 pages, 2022.

Zhao et al., "Inhibition of lysyl oxidase-like 1 (LOXL1) expression arrests liver fibrosis progression in cirrhosis by reducing elastin crosslinking", BBA—Molecular Basis of Disease, vol. 1864, pp. 1129-1137, 2018.

* cited by examiner

BICYCLIC FUSED RING DERIVATIVE OR SALT THEREOF AND PHARMACEUTICAL COMPOSITION COMPRISING SAME

TECHNICAL FIELD

The present invention relates to a bicyclic fused ring (for example, benzo[d]imidazole, benzo[d][1,2,3]triazole, or 8-oxo-8,9-dihydro-7H-purine) derivative or pharmaceutically acceptable salt thereof having an inhibitory activity against lysyl oxidase isoenzymes (LOX isoenzymes), a process for the preparation thereof, a pharmaceutical composition comprising the same and a use thereof.

BACKGROUND ART

Lysyl oxidases, which consist of five sub-families in humans, are a copper-dependent amino oxidase involved in intra- and inter-molecular cross linkage of collagen or elastin in the extracellular matrix (ECM). The increase and stabilization of extracellular matrix (ECM) stiffness through the cross linkage contributes to fibrosis progression. Lysyl oxidase isoenzymes (LOX isoenzymes) are also referred to as Lysyl Oxidase family. There are five family members in mammals, i.e., Lysyl Oxidase (LOX), Lysyl Oxidase-Like 1 (LOXL1), Lysyl Oxidase-Like 2 (LOXL2), Lysyl Oxidase-Like 3 (LOXL3), and Lysyl Oxidase-Like 4 (LOXL4). LOX isoenzymes share highly conserved carboxyl termini and non-conserved amino termini along with a copper-binding motif and a lysyl-tyrosyl-quinone cofactor (LTQ) domain. Among them, LOXL2 to LOXL4 share several scavenger receptor cysteine-rich domains [Nat Rev Cancer (2012) 12: 540-552]. It has been reported that LOXL2 is secreted and acts on the extracellular matrix (ECM) in the early stromal response of active fibrotic disease and breast cancer [Lab Invest (1998) 78(2): 143-151]. In a follow-up studies, it has been reported that LOXL2 expression is increased in several fibrotic diseases occurring in the liver, heart, cancer, eyes, lung, and kidney [J Hepatol (2005) 43(3): 49-507, Int J Mol Sci (2019) 20: 1634, Gut (2017) 6(9): 1697-1708, Nat Commun (2016) 14(7): 13710, Mol cell Biochem (2008) 307(1-2): 159-167, Clin Cancer Res (2015) 21(21): 4892-4902, Invest Ophthalmol Vis Sci (2013) 54(8): 5788-5796, Sci Rep (2017) 7(1): 149, Sci Rep (2021) (11): 12437, Int. J. Mol. Sci (2022) 53: 5533]. Especially, although the expression of LOX isoenzymes is strictly controlled during liver development, abnormal expressions thereof and increased collagen and elastin cross-linking activities are shown in fibrotic livers and kidney tissues [Biochim Biophys Acta (2018) 1864: 1129-1137, FASEB J (2016) 30: 1599-1609, Gut (2017) 66: 1697-1708, Sci Rep (2017) 7(1): 149, Sci Rep (2021) (11): 12437, Int. J. Mol. Sci (2022) 53: 5533].

The catalytic action of LOX isoenzymes leads to oxidative deamination of the substrate (i.e., lysyl and hydroxylysyl residues of collagen), thereby resulting in generating allysine or hydroxyallysine residues known as α-aminoadipic b-semialdehydes. These activated aldehydes undergo spontaneous condensation reactions with other aldehydes or with the ε-amino groups of lysine and hydroxylysine residues to form intermolecular and intramolecular crosslinks in collagen and elastin. These types of crosslinks include a bifunctional form (which is a reducible crosslink of collagen and elastin), a trifunctional form (which is a mature collagen crosslink such as pyridinoline, pyrrole, and arginoline), or a tetrafunctional form (which is a mature elastin cross-link such as desmosine and isodesmosine) [Essays in Biochemistry (2019) 63: 349-364].

It is well known in the art that certain LOX isoenzymes, particularly LOX, LOXL1 and LOXL2, are generally up-regulated in fibrosis, especially in the fibrotic liver. Their increased activity stabilizes collagen and elastin through covalent cross-linking, thereby making fibrotic scars less reversible and increasing the stiffness of the ECM, which promotes the activation of central fibrogenic effector cells, hepatic stellate cells (HSC) and myofibroblasts. Therefore, lysyl oxidase inhibitors can act as an effective antifibrotic agent in various human fibrotic diseases.

Nonalcoholic fatty liver disease (NAFLD) is a disease that histologically includes simple steatosis, nonalcoholic hepatosteatosis (NASH), and liver cirrhosis. Among them, NASH, unlike simple steatosis (non-alcoholic fatty liver, NAFL), has the potential to progress to liver cirrhosis, hepatocellular carcinoma, etc. In NASH, oxidative stress, inflammatory cascade, and fibrosis, along with insulin resistance, are known to play important roles in the progression of the disease.

Several studies have reported that LOX isoenzymes are involved in the development of liver fibrosis of various etiologies. Siegel et al. have reported that the activity of hepatic LOX isoenzymes is increased in a rat model of liver fibrosis [Proc Natl Acad Sci USA, (1978) 75: 2945-2949]. And, it has been reported that the activity of LOX isoenzymes is increased in the cohort of patients with chronic active hepatitis, liver cirrhosis, and hepatocellular carcinoma [Hepatology (1991) 14: 1167-1173]. It has been also reported that the expression of hepatic LOX isoenzymes is increased in patients with primary biliary cirrhosis and Wilson disease [J Hepatol (2005) 43: 499-507]. In addition, two major phase 2 clinical trials have been carried out with Simtuzumab, a monoclonal antibody against LOXL2, in NASH patients with advanced liver fibrosis and liver cirrhosis. According to the results, although the clinical trials were discontinued due to failure to prove histological efficacy after 4 years of the treatment, the natural course of liver fibrosis progression in NASH can be predicted [Korean J Gastroenterol 69(6): 353-358].

According to the recent research results, LOX isoenzymes have been reported to be the cause of not only liver fibrosis but also kidney disease. After ureteral obstruction, renal failure and severe hypertension begin, and rapid development of renal fibrosis leads to changes in kidney thickness and weight. When kidney disease develops after ureteral obstruction, the increase and stabilization of extracellular matrix (ECM) stiffness through cross linkage contributes to the progression of renal fibrosis. In the animal model tissues that induced kidney disease, mRNA analyses of specific LOX isoenzymes, especially LOX, LOXL1, and LOXL2, showed significant increases by about 70-fold, especially increase by 250-fold in case of LOXL3 [Sci Rep (2017) 7(1): 149, Sci Rep (2021) (11): 12437, Int. J. Mol. Sci (2022) 53: 5533].

As described above, a strong association between liver and kidney fibrosis and elevated LOX isoenzyme activity has been variously demonstrated. For example, LOX isoenzyme inhibitors have been shown to significantly reduce fibrosis in the animal models. β-Aminopropionitrile (BARN), a small molecule inhibitor against LOX isoenzymes, has shown the experimental results to improve liver and cardiacfibrosis [Nat. Med. (2010) 16: 1009-1017, FASEB J. (2016) 30: 1599-1609, J. Biol. Chem. (2016) 291: 72-88]. PAT-1251, which is known as a selective and irreversible LOXL2 inhibitor, has significantly reduced fibrosis in a mouse bleomycin-mediated lung injury model [J. Med. Chem. (2017) 60: 4403-4423]. PXS-5505, which is known as a pan-LOX inhibitor, has significantly reduced renal fibrosis in a UUO animal model causing kidney disease [Int. J. Mol. Sci (2022) 53: 5533].

Other LOX isoenzyme inhibitors have been reported to improve liver fibrosis in several animal models, such as the 0014-induced liver fibrosis model, the streptozotocin/high fat diet-induced NASH mouse model, the TAA mouse model, and the 3,5-diethoxycarbonyl-1,4-dihydrocollidine (DDC) dietary model [J Cell Mol Med. (2019) 23(3): 1759-1770, Gut (2017) 66(9): 1697-1708].

Therefore, LOX isoenzyme inhibitors have the potential to treat fibrotic diseases, and thus the materials that inhibit LOX isoenzymes can be usefully applied for the prevention and treatment of various fibrotic diseases.

DISCLOSURE

Technical Problem

The present inventors have found that a bicyclic fused ring (for example, benzo[d]imidazole, benzo[d][1,2,3]triazole, or 8-oxo-8,9-dihydro-7H-purine) derivative or pharmaceutically acceptable salt thereof has an inhibitory activity against LOX isoenzymes. Therefore, the bicyclic fused ring derivative or pharmaceutically acceptable salt thereof can be usefully applied for preventing or treating various fibrotic diseases associated with LOX isoenzymes, e.g., nonalcoholic hepatosteatosis (NASH), etc.

Therefore, the present invention provides said bicyclic fused ring derivative or pharmaceutically acceptable salt thereof, a process for the preparation thereof, a pharmaceutical composition comprising the same, and a use thereof.

Technical Solution

According to an aspect of the present invention, there is provided a bicyclic fused ring (for example, benzo[d]imidazole, benzo[d][1,2,3]triazole, or 8-oxo-8,9-dihydro-7H-purine) derivative or pharmaceutically acceptable salt thereof.

According to another aspect of the present invention, there is provided a process for preparing said bicyclic fused ring derivative or pharmaceutically acceptable salt thereof.

According to still another aspect of the present invention, there is provided a pharmaceutical composition comprising said bicyclic fused ring derivative or pharmaceutically acceptable salt thereof as an active ingredient.

According to still another aspect of the present invention, there is provided a therapeutic method comprising administering said bicyclic fused ring derivative or pharmaceutically acceptable salt thereof.

According to still another aspect of the present invention, there is provided a use of said bicyclic fused ring derivative or pharmaceutically acceptable salt thereof for the manufacture of a medicament for inhibiting lysyl oxidase isoenzymes.

Advantageous Effects

It has been found by the present invention that the bicyclic fused ring (for example, benzo[d]imidazole, benzo[d][1,2,3]triazole, or 8-oxo-8,9-dihydro-7H-purine) derivative or pharmaceutically acceptable salt thereof has an inhibitory activity against LOX isoenzymes. Therefore, the compound or pharmaceutically acceptable salt thereof according to the present invention can be usefully applied for preventing or treating various diseases associated with LOX isoenzymes, e.g., idiopathic pulmonary fibrosis (IPF), nonalcoholic hepatosteatosis (NASH), chronic kidney disease (CKD), or liver cirrhosis, etc.

BEST MODE FOR CARRYING OUT THE INVENTION

As used herein, the term 'alkyl' refers to an aliphatic hydrocarbon radical, including a straight or branched aliphatic hydrocarbon radical. For example, the $C_{1-6}$ alkyl means aliphatic hydrocarbon having 1 to 6 carbon atoms, including methyl, ethyl, propyl, n-butyl, n-pentyl, n-hexyl, isopropyl, isobutyl, sec-butyl, tert-butyl, neopentyl, and isopentyl.

The term 'hydroxy' refers to the —OH group. The term 'alkoxy' refers to a radical formed by substituting the hydrogen atom in the hydroxyl group with an alkyl, unless otherwise defined. For example, the $C_{1-6}$ alkoxy includes methoxy, ethoxy, propoxy, n-butoxy, n-pentyloxy, isopropoxy, sec-butoxy, tert-butoxy, neopentyloxy, and isopentyloxy.

The term 'halogen' refers to the fluoro, bromo, chloro, or iodo group.

The term 'amino' refers to the $—NH_2$ group. The term 'alkylamino' refers to an amino group substituted with mono- or di-alkyl. For example, the $C_{1-6}$ alkylamino includes an amino group substituted with mono- or di-$C_{1-6}$ alkyl.

The term 'alkylthio' refers to the —SR group, in which R is an alkyl. The term 'cyano' refers to the —CN.

The term 'heterocyclic ring' refers to a pentagonal or hexagonal ring containing 1 to 2 nitrogen atoms. The examples thereof include pyrazole, imidazole, pyrrole, pyridine, pyrimidine, etc.

The present invention provides a compound or salt thereof having an inhibitory activity against LOX isoenzymes, i.e., a compound of Formula 1 or pharmaceutically acceptable salt thereof:

<Formula 1>

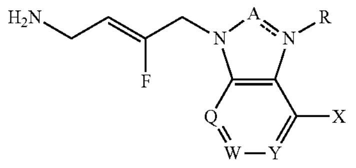

wherein,

A is $—CR_1=$, —N=, or —C(O)—, when A is $—CR_1=$ or —N=, R is absent, when A is —C(O)—, R is $C_{1-6}$ alkyl, Q is N or $CR_2$, W is N or $CR_3$, Y is N or $CR_4$, X is a heterocyclic ring or a benzene ring, the heterocyclic ring or the benzene ring is optionally substituted with 1 or 2 substituents selected from the group consisting of $C_{1-6}$ alkyl, hydroxy-$C_{1-6}$ alkyl, halogen, trifluoromethyl, $C_{1-6}$ alkoxy, $C_{1-6}$ alkylcarbonyl, $C_{1-6}$ alkoxybenzylaminosulfonyl, $C_{1-6}$ alkylsulfonyl, di-$C_{1-6}$ alkylphosphoryl, di-$C_{1-6}$ alkoxyphosphoryl, mono- or di-$C_{1-6}$ alkylaminosulfonyl, cyclopropylaminosulfonyl, pyrrolidinylsulfonyl, morpholinylsulfonyl, piperidinylsulfonyl, 3,3-difluoropyrrolidinylsulfonyl, $C_{1-3}$ alkyl-piperazinylsulfonyl, and trifluoromethylsulfonyl, $R_1$ is hydrogen, trifluoromethyl, or $C_{1-6}$ alkyl, $R_2$, $R_3$, and $R_4$ are, independently each other, selected from the group consisting of hydrogen, halogen, trifluoromethyl, cyano, nitro, hydroxycarbonyl, $C_{1-6}$ alkoxycarbonyl and —C(O)$NR_5R_6$, and C:

$R_5$ and $R_6$ are, independently each other, hydrogen, $C_{1-6}$ alkyl, or $C_{1-6}$ alkoxy; or form a 3- to 7-membered N-containing cyclic ring together with the nitrogen atom to which they are bonded.

As used herein, the expression "having an inhibitory activity against LOX isoenzymes" refers to 'having a significantly higher inhibitory activity against the human LOX isoenzymes in comparison with various amine oxidases such as MAO-A (monoamine oxidase-A), MAO-B (monoamine oxidase-B), and DAO(diamine oxidase)', especially refers to 'having a significantly higher inhibitory activity against LOXL2 known as a factor causing fibrosis'. In an embodiment, the expression "significantly higher inhibitory activity against LOXL2" means that the $IC_{50}$ against the LOXL2 obtained from an in vitro enzyme assay is at least 80 times lower than the $IC_{50}$ against the MAO-A obtained therefrom, at lease 700 times lower than the $IC_{50}$ against the MAO-B obtained therefrom, and at least 1.5 times lower than the $IC_{50}$ against the DAO obtained therefrom. In an embodiment of the present invention, A may be —$CR_1$═ or —N═, R may be absent, Q and Y may be —CH═, and W may be $CR_3$.

In another embodiment of the present invention, A may be —C(O)—, R may be $C_{1-6}$ alkyl, Q and Y may be —N═, and W may be —CH═.

In still another embodiment of the present invention, X may be a benzene ring (i.e., phenyl optionally having a substituent), a pyridine ring (i.e., pyridinyl optionally having a substituent), a pyrimidine ring (i.e., pyrimidinyl optionally having a substituent), or a pyrazole ring (i.e., pyrazolyl optionally having a substituent).

In a preferred embodiment of the present invention,

A is —$CR_1$═ or —N═,

R is absent,

Q and Y are —CH═, and

W is $CR_3$,

X is a benzene ring, a pyridine ring, a pyrimidine ring, or a pyrazole ring, the benzene ring, the pyridine ring, the pyrimidine ring, or the pyrazole ring is optionally substituted with 1 or 2 substituents selected from the group consisting of $C_{1-6}$ alkyl, hydroxy-$C_{1-6}$ alkyl, halogen, trifluoromethyl, $C_{1-6}$ alkoxy, $C_{1-6}$ alkylcarbonyl, $C_{1-6}$ alkoxybenzylaminosulfonyl, $C_{1-6}$ alkylsulfonyl, di-$C_{1-6}$ alkylphosphoryl, di-$C_{1-6}$ alkoxyphosphoryl, mono- or di-$C_{1-6}$ alkylaminosulfonyl, cyclopropylaminosulfonyl, III pyrrolidinylsulfonyl, morpholinylsulfonyl, piperidinylsulfonyl, 3,3-difluoropyrrolidinylsulfonyl, $C_{1-3}$ alkyl-piperazinylsulfonyl, and trifluoromethylsulfonyl, $R_1$ is hydrogen, trifluoromethyl or $C_{1-6}$ alkyl, $R_3$ is selected from the group consisting of hydrogen, halogen, trifluoromethyl, cyano, hydroxycarbonyl, $C_{1-6}$ alkoxycarbonyl and —C(O)$NR_5R_6$, $R_5$ and $R_6$ are, independently each other, hydrogen, $C_{1-6}$ alkyl, or $C_{1-6}$ alkoxy; or form a 3- to 7-membered N-containing cyclic ring together with the nitrogen atom to which they are bonded.

In the compound of Formula 1 or pharmaceutically acceptable salt, preferable compounds include a compound or pharmaceutically acceptable salt thereof selected from the group consisting of:

(Z)-3-fluoro-4-(6-fluoro-4-(3-fluorophenyl)-1H-benzo[d]imidazol-1-yl)but-2-en-1-amine;

(Z)-3-fluoro-4-(6-fluoro-4-(3-(trifluoromethyl)phenyl)-1H-benzo[d]imidazol-1-yl)but-2-en-1-amine;

(Z)-3-fluoro-4-(6-fluoro-4-(3-(methylsulfonyl)phenyl)-1H-benzo[d]imidazol-1-yl)but-2-en-1-amine;

(Z)-4-(1-(4-amino-2-fluorobut-2-en-1-yl)-6-fluoro-1H-benzo[d]imidazol-4-yl)-N,N-dimethylbenzenesulfonamide;

(Z)-4-(1-(4-amino-2-fluorobut-2-en-1-yl)-6-fluoro-1H-benzo[d]imidazol-4-yl)-N-cyclopropylbenzenesulfonamide;

(Z)-3-fluoro-4-(6-fluoro-4-(4-(methylsulfonyl)phenyl)-1H-benzo[d]imidazol-1-yl)but-2-en-1-amine;

(Z)-3-fluoro-4-(6-fluoro-4-(3-(pyrrolidin-1-ylsulfonyl)phenyl)-1H-benzo[d]imidazol-1-yl)but-2-en-1-amine;

(Z)-3-fluoro-4-(6-fluoro-4-(4-(morpholinosulfonyl)phenyl)-1H-benzo[d]imidazol-1-yl)but-2-en-1-amine;

(Z)-3-(1-(4-amino-2-fluorobut-2-en-1-yl)-6-fluoro-1H-benzo[d]imidazol-4-yl)-N-cyclopropylbenzenesulfonamide;

(Z)-3-(1-(4-amino-2-fluorobut-2-en-1-yl)-6-fluoro-1H-benzo[d]imidazol-4-yl)-N-methylbenzenesulfonamide;

(Z)-3-fluoro-4-(4-(3-fluorophenyl)-6-(trifluoromethyl)-1H-benzo[d]imidazol-1-yl)but-2-en-1-amine;

(Z)-3-fluoro-4-(6-(trifluoromethyl)-4-(3-(trifluoromethyl)phenyl)-1H-benzo[d]imidazol-1-yl)but-2-en-1-amine;

(Z)-3-fluoro-4-(4-(3-(methylsulfonyl)phenyl)-6-(trifluoromethyl)-1H-benzo[d]imidazol-1-yl)but-2-en-1-amine;

(Z)-4-(1-(4-amino-2-fluorobut-2-en-1-yl)-6-(trifluoromethyl)-1H-benzo[d]imidazol-4-yl)-N,N-dimethylbenzenesulfonamide;

(Z)-4-(1-(4-amino-2-fluorobut-2-en-1-yl)-6-(trifluoromethyl)-1H-benzo[d]imidazol-4-yl)-N-cyclopropylbenzenesulfonamide;

(Z)-3-fluoro-4-(4-(4-(methylsulfonyl)phenyl)-6-(trifluoromethyl)-1H-benzo[d]imidazol-1-yl)but-2-en-1-amine;

(Z)-3-fluoro-4-(4-(3-(pyrrolidin-1-ylsulfonyl)phenyl)-6-(trifluoromethyl)-1H-benzo[d]imidazol-1-yl)but-2-en-1-amine;

(Z)-3-fluoro-4-(4-(4-(morpholinosulfonyl)phenyl)-6-(trifluoromethyl)-1H-benzo[d]imidazol-1-yl)but-2-en-1-amine;

(Z)-3-(1-(4-amino-2-fluorobut-2-en-1-yl)-6-(trifluoromethyl)-1H-benzo[d]imidazol-4-yl)-N-cyclopropylbenzenesulfonamide;

(Z)-3-(1-(4-amino-2-fluorobut-2-en-1-yl)-6-(trifluoromethyl)-1H-benzo[d]imidazol-4-yl)-N-methylbenzenesulfonamide;

methyl (Z)-1-(4-amino-2-fluorobut-2-en-1-yl)-4-(3-(N,N-dimethylsulfamoyl)-4-methoxyphenyl)-1H-benzo[d]imidazol-6-carboxylate;

methyl (Z)-1-(4-amino-2-fluorobut-2-en-1-yl)-4-(3-((3,3-difluoropyrrolidin-1-yl)sulfonyl)phenyl)-1H-benzo[d]imidazol-6-carboxylate;

methyl (Z)-1-(4-amino-2-fluorobut-2-en-1-yl)-4-(3-(pyrrolidin-1-ylsulfonyl)phenyl)-1H-benzo[d]imidazol-6-carboxylate;

methyl (Z)-1-(4-amino-2-fluorobut-2-en-1-yl)-4-(2-methoxy-5-(N-m ethylsulfamoyl)phenyl)-1H-benzo[d]imidazol-6-carboxylate;

methyl (Z)-1-(4-amino-2-fluorobut-2-en-1-yl)-4-(3-(methylsulfonyl)phenyl)-1H-benzo[d]imidazol-6-carboxylate;

methyl (Z)-1-(4-amino-2-fluorobut-2-en-1-yl)-4-(5-(N,N-diethylsulfamoyl)-2-methoxyphenyl)-1H-benzo[d]imidazol-6-carboxylate;

methyl (Z)-1-(4-amino-2-fluorobut-2-en-1-yl)-4-(5-(N-cyclopropylsulfamoyl)-2-methoxyphenyl)-1H-benzo[d]imidazol-6-carboxylate;

methyl (Z)-1-(4-amino-2-fluorobut-2-en-1-yl)-4-(3-(N-isopropylsulfamoyl)-4-methoxyphenyl)-1H-benzo[d]imidazol-6-carboxylate;

methyl (Z)-1-(4-amino-2-fluorobut-2-en-1-yl)-4-(3-(N-cyclopropylsulfamoyl)phenyl)-1H-benzo[d]imidazol-6-carboxylate;

methyl (Z)-1-(4-amino-2-fluorobut-2-en-1-yl)-4-(3-(N-m ethylsulfamoyl)phenyl)-1H-benzo[d]imidazol-6-carboxylate;

methyl (Z)-1-(4-amino-2-fluorobut-2-en-1-yl)-4-(3-(N,N-dimethylsulfamoyl)phenyl)-1H-benzo[d]imidazol-6-carboxylate;

methyl (Z)-1-(4-amino-2-fluorobut-2-en-1-yl)-4-(3-(N-(4-methoxybenzyl)sulfamoyl)phenyl)-1H-benzo[d]imidazol-6-carboxylate;

methyl (Z)-1-(4-amino-2-fluorobut-2-en-1-yl)-4-(3-(piperidin-1-ylsulfonyl)phenyl)-1H-benzo[d]imidazol-6-carboxylate;

methyl (Z)-1-(4-amino-2-fluorobut-2-en-1-yl)-4-(3-(ethylsulfonyl)phenyl)-1H-benzo[d]imidazol-6-carboxylate;

methyl (Z)-1-(4-amino-2-fluorobut-2-en-1-yl)-4-(2-methyl-5-((trifluoromethyl)sulfonyl)phenyl)-1H-benzo[d]imidazol-6-carboxylate;

methyl (Z)-1-(4-amino-2-fluorobut-2-en-1-yl)-4-(3-(N-(tert-butyl)sulfamoyl)phenyl)-1H-benzo[d]imidazol-6-carboxylate;

methyl (Z)-1-(4-amino-2-fluorobut-2-en-1-yl)-4-(3-(N,N-diethylsulfamoyl)phenyl)-1H-benzo[d]imidazol-6-carboxylate;

methyl (Z)-1-(4-amino-2-fluorobut-2-en-1-yl)-4-(3-(dimethylphosphoryl)phenyl)-1H-benzo[d]imidazol-6-carboxylate;

methyl (Z)-1-(4-amino-2-fluorobut-2-en-1-yl)-4-(4-(dimethylphosphoryl)phenyl)-1H-benzo[d]imidazol-6-carboxylate;

methyl (Z)-1-(4-amino-2-fluorobut-2-en-1-yl)-4-(3-(diethoxyphosphoryl)phenyl)-1H-benzo[d]imidazol-6-carboxylate;

(Z)-1-(4-amino-2-fluorobut-2-en-1-yl)-4-(3-((3,3-difluoropyrrolidin-1-yl)sulfonyl)phenyl)-1H-benzo[d]imidazol-6-carboxylic acid;

(Z)-1-(4-amino-2-fluorobut-2-en-1-yl)-4-(3-(pyrrolidin-1-ylsulfonyl)phenyl)-1H-benzo[d]imidazol-6-carboxylic acid;

(Z)-3-fluoro-4-(4-(3-fluorophenyl)-2-(trifluoromethyl)-1H-benzo[d]imidazol-1-yl)but-2-en-1-amine;

(Z)-3-fluoro-4-(2-(trifluoromethyl)-4-(3-(trifluoromethyl)phenyl)-1H-benzo[d]imidazol-1-yl)but-2-en-1-amine;

(Z)-3-(1-(4-amino-2-fluorobut-2-en-1-yl)-2-(trifluoromethyl)-1H-benzo[d]imidazol-4-yl)-N,N-dimethylbenzenesulfonamide;

(Z)-3-fluoro-4-(4-(3-(methylsulfonyl)phenyl)-2-(trifluoromethyl)-1H-benzo[d]imidazol-1-yl)but-2-en-1-amine;

(Z)-4-(1-(4-amino-2-fluorobut-2-en-1-yl)-2-(trifluoromethyl)-1H-benzo[d]imidazol-4-yl)-N,N-dimethylbenzenesulfonamide;

(Z)-4-(1-(4-amino-2-fluorobut-2-en-1-yl)-2-(trifluoromethyl)-1H-benzo[d]imidazol-4-yl)-N-cyclopropylbenzenesulfonamide;

(Z)-3-fluoro-4-(4-(4-(methylsulfonyl)phenyl)-2-(trifluoromethyl)-1H-benzo[d]imidazol-1-yl)but-2-en-1-amine;

(Z)-3-fluoro-4-(4-(3-(pyrrolidin-1-ylsulfonyl)phenyl)-2-(trifluoromethyl)-1H-benzo[d]imidazol-1-yl)but-2-en-1-amine;

(Z)-4-(1-(4-amino-2-fluorobut-2-en-1-yl)-2-(trifluoromethyl)-1H-benzo[d]imidazol-4-yl)-N-(tert-butyl)benzenesulfonamide;

(Z)-3-(1-(4-amino-2-fluorobut-2-en-1-yl)-2-(trifluoromethyl)-1H-benzo[d]imidazol-4-yl)-N-cyclopropylbenzenesulfonamide;

(Z)-3-(1-(4-amino-2-fluorobut-2-en-1-yl)-2-(trifluoromethyl)-1H-benzo[d]imidazol-4-yl)-N-methylbenzenesulfonamide;

(Z)-4-(1-(4-amino-2-fluorobut-2-en-1-yl)-2-methyl-1H-benzo[d]imidazol-4-yl)-N,N-dimethylbenzenesulfonamide;

(Z)-3-fluoro-4-(2-methyl-4-(4-(morpholinosulfonyl)phenyl)-1H-benzo[d]imidazol-1-yl)but-2-en-1-amine;

(Z)-3-(1-(4-amino-2-fluorobut-2-en-1-yl)-2-methyl-1H-benzo[d]imidazol-4-yl)-N,N-dimethylbenzenesulfonamide;

(Z)-3-fluoro-4-(2-methyl-4-(3-(methylsulfonyl)phenyl)-1H-benzo[d]imidazol-1-yl)but-2-en-1-amine;

(Z)-3-fluoro-4-(2-methyl-4-(4-(methylsulfonyl)phenyl)-1H-benzo[d]imidazol-1-yl)but-2-en-1-amine;

(Z)-4-(1-(4-amino-2-fluorobut-2-en-1-yl)-2-methyl-1H-benzo[d]imidazol-4-yl)-N-cy clopropylbenzenesulfonamide;

(Z)-3-fluoro-4-(2-methyl-4-(3-(pyrrolidin-1-ylsulfonyl)phenyl)-1H-benzo[d]imidazol-1-yl)but-2-en-1-amine;

(Z)-4-(1-(4-amino-2-fluorobut-2-en-1-yl)-2-methyl-1H-benzo[d]imidazol-4-yl)-N-(tert-butyl)benzenesulfonamide;

(Z)-3-(1-(4-amino-2-fluorobut-2-en-1-yl)-2-methyl-1H-benzo[d]imidazol-4-yl)-N-cy clopropylbenzenesulfonamide;

(Z)-3-(1-(4-amino-2-fluorobut-2-en-1-yl)-2-methyl-1H-benzo[d]imidazol-4-yl)-N-methylbenzenesulfonamide;

methyl (Z)-1-(4-amino-2-fluorobut-2-en-1-yl)-4-(4-(N,N-dimethylsulfamoyl)phenyl)-2-methyl-1H-benzo[d]imidazol-6-carboxylate;

methyl (Z)-1-(4-amino-2-fluorobut-2-en-1-yl)-2-methyl-4-(4-(morpholinosulfonyl)phenyl)-1H-benzo[d]imidazol-6-carboxylate;

methyl (Z)-1-(4-amino-2-fluorobut-2-en-1-yl)-4-(3-(N,N-dimethylsulfamoyl)phenyl)-2-methyl-1H-benzo[d]imidazol-6-carboxylate;

methyl (Z)-1-(4-amino-2-fluorobut-2-en-1-yl)-2-methyl-4-(3-(methylsulfonyl)phenyl)-1H-benzo[d]imidazol-6-carboxylate;

methyl (Z)-1-(4-amino-2-fluorobut-2-en-1-yl)-2-methyl-4-(4-(methylsulfonyl)phenyl)-1H-benzo[d]imidazol-6-carboxylate;
methyl
(Z)-1-(4-amino-2-fluorobut-2-en-1-yl)-4-(4-(N-cyclopropylsulfamoyl)phenyl)-2-methyl-1H-benzo[d]imidazol-6-carboxylate;
methyl
(Z)-1-(4-amino-2-fluorobut-2-en-1-yl)-2-methyl-4-(3-(pyrrolidin-1-ylsulfonyl)phenyl)-1H-benzo[d]imidazol-6-carboxylate;
methyl
(Z)-1-(4-amino-2-fluorobut-2-en-1-yl)-4-(4-(N-(tert-butyl)sulfamoyl)phenyl)-2-methyl-1H-benzo[d]imidazol-6-carboxylate;
methyl
(Z)-1-(4-amino-2-fluorobut-2-en-1-yl)-4-(3-(N-cyclopropylsulfamoyl)phenyl)-2-methyl-1H-benzo[d]imidazol-6-carboxylate;
methyl
(Z)-1-(4-amino-2-fluorobut-2-en-1-yl)-2-methyl-4-(3-(N-methylsulfamoyl)phenyl)-1H-benzo[d]imidazol-6-carboxylate;
(Z)-1-(4-amino-2-fluorobut-2-en-1-yl)-4-(4-(N,N-dimethylsulfamoyl)phenyl)-N,N,2-trimethyl-1H-benzo[d]imidazol-6-carboxamide;
(Z)-1-(4-amino-2-fluorobut-2-en-1-yl)-N,N,2-trimethyl-4-(4-(morpholinosulfonyl)phenyl)-1H-benzo[d]imidazol-6-carboxamide;
(Z)-1-(4-amino-2-fluorobut-2-en-1-yl)-4-(3-(N,N-dimethylsulfamoyl)phenyl)-N,N,2-trimethyl-1H-benzo[d]imidazol-6-carboxamide;
(Z)-1-(4-amino-2-fluorobut-2-en-1-yl)-N,N,2-trimethyl-4-(3-(methylsulfonyl)phenyl)-1H-benzo[d]imidazol-6-carboxamide;
(Z)-1-(4-amino-2-fluorobut-2-en-1-yl)-N,N,2-trimethyl-4-(4-(methylsulfonyl)phenyl)-1H-benzo[d]imidazol-6-carboxamide;
(Z)-1-(4-amino-2-fluorobut-2-en-1-yl)-4-(4-(N-cyclopropylsulfamoyl)phenyl)-N,N,2-trimethyl-1H-benzo[d]imidazol-6-carboxamide;
(Z)-1-(4-amino-2-fluorobut-2-en-1-yl)-4-(3-(N-cyclopropylsulfamoyl)phenyl)-N,N,2-trimethyl-1H-benzo[d]imidazol-6-carboxamide;
(Z)-1-(4-amino-2-fluorobut-2-en-1-yl)-N,N,2-trimethyl-4-(3-(N-methylsulfamoyl)phenyl)-1H-benzo[d]imidazol-6-carboxamide;
(Z)-4-(1-(4-amino-2-fluorobut-2-en-1-yl)-2-ethyl-1H-benzo[d]imidazol-4-yl)-N,N-dimethylbenzenesulfonamide;
(Z)-4-(2-ethyl-4-(4-(morpholinosulfonyl)phenyl)-1H-benzo[d]imidazol-1-yl)-3-fluorobut-2-en-1-amine;
(Z)-3-(1-(4-amino-2-fluorobut-2-en-1-yl)-2-ethyl-1H-benzo[d]imidazol-4-yl)-N,N-dimethylbenzenesulfonamide;
(Z)-4-(2-ethyl-4-(3-(methylsulfonyl)phenyl)-1H-benzo[d]imidazol-1-yl)-3-fluorobut-2-en-1-amine;
(Z)-4-(2-ethyl-4-(4-(methylsulfonyl)phenyl)-1H-benzo[d]imidazol-1-yl)-3-fluorobut-2-en-1-amine;
(Z)-4-(1-(4-amino-2-fluorobut-2-en-1-yl)-2-ethyl-1H-benzo[d]imidazol-4-yl)-N-cyclopropylbenzenesulfonamide;
(Z)-4-(2-ethyl-4-(3-(pyrrolidin-1-ylsulfonyl)phenyl)-1H-benzo[d]imidazol-1-yl)-3-fluorobut-2-en-1-amine;
(Z)-4-(1-(4-amino-2-fluorobut-2-en-1-yl)-2-ethyl-1H-benzo[d]imidazol-4-yl)-N-(tert-butyl)benzenesulfonamide;
(Z)-3-(1-(4-amino-2-fluorobut-2-en-1-yl)-2-ethyl-1H-benzo[d]imidazol-4-yl)-N-cyclopropylbenzenesulfonamide;
(Z)-3-(1-(4-amino-2-fluorobut-2-en-1-yl)-2-ethyl-1H-benzo[d]imidazol-4-yl)-N-methylbenzenesulfonamide;
(Z)-4-(1-(4-amino-2-fluorobut-2-en-1-yl)-2-isopropyl-1H-benzo[d]imidazol-4-yl)-N,N-dimethylbenzenesulfonamide;
(Z)-3-fluoro-4-(2-isopropyl-4-(4-(morpholinosulfonyl)phenyl)-1H-benzo[d]imidazol-1-yl)but-2-en-1-amine;
(Z)-3-(1-(4-amino-2-fluorobut-2-en-1-yl)-2-isopropyl-1H-benzo[d]imidazol-4-yl)-N,N-dimethylbenzenesulfonamide;
(Z)-3-fluoro-4-(2-isopropyl-4-(3-(methylsulfonyl)phenyl)-1H-benzo[d]imidazol-1-yl) but-2-en-1-amine;
(Z)-3-fluoro-4-(2-isopropyl-4-(4-(methylsulfonyl)phenyl)-1H-benzo[d]imidazol-1-yl) but-2-en-1-amine;
(Z)-4-(1-(4-amino-2-fluorobut-2-en-1-yl)-2-isopropyl-1H-benzo[d]imidazol-4-yl)-N-cyclopropylbenzenesulfonamide;
(Z)-3-fluoro-4-(2-isopropyl-4-(3-(pyrrolidin-1-ylsulfonyl)phenyl)-1H-benzo[d]imidazol-1-yl)but-2-en-1-amine;
(Z)-4-(1-(4-amino-2-fluorobut-2-en-1-yl)-2-isopropyl-1H-benzo[d]imidazol-4-yl)-N-(tert-butyl)benzenesulfonamide;
(Z)-3-(1-(4-amino-2-fluorobut-2-en-1-yl)-2-isopropyl-1H-benzo[d]imidazol-4-yl)-N-cyclopropylbenzenesulfonamide;
(Z)-3-(1-(4-amino-2-fluorobut-2-en-1-yl)-2-isopropyl-1H-benzo[d]imidazol-4-yl)-N-methylbenzenesulfonamide;
(Z)-5-(1-(4-amino-2-fluorobut-2-en-1-yl)-1H-benzo[d][1,2,3]triazol-4-yl)-2-methoxy-N,N-dimethylbenzenesulfonamide;
(Z)-4-(4-(3-((3,3-difluoropyrrolidin-1-yl)sulfonyl)phenyl)-1H-benzo[d][1,2,3]triazol-1-yl)-3-fluorobut-2-en-1-amine;
(Z)-3-fluoro-4-(4-(3-(pyrrolidin-1-ylsulfonyl)phenyl)-1H-benzo[d][1,2,3]triazol-1-yl) but-2-en-1-amine;
(Z)-3-(1-(4-amino-2-fluorobut-2-en-1-yl)-1H-benzo[d][1,2,3]triazol-4-yl)-4-methoxy-N-methylbenzenesulfonamide;
(Z)-3-fluoro-4-(4-(3-(methylsulfonyl)phenyl)-1H-benzo[d][1,2,3]triazol-1-yl)but-2-en-1-amine;
(Z)-3-(1-(4-amino-2-fluorobut-2-en-1-yl)-1H-benzo[d][1,2,3]triazol-4-yl)-N,N-diethyl-4-methoxybenzenesulfonamide;
(Z)-3-(1-(4-amino-2-fluorobut-2-en-1-yl)-1H-benzo[d][1,2,3]triazol-4-yl)-N-cyclopropyl-4-methoxybenzenesulfonamide;
(Z)-5-(1-(4-amino-2-fluorobut-2-en-1-yl)-1H-benzo[d][1,2,3]triazol-4-yl)-N-isopropyl-2-methoxybenzenesulfonamide;
(Z)-3-(1-(4-amino-2-fluorobut-2-en-1-yl)-1H-benzo[d][1,2,3]triazol-4-yl)-N-cyclopropylbenzenesulfonamide;
(Z)-3-(1-(4-amino-2-fluorobut-2-en-1-yl)-1H-benzo[d][1,2,3]triazol-4-yl)-N-methylbenzenesulfonamide;
(Z)-3-(1-(4-amino-2-fluorobut-2-en-1-yl)-1H-benzo[d][1,2,3]triazol-4-yl)-N,N-dimethylbenzenesulfonamide;
(Z)-3-fluoro-4-(4-(2-methoxy-5-((4-methylpiperazin-1-yl)sulfonyl)phenyl)-1H-benzo[d][1,2,3]triazol-1-yl)but-2-en-1-amine;
methyl
(Z)-1-(4-amino-2-fluorobut-2-en-1-yl)-4-(3-(N,N-dimethylsulfamoyl)-4-methoxyphenyl)-1H-benzo[d][1,2,3]triazol-6-carboxylate;
methyl
(Z)-1-(4-amino-2-fluorobut-2-en-1-yl)-4-(3-((3,3-difluoropyrrolidin-1-yl)sulfonyl)phenyl)-1H-benzo[d][1,2,3]triazol-6-carboxylate;
methyl (Z)-1-(4-amino-2-fluorobut-2-en-1-yl)-4-(3-(pyrrolidin-1-ylsulfonyl)phenyl)-1H-benzo[d][1,2,3]triazol-6-carboxylate;

methyl (Z)-1-(4-amino-2-fluorobut-2-en-1-yl)-4-(2-methoxy-5-(N-m ethylsulfamoyl)phenyl)-1H-benzo[d][1,2,3]triazol-6-carboxylate;

methyl (Z)-1-(4-amino-2-fluorobut-2-en-1-yl)-4-(3-(methylsulfonyl)phenyl)-1H-benzo[d][1,2,3]triazol-6-carboxylate;

methyl (Z)-1-(4-amino-2-fluorobut-2-en-1-yl)-4-(5-(N,N-diethylsulfamoyl)-2-methoxyphenyl)-1H-benzo[d][1,2,3]triazol-6-carboxylate;

methyl (Z)-1-(4-amino-2-fluorobut-2-en-1-yl)-4-(5-(N-cyclopropylsulfamoyl)-2-methoxyphenyl)-1H-benzo[d][1,2,3]triazol-6-carboxylate;

methyl (Z)-1-(4-amino-2-fluorobut-2-en-1-yl)-4-(3-(N-isopropylsulfamoyl)-4-methoxyphenyl)-1H-benzo[d][1,2,3]triazol-6-carboxylate;

methyl (Z)-1-(4-amino-2-fluorobut-2-en-1-yl)-4-(3-(N-cyclopropylsulfamoyl)phenyl)-1H-benzo[d][1,2,3]triazol-6-carboxylate;

methyl (Z)-1-(4-amino-2-fluorobut-2-en-1-yl)-4-(3-(N-m ethylsulfamoyl)phenyl)-1H-benzo[d][1,2,3]triazol-6-carboxylate;

methyl (Z)-1-(4-amino-2-fluorobut-2-en-1-yl)-4-(3-(N,N-dimethylsulfamoyl)phenyl)-1H-benzo[d][1,2,3]triazol-6-carboxylate;

methyl (Z)-1-(4-amino-2-fluorobut-2-en-1-yl)-4-(3-(N-(4-methoxybenzyl)sulfamoyl)phenyl)-1H-benzo[d][1,2,3]triazol-6-carboxylate;

methyl (Z)-1-(4-amino-2-fluorobut-2-en-1-yl)-4-(3-(piperidin-1-ylsulfonyl)phenyl)-1H-benzo[d][1,2,3]triazol-6-carboxylate;

methyl (Z)-1-(4-amino-2-fluorobut-2-en-1-yl)-4-(3-(ethylsulfonyl)phenyl)-1H-benzo[d][1,2,3]triazol-6-carboxylate;

methyl (Z)-1-(4-amino-2-fluorobut-2-en-1-yl)-4-(2-methyl-5-((trifluoromethyl)sulfonyl)phenyl)-1H-benzo[d][1,2,3]triazol-6-carboxylate;

methyl (Z)-1-(4-amino-2-fluorobut-2-en-1-yl)-4-(3-(N-(tert-butyl)sulfamoyl)phenyl)-1H-benzo[d][1,2,3]triazol-6-carboxylate;

methyl (Z)-1-(4-amino-2-fluorobut-2-en-1-yl)-4-(3-(N,N-diethylsulfamoyl)phenyl)-1H-benzo[d][1,2,3]triazol-6-carboxylate;

methyl (Z)-1-(4-amino-2-fluorobut-2-en-1-yl)-4-(3-(diethoxyphosphoryl)phenyl)-1H-benzo[d][1,2,3]triazol-6-carboxylate;

(Z)-1-(4-amino-2-fluorobut-2-en-1-yl)-4-(3-(N,N-dimethylsulfamoyl)-4-methoxyphenyl)-N-methoxy-1H-benzo[d][1,2,3]triazol-6-carboxamide;

(Z)-1-(4-amino-2-fluorobut-2-en-1-yl)-N-methoxy-4-(3-(pyrrolidin-1-ylsulfonyl)phenyl)-1H-benzo[d][1,2,3]triazol-6-carboxamide;

(Z)-1-(4-amino-2-fluorobut-2-en-1-yl)-N-methoxy-4-(2-methoxy-5-(N-methylsulfamoyl)phenyl)-1H-benzo[d][1,2,3]triazol-6-carboxamide;

(Z)-1-(4-amino-2-fluorobut-2-en-1-yl)-4-(5-(N,N-diethylsulfamoyl)-2-methoxyphen yl)-N-methoxy-1H-benzo[d][1,2,3]triazol-6-carboxamide;

(Z)-1-(4-amino-2-fluorobut-2-en-1-yl)-4-(5-(N-cyclopropylsulfamoyl)-2-methoxyphenyl)-N-methoxy-1H-benzo[d][1,2,3]triazol-6-carboxamide;

(Z)-1-(4-amino-2-fluorobut-2-en-1-yl)-N-methoxy-N-methyl-4-(3-(pyrrolidin-1-ylsulfonyl)phenyl)-1H-benzo[d][1,2,3]triazol-6-carboxamide;

(Z)-1-(4-amino-2-fluorobut-2-en-1-yl)-4-(5-(N,N-diethylsulfamoyl)-2-methoxyphen yl)-N-methoxy-N-methyl-1H-benzo[d][1,2,3]triazol-6-carboxamide;

(Z)-1-(4-amino-2-fluorobut-2-en-1-yl)-4-(3-(N,N-dimethylsulfamoyl)phenyl)-N-methoxy-N-methyl-1H-benzo[d][1,2,3]triazol-6-carboxamide;

(Z)-9-(4-amino-2-fluorobut-2-en-1-yl)-7-methyl-6-(3-(pyrrolidin-1-ylsulfonyl)phenyl)-7,9-dihydro-8H-purin-8-one;

(Z)-3-(9-(4-amino-2-fluorobut-2-en-1-yl)-7-methyl-8-oxo-8,9-dihydro-7H-purin-6-yl)-N-cyclopropylbenzenesulfonamide;

(Z)-3-(9-(4-amino-2-fluorobut-2-en-1-yl)-7-methyl-8-oxo-8,9-dihydro-7H-purin-6-yl)-N-methylbenzenesulfonamide;

(Z)-9-(4-amino-2-fluorobut-2-en-1-yl)-7-methyl-6-(3-(methylsulfonyl)phenyl)-7,9-dihydro-8H-purin-8-one;

(Z)-3-(9-(4-amino-2-fluorobut-2-en-1-yl)-7-methyl-8-oxo-8,9-dihydro-7H-purin-6-yl)-N,N-dimethylbenzenesulfonamide;

(Z)-1-(4-amino-2-fluorobut-2-en-1-yl)-4-(3-(N,N-dimethylsulfamoyl)-4-methoxyphenyl)-N-methyl-1H-benzo[d][1,2,3]triazol-6-carboxamide;

(Z)-1-(4-amino-2-fluorobut-2-en-1-yl)-4-(3-((3,3-difluoropyrrolidin-1-yl)sulfonyl)phenyl)-N-methyl-1H-benzo[d][1,2,3]triazol-6-carboxamide;

(Z)-1-(4-amino-2-fluorobut-2-en-1-yl)-N-methyl-4-(3-(pyrrolidin-1-ylsulfonyl)phenyl)-1H-benzo[d][1,2,3]triazol-6-carboxamide;

(Z)-1-(4-amino-2-fluorobut-2-en-1-yl)-4-(2-methoxy-5-(N-m ethylsulfamoyl)phenyl)-N-methyl-1H-benzo[d][1,2,3]triazol-6-carboxamide;

(Z)-1-(4-amino-2-fluorobut-2-en-1-yl)-N-methyl-4-(3-(methylsulfonyl)phenyl)-1H-benzo[d][1,2,3]triazol-6-carboxamide;

(Z)-1-(4-amino-2-fluorobut-2-en-1-yl)-4-(5-(N,N-diethylsulfamoyl)-2-methoxyphen yl)-N-methyl-1H-benzo[d][1,2,3]triazol-6-carboxamide;

(Z)-1-(4-amino-2-fluorobut-2-en-1-yl)-4-(3-(N-cyclopropylsulfamoyl)-4-methoxyphenyl)-N-methyl-1H-benzo[d][1,2,3]triazol-6-carboxamide;

(Z)-1-(4-amino-2-fluorobut-2-en-1-yl)-4-(3-(N-isopropylsulfamoyl)-4-methoxyphen yl)-N-methyl-1H-benzo[d][1,2,3]triazol-6-carboxamide;

(Z)-1-(4-amino-2-fluorobut-2-en-1-yl)-4-(3-(N-cyclopropylsulfamoyl)phenyl)-N-methyl-1H-benzo[d][1,2,3]triazol-6-carboxamide;

(Z)-1-(4-amino-2-fluorobut-2-en-1-yl)-N-methyl-4-(3-(N-methylsulfamoyl)phenyl)-1H-benzo[d][1,2,3]triazol-6-carboxamide;

(Z)-1-(4-amino-2-fluorobut-2-en-1-yl)-4-(3-(N,N-dimethylsulfamoyl)phenyl)-N-methyl-1H-benzo[d][1,2,3]triazol-6-carboxamide;

(Z)-1-(4-amino-2-fluorobut-2-en-1-yl)-4-(3-(ethylsulfonyl)phenyl)-N-methyl-1H-benzo[d][1,2,3]triazol-6-carboxamide;
(Z)-5-(1-(4-amino-2-fluorobut-2-en-1-yl)-6-(pyrrolidin-1-carbonyl)-1H-benzo[d][1,2,3]triazol-4-yl)-2-methoxy-N,N-dimethylbenzenesulfonamide;
(Z)-(1-(4-amino-2-fluorobut-2-en-1-yl)-4-(3-((3,3-difluoropyrrolidin-1-yl)sulfonyl)phenyl)-1H-benzo[d][1,2,3]triazol-6-yl)(pyrrolidin-1-yl)methanone;
(Z)-(1-(4-amino-2-fluorobut-2-en-1-yl)-4-(3-(pyrrolidin-1-ylsulfonyl)phenyl)-1H-benzo[d][1,2,3]triazol-6-yl)(pyrrolidin-1-yl)methanone;
(Z)-3-(1-(4-amino-2-fluorobut-2-en-1-yl)-6-(pyrrolidin-1-carbonyl)-1H-benzo[d][1,2,3]triazol-4-yl)-4-methoxy-N-methylbenzenesulfonamide;
(Z)-(1-(4-amino-2-fluorobut-2-en-1-yl)-4-(3-(methylsulfonyl)phenyl)-1H-benzo[d][1,2,3]triazol-6-yl)(pyrrolidin-1-yl)methanone;
(Z)-3-(1-(4-amino-2-fluorobut-2-en-1-yl)-6-(pyrrolidin-1-carbonyl)-1H-benzo[d][1,2,3]triazol-4-yl)-N,N-diethyl-4-methoxybenzenesulfonamide;
(Z)-5-(1-(4-amino-2-fluorobut-2-en-1-yl)-6-(pyrrolidin-1-carbonyl)-1H-benzo[d][1,2,3]triazol-4-yl)-N-cyclopropyl-2-methoxybenzenesulfonamide;
(Z)-5-(1-(4-amino-2-fluorobut-2-en-1-yl)-6-(pyrrolidin-1-carbonyl)-1H-benzo[d][1,2,3]triazol-4-yl)-N-isopropyl-2-methoxybenzenesulfonamide;
(Z)-3-(1-(4-amino-2-fluorobut-2-en-1-yl)-6-(pyrrolidin-1-carbonyl)-1H-benzo[d][1,2,3]triazol-4-yl)-N-cyclopropylbenzenesulfonamide;
(Z)-3-(1-(4-amino-2-fluorobut-2-en-1-yl)-6-(pyrrolidin-1-carbonyl)-1H-benzo[d][1,2,3]triazol-4-yl)-N-methylbenzenesulfonamide;
(Z)-3-(1-(4-amino-2-fluorobut-2-en-1-yl)-6-(pyrrolidin-1-carbonyl)-1H-benzo[d][1,2,3]triazol-4-yl)-N,N-dimethylbenzenesulfonamide;
(Z)-(1-(4-amino-2-fluorobut-2-en-1-yl)-4-(3-(ethylsulfonyl)phenyl)-1H-benzo[d][1,2,3]triazol-6-yl)(pyrrolidin-1-yl)methanone;
(Z)-1-(3-(1-(4-amino-2-fluorobut-2-en-1-yl)-6-(trifluoromethyl)-1H-benzo[d]imidazol-4-yl)-4-fluorophenyl)ethan-1-one;
(Z)-(3-(1-(4-amino-2-fluorobut-2-en-1-yl)-6-(trifluoromethyl)-1H-benzo[d]imidazol-4-yl)-4-fluorophenyl)methanol;
(Z)-(3-(1-(4-amino-2-fluorobut-2-en-1-yl)-6-(trifluoromethyl)-1H-benzo[d]imidazol-4-yl)-2-chlorophenyl)methanol;
(Z)-3-fluoro-4-(4-(pyridin-3-yl)-6-(trifluoromethyl)-1H-benzo[d]imidazol-1-yl)but-2-en-1-amine;
(Z)-3-fluoro-4-(4-(5-fluoropyridin-3-yl)-6-(trifluoromethyl)-1H-benzo[d]imidazol-1-yl)but-2-en-1-amine;
(Z)-4-(4-(5-chloropyridin-3-yl)-6-(trifluoromethyl)-1H-benzo[d]imidazol-1-yl)-3-fluoro-but-2-en-1-amine;
(Z)-3-fluoro-4-(4-(pyrimidin-5-yl)-6-(trifluoromethyl)-1H-benzo[d]imidazol-1-yl)but-2-en-1-amine;
(Z)-3-fluoro-4-(4-(1-methyl-1H-pyrazol-5-yl)-6-(trifluoromethyl)-1H-benzo[d]imidazol-1-yl)but-2-en-1-ylamine;
(Z)-4-(4-(1-ethyl-1H-pyrazol-5-yl)-6-(trifluoromethyl)-1H-benzo[d]imidazol-1-yl)-3-fluoro-but-2-en-1-amine;
(Z)-3-fluoro-4-(4-(1-isopropyl-1H-pyrazol-5-yl)-6-(trifluoromethyl)-1H-benzo[d]imidazol-1-yl)but-2-en-1-amine;
(Z)-3-fluoro-4-(4-[1-methyl-3-(trifluoromethyl)-1H-pyrazol-5-yl]-6-(trifluoromethyl)-1H-benzo[d]imidazol-1-yl)but-2-en-1-amine;
(Z)-2-(4-(1-(4-amino-2-fluorobut-2-en-1-yl)-6-(trifluoromethyl)-1H-benzo[d]imidazol-4-yl)-1H-pyrazol-1-yl)ethan-1-ol;
(Z)-1-(4-amino-2-fluorobut-2-en-1-yl)-4-(3-(pyrrolidin-1-ylsulfonyl)phenyl)-1H-benzo[d]imidazol-6-carbonitrile;
(Z)-3-(1-(4-amino-2-fluorobut-2-en-1-yl)-6-cyano-1H-benzo[d]imidazol-4-yl)-N,N-dimethylbenzenesulfonamide;
(Z)-3-(1-(4-amino-2-fluorobut-2-en-1-yl)-6-cyano-1H-benzo[d]imidazol-4-yl)-4-methoxy-N-methylbenzenesulfonamide;
(Z)-4-(5-acetyl-2-fluorophenyl)-1-(4-amino-2-fluorobut-2-en-1-yl)-1H-benzo[d]imidazol-6-carbonitrile;
(Z)-1-(4-amino-2-fluorobut-2-en-1-yl)-4-(2-fluoro-5-(hydroxymethyl)phenyl)-1H-benzo[d]imidazol-6-carbonitrile;
(Z)-1-(4-amino-2-fluoro-2-but-1-yl)-4-(2-chloro-3-(hydroxymethyl)phenyl)-1H-benzo[d]imidazol-6-carbonitrile;
(Z)-1-(4-amino-2-fluorobut-2-en-1-yl)-4-(pyridin-3-yl)-1H-benzo[d]imidazol-6-carbonitrile;
(Z)-1-(4-amino-2-fluorobut-2-en-1-yl)-4-(5-fluoropyridin-3-yl)-1H-benzo[d]imidazol-6-carbonitrile;
(Z)-1-(4-amino-2-fluorobut-2-en-1-yl)-4-(5-chloropyridin-3-yl)-1H-benzo[d]imidazol-6-carbonitrile;
(Z)-1-(4-amino-2-fluorobut-2-en-1-yl)-4-(pyrimidin-5-yl)-1H-benzo[d]imidazol-6-carbonitrile;
(Z)-1-(4-amino-2-fluorobut-2-en-1-yl)-4-(1-methyl-1H-pyrazol-5-yl)-1H-benzo[d]imidazol-6-carbonitrile;
(Z)-1-(4-amino-2-fluorobut-2-en-1-yl)-4-(1-ethyl-1H-pyrazol-5-yl)-1H-benzo[d]imidazol-6-carbonitrile;
(Z)-1-(4-amino-2-fluorobut-2-en-1-yl)-4-(1-methyl-3-(trifluoromethyl)-1H-pyrazol-5-yl)-1H-benzo[d]imidazol-6-carbonitrile;
(Z)-1-(4-amino-2-fluorobut-2-en-1-yl)-4-(1,3-dimethyl-1H-pyrazol-5-yl)-1H-benzo[d]imidazol-6-carbonitrile;
(Z)-1-(4-amino-2-fluorobut-2-en-1-yl)-4-(1-(2-hydroxyethyl)-1H-pyrazol-3-yl)-1H-benzo[d]imidazol-6-carbonitrile;
(Z)-3-(1-(4-amino-2-fluorobut-2-en-1-yl)-6-(trifluoromethyl)-1H-benzo[d][1,2,3]triazol-4-yl)-N,N-dimethylbenzenesulfonamide;
(Z)-1-(3-(1-(4-amino-2-fluorobut-2-en-1-yl)-6-(trifluoromethyl)-1H-benzo[d][1,2,3]triazol-4-yl)-4-fluorophenyl)ethan-1-one;
(Z)-(3-(1-(4-amino-2-fluorobut-2-en-1-yl)-6-(trifluoromethyl)-1H-benzo[d][1,2,3]triazol-4-yl)-4-fluorophenyl)methanol;
(Z)-(3-(1-(4-amino-2-fluoro-2-en-1-yl)-6-(trifluoromethyl)-1H-benzo[d][1,2,3]triazol-4-yl)-2-chlorophenyl)methanol;
(Z)-3-fluoro-4-(4-(5-fluoropyridin-3-yl)-6-(trifluoromethyl)-1H-benzo[d][1,2,3]triazol-1-yl)but-2-en-1-amine;
(Z)-4-(4-(5-chloropyridin-3-yl)-6-(trifluoromethyl)-1H-benzo[d][1,2,3]triazol-1-yl)-3-fluorobut-2-en-1-amine;
(Z)-3-fluoro-4-(4-(pyrimidin-5-yl)-6-(trifluoromethyl)-1H-benzo[d][1,2,3]triazol-1-yl) but-2-en-1-amine;
(Z)-4-(4-(1-ethyl-1H-pyrazol-5-yl)-6-(trifluoromethyl)-1H-benzo[d][1,2,3]triazol-1-yl)-3-fluorobut-2-en-1-amine;
(Z)-4-[4-(1,3-dimethyl-1H-pyrazol-5-yl)-6-(trifluoromethyl)-1H-benzo[d][1,2,3]triazol-1-yl]-3-fluorobut-2-en-1-amine;
(Z)-2-(4-(1-(4-amino-2-fluorobut-2-en-1-yl)-6-(trifluoromethyl)-1H-benzo[d][1,2,3]triazol-4-yl]-1H-pyrazol-1-yl)ethan-1-ol;

(Z)-1-(4-amino-2-fluorobut-2-en-1-yl)-4-[2-fluoro-5-(hydroxymethyl)phenyl]-1H-benzo[d][1,2,3]triazol-6-carbonitrile;

(Z)-1-(4-amino-2-fluorobut-2-en-1-yl)-4-[2-chloro-3-(hydroxymethyl)phenyl]-1H-benzo[d][1,2,3]triazol-6-carbonitrile;

(Z)-1-(4-amino-2-fluorobut-2-en-1-yl)-4-(5-fluoropyridin-3-yl)-1H-benzo[d][1,2,3]triazol-6-carbonitrile;

(Z)-1-(4-amino-2-fluorobut-2-en-1-yl)-4-(5-chloropyridin-3-yl)-1H-benzo[d][1,2,3]triazol-6-carbonitrile;

(Z)-1-(4-amino-2-fluorobut-2-en-1-yl)-4-(pyrimidin-5-yl)-1H-benzo[d][1,2,3]triazol-6-carbonitrile; and (Z)-1-(4-amino-2-fluorobut-2-en-1-yl)-4-(1-methyl-1H-pyrazol-5-yl)-1H-benzo[d][1,2,3]triazol-6-carbonitrile.

In the compound of Formula 1 or pharmaceutically acceptable salt, more preferable compounds include a compound or pharmaceutically acceptable salt thereof selected from the group consisting of:

(Z)-3-fluoro-4-(6-fluoro-4-(3-(methylsulfonyl)phenyl)-1H-benzo[d]imidazol-1-yl)but-2-en-1-amine;

(Z)-3-fluoro-4-(6-fluoro-4-(3-(pyrrolidin-1-ylsulfonyl)phenyl)-1H-benzo[d]imidazol-1-yl)but-2-en-1-amine;

(Z)-3-(1-(4-amino-2-fluorobut-2-en-1-yl)-6-fluoro-1H-benzo[d]imidazol-4-yl)-N-cyclopropylbenzenesulfonamide;

(Z)-3-(1-(4-amino-2-fluorobut-2-en-1-yl)-6-fluoro-1H-benzo[d]imidazol-4-yl)-N-methylbenzenesulfonamide;

(Z)-3-fluoro-4-(4-(3-(methylsulfonyl)phenyl)-6-(trifluoromethyl)-1H-benzo[d]imidazol-1-yl)but-2-en-1-amine;

(Z)-3-(1-(4-amino-2-fluorobut-2-en-1-yl)-6-(trifluoromethyl)-1H-benzo[d]imidazol-4-yl)-N-methylbenzenesulfonamide;

methyl (Z)-1-(4-amino-2-fluorobut-2-en-1-yl)-4-(3-(N,N-dimethylsulfamoyl)-4-methoxyphenyl)-1H-benzo[d]imidazol-6-carboxylate;

methyl (Z)-1-(4-amino-2-fluorobut-2-en-1-yl)-4-(3-((3,3-difluoropyrrolidin-1-yl)sulfonyl)phenyl)-1H-benzo[d]imidazol-6-carboxylate;

methyl (Z)-1-(4-amino-2-fluorobut-2-en-1-yl)-4-(3-(pyrrolidin-1-ylsulfonyl)phenyl)-1H-benzo[d]imidazol-6-carboxylate;

methyl (Z)-1-(4-amino-2-fluorobut-2-en-1-yl)-4-(2-methoxy-5-(N-m ethylsulfamoyl)phenyl)-1H-benzo[d]imidazol-6-carboxylate;

methyl (Z)-1-(4-amino-2-fluorobut-2-en-1-yl)-4-(3-(methylsulfonyl)phenyl)-1H-benzo[d]imidazol-6-carboxylate;

methyl (Z)-1-(4-amino-2-fluorobut-2-en-1-yl)-4-(5-(N,N-diethylsulfamoyl)-2-methoxyphenyl)-1H-benzo[d]imidazol-6-carboxylate;

methyl (Z)-1-(4-amino-2-fluorobut-2-en-1-yl)-4-(5-(N-cyclopropylsulfamoyl)-2-methoxyphenyl)-1H-benzo[d]imidazol-6-carboxylate;

methyl (Z)-1-(4-amino-2-fluorobut-2-en-1-yl)-4-(3-(N-isopropylsulfamoyl)-4-methoxyphenyl)-1H-benzo[d]imidazol-6-carboxylate;

methyl (Z)-1-(4-amino-2-fluorobut-2-en-1-yl)-4-(3-(N-cyclopropylsulfamoyl)phenyl)-1H-benzo[d]imidazol-6-carboxylate;

methyl (Z)-1-(4-amino-2-fluorobut-2-en-1-yl)-4-(3-(N-methylsulfamoyl)phenyl)-1H-benzo[d]imidazol-6-carboxylate;

methyl (Z)-1-(4-amino-2-fluorobut-2-en-1-yl)-4-(3-(N,N-dimethylsulfamoyl)phenyl)-1H-benzo[d]imidazol-6-carboxylate;

methyl (Z)-1-(4-amino-2-fluorobut-2-en-1-yl)-4-(3-(N-(4-methoxybenzyl)sulfamoyl)phenyl)-1H-benzo[d]imidazol-6-carboxylate;

methyl (Z)-1-(4-amino-2-fluorobut-2-en-1-yl)-4-(3-(piperidin-1-ylsulfonyl)phenyl)-1H-benzo[d]imidazol-6-carboxylate;

methyl (Z)-1-(4-amino-2-fluorobut-2-en-1-yl)-4-(3-(ethylsulfonyl)phenyl)-1H-benzo[d]imidazol-6-carboxylate;

methyl (Z)-1-(4-amino-2-fluorobut-2-en-1-yl)-4-(2-methyl-5-((trifluoromethyl)sulfonyl)phenyl)-1H-benzo[d]imidazol-6-carboxylate;

methyl (Z)-1-(4-amino-2-fluorobut-2-en-1-yl)-4-(3-(N,N-diethylsulfamoyl)phenyl)-1H-benzo[d]imidazol-6-carboxylate;

methyl (Z)-1-(4-amino-2-fluorobut-2-en-1-yl)-4-(3-(dimethylphosphoryl)phenyl)-1H-benzo[d]imidazol-6-carboxylate;

(Z)-3-(1-(4-amino-2-fluorobut-2-en-1-yl)-2-(trifluoromethyl)-1H-benzo[d]imidazol-4-yl)-N-methylbenzenesulfonamide;

(Z)-3-(1-(4-amino-2-fluorobut-2-en-1-yl)-2-methyl-1H-benzo[d]imidazol-4-yl)-N,N-dimethylbenzenesulfonamide;

(Z)-3-fluoro-4-(2-methyl-4-(3-(pyrrolidin-1-ylsulfonyl)phenyl)-1H-benzo[d]imidazol-1-yl)but-2-en-1-amine;

methyl (Z)-1-(4-amino-2-fluorobut-2-en-1-yl)-4-(3-(N,N-dimethylsulfamoyl)phenyl)-2-methyl-1H-benzo[d]imidazol-6-carboxylate;

methyl (Z)-1-(4-amino-2-fluorobut-2-en-1-yl)-2-methyl-4-(3-(methylsulfonyl)phenyl)-1H-benzo[d]imidazol-6-carboxylate;

methyl (Z)-1-(4-amino-2-fluorobut-2-en-1-yl)-2-methyl-4-(3-(pyrrolidin-1-ylsulfonyl)phenyl)-1H-benzo[d]imidazol-6-carboxylate;

methyl (Z)-1-(4-amino-2-fluorobut-2-en-1-yl)-2-methyl-4-(3-(N-m ethylsulfamoyl)phenyl)-1H-benzo[d]imidazol-6-carboxylate;

(Z)-1-(4-amino-2-fluorobut-2-en-1-yl)-4-(3-(N,N-dimethylsulfamoyl)phenyl)-N,N,2-trimethyl-1H-benzo[d]imidazol-6-carboxamide;

(Z)-3-(1-(4-amino-2-fluorobut-2-en-1-yl)-2-ethyl-1H-benzo[d]imidazol-4-yl)-N,N-di methylbenzenesulfonamide;

(Z)-5-(1-(4-amino-2-fluorobut-2-en-1-yl)-1H-benzo[d][1,2,3]triazol-4-yl)-2-methoxy-N,N-dimethylbenzenesulfonamide;

(Z)-4-(4-(3-((3,3-difluoropyrrolidin-1-yl)sulfonyl)phenyl)-1H-benzo[d][1,2,3]triazol-1-yl)-3-fluorobut-2-en-1-amine;

(Z)-3-fluoro-4-(4-(3-(pyrrolidin-1-ylsulfonyl)phenyl)-1H-benzo[d][1,2,3]triazol-1-yl) but-2-en-1-amine;

(Z)-3-(1-(4-amino-2-fluorobut-2-en-1-yl)-1H-benzo[d][1,2,3]triazol-4-yl)-4-methoxy-N-methylbenzenesulfonamide;

(Z)-3-fluoro-4-(4-(3-(methylsulfonyl)phenyl)-1H-benzo[d][1,2,3]triazol-1-yl)but-2-en-1-amine;

(Z)-3-(1-(4-amino-2-fluorobut-2-en-1-yl)-1H-benzo[d][1,2,3]triazol-4-yl)-N-cyclopropyl-4-methoxybenzenesulfonamide;
(Z)-5-(1-(4-amino-2-fluorobut-2-en-1-yl)-1H-benzo[d][1,2,3]triazol-4-yl)-N-isopropyl-2-methoxybenzenesulfonamide;
(Z)-3-(1-(4-amino-2-fluorobut-2-en-1-yl)-1H-benzo[d][1,2,3]triazol-4-yl)-N-cyclopropylbenzenesulfonamide;
(Z)-3-(1-(4-amino-2-fluorobut-2-en-1-yl)-1H-benzo[d][1,2,3]triazol-4-yl)-N-methylbenzenesulfonamide;
(Z)-3-(1-(4-amino-2-fluorobut-2-en-1-yl)-1H-benzo[d][1,2,3]triazol-4-yl)-N,N-dimethylbenzenesulfonamide;
(Z)-3-fluoro-4-(4-(2-methoxy-5-((4-methyl piperazin-1-yl)sulfonyl)phenyl)-1H-benzo[d][1,2,3]triazol-1-yl)but-2-en-1-amine;
methyl
(Z)-1-(4-amino-2-fluorobut-2-en-1-yl)-4-(3-(N,N-dimethylsulfamoyl)-4-methoxyphenyl)-1H-benzo[d][1,2,3]triazol-6-carboxylate;
methyl
(Z)-1-(4-amino-2-fluorobut-2-en-1-yl)-4-(3-((3,3-difluoropyrrolidin-1-yl)sulfonyl)phenyl)-1H-benzo[d][1,2,3]triazol-6-carboxylate;
methyl
(Z)-1-(4-amino-2-fluorobut-2-en-1-yl)-4-(3-(pyrrolidin-1-ylsulfonyl)phenyl)-1H-benzo[d][1,2,3]triazol-6-carboxylate;
methyl
(Z)-1-(4-amino-2-fluorobut-2-en-1-yl)-4-(2-methoxy-5-(N-m ethylsulfamoyl)phenyl)-1H-benzo[d][1,2,3]triazol-6-carboxylate;
methyl
(Z)-1-(4-amino-2-fluorobut-2-en-1-yl)-4-(3-(methylsulfonyl)phenyl)-1H-benzo[d][1,2,3]triazol-6-carboxylate;
methyl
(Z)-1-(4-amino-2-fluorobut-2-en-1-yl)-4-(5-(N,N-diethylsulfamoyl)-2-methoxyphenyl)-1H-benzo[d][1,2,3]triazol-6-carboxylate;
methyl
(Z)-1-(4-amino-2-fluorobut-2-en-1-yl)-4-(5-(N-cyclopropylsulfamoyl)-2-methoxyphenyl)-1H-benzo[d][1,2,3]triazol-6-carboxylate;
methyl
(Z)-1-(4-amino-2-fluorobut-2-en-1-yl)-4-(3-(N-isopropylsulfamoyl)-4-methoxyphenyl)-1H-benzo[d][1,2,3]triazol-6-carboxylate;
methyl
(Z)-1-(4-amino-2-fluorobut-2-en-1-yl)-4-(3-(N-cyclopropylsulfamoyl)phenyl)-1H-benzo[d][1,2,3]triazol-6-carboxylate;
methyl
(Z)-1-(4-amino-2-fluorobut-2-en-1-yl)-4-(3-(N-m ethylsulfamoyl)phenyl)-1H-benzo[d][1,2,3
]triazol-6-carboxylate;
methyl
(Z)-1-(4-amino-2-fluorobut-2-en-1-yl)-4-(3-(N,N-dimethylsulfamoyl)phenyl)-1H-benzo[d][1,2,3]triazol-6-carboxylate;
methyl
(Z)-1-(4-amino-2-fluorobut-2-en-1-yl)-4-(3-(N-(4-methoxybenzyl)sulfamoyl)phenyl)-1H-benzo[d][1,2,3]triazol-6-carboxylate;
methyl
(Z)-1-(4-amino-2-fluorobut-2-en-1-yl)-4-(3-(ethylsulfonyl)phenyl)-1H-benzo[d][1,2,3]triazol-6-carboxylate;
methyl
(Z)-1-(4-amino-2-fluorobut-2-en-1-yl)-4-(2-methyl-5-((trifluoromethyl)sulfonyl)phenyl)-1H-benzo[d][1,2,3]triazol-6-carboxylate;
(Z)-1-(4-amino-2-fluorobut-2-en-1-yl)-4-(3-(N,N-dimethylsulfamoyl)-4-methoxyphenyl)-N-methoxy-1H-benzo[d][1,2,3]triazol-6-carboxamide;
(Z)-1-(4-amino-2-fluorobut-2-en-1-yl)-N-methoxy-4-(3-(pyrrolidin-1-ylsulfonyl)phenyl)-1H-benzo[d][1,2,3]triazol-6-carboxamide;
(Z)-1-(4-amino-2-fluorobut-2-en-1-yl)-N-methoxy-4-(2-methoxy-5-(N-methylsulfamoyl)phenyl)-1H-benzo[d][1,2,3]triazol-6-carboxamide;
(Z)-1-(4-amino-2-fluorobut-2-en-1-yl)-4-(5-(N,N-diethylsulfamoyl)-2-methoxyphen yl)-N-methoxy-1H-benzo[d][1,2,3]triazol-6-carboxamide;
(Z)-1-(4-amino-2-fluorobut-2-en-1-yl)-4-(5-(N-cyclopropylsulfamoyl)-2-methoxyphenyl)-N-methoxy-1H-benzo[d][1,2,3]triazol-6-carboxamide;
(Z)-1-(4-amino-2-fluorobut-2-en-1-yl)-N-methoxy-N-methyl-4-(3-(pyrrolidin-1-ylsulfonyl)phenyl)-1H-benzo[d][1,2,3]triazol-6-carboxamide;
(Z)-1-(4-amino-2-fluorobut-2-en-1-yl)-4-(5-(N,N-diethylsulfamoyl)-2-methoxyphen yl)-N-methoxy-N-methyl-1H-benzo[d][1,2,3]triazol-6-carboxamide;
(Z)-1-(4-amino-2-fluorobut-2-en-1-yl)-4-(3-(N,N-dimethylsulfamoyl)phenyl)-N-methoxy-N-methyl-1H-benzo[d][1,2,3]triazol-6-carboxamide;
(Z)-1-(3-(1-(4-amino-2-fluorobut-2-en-1-yl)-6-(trifluoromethyl)-1H-benzo[d]imidazol-4-yl)-4-fluorophenyl)ethan-1-one;
(Z)-3-fluoro-4-(4-(pyridin-3-yl)-6-(trifluoromethyl)-1H-benzo[d]imidazol-1-yl)but-2-en-1-amine;
(Z)-3-fluoro-4-(4-(5-fluoropyridin-3-yl)-6-(trifluoromethyl)-1H-benzo[d]imidazol-1-yl)but-2-en-1-amine;
(Z)-4-(4-(5-chloropyridin-3-yl)-6-(trifluoromethyl)-1H-benzo[d]imidazol-1-yl)-3-fluoro-but-2-en-1-amine;
(Z)-3-fluoro-4-(4-(pyrimidin-5-yl)-6-(trifluoromethyl)-1H-benzo[d]imidazol-1-yl)but-2-en-1-amine;
(Z)-3-fluoro-4-(4-(1-methyl-1H-pyrazol-5-yl)-6-(trifluoromethyl)-1H-benzo[d]imidazol-1-yl)but-2-en-1-yl-amine;
(Z)-4-(4-(1-ethyl-1H-pyrazol-5-yl)-6-(trifluoromethyl)-1H-benzo[d]imidazol-1-yl]-3-fluoro-but-2-en-1-amine;
(Z)-3-fluoro-4-(4-(1-isopropyl-1H-pyrazol-5-yl)-6-(trifluoromethyl)-1H-benzo[d]imidazol-1-yl)but-2-en-1-amine;
(Z)-3-fluoro-4-(4-[1-methyl-3-(trifluoromethyl)-1H-pyrazol-5-yl]-6-(trifluoromethyl)-1H-benzo[d]imidazol-1-yl)but-2-en-1-amine;
(Z)-2-(4-(1-(4-amino-2-fluorobut-2-en-1-yl)-6-(trifluoromethyl)-1H-benzo[d]imidazol-4-yl)-1H-pyrazol-1-yl)ethan-1-ol;
(Z)-1-(4-amino-2-fluorobut-2-en-1-yl)-4-(3-(pyrrolidin-1-ylsulfonyl)phenyl)-1H-benzo[d]imidazol-6-carbonitrile;
(Z)-3-(1-(4-amino-2-fluorobut-2-en-1-yl)-6-cyano-1H-benzo[d]imidazol-4-yl)-N,N-dimethylbenzenesulfonamide;
(Z)-3-(1-(4-amino-2-fluorobut-2-en-1-yl)-6-cyano-1H-benzo[d]imidazol-4-yl)-4-methoxy-N-methylbenzenesulfonamide;
(Z)-4-(5-acetyl-2-fluorophenyl)-1-(4-amino-2-fluorobut-2-en-1-yl)-1H-benzo[d]imidazol-6-carbonitrile;
(Z)-1-(4-amino-2-fluorobut-2-en-1-yl)-4-(2-fluoro-5-(hydroxymethyl)phenyl)-1H-benzo[d]imidazol-6-carbonitrile;
(Z)-1-(4-amino-2-fluoro-2-but-1-yl)-4-(2-chloro-3-(hydroxymethyl)phenyl)-1H-benzo[d]imidazol-6-carbonitrile;

(Z)-1-(4-amino-2-fluorobut-2-en-1-yl)-4-(pyridin-3-yl)-1H-benzo[d]imidazol-6-carbonitrile;

(Z)-1-(4-amino-2-fluorobut-2-en-1-yl)-4-(5-fluoropyridin-3-yl)-1H-benzo[d]imidazol-6-carbonitrile;

(Z)-1-(4-amino-2-fluorobut-2-en-1-yl)-4-(5-chloropyridin-3-yl)-1H-benzo[d]imidazol-6-carbonitrile;

(Z)-1-(4-amino-2-fluorobut-2-en-1-yl)-4-(pyrimidin-5-yl)-1H-benzo[d]imidazol-6-carbonitrile;

(Z)-1-(4-amino-2-fluorobut-2-en-1-yl)-4-(1-methyl-1H-pyrazol-5-yl)-1H-benzo[d]imidazol-6-carbonitrile;

(Z)-1-(4-amino-2-fluorobut-2-en-1-yl)-4-(1-ethyl-1H-pyrazol-5-yl)-1H-benzo[d]imidazol-6-carbonitrile;

(Z)-1-(4-amino-2-fluorobut-2-en-1-yl)-4-(1-methyl-3-(trifluoromethyl)-1H-pyrazol-5-yl)-1H-benzo[d]imidazol-6-carbonitrile;

(Z)-1-(4-amino-2-fluorobut-2-en-1-yl)-4-(1,3-dimethyl-1H-pyrazol-5-yl)-1H-benzo[d]imidazol-6-carbonitrile;

(Z)-1-(4-amino-2-fluorobut-2-en-1-yl)-4-(1-(2-hydroxyethyl)-1H-pyrazol-3-yl)-1H-benzo[d]imidazol-6-carbonitrile;

(Z)-3-(1-(4-amino-2-fluorobut-2-en-1-yl)-6-(trifluoromethyl)-1H-benzo[d][1,2,3]triazol-4-yl)-N,N-dimethylbenzenesulfonamide;

(Z)-1-(3-(1-(4-amino-2-fluorobut-2-en-1-yl)-6-(trifluoromethyl)-1H-benzo[d][1,2,3]triazol-4-yl)-4-fluorophenyl) ethan-1-one;

(Z)-(3-(1-(4-amino-2-fluorobut-2-en-1-yl)-6-(trifluoromethyl)-1H-benzo[d][1,2,3]triazol-4-yl)-4-fluorophenyl) methanol;

(Z)-(3-(1-(4-amino-2-fluoro-2-en-1-yl)-6-(trifluoromethyl)-1H-benzo[d][1,2,3]triazol-4-yl)-2-chlorophenyl)methanol;

(Z)-3-fluoro-4-(4-(5-fluoropyridin-3-yl)-6-(trifluoromethyl)-1H-benzo[d][1,2,3]triazol-1-yl)but-2-en-1-amine;

(Z)-4-(4-(5-chloropyridin-3-yl)-6-(trifluoromethyl)-1H-benzo[d][1,2,3]triazol-1-yl)-3-fluorobut-2-en-1-amine;

(Z)-3-fluoro-4-(4-(pyrimidin-5-yl)-6-(trifluoromethyl)-1H-benzo[d][1,2,3]triazol-1-yl) but-2-en-1-amine;

(Z)-4-(4-(1-ethyl-1H-pyrazol-5-yl)-6-(trifluoromethyl)-1H-benzo[d][1,2,3]triazol-1-yl)-3-fluorobut-2-en-1-amine;

(Z)-4-[4-(1,3-dimethyl-1H-pyrazol-5-yl)-6-(trifluoromethyl)-1H-benzo[d][1,2,3]triazol-1-yl]-3-fluorobut-2-en-1-amine;

(Z)-2-(4-(1-(4-amino-2-fluorobut-2-en-1-yl)-6-(trifluoromethyl)-1H-benzo[d][1,2,3]triazol-4-yl]-1H-pyrazol-1-yl) ethan-1-ol;

(Z)-1-(4-amino-2-fluorobut-2-en-1-yl)-4-[2-fluoro-5-(hydroxymethyl)phenyl]-1H-benzo[d][1,2,3]triazol-6-carbonitrile;

(Z)-1-(4-amino-2-fluorobut-2-en-1-yl)-4-[2-chloro-3-(hydroxymethyl)phenyl]-1H-benzo[d][1,2,3]triazol-6-carbonitrile;

(Z)-1-(4-amino-2-fluorobut-2-en-1-yl)-4-(5-fluoropyridin-3-yl)-1H-benzo[d][1,2,3]triazol-6-carbonitrile;

(Z)-1-(4-amino-2-fluorobut-2-en-1-yl)-4-(5-chloropyridin-3-yl)-1H-benzo[d][1,2,3]triazol-6-carbonitrile;

(Z)-1-(4-amino-2-fluorobut-2-en-1-yl)-4-(pyrimidin-5-yl)-1H-benzo[d][1,2,3]triazol-6-carbonitrile; and (Z)-1-(4-amino-2-fluorobut-2-en-1-yl)-4-(1-methyl-1H-pyrazol-5-yl)-1H-benzo[d][1,2,3]triazol-6-carbonitrile.

In the compound of Formula 1 or pharmaceutically acceptable salt, still more preferable compounds include a compound or pharmaceutically acceptable salt thereof selected from the group consisting of:

(Z)-1-(3-(1-(4-amino-2-fluorobut-2-en-1-yl)-6-(trifluoromethyl)-1H-benzo[d]imidazol-4-yl)-4-fluorophenyl)ethan-1-one;

(Z)-3-fluoro-4-(4-(pyridin-3-yl)-6-(trifluoromethyl)-1H-benzo[d]imidazol-1-yl)but-2-en-1-amine;

(Z)-3-fluoro-4-(4-(5-fluoropyridin-3-yl)-6-(trifluoromethyl)-1H-benzo[d]imidazol-1-yl)but-2-en-1-amine;

(Z)-4-(4-(5-chloropyridin-3-yl)-6-(trifluoromethyl)-1H-benzo[d]imidazol-1-yl)-3-fluoro-but-2-en-1-amine;

(Z)-3-fluoro-4-(4-(pyrimidin-5-yl)-6-(trifluoromethyl)-1H-benzo[d]imidazol-1-yl)but-2-en-1-amine;

(Z)-3-fluoro-4-(4-(1-methyl-1H-pyrazol-5-yl)-6-(trifluoromethyl)-1H-benzo[d]imidazol-1-yl)but-2-en-1-yl-amine;

(Z)-4-(4-(1-ethyl-1H-pyrazol-5-yl)-6-(trifluoromethyl)-1H-benzo[d]imidazol-1-yl]-3-fluoro-but-2-en-1-amine;

(Z)-3-fluoro-4-(4-(1-isopropyl-1H-pyrazol-5-yl)-6-(trifluoromethyl)-1H-benzo[d]imidazol-1-yl)but-2-en-1-amine;

(Z)-3-fluoro-4-(4-[1-methyl-3-(trifluoromethyl)-1H-pyrazol-5-yl]-6-(trifluoromethyl)-1H-benzo[d]imidazol-1-yl) but-2-en-1-amine;

(Z)-2-(4-(1-(4-amino-2-fluorobut-2-en-1-yl)-6-(trifluoromethyl)-1H-benzo[d]imidazol-4-yl)-1H-pyrazol-1-yl) ethan-1-ol;

(Z)-1-(4-amino-2-fluorobut-2-en-1-yl)-4-(3-(pyrrolidin-1-ylsulfonyl)phenyl)-1H-benzo[d]imidazol-6-carbonitrile;

(Z)-3-(1-(4-amino-2-fluorobut-2-en-1-yl)-6-cyano-1H-benzo[d]imidazol-4-yl)-N,N-dimethylbenzenesulfonamide;

(Z)-3-(1-(4-amino-2-fluorobut-2-en-1-yl)-6-cyano-1H-benzo[d]imidazol-4-yl)-4-methoxy-N-methylbenzenesulfonamide;

(Z)-4-(5-acetyl-2-fluorophenyl)-1-(4-amino-2-fluorobut-2-en-1-yl)-1H-benzo[d]imidazol-6-carbonitrile;

(Z)-1-(4-amino-2-fluorobut-2-en-1-yl)-4-(2-fluoro-5-(hydroxymethyl)phenyl)-1H-benzo[d]imidazol-6-carbonitrile;

(Z)-1-(4-amino-2-fluoro-2-but-1-yl)-4-(2-chloro-3-(hydroxymethyl)phenyl)-1H-benzo[d]imidazol-6-carbonitrile;

(Z)-1-(4-amino-2-fluorobut-2-en-1-yl)-4-(pyridin-3-yl)-1H-benzo[d]imidazol-6-carbonitrile;

(Z)-1-(4-amino-2-fluorobut-2-en-1-yl)-4-(5-fluoropyridin-3-yl)-1H-benzo[d]imidazol-6-carbonitrile;

(Z)-1-(4-amino-2-fluorobut-2-en-1-yl)-4-(5-chloropyridin-3-yl)-1H-benzo[d]imidazol-6-carbonitrile;

(Z)-1-(4-amino-2-fluorobut-2-en-1-yl)-4-(pyrimidin-5-yl)-1H-benzo[d]imidazol-6-carbonitrile;

(Z)-1-(4-amino-2-fluorobut-2-en-1-yl)-4-(1-methyl-1H-pyrazol-5-yl)-1H-benzo[d]imidazol-6-carbonitrile;

(Z)-1-(4-amino-2-fluorobut-2-en-1-yl)-4-(1-ethyl-1H-pyrazol-5-yl)-1H-benzo[d]imidazol-6-carbonitrile;

(Z)-1-(4-amino-2-fluorobut-2-en-1-yl)-4-(1-methyl-3-(trifluoromethyl)-1H-pyrazol-5-yl)-1H-benzo[d]imidazol-6-carbonitrile;

(Z)-1-(4-amino-2-fluorobut-2-en-1-yl)-4-(1,3-dimethyl-1H-pyrazol-5-yl)-1H-benzo[d]imidazol-6-carbonitrile;

(Z)-1-(4-amino-2-fluorobut-2-en-1-yl)-4-(1-(2-hydroxyethyl)-1H-pyrazol-3-yl)-1H-benzo[d]imidazol-6-carbonitrile;

(Z)-3-(1-(4-amino-2-fluorobut-2-en-1-yl)-6-(trifluoromethyl)-1H-benzo[d][1,2,3]triazol-4-yl)-N,N-dimethylbenzenesulfonamide;

(Z)-1-(3-(1-(4-amino-2-fluorobut-2-en-1-yl)-6-(trifluoromethyl)-1H-benzo[d][1,2,3]triazol-4-yl)-4-fluorophenyl) ethan-1-one;

(Z)-(3-(1-(4-amino-2-fluorobut-2-en-1-yl)-6-(trifluoromethyl)-1H-benzo[d][1,2,3]triazol-4-yl)-4-fluorophenyl) methanol;

(Z)-(3-(1-(4-amino-2-fluoro-2-en-1-yl)-6-(trifluoromethyl)-1H-benzo[d][1,2,3]triazol-4-yl)-2-chlorophenyl)methanol;
(Z)-3-fluoro-4-(4-(5-fluoropyridin-3-yl)-6-(trifluoromethyl)-1H-benzo[d][1,2,3]triazol-1-yl)but-2-en-1-amine;
(Z)-4-(4-(5-chloropyridin-3-yl)-6-(trifluoromethyl)-1H-benzo[d][1,2,3]triazol-1-yl)-3-fluorobut-2-en-1-amine;
(Z)-3-fluoro-4-(4-(pyrimidin-5-yl)-6-(trifluoromethyl)-1H-benzo[d][1,2,3]triazol-1-yl) but-2-en-1-amine;
(Z)-4-(4-(1-ethyl-1H-pyrazol-5-yl)-6-(trifluoromethyl)-1H-benzo[d][1,2,3]triazol-1-yl)-3-fluorobut-2-en-1-amine;
(Z)-4-[4-(1,3-dimethyl-1H-pyrazol-5-yl)-6-(trifluoromethyl)-1H-benzo[d][1,2,3]triazol-1-yl]-3-fluorobut-2-en-1-amine;
(Z)-2-(4-(1-(4-amino-2-fluorobut-2-en-1-yl)-6-(trifluoromethyl)-1H-benzo[d][1,2,3]triazol-4-yl]-1H-pyrazol-1-yl) ethan-1-ol;
(Z)-1-(4-amino-2-fluorobut-2-en-1-yl)-4-[2-fluoro-5-(hydroxymethyl)phenyl]-1H-benzo[d][1,2,3]triazol-6-carbonitrile;
(Z)-1-(4-amino-2-fluorobut-2-en-1-yl)-4-[2-chloro-3-(hydroxymethyl)phenyl]-1H-benzo[d][1,2,3]triazol-6-carbonitrile;
(Z)-1-(4-amino-2-fluorobut-2-en-1-yl)-4-(5-fluoropyridin-3-yl)-1H-benzo[d][1,2,3]triazol-6-carbonitrile;
(Z)-1-(4-amino-2-fluorobut-2-en-1-yl)-4-(5-chloropyridin-3-yl)-1H-benzo[d][1,2,3]triazol-6-carbonitrile;
(Z)-1-(4-amino-2-fluorobut-2-en-1-yl)-4-(pyrimidin-5-yl)-1H-benzo[d][1,2,3]triazol-6-carbonitrile; and
(Z)-1-(4-amino-2-fluorobut-2-en-1-yl)-4-(1-methyl-1H-pyrazol-5-yl)-1H-benzo[d][1,2,3]triazol-6-carbonitrile.

In the compound of Formula 1 or pharmaceutically acceptable salt, especially preferable compounds include a compound or pharmaceutically acceptable salt thereof selected from the group consisting of:
(Z)-3-fluoro-4-(4-(1-methyl-1H-pyrazol-5-yl)-6-(trifluoromethyl)-1H-benzo[d]imidazol-1-yl)but-2-en-1-yl-amine;
(Z)-4-(4-(1-ethyl-1H-pyrazol-5-yl)-6-(trifluoromethyl)-1H-benzo[d]imidazol-1-yl]-3-fluoro-but-2-en-1-amine;
(Z)-3-fluoro-4-(4-(1-isopropyl-1H-pyrazol-5-yl)-6-(trifluoromethyl)-1H-benzo[d]imidazol-1-yl)but-2-en-1-amine;
(Z)-2-(4-(1-(4-amino-2-fluorobut-2-en-1-yl)-6-(trifluoromethyl)-1H-benzo[d]imidazol-4-yl)-1H-pyrazol-1-yl) ethan-1-ol;
(Z)-1-(4-amino-2-fluorobut-2-en-1-yl)-4-(3-(pyrrolidin-1-ylsulfonyl)phenyl)-1H-benzo[d]imidazol-6-carbonitrile;
(Z)-1-(4-amino-2-fluorobut-2-en-1-yl)-4-(1-methyl-1H-pyrazol-5-yl)-1H-benzo[d]imidazol-6-carbonitrile;
(Z)-1-(4-amino-2-fluorobut-2-en-1-yl)-4-(1-(2-hydroxyethyl)-1H-pyrazol-3-yl)-1H-benzo[d]imidazol-6-carbonitrile;
(Z)-3-(1-(4-amino-2-fluorobut-2-en-1-yl)-6-(trifluoromethyl)-1H-benzo[d][1,2,3]triazol-4-yl)-N,N-dimethylbenzenesulfonamide;
(Z)-4-[4-(1,3-dimethyl-1H-pyrazol-5-yl)-6-(trifluoromethyl)-1H-benzo[d][1,2,3]triazol-1-yl]-3-fluorobut-2-en-1-amine; and
(Z)-2-(4-(1-(4-amino-2-fluorobut-2-en-1-yl)-6-(trifluoromethyl)-1H-benzo[d][1,2,3]triazol-4-yl]-1H-pyrazol-1-yl) ethan-1-ol.

The compound of Formula 1 of the present invention may be in a pharmaceutically acceptable salt form. The salt may be a conventional acid addition salt form, which includes e.g., salts derived from an inorganic acid an organic acid.

The compound of Formula 1 or pharmaceutically acceptable salt thereof according to the present invention may be prepared by various methods. For example, the compound of Formula 1 or pharmaceutically acceptable salt thereof according to the present invention by a process which comprises reacting a compound of Formula 2 with a compound of Formula 3 to obtain a compound of Formula 1a; deprotecting the compound of Formula 1a to obtain a compound of Formula 1; and optionally converting the compound of Formula 1 to a pharmaceutically acceptable salt thereof:

<Formula 1>

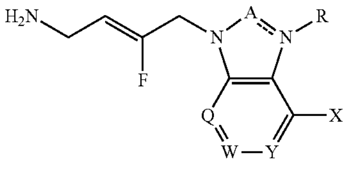

<Formula 1a>

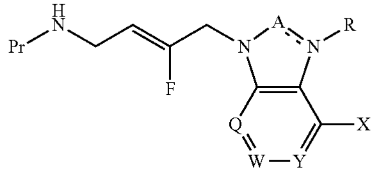

<Formula 2>

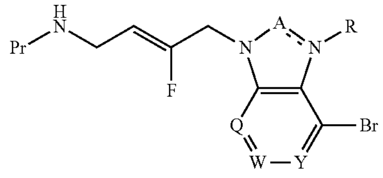

<Formula 3>

B—X

In Formulas 1, 1a, 2, and 3, Pr is an amine protecting group (e.g., tert-butoxycarbonyl, 9-fluorenylmethyloxycarbonyl (FMOC), benzyloxycarbonyl (CBZ), tri phenylmethyl (trityl), etc.), B is boronic acid ($B(OH)_2$) or boronic acid pinacol ester, and A, R, Q, W, Y, and X are the same as defined above.

The reaction between the compound of Formula 2 and the commercially available compound of Formula 3 may be carried out according to the Suzuki reaction. Said reaction may be carried out using a palladium catalyst, such as palladium diacetate ($Pd(OAc)_2$), tris(dibenzylideneacetone) dipalladium ($Pd_2(dba)_3$), tetrakis(triphenylphosphine)palladium ($Pd(PPh_3)_4$) or palladium di[1,1'-bis(diphenylphosphino)ferrocene]dichloride ($PdCl_2(dppf)_2$), etc. When performing the reaction under a palladium catalyst, a ligand and a base may be added in addition to the palladium catalyst. The ligand includes (S)-2,2-bis(diphenylphosphino)-1,1-binaphthyl (BINAP), 1,1'-bis(diphenylphosphino)ferrocene (dppf), or (tri-O-tolyl)phosphine ($P(O-Tol)_3$), etc. The base includes an inorganic base such as cesium carbonate ($Cs_2CO_3$), sodium carbonate ($Na_2CO_3$), potassium carbonate ($K_2CO_3$), potassium fluoride (KF), cesium fluoride (CsF), sodium hydroxide (NaOH), potassium phosphonate ($K_3PO_4$), sodium tert-butoxide (tert-BuONa) or potassium tert-butoxide (tert-BuOK), etc. Said reaction may be carried out in a non-polar organic solvent such as benzene or toluene or a polar organic solvent such as dioxane, tetrahydrofuran, acetonitrile, 1,2-dimethoxy ethane, or N,N-dimethylformamide, at 50° C., to 150° C., preferably 80° C. to 110° C. Other reaction conditions including a reaction time may be determined according to known methods for the Suzuki reaction (Barbara Czako and Laszlo Kurti, *STRATEGIC APPLICATIONS of NAMED REACTIONS in ORGANIC SYNTHESIS,* 2005).

The deprotection of the compound of Formula 1a may be carried out according to known methods (e.g., Theodora W. Greene and Peter G. M. Wuts, *Protective groups in organic synthesis,* 3rd Ed., 1999). For example, the amine protecting group may be removed at room temperature using an acid such as trifluoroacetic acid or hydrochloric acid gas, in an organic solvent such as dichloromethane, dioxane, ethyl acetate, etc.

The compound of Formula 2 may be prepared according to a process pf the following Reaction Scheme 1.

<Reaction Scheme 1>

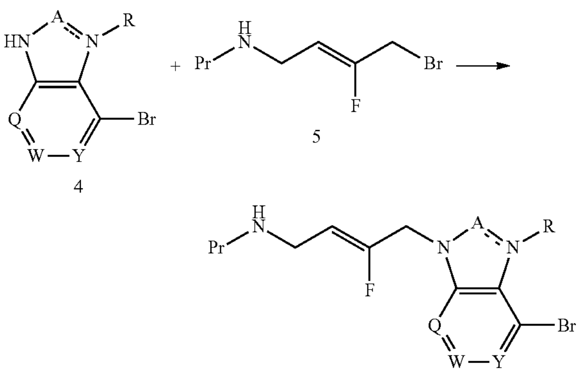

4 5 2

In Reaction Scheme 1, A, R, Q, W, Y, X, and Pr are the same as defined above.

The compounds of Formulas 4 and 5 are commercially available. The coupling reaction between the compound of Formula 4 and the compound of Formula 5 may be carried out in the presence of a base and a solvent. The base may be cesium carbonate, potassium carbonate, sodium carbonate, etc., and the solvent may be an organic solvent such as N,N-dimethylformamide, dioxane, tetrahydrofuran, etc. And, the reaction may be carried out at room temperature to 100° C.

The bicyclic fused ring derivative according to the present invention (i.e., the compound of Formula 1 or pharmaceutically acceptable salt thereof) has an inhibitory activity against lysyl oxidase isozymes and thus can be effectively applied for the prevention or treatment of diseases mediated by lysyl oxidase isozymes. Preferably, the compound of Formula 1 or pharmaceutically acceptable salt thereof according to the present invention may be usefully applied for preventing or treating various fibrotic diseases, such as idiopathic pulmonary fibrosis (IPF), nonalcoholic hepatosteatosis (NASH), chronic kidney disease (CKD), or liver cirrhosis, preferably nonalcoholic hepatosteatosis (NASH).

Therefore, the present invention includes, within its scope, a pharmaceutical composition for inhibiting lysyl oxidase isoenzymes comprising a therapeutically effective amount of the compound of Formula 1 or pharmaceutically acceptable salt thereof as an active ingredient. In an embodiment, the present invention provides a pharmaceutical composition for preventing or treating idiopathic pulmonary fibrosis (IPF), nonalcoholic hepatosteatosis (NASH), chronic kidney disease (CKD), or liver cirrhosis, preferably nonalcoholic hepatosteatosis (NASH), comprising a therapeutically effective amount of the compound of Formula 1 or pharmaceutically acceptable salt thereof as an active ingredient.

The pharmaceutical composition of the present invention may comprise a pharmaceutically acceptable carrier, such as diluents, disintegrants, sweeteners, lubricants, or flavoring agents, which is conventionally used in the art. The pharmaceutical composition may be formulated to an oral dosage form such as tablets, capsules, powders, granules, suspensions, emulsions, or syrups; or a parenteral dosage form such as solutions for external use, suspensions for external use, emulsions for external use, gels (e.g., ointment), inhalations, nebulizations, injections, according to conventional methods. The dosage form may be formulated to various forms, e.g., dosage forms for single administration or for multiple administrations.

The pharmaceutical composition of the present invention may comprise, for example, a diluent (e.g., lactose, corn starch, etc.); a lubricant (e.g., magnesium stearate); an emulsifying agent; a suspending agent; a stabilizer; and/or an isotonic agent. If necessary, the composition further comprises sweeteners and/or flavoring agents.

The composition of the present invention may be administered orally or parenterally, including inhalant, intravenous, intraperitoneal, subcutaneous, rectal and topical routes of administration. Therefore, the composition of the present invention may be formulated into various forms such as tablets, capsules, aqueous solutions or suspensions. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient may be combined with emulsifying and/or suspending agents. If desired, certain sweetening and/or flavoring agents may be used. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present invention may be in the form of an aqueous solution containing pharmaceutically acceptable carriers, e.g., saline having a pH level of 7.4. The solutions may be introduced into a patient's intramuscular bloodstream by local bolus injection.

The bicyclic fused ring derivative, i.e., the compound of Formula 1 or pharmaceutically acceptable salt thereof may be administered in an effective amount ranging from about 0.001 mg/kg to about 100 mg/kg per day to a subject patient. Of course, the dosage may be changed according to the patient's age, weight, susceptibility, symptom, or activity of the compound.

The present invention includes, within its scope, a method for inhibiting lysyl oxidase isoenzymes in a mammal, comprising administering a therapeutically effective amount of the compound of Formula 1 or pharmaceutically acceptable salt thereof to the mammal in need thereof. In an embodiment, the present invention provides a method for treating idiopathic pulmonary fibrosis (IPF), nonalcoholic hepatosteatosis (NASH), chronic kidney disease (CKD), or liver cirrhosis, preferably nonalcoholic hepatosteatosis (NASH), comprising administering a therapeutically effective amount of the compound of Formula 1 or pharmaceutically acceptable salt thereof to the mammal in need thereof.

The present invention also provides a use of the compound of Formula 1 or pharmaceutically acceptable salt thereof for the manufacture of a medicament for inhibiting lysyl oxidase isoenzymes in a mammal. In an embodiment, the present invention provides a use of the compound of Formula 1 or pharmaceutically acceptable salt thereof for the manufacture of a medicament for preventing or treating idiopathic pulmonary fibrosis (IPF), nonalcoholic hepatosteatosis (NASH), chronic kidney disease (CKD), or liver cirrhosis, preferably nonalcoholic hepatosteatosis (NASH).

Hereinafter, the present invention will be described in more detail through examples and test examples. However, these examples and test examples are provided for illustration purposes only and are not intended to limit the scope of the invention.

The analyses of the compounds prepared in the following Examples were carried out as follows: Nuclear magnetic resonance (NMR) spectrum analysis was carried out using Bruker 400 MHz spectrometer and Agilent 600 MHz spectrometer and the chemical shifts thereof were analyzed in ppm. And, the indicated molecular weights were measured by using liquid chromatograph/mass selective detector (MSD) of Agilent 1260 Infinity series equipped with an electrostatic spray interface, using a single quadrupole for ESI+ (electrospray ionization positive mode) MS, which depicts the m/z ratio values, with the [M+H]+ peak represented. Column chromatography was carried out on silica gel (Merck, 70-230 mesh) (W. C. Still, J. Org. Chem., 43, 2923, 1978). The abbreviation used in the following Examples are as follows: methyl is abbreviated as Me, ethyl is abbreviated as Et, phenyl is abbreviated as Ph, and tert-butyloxycarbonyl is abbreviated as BOC. In addition, the starting materials for each example were known compounds that were synthesized according to literatures or purchased from the market such as Sigma-Aldrich.

Preparation 1. tert-butyl N—[(Z)-4-(4-bromo-6-fluoro-benzimidazol-1-yl)-3-fluoro-but-2-enyl]carbamate 4-Bromo-6-fluoro-1H-benzoimidazole (215 mg) and cesium carbonate (651 mg) were dissolved in N,N-dimethylformamide (3.0 mL) and then tert-butyl N—[(Z)-4-bromo-3-fluoro-but-2-enyl]carbamate (343 mg) was added thereto. The mixture was stirred at room temperature for 16 hours. After diethyl ether was added thereto, the reaction mixture was washed with distilled water, dried over anhydrous magnesium sulfate, and then concentrated under reduced pressure to obtain a yellow liquid residue. The residue was purified by silica gel column chromatography (developing solvent: n-hexane/ethyl acetate=1/1) to prepare 361 mg of the titled compound as a light green liquid. (Yield: 77.1%)

$^1$H-NMR (MeOD, 400 MHz) δ 7.93 (s, 1H), 7.44-7.35 (m, 2H), 5.20 (dt, 1H), 5.05 (d, 2H), 3.73 (s, 2H), 1.38 (s, 9H)

Preparation 2. tert-Butyl N—[(Z)-4-[4-bromo-6-(trifluoromethyl)benzimidazol-1-yl]-3-fluoro-but-2-enyl]carbamate The titled compound (333 mg) was prepared as a yellow solid in accordance with the same procedures as in Preparation 1, except for using 4-bromo-6-(trifluoromethyl)-1H-benzo[d]imidazole (265 mg) instead of 4-bromo-6-fluoro-1H-benzoimidazole. (Yield: 73.7%)

$^1$H-NMR (MeOD, 400 MHz) δ 8.50 (s, 1H), 8.04 (s, 1H), 7.79 (s, 1H), 5.33-5.23 (m, 3H), 3.73 (d, 2H), 1.42 (s, 9H)

Preparation 3. methyl 7-bromo-3-[(Z)-4-(tert-butoxycarbonylamino)-2-fluoro-but-2-enyl]benzimidazol-5-carboxylate The titled compound (75 mg) was prepared as a white solid in accordance with the same procedures as in Preparation 1, except for using methyl 4-bromo-1H-benzo[d]imidazol-6-carboxylate (255 mg) instead of 4-bromo-6-fluoro-1H-benzoimidazole. (Yield: 17.0%)

$^1$H-NMR (MeOD, 400 MHz) δ 8.46 (s, 1H), 8.31 (s, 1H), 8.15 (s, 1H), 5.30-5.14 (m, 3H), 4.10 (s, 3H), 3.74 (d, 2H), 1.40 (s, 9H)

Preparation 4. 7-bromo-3-[(Z)-4-(tert-butoxycarbonylamino)-2-fluoro-but-2-enyl]benzimidazol-5-carboxylic acid Methyl 7-bromo-3-[(Z)-4-(tert-butoxycarbonylamino)-2-fluoro-but-2-enyl]benzimidazol-5-carboxy late prepared in Preparation 3 (40 mg) was dissolved in 1.4 mL of a mixed solvent of tetrahydrofuran/distilled water (6/1) and then a lithium hydroxide solution (40 mg/1.0 mL) was added thereto. The mixture was stirred at room temperature for 16 hours. Distilled water (30 mL) was added to the reaction mixture and then the pH thereof was adjusted to 3-4 with a saturated citric acid solution. After ethyl acetate was added thereto, the reaction mixture was washed with a sodium hydrogen carbonate solution and brine, dried over anhydrous sodium sulfate, and then concentrated under reduced pressure to prepare 37 mg of the titled compound as a white solid. (Yield: 95.0%)

$^1$H-NMR (MeOD, 400 MHz) δ 8.46 (s, 1H), 8.31 (s, 1H), 8.15 (s, 1H), 5.34-5.19 (m, 3H), 3.75 (d, 2H), 1.41 (s, 9H)

Preparation 5. tert-butyl N—[(Z)-4-[4-bromo-2-(trifluoromethyl)benzimidazol-1-yl]-3-fluoro-but-2-enyl]carbamate The titled compound (393 mg) was prepared as a white solid in accordance with the same procedures as in Preparation 1, except for using 4-bromo-2-(trifluoromethyl)-1H-benzo[d]imidazole (265 mg) instead of 4-bromo-6-fluoro-1H-benzoimidazole. (Yield: 86.8%)

$^1$H-NMR (MeOD, 400 MHz) δ 7.58 (d, 1H), 7.43 (d, 1H), 7.11 (dd, 1H), 5.33-5.17 (m, 3H), 3.75 (d, 2H), 1.40 (s, 9H)

Preparation 6. tert-butyl N—[(Z)-4-(4-bromo-2-methyl-benzimidazol-1-yl)-3-fluoro-but-2-enyl]carbamate The titled compound (147 mg) was prepared as a white solid in accordance with the same procedures as in Preparation 1, except for using 4-bromo-2-methyl-1H-benzo[d]imidazole (211 mg) instead of 4-bromo-6-fluoro-1H-benzoimidazole. (Yield: 37.0%)

$^1$H-NMR (MeOD, 400 MHz) δ 7.50 (d, 1H), 7.41 (d, 1H), 7.17 (dd, 1H), 5.30-5.14 (m, 3H), 3.72 (d, 2H), 2.65 (s, 3H), 1.41 (s, 9H)

Preparation 7. methyl 7-bromo-3-[(Z)-4-(tert-butoxycarbonylamino)-2-fluoro-but-2-enyl]-2-methyl-benzimidazol-5-carboxylate The titled compound (263 mg) was prepared as a white solid in accordance with the same procedures as in Preparation 1, except for using methyl 4-bromo-2-methyl-1H- benzo[d]imidazol-6-carboxylate (269 mg) instead of 4-bromo-6-fluoro-1H-benzoimidazole. (Yield: 57.6%)

$^1$H-NMR (MeOD, 400 MHz) δ 8.20 (s, 1H), 8.09 (s, 1H), 5.20-5.11 (m, 3H), 3.94 (s, 3H), 3.71 (d, 2H), 2.69 (s, 3H), 1.41 (s, 9H)

Preparation 8. tert-butyl N—[(Z)-4-[4-bromo-6-(di methylcarbamoyl)-2-methyl-benzimidazol-1-yl]-3-fluoro-but-2-enyl]carbamate

Step 1: 7-bromo-3-[(Z)-4-(tert-butoxycarbonylamino)-2-fluoro-but-2-enyl]-2-methyl-benzimidazol-5-carboxylic acid Methyl 7-bromo-3-[(Z)-4-(tert-butoxycarbonylamino)-2-fluoro-but-2-enyl]-2-methyl-benzimidazol-5-carboxylate prepared in Preparation 7 (186 mg) was dissolved in 5.0 mL of a mixed solvent of tetrahydrofuran/distilled water (6/1) and then a lithium hydroxide solution (196 mg/6.0 mL) was added thereto. The mixture was stirred at room temperature for 16 hours. Distilled water (30 mL) was added to the reaction mixture and then the pH thereof was adjusted to 3-4 with a saturated citric acid solution. After ethyl acetate was added thereto, the reaction mixture was washed with a sodium hydrogen carbonate solution and brine, dried over anhydrous sodium sulfate, and then concentrated under reduced pressure to prepare 177 mg of the titled compound as a white solid. (Yield: 97.9%)

$^1$H-NMR (MeOD, 400 MHz) δ 8.19 (s, 1H), 8.11 (s, 1H), 5.23-5.15 (m, 3H), 3.71 (d, 2H), 2.68 (s, 3H), 1.41 (s, 9H)

Step 2: tert-butyl N—[(Z)-4-[4-bromo-6-(di methyl-carbamoyl)-2-methyl-benzimidazol-1-yl]-3-fluoro-but-2-enyl]carbamate 7-Bromo-3-[(Z)-4-(tert-butoxycarbonylamino)-2-fluoro-but-2-enyl]-2-methyl-benzimidazol-5-carboxylic acid prepared in Step 1 (100 mg) was dissolved in 2.0 mL of a mixed solvent of dichloromethane/dimethylformamide (3/1) and then 1-[bis(dimethylamino)methylene]-1H-1,2,3-triazolo[4,5-b]pyridinium 3-oxide hexafluorophosphate (HATU) (129 mg) was added thereto. The mixture was stirred at room temperature for 20 minutes. Dimethylamine hydrochloride (37 mg) and diisopropylethylamine (117 mg) were added to the reaction mixture, which was then stirred at room temperature for 2.5 hours. The reaction mixture was concentrated under reduced pressure, ethyl acetate was added thereto. The reaction mixture was washed with distilled water, dried over anhydrous sodium sulfate, and then concentrated under reduced pressure to obtain a yellow liquid residue. The residue was purified by silica gel column chromatography (developing solvent: n-hexane/ethyl acetate=1/4) to prepare 85 mg of the titled compound as a white solid. (Yield: 80.0%)

$^1$H-NMR (MeOD, 400 MHz) δ 7.65 (s, 1H), 7.55 (s, 1H), 5.25-5.16 (m, 3H), 3.76 (d, 2H), 3.17 (s, 3H), 3.05 (s, 3H), 2.70 (s, 3H), 1.41 (s, 9H)

Preparation 9. tert-butyl N—[(Z)-4-(4-bromo-2-ethyl-benzimidazol-1-yl)-3-fluoro-but-2-enyl]carbamate The titled compound (139 mg) was prepared as a white solid in accordance with the same procedures as in Preparation 1, except for using 4-bromo-2-ethyl-1H-benzimidazole (225 mg) instead of 4-bromo-6-fluoro-1H-benzoimidazole. (Yield: 33.6%)

$^1$H-NMR (MeOD, 400 MHz) δ 7.50 (d, 1H), 7.44 (d, 1H), 7.17 (dd, 1H), 5.18-5.05 (m, 3H), 3.74 (d, 2H), 2.87 (q, 2H), 1.44 (t, 3H), 1.41 (s, 9H)

Preparation 10. tert-butyl N—[(Z)-4-(4-bromo-2-isopropyl-benzimidazol-1-yl)-3-fluoro-but-2-enyl] carbamate The titled compound (152 mg) was prepared as a white solid in accordance with the same procedures as in Preparation 1, except for using 4-bromo-2-isopropyl-1H-benzimidazole (239 mg) instead of 4-bromo-6-fluoro-1H-benzoimidazole. (Yield: 35.6%)

$^1$H-NMR (MeOD, 400 MHz) δ 7.51 (d, 1H), 7.43 (d, 1H), 7.15 (dd, 1H), 5.15-5.06 (m, 3H), 3.74 (d, 2H), 3.32 (m, 1H), 1.41 (s, 9H), 1.26 (s, 3H), 1.24 (s, 3H)

Preparation 11. tert-butyl N—[(Z)-4-(4-bromobenzotriazol-1-yl)-3-fluoro-but-2-enyl]carbamate The titled compound (84 mg) was prepared as a white solid in accordance with the same procedures as in Preparation 1, except for using 4-bromo-1H-benzotriazole (198 mg) instead of 4-bromo-6-fluoro-1H-benzoimidazole. (Yield: 21.7%)

$^1$H-NMR (MeOD, 400 MHz) δ 7.81 (d, 1H), 7.66 (d, 1H), 7.48 (dd, 1H), 5.50 (d, 2H), 5.30 (dt, 1H), 3.94 (d, 2H), 1.43 (s, 9H)

Preparation 12. methyl 7-bromo-3-[(Z)-4-(tert-butoxycarbonylamino)-2-fluoro-but-2-enyl]benzotriazol-5-carboxylate The titled compound (133 mg) was prepared as a yellow solid in accordance with the same procedures as in Preparation 1, except for using methyl 7-bromo-3H-benzotriazol-5-carboxylate (256 mg) instead of 4-bromo-6-fluoro-1H-benzoimidazole. (Yield: 29.9%)

$^1$H-NMR (MeOD, 400 MHz) δ 8.47 (s, 1H), 8.18 (s, 1H), 5.60 (d, 2H), 5.40 (dt, 1H), 3.98 (s, 3H), 3.75 (d, 2H), 1.41 (s, 9H)

Preparation 13. tert-butyl N—[(Z)-4-[4-bromo-6-(methoxycarbamoyl)benzotriazol-1-yl]-3-fluoro-but-2-enyl]carbamate

Step 1: 7-bromo-3-[(Z)-4-(tert-butoxycarbonylamino)-2-fluoro-but-2-enyl]benzotriazol-5-carboxylic acid Methyl 7-bromo-3-[(Z)-4-(tert-butoxycarbonylamino)-2-fluoro-but-2-enyl]benzotriazol-5-carboxylate prepared in Preparation 12 (200 mg) was dissolved in 5.0 mL of a mixed solvent of tetrahydrofuran/distilled water (6/1) and then a lithium hydroxide solution (216 mg/6.0 mL) was added thereto. The mixture was stirred at room temperature for 16 hours. Distilled water (30 mL) was added to the reaction mixture and then the pH thereof was adjusted to 3-4 with a saturated citric acid solution. After ethyl acetate was added thereto, the reaction mixture was washed with a sodium hydrogen carbonate solution and brine, dried over anhydrous sodium sulfate, and then concentrated under reduced pressure to prepare 174 mg of the titled compound as a white solid. (Yield: 89.8%)

$^1$H-NMR (MeOD, 400 MHz) δ 8.49 (s, 1H), 8.23 (s, 1H), 5.60 (d, 2H), 5.35 (dt, 1H), 3.75 (d, 2H), 1.41 (s, 9H)

Step 2: tert-butyl N—[(Z)-4-[4-bromo-6-(methoxycarbamoyl)benzotriazol-1-yl]-3-fluoro-but-2-enyl] carbamate 7-Bromo-3-[(Z)-4-(tert-butoxycarbonylamino)-2-fluoro-but-2-enyl]benzotriazol-5-carboxyli acid prepared in Step 1 (100 mg) was dissolved in 2.0 mL of a mixed solvent of dichloromethane/dimethylformamide (3/1) and then 1-[bis(dimethylamino)methylene]-1H-1,2,3-triazolo[4,5-b]pyridinium 3-oxide hexafluorophosphate (HATU) (159 mg) was added thereto. The mixture was stirred at room temperature for 20 minutes. Methoxylamine hydrochloride (29 mg) and diisopropylethylamine (151 mg) were added to the reaction mixture, which was then stirred at room temperature for 2.5 hours. The reaction mixture was concentrated under reduced pressure, ethyl acetate was added thereto. The reaction mixture was washed with distilled water, dried over anhydrous sodium sulfate, concentrated under reduced pressure to obtain a yellow liquid residue. The residue was purified by silica gel column chromatography (developing solvent: n-hexane/ethyl acetate=1/4) to prepare 30 mg of the titled compound as yellow liquid. (Yield: 28.1%)

$^1$H-NMR (MeOD, 400 MHz) δ 8.24 (s, 1H), 8.01 (s, 1H), 5.58 (d, 2H), 5.35 (dt, 1H), 3.86 (s, 3H), 3.76 (d, 2H), 1.41 (s, 9H)

Preparation 14. tert-butyl N—[(Z)-4-[4-bromo-6-[methoxy(methyl)carbamoyl]benzotriazol-1-yl]-3-fluoro-but-2-enyl]c arbamate The titled compound (36.3 mg) was prepared as a light pink liquid in accordance with the same procedures as in Step 2 of Preparation 13, except for using N,O-dimethylhydroxylamine hydrochloride (34 mg) instead of methoxylamine hydrochloride. (Yield: 33.0%)

$^1$H-NMR (MeOD, 400 MHz) δ 8.14 (s, 1H), 7.89 (s, 1H), 5.59 (d, 2H), 5.40 (dt, 1H), 3.76 (d, 2H), 3.61 (s, 3H), 1.41 (s, 9H)

Preparation 15. tert-butyl N—[(Z)-4-(6-chloro-7-methyl-8-oxo-purin-9-yl)-3-fluoro-but-2-enyl]carbamate The titled compound (241 mg) was prepared as a yellow solid in accordance with the same procedures as in Preparation 1, except for using 6-chloro-7-methyl-7,9-dihydro-8H-purin-8-one (228 mg) instead of 4-bromo-6-fluoro-1H-benzoimidazole. (Yield: 58.0%)

$^1$H-NMR (MeOD, 400 MHz) δ 8.85 (s, 1H), 5.33 (d, 2H), 4.92-4.89 (m, 1H), 3.70 (d, 2H), 3.28 (s, 3H), 1.40 (s, 9H)

Preparation 16. tert-butyl N—[(Z)-4-[4-bromo-6-(methylcarbamoyl)benzotriazol-1-yl]-3-fluoro-but-2-enyl]carbamate The titled compound (24.0 mg) was prepared as a yellow liquid in accordance with the same procedures as in Step 2 of Preparation 13, except for using methanamine hydrochloride (24 mg) instead of methoxylamine hydrochloride. (Yield: 23.0%)

$^1$H-NMR (MeOD, 400 MHz) δ 8.21 (s, 1H), 8.00 (s, 1H), 5.60 (d, 2H), 5.33 (dt, 1H), 3.74 (d, 2H), 2.78 (s, 3H), 1.41 (s, 9H)

Preparation 17. tert-butyl N—[(Z)-4-[4-bromo-6-(pyrrolidin-1-carbonyl)benzotriazol-1-yl]-3-fluoro-but-2-enyl]carbamate The titled compound (56.0 mg) was prepared as a yellow liquid in accordance with the same procedures as in Step 2 of Preparation 13, except for using pyrrolidine (25 mg) instead of methoxylamine hydrochloride. (Yield: 49.5%)

$^1$H-NMR (MeOD, 400 MHz) δ 8.06 (s, 1H), 7.80 (s, 1H), 5.57 (d, 2H), 5.34 (dt, 1H), 3.76 (d, 2H), 3.63 (t, 2H), 3.50 (t, 2H), 2.07-1.94 (m, 4H), 1.41 (s, 9H)

Preparation 18. tert-butyl (Z)-(4-(4-bromo-6-cyano-1H-benzo[d]imidazol-1-yl)-3-fluorobut-2-en-1-yl) carbamate The titled compound (172 mg) was prepared as a pale yellow solid in accordance with the same procedures as in Preparation 1, except for using 4-bromo-6-(carbonitrile)-1H-benzo[d]imidazole (222 mg) instead of 4-bromo-6-fluoro-1H-benzoimidazole. (Yield: 42.0%)

$^1$H-NMR (MeOD, 400 MHz) δ 8.91 (s, 1H), 8.11 (s, 1H), 7.85 (s, 1H), 5.45-5.18 (m, 3H), 3.74 (d, 2H), 1.42 (s, 9H)

Preparation 19. tert-butyl (Z)-(4-(4-bromo-6-(trifluoromethyl)-1H-benzo[d][1,2,3]triazol-1-yl)-3-fluorobut-2-en-1-yl)carbamate The titled compound (150 mg) was prepared as a yellow solid in accordance with the same procedures as in Preparation 1, except for using 4-bromo-6-(trifluoromethyl)-1H-benzo[d][1,2,3]triazole (266 mg) instead of 4-bromo-6-fluoro-1H-benzoimidazole. (Yield: 33.0%)

$^1$H-NMR (MeOD, 600 MHz) δ 8.30 (s, 1H), 7.91 (s, 1H), 5.62 (d, 2H), 5.38-5.34 (m, 1H), 3.75 (d, 2H), 1.41 (s, 9H)

Preparation 20. tert-butyl (Z)-(4-(4-bromo-6-cyano-1H-benzo[d][1,2,3]triazol-1-yl)-3-fluorobut-2-en-1-yl)carbamate The titled compound (183 mg) was prepared as a yellow solid in accordance with the same procedures as in Preparation 1, except for using 4-bromo-1H-benzo[d][1,2,3]triazol-6-carbonitrile (223 mg) instead of 4-bromo-6-fluoro-1H-benzoimidazole. (Yield: 44.7%)

$^1$H-NMR (MeOD, 400 MHz) δ 8.40 (s, 1H), 7.98 (s, 1H), 5.62-5.32 (m, 3H), 3.75 (d, 2H), 1.43 (s, 9H)

Example 1. (Z)-3-fluoro-4-(6-fluoro-4-(3-fluorophenyl)-1H-benzo[d]imidazol-1-yl)but-2-en-1-amine hydrochloride tert-Butyl N—[(Z)-4-(4-bromo-6-fluoro-benzimidazol-1-yl)-3-fluoro-but-2-enyl]carbamate prepared in Preparation 1 (20 mg) and 3-fluorophenylboronic acid (7.0 mg) were dissolved in 1,4-dioxane (2.0 mL) and distilled water (0.4 mL) and then tetrakis(triphenylphosphine)palladium ($Pd(PPh_3)_4$) (4.0 mg) and potassium phosphate tribasic (50 mg) were added thereto. The mixture was stirred at 120° C. for 2 hours. The reaction mixture was cooled to room temperature and then dichloromethane was added thereto. The reaction mixture was washed with a saturated sodium hydrogen carbonate solution, dried over anhydrous magnesium sulfate, and then concentrated under reduced pressure to obtain a yellow liquid residue. A Hydrogen chloride solution (4.0 M in dioxane, 3.0 mL) was added to the residue and the resulting mixture was stirred at 70° C. for 2 hours. The reaction mixture was concentrated under reduced pressure and the resulting residue was purified by silica gel column chromatography (developing solvent: dichloromethane/methanol=10/1) to prepare 8.3 mg of the titled compound. (Yield: 47.2%)

$^1$H-NMR (MeOD, 400 MHz) δ 8.27 (s, 1H), 7.72-7.68 (m, 2H), 7.53-7.51 (m, 1H), 7.43-7.41 (m, 1H), 7.28 (d, 1H), 7.17 (t, 1H), 5.30, dt, 1H), 5.20 (d, 2H), 3.60 (d, 2H)

Example 2. (Z)-3-fluoro-4-(6-fluoro-4-(3-(trifluoromethyl)phenyl)-1H-benzo[d]imidazol-1-yl)but-2-en-1-amine hydrochloride The titled compound (9.8 mg) was prepared in accordance with the same procedures as in Example 1, except for using 3-(trifluoromethyl)phenylboronic acid (9.4 mg) instead of 3-fluorophenylboronic acid. (Yield: 48.8%)

$^1$H-NMR (MeOD, 400 MHz) δ 8.28-8.25 (m, 2H), 8.14 (d, 1H), 7.97-7.71 (m, 2H), 7.39 (d, 1H), 7.33 (d, 1H), 5.32-5.20 (m, 3H), 3.58 (d, 2H)

Example 3. (Z)-3-fluoro-4-(6-fluoro-4-(3-(methylsulfonyl)phenyl)-1H-benzo[d]imidazol-1-yl)but-2-en-1-amine hydrochloride The titled compound (12.4 mg) was prepared in accordance with the same procedures as in Example 1, except for using 3-(methanesulfonyl)phenylboronic acid (10.0 mg) instead of 3-fluorophenylboronic acid. (Yield: 60.3%)

$^1$H-NMR (MeOD, 400 MHz) δ 8.31 (s, 1H), 8.24 (s, 1H), 8.22-8.16 (m, 1H), 8.06 (d, 1H), 7.84 (dd, 1H), 7.51 (d, 1H), 7.36 (d, 1H), 5.35-5.24 (m, 3H), 3.65 (d, 2H), 3.24 (s, 3H)

Example 4. (Z)-4-(1-(4-amino-2-fluorobut-2-en-1-yl)-6-fluoro-1H-benzo[d]imidazol-4-yl)-N,N-dimethyl benzenesulfonamide hydrochloride The titled compound (13.3 mg) was prepared in accordance with the same procedures as in Example 1, except for using N,N-dimethyl-4-(4,4,5,5-tetramethyl-1,3,2-dioxaborolan-2-yl)benzenesulfonamide (15.5 mg) instead of 3-fluorophenylboronic acid. (Yield: 60.4%)

$^1$H-NMR (MeOD, 400 MHz) δ 8.32 (s, 1H), 8.16 (d, 2H), 7.93 (d, 2H), 7.50 (d, 1H), 7.36 (d, 1H), 5.40-5.23 (m, 3H), 3.65 (d, 2H), 2.73 (s, 6H)

Example 5. (Z)-4-(1-(4-amino-2-fluorobut-2-en-1-yl)-6-fluoro-1H-benzo[d]imidazol-4-yl)-N-cyclopropylbenzenesulfonamide hydrochloride The titled compound (9.6 mg) was prepared in accordance with the same procedures as in Example 1, except for using N-cyclopropyl-4-(4,4,5,5-tetramethyl-1,3,2-dioxaborolan-2-yl)benzenesulfonamide (16.1 mg) instead of 3-fluorophenylboronic acid. (Yield: 42.4%)

$^1$H-NMR (MeOD, 400 MHz) δ 8.30 (s, 1H), 8.13 (d, 2H), 8.03 (d, 2H), 7.46 (d, 1H), 7.36 (d, 1H), 5.36-5.22 (m, 3H), 3.64 (d, 2H), 2.25-2.22 (m, 1H), 0.59-0.55 (m, 4H)

Example 6. (Z)-3-fluoro-4-(6-fluoro-4-(4-(methylsulfonyl)phenyl)-1H-benzo[d]imidazol-1-yl)but-2-en-1-amine hydrochloride The titled compound (7.1 mg) was prepared in accordance with the same procedures as in Example 1, except for using 4-(methanesulfonyl)phenylboronic acid (14.3 mg) instead of 3-fluorophenylboronic acid. (Yield: 34.5%)

$^1$H-NMR (MeOD, 400 MHz) δ 8.75 (s, 1H), 8.15-8.09 (m, 3H), 7.80 (d, 1H), 7.60 (d, 1H), 7.42 (d, 1H), 5.44-5.28 (m, 3H), 3.67 (d, 2H), 3.19 (s, 3H)

Example 7. (Z)-3-fluoro-4-(6-fluoro-4-(3-(pyrrolidin-1-ylsulfonyl)phenyl)-1H-benzo[d]imidazol-1-yl)but-2-en-1-amine hydrochloride The titled compound (13.9 mg) was prepared in accordance with the same procedures as in Example 1, except for using (3-pyrrolidin-1-ylsulfonylphenyl)boronic acid (12.7 mg) instead of 3-fluorophenylboronic acid. (Yield: 59.6%)

$^1$H-NMR (MeOD, 400 MHz) δ 8.66 (s, 1H), 8.49 (s, 1H), 8.15 (d, 1H), 7.92-7.77 (m, 2H), 7.54 (d, 1H), 7.35 (d, 1H), 5.44-5.30 (m, 3H), 3.69 (d, 2H), 3.55-3.25 (m, 4H), 2.01-1.78 (m, 4H)

Example 8. (Z)-3-fluoro-4-(6-fluoro-4-(4-(morpholinosulfonyl)phenyl)-1H-benzo[d]imidazol-1-yl)but-2-en-1-amine hydrochloride The titled compound (14.7 mg) was prepared in accordance with the same procedures as in Example 1, except for using 4-(morpholinosulfonyl)phenylboronic acid pinacol ester (17.6 mg) instead of 3-fluorophenylboronic acid. (Yield: 61.0%)

$^1$H-NMR (MeOD, 400 MHz) δ 9.35 (s, 1H), 8.43-8.15 (m, 4H), 7.81 (d, 1H), 7.58 (d, 1H), 5.66-5.41 (m, 3H), 3.75-3.71 (m, 6H), 3.07-3.04 (m, 4H)

Example 9. (Z)-3-(1-(4-amino-2-fluorobut-2-en-1-yl)-6-fluoro-1H-benzo[d]imidazol-4-yl)-N-cyclopropylbenzenesulfonamide hydrochloride The titled compound (7.8 mg) was prepared in accordance with the same procedures as in Example 1, except for using (3-(N-cyclopropylsulfamoyl)phenylboronic acid (12.0 mg) instead of 3-fluorophenylboronic acid. (Yield: 34.5%)

$^1$H-NMR (MeOD, 400 MHz) δ 9.02 (s, 1H), 8.13 (s, 1H), 8.08 (d, 1H), 8.04 (d, 1H), 7.84-7.71 (m, 3H), 5.55-5.37 (m, 3H), 3.69 (d, 2H), 2.25-2.23 (m, 1H), 0.60-0.54 (m, 4H)

Example 10. (Z)-3-(1-(4-amino-2-fluorobut-2-en-1-yl)-6-fluoro-1H-benzo[d]imidazol-4-yl)-N-methylbenzenesulfonamide hydrochloride The titled compound (10.1 mg) was prepared in accordance with the same procedures as in Example 1, except for using 3-(N-methylsulfamoyl)phenylboronic acid (10.7 mg) instead of 3-fluorophenylboronic acid. (Yield: 47.4%)

$^1$H-NMR (MeOD, 400 MHz) δ 8.32 (s, 1H), 8.24 (s, 1H), 8.15 (s, 1H), 8.03-7.81 (d, 1H), 7.75-7.70 (m, 1H), 7.50 (d, 1H), 7.35 (d, 1H), 5.39-5.23 (m, 3H), 3.68 (d, 2H), 2.61 (s, 3H)

Example 11. (Z)-3-fluoro-4-(4-(3-fluorophenyl)-6-(trifluoromethyl)-1H-benzo[d]imidazol-1-yl)but-2-en-1-amine hydrochloride The titled compound (7.1 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate. (Yield: 39.8%)

$^1$H-NMR (MeOD, 400 MHz) δ 8.97 (s, 1H), 8.20 (s, 1H), 7.81 (s, 1H), 7.67-7.56 (m, 3H), 7.26-7.22 (m, 1H), 5.53-5.43 (m, 3H), 3.68 (d, 2H)

Example 12. (Z)-3-fluoro-4-(6-(trifluoromethyl)-4-(3-(trifluoromethyl)phenyl)-1H-benzo[d]imidazol-1-yl) but-2-en-1-amine hydrochloride The titled compound (8.8 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and 3-(trifluoromethyl)phenylboronic acid (8.4 mg) instead of 3-fluorophenylboronic acid. (Yield: 43.9%)

$^1$H-NMR (MeOD, 400 MHz) δ 8.50 (s, 1H), 8.28 (s, 1H), 8.16 (d, 1H), 8.09 (s, 1H), 7.71-7.12 (m, 3H), 5.42-5.30 (m, 3H), 3.67 (d, 2H)

Example 13. (Z)-3-fluoro-4-(4-(3-(methylsulfonyl) phenyl)-6-(trifluoromethyl)-1H-benzo[d]imidazol-1-yl) but-2-en-1-amine hydrochloride The titled compound (8.1 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and 3-(methanesulfonyl)phenylboronic acid (8.9 mg) instead of 3-fluorophenylboronic acid. (Yield: 39.5%)

$^1$H-NMR (MeOD, 400 MHz) δ 8.54 (d, 2H), 8.25 (d, 1H), 8.11 (s, 1H), 8.04 (d, 1H), 7.83-7.79 (m, 2H), 5.43-5.31 (m, 3H), 3.67 (d, 2H), 3.25 (s, 3H)

Example 14. (Z)-4-(1-(4-amino-2-fluorobut-2-en-1-yl)-6-(trifluoromethyl)-1H-benzo[d]imidazol-4-yl)-N, N-dimethylbenzenesulfonamide hydrochloride The titled compound (8.5 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and N,N-dimethyl-4-(4,4,5,5-tetramethyl-1,3,2-dioxaborolan-2-yl)benzenesulfonamide (13.8 mg) instead of 3-fluorophenylboronic acid. (Yield: 39.0%)

$^1$H-NMR (MeOD, 400 MHz) δ 8.52 (s, 1H), 8.18 (d, 2H), 8.11 (s, 1H), 7.94 (d, 2H), 7.79 (s, 1H), 5.45-5.35 (m, 3H), 3.67 (d, 1H), 2.76 (s, 6H)

Example 15. (Z)-4-(1-(4-amino-2-fluorobut-2-en-1-yl)-6-(trifluoromethyl)-1H-benzo[d]imidazol-4-yl)-N-cyclopropylbenzenesulfonamide hydrochloride The titled compound (6.6 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and N-cyclopropyl-4-(4,4,5,5-tetramethyl-1,3,2-dioxaborolan-2-yl)benzenesulfonamide (13.7 mg) instead of 3-fluorophenylboronic acid. (Yield: 29.6%)

$^1$H-NMR (MeOD, 400 MHz) δ 8.51 (s, 1H), 8.15 (d, 2H), 8.10 (s, 1H), 8.03 (d, 2H), 7.79 (s, 1H), 5.44-5.31 (m, 3H), 3.67 (d, 2H), 2.25-2.20 (m, 1H), 0.60-0.57 (m, 4H)

Example 16. (Z)-3-fluoro-4-(4-(4-(methylsulfonyl) phenyl)-6-(trifluoromethyl)-1H-benzo[d]imidazol-1-yl) but-2-en-1-amine hydrochloride The titled compound (7.4 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and 4-(methanesulfonyl)phenylboronic acid (12.5 mg) instead of 3-fluorophenylboronic acid. (Yield: 36.1%)

$^1$H-NMR (MeOD, 400 MHz) δ 9.04 (s, 1H), 8.27 (s, 1H), 8.17-8.10 (m, 4H), 7.82 (s, 1H), 5.56-5.44 (m, 3H), 3.69 (d, 2H), 3.21 (s, 3H)

Example 17. (Z)-3-fluoro-4-(4-(3-(pyrrolidin-1-ylsulfonyl)phenyl)-6-(trifluoromethyl)-1H-benzo[d] imidazol-1-yl)but-2-en-1-amine hydrochloride The titled compound (12.3 mg) was prepared in accordance with the same procedures as in Example 1, except for using tert-butyl N—[(Z)-4-[4-bromo-6-(trifluoromethyl) benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (3-pyrrolidin-1-ylsulfonylphenyl)boronic acid (11.3 mg) instead of 3-fluorophenylboronic acid. (Yield: 53.6%)

$^1$H-NMR (MeOD, 400 MHz) δ 8.63 (s, 1H), 8.44 (s, 1H), 8.19-8.13 (m, 2H), 7.92 (d, 1H), 7.80-7.73 (m, 2H), 5.55-5.37 (m, 3H), 3.67 (d, 2H), 3.28-3.25 (m, 4H), 1.82-1.78 (m, 4H)

Example 18. (Z)-3-fluoro-4-(4-(4-(morpholinosulfonyl)phenyl)-6-(trifluoromethyl)-1H-benzo[d]imidazol-1-yl)but-2-en-1-amine hydrochloride The titled compound (11.6 mg) was prepared in accordance with the same procedures as in Example 1, except for using tert-butyl N—[(Z)-4-[4-bromo-6-(trifluoromethyl) benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and 4-(morpholinosulfonyl)phenylboronic acid pinacol ester (15.6 mg) instead of 3-fluorophenylboronic acid. (Yield: 49.0%)

$^1$H-NMR (MeOD, 400 MHz) δ 9.03 (s, 1H), 8.43 (d, 1H), 8.26-8.19 (m, 3H), 8.10-7.89 (m, 2H), 5.55-5.41 (m, 3H), 3.74-3.69 (m, 6H), 3.17-3.05 (m, 4H)

Example 19. (Z)-3-(1-(4-amino-2-fluorobut-2-en-1-yl)-6-(trifluoromethyl)-1H-benzo[d]imidazol-4-yl)-N-cyclopropylbenzenesulfonamide hydrochloride The titled compound (7.1 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (3-(N-cyclopropylsulfamoyl)phenylboronic acid (10.7 mg) instead of 3-fluorophenylboronic acid. (Yield: 31.8%)

$^1$H-NMR (MeOD, 400 MHz) δ 8.52 (s, 1H), 8.46 (s, 1H), 8.21 (d, 1H), 8.09 (s, 1H), 7.96 (d, 1H), 7.78-7.74 (m, 2H), 5.42-5.30 (m, 3H), 3.67 (d, 2H), 2.28-2.25 (m, 1H), 0.60-0.55 (m, 4H)

Example 20. (Z)-3-(1-(4-amino-2-fluorobut-2-en-1-yl)-6-(trifluoromethyl)-1H-benzo[d]imidazol-4-yl)-N-methylbenzenesulfonamide hydrochloride The titled compound (10 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and 3-(N-methylsulfamoyl)phenylboronic acid (9.5 mg) instead of 3-fluorophenylboronic acid. (Yield: 47.2%)

$^1$H-NMR (MeOD, 400 MHz) δ 8.57 (s, 1H), 8.41 (s, 1H), 8.18 (d, 1H), 8.11 (s, 1H), 7.92 (d, 1H), 7.77-7.74 (m, 2H), 5.50-5.36 (m, 3H), 3.67 (d, 2H), 2.61 (s, 3H)

Example 21. methyl (Z)-1-(4-amino-2-fluorobut-2-en-1-yl)-4-(3-(N,N-dimethylsulfamoyl)-4-methoxyphenyl)-1H-benzo[d]imidazol-6-carboxylate hydrochloride The titled compound (6.5 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and (3-(N,N-dim ethylsulfamoyl)-4-methoxyphenyl)boronic acid (11.7 mg) instead of 3-fluorophenylboronic acid. (Yield: 28.0%)

$^1$H-NMR (MeOD, 400 MHz) δ 8.46 (s, 1H), 8.43 (d, 1H), 8.32 (s, 1H), 8.21 (d, 1H), 8.09 (s, 1H), 7.39 (d, 1H), 5.39-5.28 (m, 3H), 4.03 (s, 3H), 3.97 (s, 3H), 3.67 (d, 2H), 2.77 (s, 6H)

Example 22. methyl (Z)-1-(4-amino-2-fluorobut-2-en-1-yl)-4-(3-((3,3-difluoropyrrolidine-1-yl)sulfonyl)phenyl)-1H-benzo[d]imidazol-6-carboxylate hydrochloride The titled compound (9.3 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and 3,3-difluoro-1-((3-(4,4,5,5-tetramethyl-1,3,2-dioxaborolan-2-yl)phenyl)sulfonyl)pyrrolidine (16.9 mg) instead of 3-fluorophenylboronic acid. (Yield: 37.4%)

$^1$H-NMR (MeOD, 400 MHz) δ 8.50 (s, 1H), 8.49 (s, 1H), 8.46 (s, 1H), 8.25 (d, 1H), 8.18 (s, 1H), 7.92 (d, 1H), 7.77 (dd, 1H), 5.40-5.29 (m, 3H), 3.99 (s, 3H), 3.67-3.54 (m, 4H), 3.52-3.50 (m, 2H), 2.40-2.29 (m, 2H)

Example 23. methyl (Z)-1-(4-amino-2-fluorobut-2-en-1-yl)-4-(3-(pyrrolidin-1-ylsulfonyl)phenyl)-1H-benzo[d]imidazol-6-carboxylate hydrochloride The titled compound (9.8 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and (3-pyrrolidin-1-ylsulfonylphenyl)boronic acid (11.5 mg) instead of 3-fluorophenylboronic acid. (Yield: 42.6%)

$^1$H-NMR (MeOD, 400 MHz) δ 8.50-8.48 (m, 2H), 8.45 (s, 1H), 8.37 (d, 1H), 8.23 (s, 1H), 7.91 (d, 1H), 7.50 (dd, 1H), 5.40-5.30 (m, 3H), 3.99 (s, 3H), 3.62 (d, 2H), 3.31-3.27 (m, 4H), 1.81-1.77 (m, 4H)

Example 24. methyl (Z)-1-(4-amino-2-fluorobut-2-en-1-yl)-4-(2-methoxy-5-(N-m ethylsulfamoyl)phenyl)-1H-benzo[d]imidazol-6-carboxylate hydrochloride The titled compound (2.7 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and [2-methoxy-5-(methylsulfamoyl)phenyl]boronic acid (11.1 mg) instead of 3-fluorophenylboronic acid. (Yield: 11.0%)

$^1$H-NMR (MeOD, 400 MHz) δ 8.40 (s, 1H), 8.37 (s, 1H), 8.00 (s, 1H), 7.93 (d, 1H), 7.86 (s, 1H), 7.34 (d, 1H), 5.39-5.28 (m, 3H), 3.97 (s, 3H), 3.86 (s, 3H), 3.35 (d, 2H), 2.58 (s, 3H)

Example 25. methyl (Z)-1-(4-amino-2-fluorobut-2-en-1-yl)-4-(3-(methylsulfonyl)phenyl)-1H-benzo[d]imidazol-6-carboxylate hydrochloride The titled compound (7.1 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and 3-(methanesulfonyl)phenylboronic acid (9.0 mg) instead of 3-fluorophenylboronic acid. (Yield: 34.6%)

$^1$H-NMR (MeOD, 400 MHz) δ 8.54-8.52 (m, 2H), 8.50 (s, 1H), 8.40 (d, 1H), 8.27 (s, 1H), 8.18 (d, 1H), 7.81 (dd, 1H), 5.41-5.31 (m, 3H), 3.99 (s, 3H), 3.63 (d, 2H), 3.25 (s, 3H)

Example 26. methyl (Z)-1-(4-amino-2-fluorobut-2-en-1-yl)-4-(5-(N,N-diethylsulfamoyl)-2-methoxyphenyl)-1H-benzo[d]imidazol-6-carboxylate hydrochloride The titled compound (8.9 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and (5-(N,N-diethylsulfamoyl)-2-methoxyphenyl)boronic acid (13.0 mg) instead of 3-fluorophenylboronic acid. (Yield: 36.4%)

$^1$H-NMR (MeOD, 400 MHz) δ 8.39 (s, 1H), 8.36 (d, 1H), 7.96 (s, 1H), 7.91 (d, 1H), 7.89 (s, 1H), 7.31 (d, 1H), 5.42-5.29 (m, 3H), 3.96 (s, 3H), 3.85 (s, 3H), 3.63 (d, 2H), 3.24 (q, 4H), 1.16 (t, 6H)

Example 27. methyl (Z)-1-(4-amino-2-fluorobut-2-en-1-yl)-4-(5-(N-cyclopropylsulfamoyl)-2-methoxyphenyl)-1H-benzo[d]imidazol-6-carboxylate hydrochloride The titled compound (5.2 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and (5-(N-cyclopropylsulfamoyl)-2-methoxyphenyl)boronic acid (12.3 mg) instead of 3-fluorophenylboronic acid. (Yield: 21.9%)

$^1$H-NMR (MeOD, 400 MHz) δ 8.42 (s, 1H), 8.41 (d, 1H), 7.99 (s, 1H), 7.98 (d, 1H), 7.89 (s, 1H), 7.35 (d, 1H), 5.42-5.30 (m, 3H), 3.97 (s, 3H), 3.84 (s, 3H), 3.64 (d, 2H), 2.28-2.23 (m, 1H), 0.58-0.55 (m, 4H)

Example 28. methyl (Z)-1-(4-amino-2-fluorobut-2-en-1-yl)-4-(3-(N-isopropylsulfamoyl)-4-methoxyphenyl)-1H-benzo[d]imidazol-6-carboxylate hydrochloride The titled compound (7.0 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and [3-(isopropylsulfamoyl)-4-methoxyphenyl] boronic acid (12.4 mg) instead of 3-fluorophenylboronic acid. (Yield: 29.4%)

$^1$H-NMR (MeOD, 400 MHz) δ 8.45 (s, 1H), 8.43 (d, 1H), 8.32 (s, 1H), 8.21 (d, 1H), 8.09 (s, 1H), 7.37 (d, 1H), 5.38-5.26 (m, 3H), 4.06 (s, 3H), 3.98 (s, 3H), 3.61 (d, 2H), 3.46-3.44 (m, 1H), 1.08 (s, 6H)

Example 29. methyl (Z)-1-(4-amino-2-fluorobut-2-en-1-yl)-4-(3-(N-cyclopropylsulfamoyl)phenyl)-1H-benzo[d]imidazol-6-carboxylate hydrochloride The titled compound (8.1 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and (3-(N-cyclopropylsulfamoyl)phenylboronic acid (10.9 mg) instead of 3-fluorophenylboronic acid. (Yield: 36.2%)

$^1$H-NMR (MeOD, 400 MHz) δ 8.49 (s, 1H), 8.45 (d, 1H), 8.44 (s, 1H), 8.38 (d, 1H), 8.37 (s, 1H), 8.17 (d, 1H), 7.75 (dd, 1H), 5.42-5.29 (m, 3H), 3.97 (s, 3H), 3.62 (d, 2H), 2.29-2.24 (m, 1H), 0.59-0.56 (m, 4H)

Example 30. methyl (Z)-1-(4-amino-2-fluorobut-2-en-1-yl)-4-(3-(N-m ethylsulfamoyl)phenyl)-1H-benzo[d]imidazol-6-carboxylate hydrochloride The titled compound (8.5 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and 3-(N-methylsulfamoyl)phenylboronic acid (10.4 mg) instead of 3-fluorophenylboronic acid. (Yield: 40.1%)

$^1$H-NMR (MeOD, 400 MHz) δ 8.49 (s, 1H), 8.41 (d, 1H), 8.40 (s, 1H), 8.38 (d, 1H), 8.37 (s, 1H), 7.91 (d, 1H), 7.74 (dd, 1H), 5.42-5.32 (m, 3H), 3.99 (s, 3H), 3.62 (d, 2H), 2.61 (s, 3H)

Example 31. methyl (Z)-1-(4-amino-2-fluorobut-2-en-1-yl)-4-(3-(N,N-dimethysulfamoyl)phenyl)-1H-benzo[d]imidazol-6-carboxylate hydrochloride The titled compound (8.2 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and [3-(dimethylsulfamoyl)phenyl]boronic acid (10.4 mg) instead of 3-fluorophenylboronic acid. (Yield: 37.6%)

$^1$H-NMR (MeOD, 400 MHz) δ 8.47 (s, 1H), 8.38 (s, 1H), 8.37 (d, 1H), 8.24 (d, 1H), 8.22 (s, 1H), 7.85 (d, 1H), 7.78 (dd, 1H), 5.42-5.31 (m, 3H), 3.99 (s, 3H), 3.65 (d, 2H), 2.79 (s, 6H)

Example 32. methyl (Z)-1-(4-amino-2-fluorobut-2-en-1-yl)-4-(3-(N-(4-methoxybenzyl)sulfamoyl)phenyl)-1H-benzo[d]imidazol-6-carboxylate hydrochloride The titled compound (10 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and [3-[(4-methoxyphenyl)methylsulfamoyl] phenyl]boronic acid (14.5 mg) instead of 3-fluorophenylboronic acid. (Yield: 38.5%)

$^1$H-NMR (MeOD, 400 MHz) δ 8.48 (s, 1H), 8.38 (d, 1H), 8.36 (s, 1H), 8.32-8.30 (m, 2H), 7.88 (d, 1H), 7.67 (dd, 1H), 7.14 (d, 2H), 6.75 (d, 2H), 5.42-5.30 (m, 3H), 4.09 (s, 2H), 3.99 (s, 3H), 3.60 (s, 3H), 3.59 (d, 2H)

Example 33. methyl (Z)-1-(4-amino-2-fluorobut-2-en-1-yl)-4-(3-(piperidin-1-ylsulfonyl)phenyl)-1H-benzo[d]imidazol-6-carboxylate hydrochloride The titled compound (11.8 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl]carbamate; and [3-(1-piperidylsulfonyl)phenyl] boronic acid (12.2 mg) instead of 3-fluorophenylboronic acid. (Yield: 49.9%)

$^1$H-NMR (MeOD, 400 MHz) δ 8.46 (s, 1H), 8.37 (s, 1H), 8.36 (s, 1H), 8.21 (d, 1H), 8.14 (s, 1H), 7.83-7.73 (m, 2H), 5.41-5.30 (m, 3H), 3.99 (s, 3H), 3.61 (d, 2H), 3.31-3.06 (m, 4H), 1.68-1.62 (m, 4H), 1.49-1.43 (m, 2H)

Example 34. methyl (Z)-1-(4-amino-2-fluorobut-2-en-1-yl)-4-(3-(ethylsulfonyl)phenyl)-1H-benzo[d]imidazol-6-carboxylate hydrochloride The titled compound (9.8 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and (3-ethylsulfonylphenyl)boronic acid (9.7 mg) instead of 3-fluorophenylboronic acid. (Yield: 46.3%)

$^1$H-NMR (MeOD, 400 MHz) δ 8.49 (s, 1H), 8.48 (s, 1H), 8.39 (s, 1H), 8.37 (d, 1H), 8.27 (s, 1H), 7.99 (d, 1H), 7.81 (dd, 1H), 5.42-5.32 (m, 3H), 3.99 (s, 3H), 3.62 (d, 2H), 3.32 (q, 2H), 1.31 (t, 3H)

Example 35. methyl (Z)-1-(4-amino-2-fluorobut-2-en-1-yl)-4-(2-methyl-5-((trifluoromethyl)sulfonyl) phenyl)-1H-benzo[d]imidazol-6-carboxylate hydrochloride The titled compound (11 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and 4,4,5,5-tetramethyl-2-[2-methyl-5-(trifluoromethylsulfonyl)phenyl]-1,3,2-dioxaborolane (15.8 mg) instead of 3-fluorophenylboronic acid. (Yield: 46.6%)

$^1$H-NMR (MeOD, 400 MHz) δ 8.47-8.45 (m, 2H), 8.08 (d, 1H), 8.06-8.04 (m, 2H), 7.80 (d, 1H), 5.45-5.35 (m, 3H), 3.98 (s, 3H), 3.61 (d, 2H), 2.32 (s, 3H)

Example 36. methyl (Z)-1-(4-amino-2-fluorobut-2-en-1-yl)-4-(3-(N-(tert-butyl)sulfamoyl)phenyl)-1H-benzo[d]imidazol-6-carboxylate hydrochloride The titled compound (6 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and [3-(tert-butylsulfamoyl)phenyl]boronic acid (11.6 mg) instead of 3-fluorophenylboronic acid. (Yield: 26.0%)

$^1$H-NMR (MeOD, 400 MHz) δ 8.51 (s, 1H), 8.50 (s, 1H), 8.46 (d, 1H), 8.38-8.27 (m, 1H), 8.17 (d, 1H), 7.70 (dd, 1H), 5.41-5.30 (m, 3H), 3.97 (s, 3H), 3.62 (d, 2H), 1.24 (s, 9H)

Example 37. methyl (Z)-1-(4-amino-2-fluorobut-2-en-1-yl)-4-(3-(N,N-diethylsulfamoyl)phenyl)-1H-benzo[d]imidazol-6-carboxylate hydrochloride The titled compound (12.3 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl]carbamate; and [3-(diethylsulfamoyl)phenyl]boronic acid (9.7 mg) instead of 3-fluorophenylboronic acid. (Yield: 53.2%)

$^1$H-NMR (MeOD, 400 MHz) δ 8.46 (s, 1H), 8.43 (s, 1H), 8.42 (s, 1H), 8.37 (d, 1H), 8.19 (s, 1H), 7.89 (d, 1H), 7.73 (dd, 1H), 5.41-5.30 (m, 3H), 3.99 (s, 3H), 3.61 (d, 2H), 3.32-3.30 (q, 4H), 1.19-1.15 (t, 6H)

Example 38. methyl (Z)-1-(4-amino-2-fluorobut-2-en-1-yl)-4-(3-(dimethylphosphoryl)phenyl)-1H-benzo[d]imidazol-6-carboxylate hydrochloride The titled compound (6.4 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and 2-(3-dimethylphosphorylphenyl)-4,4,5,5-tetramethyl-1,3,2-dioxaborolane (12.7 mg) instead of 3-fluorophenylboronic acid. (Yield: 31.3%)

$^1$H-NMR (MeOD, 400 MHz) δ 9.21 (s, 1H), 8.54 (s, 1H), 8.27 (s, 1H), 8.23 (d, 1H), 7.95 (d, 1H), 7.83 (d, 1H), 7.76-7.75 (m, 1H), 5.62-5.49 (m, 3H), 4.01 (s, 3H), 3.69 (d, 2H), 1.91 (s, 3H), 1.87 (s, 3H)

Example 39. methyl (Z)-1-(4-amino-2-fluorobut-2-en-1-yl)-4-(4-(dimethylphosphoryl)phenyl)-1H-benzo[d]imidazol-6-carboxylate hydrochloride The titled compound (5.9 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and (4-dimethylphosphorylphenyl)boronic acid (9.0 mg) instead of 3-fluorophenylboronic acid. (Yield: 28.9%)

$^1$H-NMR (MeOD, 400 MHz) δ 9.13 (s, 1H), 8.53 (s, 1H), 8.26 (s, 1H), 8.03-7.92 (m, 4H), 5.60-5.42 (m, 3H), 4.01 (s, 3H), 3.69 (d, 2H), 1.89 (s, 3H), 1.86 (s, 3H)

Example 40. methyl (Z)-1-(4-amino-2-fluorobut-2-en-1-yl)-4-(3-(diethoxyphosphoryl)phenyl)-1H-benzo[d]imidazol-6-carboxylate hydrochloride The titled compound (6.6 mg) was prepared in accordance with the same procedures as in Example 1, except for using methyl 7-bromo-3-[(Z)-4-(tert-butoxycarbonylamino)-2-fluoro-but-2-enyl]benzimidazol-5-carboxy late prepared in Preparation 3 (20 mg) instead of tert-butyl N—[(Z)-4-(4-bromo-6-fluoro-benzimidazol-1-yl)-3-fluoro-but-2-enyl] carbamate; and 2-(3-diethoxyphosphorylphenyl)-4,4,5,5-tetramethyl-1,3,2-dioxaborolane (15.4 mg) instead of 3-fluorophenylboronic acid. (Yield: 28.5%)

$^1$H-NMR (MeOD, 400 MHz) δ 8.51 (s, 1H), 8.38 (s, 1H), 8.36 (d, 1H), 8.20 (d, 1H), 8.15 (s, 1H), 7.88-7.83 (m, 1H), 7.75-7.71 (m, 1H), 5.50-5.30 (m, 3H), 4.18 (q, 4H), 3.68 (d, 2H), 1.37 (t, 6H)

Example 41. (Z)-1-(4-amino-2-fluorobut-2-en-1-yl)-4-(3-((3,3-difluoropyrrolidin-1-yl)sulfonyl)phenyl)-1H-benzo[d]imidazol-6-carboxylic acid hydrochloride The titled compound (3.8 mg) was prepared in accordance with the same procedures as in Example 1, except for using 7-bromo-3-[(Z)-4-(tert-butoxycarbonylamino)-2-fluoro-but-2-enyl]benzimidazol-5-carboxylic acid prepared in Preparation 4 (20 mg) instead of tert-butyl N—[(Z)-4-(4-bromo-6-fluoro-benzimidazol-1-yl)-3-fluoro-but-2-enyl] carbamate; and 3,3-difluoro-1-((3-(4,4,5,5-tetramethyl-1,3,2-dioxaborolan-2-yl)phenyl)sulfonyl)pyrrolidine (16.9 mg) instead of 3-fluorophenylboronic acid. (Yield: 15.8%)

$^1$H-NMR (MeOD, 400 MHz) δ 8.49 (s, 1H), 8.45 (s, 1H), 8.37 (s, 1H), 8.25 (d, 1H), 8.20 (s, 1H), 7.87 (d, 1H), 7.80 (dd, 1H), 5.50-5.28 (m, 3H), 3.70-3.64 (m, 4H), 3.56-3.52 (m, 2H), 2.38-2.32 (m, 2H)

Example 42. (Z)-1-(4-amino-2-fluorobut-2-en-1-yl)-4-(3-(pyrrolidin-1-ylsulfonyl)phenyl)-1H-benzo[d]imidazol-6-carboxylic acid hydrochloride The titled compound (4.0 mg) was prepared in accordance with the same procedures as in Example 1, except for using 7-bromo-3-[(Z)-4-(tert-butoxycarbonylamino)-2-fluoro-but-2-enyl]benzimidazol-5-carboxylic acid prepared in Preparation 4 (20 mg) instead of tert-butyl N—[(Z)-4-(4-bromo-6-fluoro-benzimidazol-1-yl)-3-fluoro-but-2-enyl] carbamate; and (3-pyrrolidin-1-ylsulfonylphenyl)boronic acid (11.5 mg) instead of 3-fluorophenylboronic acid. (Yield: 17.9%)

$^1$H-NMR (MeOD, 400 MHz) δ 8.45-8.43 (m, 2H), 8.36 (s, 1H), 8.23 (d, 1H), 8.22 (s, 1H), 7.90 (d, 1H), 7.77 (dd, 1H), 5.40-5.28 (m, 3H), 3.67 (d, 2H), 3.36-3.32 (m, 4H), 1.81-1.77 (m, 4H)

Example 43. (Z)-3-fluoro-4-(4-(3-fluorophenyl)-2-(trifluoromethyl)-1H-benzo[d]imidazol-1-yl)but-2-en-1-amine hydrochloride The titled compound (6.9 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl] carbamate. (Yield: 38.8%)

$^1$H-NMR (MeOD, 400 MHz) δ 7.75-7.63 (m, 3H), 7.62-7.54 (m, 2H), 7.52-7.49 (m, 1H), 7.18-7.13 (m, 1H), 5.35 (d, 2H), 5.30 (dt, 1H), 3.61 (d, 2H)

Example 44. (Z)-3-fluoro-4-(2-(trifluoromethyl)-4-(3-(trifluoromethyl)phenyl)-1H-benzo[d]imidazol-1-yl) but-2-en-1-amine hydrochloride The titled compound (7.1 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl] carbamate; and 3-(trifluoromethyl)phenylboronic acid (8.4 mg) instead of 3-fluorophenylboronic acid. (Yield: 35.6%)

$^1$H-NMR (MeOD, 400 MHz) δ 8.34 (s, 1H), 8.26 (s, 1H), 7.79-7.62 (m, 5H), 5.37 (d, 2H), 5.27 (dt, 1H), 3.61 (d, 2H)

Example 45. (Z)-3-(1-(4-amino-2-fluorobut-2-en-1-yl)-2-(trifluoromethyl)-1H-benzo[d]imidazol-4-yl)-N, N-dimethylbenzenesulfonamide hydrochloride The titled compound (7.0 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl] carbamate; and [3-(dimethylsulfamoyl)phenyl]boronic acid (10.1 mg) instead of 3-fluorophenylboronic acid. (Yield: 31.9%)

$^1$H-NMR (MeOD, 400 MHz) δ 8.23 (s, 1H), 8.20 (d, 1H), 7.85-7.63 (m, 5H), 5.30 (d, 2H), 5.25 (dt, 1H), 3.64 (d, 2H), 2.80 (s, 6H)

Example 46. (Z)-3-fluoro-4-(4-(3-(methylsulfonyl) phenyl)-2-(trifluoromethyl)-1H-benzo[d]imidazol-1-yl) but-2-en-1-amine hydrochloride The titled compound (7.7 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl] carbamate; and 3-(methanesulfonyl)phenylboronic acid (8.9 mg) instead of 3-fluorophenylboronic acid. (Yield: 33.7%)

$^1$H-NMR (MeOD, 400 MHz) δ 8.60 (s, 1H), 8.34 (d, 1H), 8.02 (d, 1H), 7.81-7.63 (m, 4H), 5.43 (d, 2H), 5.25 (dt, 1H), 3.58 (d, 2H), 3.21 (s, 3H)

Example 47. (Z)-4-(1-(4-amino-2-fluorobut-2-en-1-yl)-2-(trifluoromethyl)-1H-benzo[d]imidazol-4-yl)-N, N-dimethylbenzenesulfonamide hydrochloride The titled compound (6.5 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl] carbamate; and N,N-dimethyl-4-(4,4,5,5-tetramethyl-1,3,2-dioxaborolan-2-yl)benzenesulfonamide (13.8 mg) instead of 3-fluorophenylboronic acid. (Yield: 30.0%)

$^1$H-NMR (MeOD, 400 MHz) δ 8.62 (s, 1H), 8.60 (s, 1H), 8.23 (d, 2H), 7.93 (d, 1H), 7.81 (d, 1H), 7.70-7.63 (m, 1H), 5.37 (d, 2H), 5.28 (dt, 1H), 3.61 (d, 2H), 2.74 (s, 6H)

Example 48. (Z)-4-(1-(4-amino-2-fluorobut-2-en-1-yl)-2-(trifluoromethyl)-1H-benzo[d]imidazol-4-yl)-N-cyclopropylbenzenesulfonamide hydrochloride The titled compound (8.3 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl] carbamate; and N-cyclopropyl-4-(4,4,5,5-tetramethyl-1,3,2-dioxaborolan-2-yl)benzenesulfonamide (14.3 mg) instead of 3-fluorophenylboronic acid. (Yield: 37.3%)

$^1$H-NMR (MeOD, 400 MHz) δ 8.23 (d, 2H), 8.02 (d, 2H), 7.81 (d, 1H), 7.72 (d, 1H), 7.70-7.63 (m, 1H), 5.40 (d, 2H), 5.30 (dt, 1H), 3.64 (d, 2H), 2.26-2.21 (m, 1H), 0.59-0.55 (m, 4H)

Example 49. (Z)-3-fluoro-4-(4-(4-(methylsulfonyl) phenyl)-2-(trifluoromethyl)-1H-benzo[d]imidazol-1-yl) but-2-en-1-amine hydrochloride The titled compound (5.6 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl] carbamate; and 4-(methanesulfonyl)phenylboronic acid (11.5 mg) instead of 3-fluorophenylboronic acid. (Yield: 29.1%)

$^1$H-NMR (MeOD, 400 MHz) δ 8.28 (d, 2H), 8.26 (d, 2H), 7.82 (d, 1H), 7.73 (d, 1H), 7.67-7.64 (m, 1H), 5.38 (d, 2H), 5.26 (dt, 1H), 3.63 (d, 2H), 3.19 (s, 3H)

Example 50. (Z)-3-fluoro-4-(4-(3-(pyrrolidin-1-ylsulfonyl)phenyl)-2-(trifluoromethyl)-1H-benzo[d]imidazol-1-yl)but-2-en-1-amine hydrochloride The titled compound (7.6 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl]carbamate; and (3-pyrrolidin-1-ylsulfonylphenyl)boronic acid (11.3 mg) instead of 3-fluorophenylboronic acid. (Yield: 33.3%)

$^1$H-NMR (MeOD, 400 MHz) δ 8.87 (s, 1H), 8.17 (d, 1H), 7.88 (d, 1H), 7.78-7.63 (m, 4H), 5.40 (d, 2H), 5.21 (dt, 1H), 3.61 (d, 2H), 3.40-3.32 (m, 4H), 1.80-1.77 (m, 4H)

Example 51. (Z)-4-(1-(4-amino-2-fluorobut-2-en-1-yl)-2-(trifluoromethyl)-1H-benzo[d]imidazol-4-yl)-N-(tert-butyl)benzenesulfonamide hydrochloride The titled compound (8.1 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl]carbamate; and N-tert-butyl-4-(4,4,5,5-tetramethyl-1,3,2-dioxaborolan-2-yl)benzenesulfonamide (15 mg) instead of 3-fluorophenylboronic acid. (Yield: 35.0%)

$^1$H-NMR (MeOD, 400 MHz) δ 8.28 (d, 2H), 7.92 (d, 2H), 7.89 (d, 1H), 7.71 (d, 1H), 7.68-7.63 (m, 1H), 5.34 (d, 2H), 5.22 (dt, 1H), 3.76-3.64 (m, 4H), 3.61 (d, 2H), 3.06-3.04 (m, 4H)

Example 52. (Z)-3-(1-(4-amino-2-fluorobut-2-en-1-yl)-2-(trifluoromethyl)-1H-benzo[d]imidazol-4-yl)-N-cyclopropylbenzenesulfonamide hydrochloride The titled compound (6.4 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl]carbamate; and (3-(N-cyclopropylsulfamoyl)phenylboronic acid (10.7 mg) instead of 3-fluorophenylboronic acid. (Yield: 28.8%)

$^1$H-NMR (MeOD, 400 MHz) δ 8.52 (s, 1H), 8.25 (d, 1H), 7.94 (d, 1H), 7.92-7.62 (m, 4H), 5.37 (d, 2H), 5.20 (dt, 1H), 3.61 (d, 2H), 2.36-2.33 (m, 1H), 0.61-0.57 (m, 4H)

Example 53. (Z)-3-(1-(4-amino-2-fluorobut-2-en-1-yl)-2-(trifluoromethyl)-1H-benzo[d]imidazol-4-yl)-N-methylbenzenesulfonamide hydrochloride The titled compound (7.8 mg) was prepared in accordance with the same procedures as in Example 1, except for using tert-butyl N—[(Z)-4-[4-bromo-2-(trifluoromethyl)benzimidazol-1-yl]-3-fluoro-but-2-enyl]carbamate prepared in Preparation 5 (20 mg) instead of tert-butyl N—[(Z)-4-(4-bromo-6-fluoro-benzimidazol-1-yl)-3-fluoro-but-2-enyl]carbamate; and 3-(N-methylsulfamoyl)phenylboronic acid (9.5 mg) instead of 3-fluorophenylboronic acid. (Yield: 36.9%)

$^1$H-NMR (MeOD, 400 MHz) δ 8.50 (s, 1H), 8.24 (d, 1H), 7.88 (d, 1H), 7.83-7.62 (m, 4H), 5.37 (d, 2H), 5.17 (dt, 1H), 3.62 (d, 2H), 2.66 (s, 3H)

Example 54. (Z)-4-(1-(4-amino-2-fluorobut-2-en-1-yl)-2-methyl-1H-benzo[d]imidazol-4-yl)-N,N-dimeth ylbenzenesulfonamide hydrochloride The titled compound (11.7 mg) was prepared in accordance with the same procedures as in Example 1, except for using tert-butyl N—[(Z)-4-(4-bromo-2-methyl-benzimidazol-1-yl)-3-fluoro-but-2-enyl]carbamate prepared in Preparation 6 (20 mg) instead of tert-butyl N—[(Z)-4-(4-bromo-6-fluoro-benzimidazol-1-yl)-3-fluoro-but-2-enyl]carbamate; and N,N-dimethyl-4-(4,4,5,5-tetramethyl-1,3,2-dioxaborolan-2-yl)benzenesulfonamide (15.6 mg) instead of 3-fluorophenylboronic acid. (Yield: 53.1%)

$^1$H-NMR (MeOD, 400 MHz) δ 8.02-7.80 (m, 5H), 7.73-7.63 (m, 2H), 5.67-5.48 (m, 3H), 3.67 (d, 2H), 2.96 (s, 3H), 2.76 (s, 6H)

Example 55. (Z)-3-fluoro-4-(2-methyl-4-(4-(morpholinosulfonyl)phenyl)-1H-benzo[d]imidazol-1-yl)but-2-en-1-amine hydrochloride The titled compound (12.3 mg) was prepared in accordance with the same procedures as in Example 1, except for using tert-butyl N—[(Z)-4-(4-bromo-2-methyl-benzimidazol-1-yl)-3-fluoro-but-2-enyl]carbamate prepared in Preparation 6 (20 mg) instead of tert-butyl N—[(Z)-4-(4-bromo-6-fluoro-benzimidazol-1-yl)-3-fluoro-but-2-enyl]carbamate; and 4-(morpholinosulfonyl)phenylboronic acid pinacol ester (17.7 mg) instead of 3-fluorophenylboronic acid. (Yield: 50.9%)

$^1$H-NMR (MeOD, 400 MHz) δ 8.05-7.90 (m, 5H), 7.71-7.64 (m, 2H), 5.63-5.45 (m, 3H), 3.76-3.60 (m, 6H), 3.08-3.02 (m, 4H), 2.94 (s, 3H)

Example 56. (Z)-3-(1-(4-amino-2-fluorobut-2-en-1-yl)-2-methyl-1H-benzo[d]imidazol-4-yl)-N,N-dimeth ylbenzenesulfonamide hydrochloride The titled compound (10.1 mg) was prepared in accordance with the same procedures as in Example 1, except for using tert-butyl N—[(Z)-4-(4-bromo-2-methyl-benzimidazol-1-yl)-3-fluoro-but-2-enyl]carbamate prepared in Preparation 6 (20 mg) instead of tert-butyl N—[(Z)-4-(4-bromo-6-fluoro-benzimidazol-1-yl)-3-fluoro-but-2-enyl]carbamate; and [3-(dimethylsulfamoyl)phenyl]boronic acid (15.6 mg) instead of 3-fluorophenylboronic acid. (Yield: 45.8%)

$^1$H-NMR (MeOD, 400 MHz) δ 8.15 (s, 1H), 8.10 (d, 1H), 7.87 (d, 1H), 7.76-7.50 (m, 2H), 7.50-7.47 (m, 2H), 5.38-5.27 (m, 3H), 3.66 (d, 2H), 2.82 (s, 3H), 2.77 (s, 6H)

Example 57. (Z)-3-fluoro-4-(2-methyl-4-(3-(methylsulfonyl)phenyl)-1H-benzo[d]imidazol-1-yl)but-2-en-1-amine hydrochloride The titled compound (7.4 mg) was prepared in accordance with the same procedures as in Example 1, except for using tert-butyl N—[(Z)-4-(4-bromo-2-methyl-benzimidazol-1-yl)-3-fluoro-but-2-enyl]carbamate prepared in Preparation 6 (20 mg) instead of tert-butyl N—[(Z)-4-(4-bromo-6-fluoro-benzimidazol-1-yl)-3-fluoro-but-2-enyl]carbamate; and 3-(methanesulfonyl)phenylboronic acid (10.0 mg) instead of 3-fluorophenylboronic acid. (Yield: 36.0%)

$^1$H-NMR (MeOD, 400 MHz) δ 8.33 (s, 1H), 8.32 (d, 1H), 8.11 (d, 1H), 7.85-7.78 (m, 2H), 7.58-7.55 (m, 2H), 5.43-5.31 (m, 3H), 3.67 (d, 2H), 3.31 (s, 3H), 2.82 (s, 3H)

Example 58. (Z)-3-fluoro-4-(2-methyl-4-(4-(methylsulfonyl)phenyl)-1H-benzo[d]imidazol-1-yl)but-2-en-1-amine hydrochloride The titled compound (4.0 mg) was prepared in accordance with the same procedures as in Example 1, except for using tert-butyl N—[(Z)-4-(4-bromo-2-methyl-benzimidazol-1-yl)-3-fluoro-but-2-enyl]carbamate prepared in Preparation 6 (20 mg) instead of tert-butyl N—[(Z)-4-(4-bromo-6-fluoro-benzimidazol-1-yl)-3-fluoro-but-2-enyl]carbamate; and 4-(methanesulfonyl)phenylboronic acid (10.0 mg) instead of 3-fluorophenylboronic acid. (Yield: 19.4%)

$^1$H-NMR (MeOD, 400 MHz) δ 8.14 (d, 2H), 8.01 (d, 2H), 7.86 (d, 1H), 7.68-7.63 (m, 2H), 5.54-5.50 (m, 3H), 3.68 (d, 2H), 3.31 (s, 3H), 2.87 (s, 3H)

Example 59. (Z)-4-(1-(4-amino-2-fluorobut-2-en-1-yl)-2-methyl-1H-benzo[d]imidazol-4-yl)-N-cyclopropylbenzenesulfonamide hydrochloride The titled compound (2.1 mg) was prepared in accordance with the same procedures as in Example 1, except for using tert-butyl N—[(Z)-4-(4-bromo-2-methyl-benzimidazol-1-yl)-3-fluoro-but-2-enyl]carbamate prepared in Preparation 6 (20 mg) instead of tert-butyl N—[(Z)-4-(4-bromo-6-fluoro-benzimidazol-1-yl)-3-fluoro-but-2-enyl]carbamate; and N-cyclopropyl-4-(4,4,5,5-tetramethyl-1,3,2-dioxaborolan-2-yl)benzenesulfonamide (16.2 mg) instead of 3-fluorophenylboronic acid. (Yield: 9.3%)

$^1$H-NMR (MeOD, 400 MHz) δ 8.06 (d, 2H), 8.00 (d, 2H), 7.58-7.50 (m, 1H), 7.46-7.38 (m, 2H), 5.20-5.08 (m, 3H), 3.58 (d, 2H), 2.67 (s, 3H), 2.21-2.14 (m, 1H), 0.60-0.56 (m, 4H)

Example 60. (Z)-3-fluoro-4-(2-methyl-4-(3-(pyrrolidin-1-ylsulfonyl)phenyl)-1H-benzo[d]imidazol-1-yl)but-2-en-1-amine hydrochloride The titled compound (16.8 mg) was prepared in accordance with the same procedures as in Example 1, except for using tert-butyl N—[(Z)-4-(4-bromo-2-methyl-benzimidazol-1-yl)-3-fluoro-but-2-enyl]carbamate prepared in Preparation 6 (20 mg) instead of tert-butyl N—[(Z)-4-(4-bromo-6-fluoro-benzimidazol-1-yl)-3-fluoro-but-2-enyl]carbamate; and (3-pyrrolidin-1-ylsulfonylphenyl)boronic acid (12.8 mg) instead of 3-fluorophenylboronic acid. (Yield: 72.0%)

$^1$H-NMR (MeOD, 400 MHz) δ 8.12-8.00 (m, 5H), 7.86-7.63 (m, 2H), 5.66-5.47 (m, 3H), 3.70 (d, 2H), 3.41-3.30 (m, 4H), 2.95 (s, 3H), 1.83-1.76 (m, 4H)

Example 61. (Z)-4-(1-(4-amino-2-fluorobut-2-en-1-yl)-2-methyl-1H-benzo[d]imidazol-4-yl)-N-(tert-butyl)benzenesulfonamide hydrochloride The titled compound (2.0 mg) was prepared in accordance with the same procedures as in Example 1, except for using tert-butyl N—[(Z)-4-(4-bromo-2-methyl-benzimidazol-1-yl)-3-fluoro-but-2-enyl]carbamate prepared in Preparation 6 (20 mg) instead of tert-butyl N—[(Z)-4-(4-bromo-6-fluoro-benzimidazol-1-yl)-3-fluoro-but-2-enyl]carbamate; and N-tert-butyl-4-(4,4,5,5-tetramethyl-1,3,2-dioxaborolan-2-yl)benzenesulfonamide (17.0 mg) instead of 3-fluorophenylboronic acid. (Yield: 9.7%)

$^1$H-NMR (MeOD, 400 MHz) δ 8.07-8.03 (m, 3H), 7.65-7.56 (m, 2H), 7.44-7.38 (m, 2H), 5.18-5.04 (m, 3H), 3.58 (d. 2H), 2.67 (s, 3H), 1.25 (s, 9H)

Example 62. (Z)-3-(1-(4-amino-2-fluorobut-2-en-1-yl)-2-methyl-1H-benzo[d]imidazol-4-yl)-N-cyclopropylbenzenesulfonamide hydrochloride The titled compound (6.0 mg) was prepared in accordance with the same procedures as in Example 1, except for using tert-butyl N—[(Z)-4-(4-bromo-2-methyl-benzimidazol-1-yl)-3-fluoro-but-2-enyl]carbamate prepared in Preparation 6 (20 mg) instead of tert-butyl N—[(Z)-4-(4-bromo-6-fluoro-benzimidazol-1-yl)-3-fluoro-but-2-enyl]carbamate; and N-cyclopropyl-3-(4,4,5,5-tetramethyl-1,3,2-dioxaborolan-2-yl)benzenesulfonamide (14.9 mg) instead of 3-fluorophenylboronic acid. (Yield: 26.5%)

$^1$H-NMR (CDCl3, 400 MHz) δ 8.28 (s, 1H), 8.09 (d, 1H), 7.95 (d, 1H), 7.77-7.67 (m, 2H), 7.53-7.48 (m, 2H), 5.33-5.21 (m, 3H), 3.67 (d, 2H), 2.77 (s, 3H), 2.26-2.22 (m, 1H), 0.60-0.55 (m, 4H)

Example 63. (Z)-3-(1-(4-amino-2-fluorobut-2-en-1-yl)-2-methyl-1H-benzo[d]imidazol-4-yl)-N-methylbenzenesulfonamide hydrochloride The titled compound (12.0 mg) was prepared in accordance with the same procedures as in Example 1, except for using tert-butyl N—[(Z)-4-(4-bromo-2-methyl-benzimidazol-1-yl)-3-fluoro-but-2-enyl]carbamate prepared in Preparation 6 (20 mg) instead of tert-butyl N—[(Z)-4-(4-bromo-6-fluoro-benzimidazol-1-yl)-3-fluoro-but-2-enyl]carbamate; and N-methyl-3-(4,4,5,5-tetramethyl-1,3,2-dioxaborolan-2-yl)benzenesulfonamide (14.9 mg) instead of 3-fluorophenylboronic acid. (Yield: 56.2%)

$^1$H-NMR (MeOD, 400 MHz) δ 8.30 (s, 1H), 8.11 (d, 1H), 8.07 (d, 1H), 7.73-7.69 (m, 1H), 7.60-7.57 (m, 1H), 7.43-7.39 (m, 2H), 5.20-5.04 (m, 3H), 3.61 (d, 2H), 2.67 (s. 3H), 2.61 (s, 3H)

Example 64. methyl (Z)-1-(4-amino-2-fluorobut-2-en-1-yl)-4-(4-(N,N-dimethylsulfamoyl)phenyl)-2-methyl-1H-benzo[d]imidazol-6-carboxylate hydrochloride The titled compound (7.2 mg) was prepared in accordance with the same procedures as in Example 1, except for using methyl 7-bromo-3-[(Z)-4-(tert-butoxycarbonylamino)-2-fluoro-but-2-enyl]-2-methyl-benzimidazol-5-carboxylate prepared in Preparation 7 (20 mg) instead of tert-butyl N—[(Z)-4-(4-bromo-6-fluoro-benzimidazol-1-yl)-3-fluoro-but-2-enyl]carbamate; and N,N-dimethyl-4-(4,4,5,5-tetramethyl-1,3,2-dioxaborolan-2-yl)benzenesulfonamide (13.6 mg) instead of 3-fluorophenylboronic acid. (Yield: 33.1%)

$^1$H-NMR (MeOD, 400 MHz) δ 8.34 (s, 1H), 8.15 (s, 1H), 8.10 (d, 2H), 7.94 (d, 2H), 5.36-5.27 (m, 3H), 3.95 (s, 3H), 3.67 (d, 2H), 2.80 (s, 3H), 2.75 (s, 6H)

Example 65. methyl (Z)-1-(4-amino-2-fluorobut-2-en-1-yl)-2-methyl-4-(4-(morpholinosulfonyl)phenyl)-1H-benzo[d]imidazol-6-carboxylate hydrochloride The titled compound (3.3 mg) was prepared in accordance with the same procedures as in Example 1, except for using methyl 7-bromo-3-[(Z)-4-(tert-butoxycarbonylamino)-2-fluoro-but-2-enyl]-2-methyl-benzimidazol-5-carboxylate prepared in Preparation 7 (20 mg) instead of tert-butyl N—[(Z)-4-(4-bromo-6-fluoro-benzimidazol-1-yl)-3-fluoro-but-2-enyl]carbamate; and 4-(morpholinosulfonyl)phenylboronic acid pinacol ester (15.5 mg) instead of 3-fluorophenylboronic acid. (Yield: 14.0%)

$^1$H-NMR (MeOD, 400 MHz) δ 8.29 (s, 1H), 8.16 (s, 1H), 8.14 (d, 2H), 7.92 (d, 2H), 5.50-5.30 (m, 3H), 3.98 (s, 3H), 3.76-3.74 (m, 4H), 3.66 (d, 2H), 3.05-3.04 (m, 4H), 2.72 (s, 3H)

Example 66. methyl (Z)-1-(4-amino-2-fluorobut-2-en-1-yl)-4-(3-(N,N-dimethylsulfamoyl)phenyl)-2-methyl-1H-benzo[d]imidazol-6-carboxylate hydrochloride The titled compound (5.6 mg) was prepared in accordance with the same procedures as in Example 1, except for using methyl 7-bromo-3-[(Z)-4-(tert-butoxycarbonylamino)-2-fluoro-but-2-enyl]-2-methyl-benzimidazol-5-carboxylate prepared in Preparation 7 (20 mg) instead of tert-butyl N—[(Z)-4-(4-bromo-6-fluoro-benzimidazol-1-yl)-3-fluoro-but-2-enyl]carbamate; and [3-(dimethylsulfamoyl)phenyl]boronic acid (13.6 mg) instead of 3-fluorophenylboronic acid. (Yield: 25.7%)

$^1$H-NMR (MeOD, 400 MHz) δ 8.60 (s, 1H), 8.24 (s, 1H), 8.06 (s, 1H), 8.03-7.86 (m, 3H), 5.86-5.60 (m, 3H), 4.02 (s, 3H), 3.69 (d, 2H), 2.97 (s, 3H), 2.75 (s, 6H)

Example 67. methyl (Z)-1-(4-amino-2-fluorobut-2-en-1-yl)-2-methyl-4-(3-(methylsulfonyl)phenyl)-1H-benzo[d]imidazol-6-carboxylate hydrochloride The titled compound (1.6 mg) was prepared in accordance with the same procedures as in Example 1, except for using methyl 7-bromo-3-[(Z)-4-(tert-butoxycarbonylamino)-2-fluoro-but-2-enyl]-2-methyl-benzimidazol-5-carboxylate prepared in Preparation 7 (20 mg) instead of tert-butyl N—[(Z)-4-(4-bromo-6-fluoro-benzimidazol-1-yl)-3-fluoro-but-2-enyl]carbamate; and 3-(methanesulfonyl)phenylboronic acid (8.8 mg) instead of 3-fluorophenylboronic acid. (Yield: 7.8%)

$^1$H-NMR (MeOD, 400 MHz) δ 8.47 (s, 1H), 8.30 (s, 1H), 8.23 (d, 1H), 8.13 (s, 1H), 8.04 (d, 1H), 7.81 (t, 1H), 5.29-5.21 (m, 3H), 3.98 (s, 3H), 3.60 (d, 2H), 3.31 (s, 3H), 2.72 (s, 3H)

Example 68. methyl (Z)-1-(4-amino-2-fluorobut-2-en-1-yl)-2-methyl-4-(4-(methylsulfonyl)phenyl)-1H-benzo[d]imidazol-6-carboxylate hydrochloride The titled compound (6.2 mg) was prepared in accordance with the same procedures as in Example 1, except for using methyl 7-bromo-3-[(Z)-4-(tert-butoxycarbonylamino)-2-fluoro-but-2-enyl]-2-methyl-benzimidazol-5-carboxylate prepared in Preparation 7 (20 mg) instead of tert-butyl N—[(Z)-4-(4-bromo-6-fluoro-benzimidazol-1-yl)-3-fluoro-but-2-enyl]carbamate; and 4-(methanesulfonyl)phenylboronic acid (8.8 mg) instead of 3-fluorophenylboronic acid. (Yield: 32.7%)

$^1$H-NMR (MeOD, 400 MHz) δ 8.43 (s, 1H), 8.19 (s, 1H), 8.14-8.07 (m, 4H), 5.50-5.39 (m, 3H), 3.97 (s, 3H), 3.67 (d, 2H), 3.21 (s, 3H), 2.83 (s, 3H)

Example 69. methyl (Z)-1-(4-amino-2-fluorobut-2-en-1-yl)-4-(4-(N-cyclopropylsulfamoyl)phenyl)-2-methyl-1H-benzo[d]imidazol-6-carboxylate hydrochloride The titled compound (7.6 mg) was prepared in accordance with the same procedures as in Example 1, except for using methyl 7-bromo-3-[(Z)-4-(tert-butoxycarbonylamino)-2-fluoro-but-2-enyl]-2-methyl-benzimidazol-5-carboxylate prepared in Preparation 7 (20 mg) instead of tert-butyl N—[(Z)-4-(4-bromo-6-fluoro-benzimidazol-1-yl)-3-fluoro-but-2-enyl]carbamate; and N-cyclopropyl-4-(4,4,5,5-tetramethyl-1,3,2-dioxaborolan-2-yl)benzenesulfonamide (14.2 mg) instead of 3-fluorophenylboronic acid. (Yield: 34.1%)

$^1$H-NMR (MeOD, 400 MHz) δ 8.34 (s, 1H), 8.19 (s, 1H), 8.14-8.07 (m, 4H), 5.50-5.39 (m, 3H), 3.97 (s, 3H), 3.67 (d, 2H), 2.77 (s, 3H), 2.23-2.20 (m, 1H), 0.60-0.57 (m, 4H)

Example 70. methyl (Z)-1-(4-amino-2-fluorobut-2-en-1-yl)-2-methyl-4-(3-(pyrrolidin-1-ylsulfonyl)phenyl)-1H-benzo[d]imidazol-6-carboxylate hydrochloride The titled compound (11.1 mg) was prepared in accordance with the same procedures as in Example 1, except for using methyl 7-bromo-3-[(Z)-4-(tert-butoxycarbonylamino)-2-fluoro-but-2-enyl]-2-methyl-benzimidazol-5-carboxylate prepared in Preparation 7 (20 mg) instead of tert-butyl N—[(Z)-4-(4-bromo-6-fluoro-benzimidazol-1-yl)-3-fluoro-but-2-enyl]carbamate; and (3-pyrrolidin-1-ylsulfonylphenyl)boronic acid (11.2 mg) instead of 3-fluorophenylboronic acid. (Yield: 48.4%)

$^1$H-NMR (MeOD, 400 MHz) δ 8.61 (s, 1H), 8.24 (s, 1H), 8.12 (s, 1H), 8.03-8.00 (m, 2H), 7.89-7.85 (m, 1H), 5.69-5.56 (m, 3H), 3.72 (s, 3H), 3.67 (d, 2H), 3.31-3.27 (m, 4H), 2.98 (s, 3H), 1.81-1.77 (m, 4H)

Example 71. methyl (Z)-1-(4-amino-2-fluorobut-2-en-1-yl)-4-(4-(N-(tert-butyl)sulfamoyl)phenyl)-2-methyl-1H-benzo[d]imidazol-6-carboxylate hydrochloride The titled compound (5.5 mg) was prepared in accordance with the same procedures as in Example 1, except for using methyl 7-bromo-3-[(Z)-4-(tert-butoxycarbonylamino)-2-fluoro-but-2-enyl]-2-methyl-benzimidazol-5-carboxylate prepared in Preparation 7 (20 mg) instead of tert-butyl N—[(Z)-4-(4-bromo-6-fluoro-benzimidazol-1-yl)-3-fluoro-but-2-enyl]carbamate; and N-tert-butyl-4-(4,4,5,5-tetramethyl-1,3,2-dioxaborolan-2-yl)benzenesulfonamide (14.9 mg) instead of 3-fluorophenylboronic acid. (Yield: 23.9%)

$^1$H-NMR (MeOD, 400 MHz) δ 8.58 (s, 1H), 8.28 (s, 1H), 8.10 (d, 2H), 7.91 (d, 2H), 5.66-5.50 (m, 3H), 4.01 (s, 3H), 3.70 (d, 2H), 2.97 (s, 3H), 1.26 (s, 9H)

Example 72. methyl (Z)-1-(4-amino-2-fluorobut-2-en-1-yl)-4-(3-(N-cyclopropylsulfamoyl)phenyl)-2-methyl-1H-benzo[d]imidazol-6-carboxylate hydrochloride The titled compound (11.5 mg) was prepared in accordance with the same procedures as in Example 1, except for using methyl 7-bromo-3-[(Z)-4-(tert-butoxycarbonylamino)-2-fluoro-but-2-enyl]-2-methyl-benzimidazol-5-carboxylate prepared in Preparation 7 (20 mg) instead of tert-butyl N—[(Z)-4-(4-bromo-6-fluoro-benzimidazol-1-yl)-3-fluoro-but-2-enyl]carbamate; and N-cyclopropyl-3-(4,4,5,5-tetramethyl-1,3,2-dioxaborolan-2-yl)benzenesulfonamide (14.9 mg) instead of 3-fluorophenylboronic acid. (Yield: 51.6%)

$^1$H-NMR (MeOD, 400 MHz) δ 8.35 (s, 1H), 8.31 (s, 1H), 8.15 (d, 1H), 8.12 (s, 1H), 7.94 (d, 1H), 7.74 (d, 1H), 5.33-5.23 (m, 3H), 3.94 (s, 3H), 3.67 (d, 2H), 2.75 (s, 3H), 2.28-2.25 (m, 1H), 0.59-0.57 (m, 4H)

Example 73. methyl (Z)-1-(4-amino-2-fluorobut-2-en-1-yl)-2-methyl-4-(3-(N-methylsulfamoyl)phenyl)-1H-benzo[d]imidazol-6-carboxylate hydrochloride The titled compound (6.5 mg) was prepared in accordance with the same procedures as in Example 1, except for using methyl 7-bromo-3-[(Z)-4-(tert-butoxycarbonylamino)-2-fluoro-but-2-enyl]-2-methyl-benzimidazol-5-carboxylate prepared in Preparation 7 (20 mg) instead of tert-butyl N—[(Z)-4-(4-bromo-6-fluoro-benzimidazol-1-yl)-3-fluoro-but-2-enyl]carbamate; and N-methyl-3-(4,4,5,5-tetramethyl-1,3,2-dioxaborolan-2-yl)benzenesulfonamide (13.0 mg) instead of 3-fluorophenylboronic acid. (Yield: 30.7%)

$^1$H-NMR (MeOD, 400 MHz) δ 8.32 (s, 1H), 8.30 (s, 1H), 8.15 (d, 1H), 8.11 (s, 1H), 7.90 (d, 1H), 7.30 (d, 1H), 5.32-5.21 (m, 3H), 3.98 (s, 3H), 3.67 (d, 2H), 2.74 (s, 3H), 2.61 (s, 3H)

Example 74. (Z)-1-(4-amino-2-fluorobut-2-en-1-yl)-4-(4-(N,N-dimethylsulfamoyl)phenyl)-N,N,2-trimethyl-1H-benzo[d]imidazol-6-carboxamide hydrochloride The titled compound (1.9 mg) was prepared in accordance with the same procedures as in Example 1, except for using tert-butyl N—[(Z)-4-[4-bromo-6-(di methylcarbamoyl)-2-methyl-benzimidazol-1-yl]-3-fluoro-but-2-enyl]carbamate prepared in Preparation 8 (20 mg) instead of tert-butyl N—[(Z)-4-(4-bromo-6-fluoro-benzimidazol-1-yl)-3-fluoro-but-2-enyl]carbamate; and N,N-dimethyl-4-(4,4,5,5-tetramethyl-1,3,2-dioxaborolan-2-yl)benzenesulfonamide (13.3 mg) instead of 3-fluorophenylboronic acid. (Yield: 8.7%)

$^1$H-NMR (MeOD, 400 MHz) δ 8.13 (d, 2H), 7.92 (d, 2H), 7.54 (s, 1H), 7.35 (s, 1H), 5.25-5.14 (m, 3H), 3.60 (d, 2H), 3.17 (s, 3H), 3.11 (s, 3H), 2.76 (s, 6H), 2.68 (s, 3H)

Example 75. (Z)-1-(4-amino-2-fluorobut-2-en-1-yl)-N,N,2-trimethyl-4-(4-(morpholinosulfonyl)phenyl)-1H-benzo[d]imidazol-6-carboxamide hydrochloride The titled compound (3.0 mg) was prepared in accordance with the same procedures as in Example 1, except for using tert-butyl N—[(Z)-4-[4-bromo-6-(di methylcarbamoyl)-2-methyl-benzimidazol-1-yl]-3-fluoro-but-2-enyl]carbamate prepared in Preparation 8 (20 mg) instead of tert-butyl N—[(Z)-4-(4-bromo-6-fluoro-benzimidazol-1-yl)-3-fluoro-but-2-enyl]carbamate; and 4-(morpholinosulfonyl)phenylboronic acid pinacol ester (15.1 mg) instead of 3-fluorophenylboronic acid. (Yield: 12.8%)

$^1$H-NMR (MeOD, 400 MHz) δ 8.14 (d, 2H), 7.91 (d, 2H), 7.71 (s, 1H), 7.55 (s, 1H), 5.38-5.15 (m, 3H), 3.76-3.74 (m, 4H), 3.60 (d, 2H), 3.18 (s. 3H), 3.12 (s, 3H), 3.05-3.03 (m, 4H), 2.71 (s, 3H)

Example 76. (Z)-1-(4-amino-2-fluorobut-2-en-1-yl)-4-(3-(N,N-dimethylsulfamoyl)phenyl)-N,N,2-trimethyl-1H-benzo[d]imidazol-6-carboxamide hydrochloride The titled compound (2.7 mg) was prepared in accordance with the same procedures as in Example 1, except for using tert-butyl N—[(Z)-4-[4-bromo-6-(di methylcarbamoyl)-2-methyl-benzimidazol-1-yl]-3-fluoro-but-2-enyl]carbamate prepared in Preparation 8 (20 mg) instead of tert-butyl N—[(Z)-4-(4-bromo-6-fluoro-benzimidazol-1-yl)-3-fluoro-but-2-enyl]carbamate; and 3-(N,N-dimethylaminosulfonyl) phenylboronic acid pinacol ester (13.3 mg) instead of 3-fluorophenylboronic acid. (Yield: 12.4%)

$^1$H-NMR (MeOD, 400 MHz) δ 8.31 (s, 1H), 8.18 (d, 1H), 7.85-7.79 (m, 2H), 7.77 (s, 1H), 7.50 (s, 1H), 5.25-5.12 (m, 3H), 3.61 (d, 2H), 3.17 (s, 3H), 3.11 (s, 3H), 2.70 (s, 6H), 2.68 (s, 3H)

Example 77. (Z)-1-(4-amino-2-fluorobut-2-en-1-yl)-N,N,2-trimethyl-4-(3-(methylsulfonyl)phenyl)-1H-benzo[d]imidazol-6-carboxamide hydrochloride The titled compound (3.1 mg) was prepared in accordance with the same procedures as in Example 1, except for using tert-butyl N—[(Z)-4-[4-bromo-6-(di methylcarbamoyl)-2-methyl-benzimidazol-1-yl]-3-fluoro-but-2-enyl]carbamate prepared in Preparation 8 (20 mg) instead of tert-butyl N—[(Z)-4-(4-bromo-6-fluoro-benzimidazol-1-yl)-3-fluoro-but-2-enyl]carbamate; and 3-(methanesulfonyl)phenylboronic acid (8.5 mg) instead of 3-fluorophenylboronic acid. (Yield: 15.2%)

$^1$H-NMR (MeOD, 400 MHz) δ 8.46 (s, 1H), 8.21 (d, 1H), 8.01 (d, 1H), 7.81 (dd, 1H), 7.70 (s, 1H), 7.53 (s, 1H), 5.24-5.14 (m, 3H), 3.55 (d, 2H), 3.24 (s, 3H), 3.17 (s, 3H), 3.10 (s, 3H), 2.71 (s, 3H)

Example 78. (Z)-1-(4-amino-2-fluorobut-2-en-1-yl)-N,N,2-trimethyl-4-(4-(methylsulfonyl)phenyl)-1H-benzo[d]imidazol-6-carboxamide hydrochloride The titled compound (4.0 mg) was prepared in accordance with the same procedures as in Example 1, except for using tert-butyl N—[(Z)-4-[4-bromo-6-(di methylcarbamoyl)-2-methyl-benzimidazol-1-yl]-3-fluoro-but-2-enyl]carbamate prepared in Preparation 8 (20 mg) instead of tert-butyl N—[(Z)-4-(4-bromo-6-fluoro-benzimidazol-1-yl)-3-fluoro-but-2-enyl]carbamate; and 4-(methanesulfonyl)phenylboronic acid (8.5 mg) instead of 3-fluorophenylboronic acid. (Yield: 19.5%)

$^1$H-NMR (MeOD, 400 MHz) δ 8.15 (d, 2H), 8.10 (d, 2H), 7.71 (s, 1H), 7.54 (s, 1H), 5.24-5.15 (m, 3H), 3.60 (d, 2H), 3.17 (s, 3H), 3.15 (s, 3H), 3.10 (s, 3H), 2.70 (s, 3H)

Example 79. (Z)-1-(4-amino-2-fluorobut-2-en-1-yl)-4-(4-(N-cyclopropylsulfamoyl)phenyl)-N,N,2-trimethyl-1H-benzo[d]imidazol-6-carboxamide hydrochloride The titled compound (5.2 mg) was prepared in accordance with the same procedures as in Example 1, except for using tert-butyl N—[(Z)-4-[4-bromo-6-(di methylcarbamoyl)-2-methyl-benzimidazol-1-yl]-3-fluoro-but-2-enyl]carbamate prepared in Preparation 8 (20 mg) instead of tert-butyl N—[(Z)-4-(4-bromo-6-fluoro-benzimidazol-1-yl)-3-fluoro-but-2-enyl]carbamate; and N-cyclopropyl-4-(4,4,5,5-tetramethyl-1,3,2-dioxaborolan-2-yl)benzenesulfonamide (13.8 mg) instead of 3-fluorophenylboronic acid. (Yield: 23.4%)

$^1$H-NMR (MeOD, 400 MHz) δ 8.10 (d, 2H), 8.01 (d, 2H), 7.70 (s, 1H), 7.54 (s, 1H), 5.50-5.13 (m, 3H), 3.62 (d, 2H), 3.15 (s, 3H), 3.11 (s, 3H), 2.70 (s, 3H), 2.23-2.20 (m, 1H), 0.59-0.57 (m, 4H)

Example 80. (Z)-1-(4-amino-2-fluorobut-2-en-1-yl)-4-(3-(N-cyclopropylsulfamoyl)phenyl)-N,N,2-trimethyl-1H-benzo[d]imidazol-6-carboxamide hydrochloride The titled compound (5.6 mg) was prepared in accordance with the same procedures as in Example 1, except for using tert-butyl N—[(Z)-4-[4-bromo-6-(di methylcarbamoyl)-2-methyl-benzimidazol-1-yl]-3-fluoro-but-2-enyl]carbamate prepared in Preparation 8 (20 mg) instead of tert-butyl N—[(Z)-4-(4-bromo-6-fluoro-benzimidazol-1-yl)-3-fluoro-but-2-enyl]carbamate; and N-cyclopropyl-3-(4,4,5,5-tetramethyl-1,3,2-dioxaborolan-2-yl)benzenesulfonamide (13.8 mg) instead of 3-fluorophenylboronic acid. (Yield: 25.2%)

$^1$H-NMR (MeOD, 400 MHz) δ 8.38 (s, 1H), 8.16 (d, 1H), 7.93 (d, 1H), 7.73 (dd, 1H), 7.69 (s, 1H), 7.51 (s, 1H), 5.50-5.14 (m, 3H), 3.64 (d, 2H), 3.14 (s, 3H), 3.10 (S, 3H), 2.27-2.25 (m, 1H), 0.59-0.56 (m, 4H)

Example 81. (Z)-1-(4-amino-2-fluorobut-2-en-1-yl)-N,N,2-trimethyl-4-(3-(N-methyl sulfamoyl)phenyl)-1H-benzo[d]imidazol-6-carboxamide hydrochloride The titled compound (4.4 mg) was prepared in accordance with the same procedures as in Example 1, except for using tert-butyl N—[(Z)-4-[4-bromo-6-(di methylcarbamoyl)-2-methyl-benzimidazol-1-yl]-3-fluoro-but-2-enyl]carbamate prepared in Preparation 8 (20 mg) instead of tert-butyl N—[(Z)-4-(4-bromo-6-fluoro-benzimidazol-1-yl)-3-fluoro-but-2-enyl]carbamate; and N-methyl-3-(4,4,5,5-tetramethyl-1,3,2-dioxaborolan-2-yl)benzenesulfonamide (12.7 mg) instead of 3-fluorophenylboronic acid. (Yield: 20.8%)

$^1$H-NMR (MeOD, 400 MHz) δ 8.33 (s, 1H), 8.15 (d, 1H), 7.88 (d, 1H), 7.75-7.69 (m, 2H), 7.49 (s, 1H), 5.50-5.15 (m, 3H), 3.46 (d, 2H), 3.17 (s, 3H), 3.13 (s, 3H), 2.70 (s, 3H), 2.61 (s, 3H)

Example 82. (Z)-4-(1-(4-amino-2-fluorobut-2-en-1-yl)-2-ethyl-1H-benzo[d]imidazol-4-yl)-N,N-dimethyl benzenesulfonamide hydrochloride The titled compound (8.2 mg) was prepared in accordance with the same procedures as in Example 1, except for using tert-butyl N—[(Z)-4-(4-bromo-2-ethyl-benzimidazol-1-yl)-3-fluoro-but-2-enyl]carbamate prepared in Preparation 9 (20 mg) instead of tert-butyl N—[(Z)-4-(4-bromo-6-fluoro-benzimidazol-1-yl)-3-fluoro-but-2-enyl]carbamate; and N,N-dimethyl-4-(4,4,5,5-tetramethyl-1,3,2-dioxaborolan-2-yl)benzenesulfonamide (15.1 mg) instead of 3-fluorophenylboronic acid. (Yield: 37.3%)

$^1$H-NMR (MeOD, 400 MHz) δ 7.99-7.90 (m, 5H), 7.71-7.64 (m, 2H), 5.61-5.47 (m, 3H), 3.67 (d, 2H), 3.27 (q, 2H), 2.78 (s, 6H), 1.33 (t, 3H)

Example 83. (Z)-4-(2-ethyl-4-(4-(morpholinosulfonyl)phenyl)-1H-benzo[d]imidazol-1-yl)-3-fluorobut-2-en-1-amine hydrochloride The titled compound (7.7 mg) was prepared in accordance with the same procedures as in Example 1, except for using tert-butyl N—[(Z)-4-(4-bromo-2-ethyl-benzimidazol-1-yl)-3-fluoro-but-2-enyl]carbamate prepared in Preparation 9 (20 mg) instead of tert-butyl N—[(Z)-4-(4-bromo-6-fluoro-benzimidazol-1-yl)-3-fluoro-but-2-enyl]carbamate; and 4-(morpholinosulfonyl)phenylboronic acid pinacol ester (17.1 mg) instead of 3-fluorophenylboronic acid. (Yield: 32.1%)

$^1$H-NMR (MeOD, 400 MHz) δ 7.99-7.83 (m, 5H), 7.76-7.67 (m, 2H), 5.64-5.49 (m, 3H), 4.20-4.16 (m, 4H), 3.67 (d, 2H), 3.27 (q, 2H), 3.06-3.02 (m, 4H), 1.32 (t, 3H)

Example 84. (Z)-3-(1-(4-amino-2-fluorobut-2-en-1-yl)-2-ethyl-1H-benzo[d]imidazol-4-yl)-N,N-dimethyl benzenesulfonamide hydrochloride The titled compound (8.1 mg) was prepared in accordance with the same procedures as in Example 1, except for using tert-butyl N—[(Z)-4-(4-bromo-2-ethyl-benzimidazol-1-yl)-3-fluoro-but-2-enyl]carbamate prepared in Preparation 9 (20 mg) instead of tert-butyl N—[(Z)-4-(4-bromo-6-fluoro-benzimidazol-1-yl)-3-fluoro-but-2-enyl]carbamate; and 3-(N,N-dimethylaminosulfonyl)phenylboronic acid pinacol ester (15.1 mg) instead of 3-fluorophenylboronic acid. (Yield: 36.9%)

$^1$H-NMR (MeOD, 400 MHz) δ 8.07-7.86 (m, 5H), 7.79-7.64 (m, 2H), 5.65-5.49 (m, 3H), 3.70 (d, 2H), 3.27 (q, 2H), 3.25 (s, 3H), 2.75 (s, 6H), 1.33 (t, 3H)

Example 85. (Z)-4-(2-ethyl-4-(3-(methylsulfonyl)phenyl)-1H-benzo[d]imidazol-1-yl)-3-fluorobut-2-en-1-amine hydrochloride The titled compound (12.9 mg) was prepared in accordance with the same procedures as in Example 1, except for using tert-butyl N—[(Z)-4-(4-bromo-2-ethyl-benzimidazol-1-yl)-3-fluoro-but-2-enyl]carbamate prepared in Preparation 9 (20 mg) instead of tert-butyl N—[(Z)-4-(4-bromo-6-fluoro-benzimidazol-1-yl)-3-fluoro-but-2-enyl]carbamate; and 3-(methanesulfonyl)phenylboronic acid (9.7 mg) instead of 3-fluorophenylboronic acid. (Yield: 62.7%)

$^1$H-NMR (MeOD, 400 MHz) δ 8.24 (s, 1H), 8.19-7.92 (m, 4H), 7.74-7.67 (m, 2H), 5.70-5.53 (m, 3H), 3.70 (d, 2H), 3.27 (q, 2H), 3.18 (s, 3H), 1.33 (t, 3H)

Example 86. (Z)-4-(2-ethyl-4-(4-(methylsulfonyl)phenyl)-1H-benzo[d]imidazol-1-yl)-3-fluorobut-2-en-1-amine hydrochloride The titled compound (5.6 mg) was prepared in accordance with the same procedures as in Example 1, except for using tert-butyl N—[(Z)-4-(4-bromo-2-ethyl-benzimidazol-1-yl)-3-fluoro-but-2-enyl]carbamate prepared in Preparation 9 (20 mg) instead of tert-butyl N—[(Z)-4-(4-bromo-6-fluoro-benzimidazol-1-yl)-3-fluoro-but-2-enyl]carbamate; and 4-(methanesulfonyl)phenylboronic acid (9.7 mg) instead of 3-fluorophenylboronic acid. (Yield: 27.2%)

$^1$H-NMR (MeOD, 400 MHz) δ 8.18-7.93 (m, 5H), 7.72-7.66 (m, 2H), 5.61-5.47 (m, 3H), 3.69 (d, 2H), 3.27 (q, 2H), 3.22 (s, 3H), 1.32 (t, 3H)

Example 87. (Z)-4-(1-(4-amino-2-fluorobut-2-en-1-yl)-2-ethyl-1H-benzo[d]imidazol-4-yl)-N-cyclopropyl benzenesulfonamide hydrochloride The titled compound (10.9 mg) was prepared in accordance with the same procedures as in Example 1, except for using tert-butyl N—[(Z)-4-(4-bromo-2-ethyl-benzimidazol-1-yl)-3-fluoro-but-2-enyl]carbamate prepared in Preparation 9 (20 mg) instead of tert-butyl N—[(Z)-4-(4-bromo-6-fluoro-benzimidazol-1-yl)-3-fluoro-but-2-enyl]carbamate; and N-cyclopropyl-4-(4,4,5,5-tetramethyl-1,3,2-dioxaborolan-2-yl)benzenesulfonamide (15.7 mg) instead of 3-fluorophenylboronic acid. (Yield: 48.3%)

$^1$H-NMR (MeOD, 400 MHz) δ 8.06-7.98 (m, 4H), 7.98-7.84 (m, 1H), 7.65-7.60 (m, 2H), 5.61-5.41 (m, 3H), 3.53 (d, 2H), 3.19 (q, 2H), 2.26-2.21 (m, 1H), 1.48 (t, 3H), 0.60-0.56 (m, 4H)

Example 88. (Z)-4-(2-ethyl-4-(3-(pyrrolidin-1-ylsulfonyl)phenyl)-1H-benzo[d]imidazol-1-yl)-3-fluorobut-2-en-1-amine hydrochloride The titled compound (8.5 mg) was prepared in accordance with the same procedures as in Example 1, except for using tert-butyl N—[(Z)-4-(4-bromo-2-ethyl-benzimidazol-1-yl)-3-fluoro-but-2-enyl]carbamate prepared in Preparation 9 (20 mg) instead of tert-butyl N—[(Z)-4-(4-bromo-6-fluoro-benzimidazol-1-yl)-3-fluoro-but-2-enyl]carbamate; and (3-pyrrolidin-1-ylsulfonylphenyl)boronic acid (12.4 mg) instead of 3-fluorophenylboronic acid. (Yield: 36.6%)

$^1$H-NMR (MeOD, 400 MHz) δ 8.13 (s, 1H), 8.03-7.95 (m, 4H), 7.86-7.64 (m, 2H), 5.64-5.49 (m, 3H), 3.69 (d, 2H), 3.35-3.33 (m, 4H), 3.20 (q, 2H), 1.83-1.78 (m, 4H), 1.29 (t, 3H)

Example 89. (Z)-4-(1-(4-amino-2-fluorobut-2-en-1-yl)-2-ethyl-1H-benzo[d]imidazol-4-yl)-N-(tert-butyl) benzenesulfonamide hydrochloride The titled compound (6.2 mg) was prepared in accordance with the same procedures as in Example 1, except for using tert-butyl N—[(Z)-4-(4-bromo-2-ethyl-benzimidazol-1-yl)-3-fluoro-but-2-enyl]carbamate prepared in Preparation 9 (20 mg) instead of tert-butyl N—[(Z)-4-(4-bromo-6-fluoro-benzimidazol-1-yl)-3-fluoro-but-2-enyl]carbamate; and N-tert-butyl-4-(4,4,5,5-tetramethyl-1,3,2-dioxaborolan-2-yl)benzenesulfonamide (16.5 mg) instead of 3-fluorophenylboronic acid. (Yield: 26.6%)

$^1$H-NMR (MeOD, 400 MHz) δ 8.09-7.98 (m, 4H), 7.73-7.63 (m, 1H), 7.47-7.35 (m, 2H), 5.23-5.16 (m, 3H), 3.60 (d, 2H), 3.04 (q, 2H), 1.41 (t, 3H), 1.26 (s, 9H)

Example 90. (Z)-3-(1-(4-amino-2-fluorobut-2-en-1-yl)-2-ethyl-1H-benzo[d]imidazol-4-yl)-N-cyclopropyl benzenesulfonamide hydrochloride The titled compound (2.4 mg) was prepared in accordance with the same procedures as in Example 1, except for using tert-butyl N—[(Z)-4-(4-bromo-2-ethyl-benzimidazol-1-yl)-3-fluoro-but-2-enyl]carbamate prepared in Preparation 9 (20 mg) instead of tert-butyl N—[(Z)-4-(4-bromo-6-fluoro-benzimidazol-1-yl)-3-fluoro-but-2-enyl]carbamate; and N-cyclopropyl-3-(4,4,5,5-tetramethyl-1,3,2-dioxaborolan-2-yl)benzenesulfonamide (15.7 mg) instead of 3-fluorophenylboronic acid. (Yield: 10.6%)

$^1$H-NMR (MeOD, 400 MHz) δ 8.21 (s, 1H), 8.11-7.99 (m, 3H), 7.90-7.61 (m, 3H), 5.54-5.45 (m, 3H), 3.70 (d, 2H), 3.24 (q, 2H), 2.26-2.20 (m, 1H), 1.49 (t, 3H), 0.58-0.55 (m, 4H)

Example 91. (Z)-3-(1-(4-amino-2-fluorobut-2-en-1-yl)-2-ethyl-1H-benzo[d]imidazol-4-yl)-N-methylbenzenesulfonamide hydrochloride The titled compound (2.1 mg) was prepared in accordance with the same procedures as in Example 1, except for using tert-butyl N—[(Z)-4-(4-bromo-2-ethyl-benzimidazol-1-yl)-3-fluoro-but-2-enyl]carbamate prepared in Preparation 9 (20 mg) instead of tert-butyl N—[(Z)-4-(4-bromo-6-fluoro-benzimidazol-1-yl)-3-fluoro-but-2-enyl]carbamate; and N-methyl-3-(4,4,5,5-tetramethyl-1,3,2-dioxaborolan-2-yl)benzenesulfonamide (14.4 mg) instead of 3-fluorophenylboronic acid. (Yield: 9.9%)

$^1$H-NMR (MeOD, 400 MHz) δ 7.98 (s, 1H), 7.97-7.95 (m, 1H), 7.87-7.73 (m, 3H), 7.69-7.56 (m, 2H), 5.22-5.19 (m, 3H), 3.63 (d, 2H), 3.02 (q, 2H), 2.62 (s, 3H), 1.44 (t, 3H)

Example 92. (Z)-4-(1-(4-amino-2-fluorobut-2-en-1-yl)-2-isopropyl-1H-benzo[d]imidazol-4-yl)-N,N-dimethylbenzenesulfonamide hydrochloride The titled compound (12.2 mg) was prepared in accordance with the same procedures as in Example 1, except for using tert-butyl N—[(Z)-4-(4-bromo-2-isopropyl-benzimidazol-1-yl)-3-fluoro-but-2-enyl]carbamate prepared in Preparation 10 (20 mg) instead of tert-butyl N—[(Z)-4-(4-bromo-6-fluoro-benzimidazol-1-yl)-3-fluoro-but-2-enyl] carbamate; and N,N-dimethyl-4-(4,4,5,5-tetramethyl-1,3,2-dioxaborolan-2-yl)benzenesulfonamide (14.6 mg) instead of 3-fluorophenylboronic acid. (Yield: 55.7%)

$^1$H-NMR (MeOD, 400 MHz) δ 8.05-7.96 (m, 5H), 7.74-7.65 (m, 2H), 5.73-5.50 (m, 3H), 3.82-3.61 (m, 3H), 2.79 (s, 6H), 1.56 (s, 6H)

Example 93. (Z)-3-fluoro-4-(2-isopropyl-4-(4-(morpholinosulfonyl)phenyl)-1H-benzo[d]imidazol-1-yl) but-2-en-1-amine hydrochloride The titled compound (15.1 mg) was prepared in accordance with the same procedures as in Example 1, except for using tert-butyl N—[(Z)-4-(4-bromo-2-isopropyl-benzimidazol-1-yl)-3-fluoro-but-2-enyl]carbamate prepared in Preparation 10 (20 mg) instead of tert-butyl N—[(Z)-4-(4-bromo-6-fluoro-benzimidazol-1-yl)-3-fluoro-but-2-enyl] carbamate; and 4-(morpholinosulfonyl)phenylboronic acid pinacol ester (16.6 mg) instead of 3-fluorophenylboronic acid. (Yield: 63.2%)

$^1$H-NMR (MeOD, 400 MHz) δ 8.03-7.98 (m, 5H), 7.74-7.66 (m, 2H), 5.72-5.50 (m, 3H), 3.76-3.66 (m, 7H), 3.08-3.06 (m, 4H), 1.56 (s, 6H)

Example 94. (Z)-3-(1-(4-amino-2-fluorobut-2-en-1-yl)-2-isopropyl-1H-benzo[d]imidazol-4-yl)-N,N-dimethylbenzenesulfonamide hydrochloride The titled compound (18.5 mg) was prepared in accordance with the same procedures as in Example 1, except for using tert-butyl N—[(Z)-4-(4-bromo-2-isopropyl-benzimidazol-1-yl)-3-fluoro-but-2-enyl]carbamate prepared in Preparation 10 (20 mg) instead of tert-butyl N—[(Z)-4-(4-bromo-6-fluoro-benzimidazol-1-yl)-3-fluoro-but-2-enyl] carbamate; and 3-(N,N-dimethylaminosulfonyl)phenylboronic acid pinacol ester (14.6 mg) instead of 3-fluorophenylboronic acid. (Yield: 84.4%)

$^1$H-NMR (MeOD, 400 MHz) δ 8.08-7.93 (m. 5H), 7.85-7.63 (m, 2H), 5.68-5.49 (m, 3H), 3.78-3.61 (m, 3H), 2.76 (s, 6H), 1.54 (s, 6H)

Example 95. (Z)-3-fluoro-4-(2-isopropyl-4-(3-(methylsulfonyl)phenyl)-1H-benzo[d]imidazol-1-yl) but-2-en-1-amine hydrochloride The titled compound (10.5 mg) was prepared in accordance with the same procedures as in Example 1, except for using tert-butyl N—[(Z)-4-(4-bromo-2-isopropyl-benzimidazol-1-yl)-3-fluoro-but-2-enyl]carbamate prepared in Preparation 10 (20 mg) instead of tert-butyl N—[(Z)-4-(4-bromo-6-fluoro-benzimidazol-1-yl)-3-fluoro-but-2-enyl] carbamate; and 3-(methanesulfonyl)phenylboronic acid (9.4 mg) instead of 3-fluorophenylboronic acid. (Yield: 51.1%)

$^1$H-NMR (MeOD, 400 MHz) δ 8.26 (s, 1H), 8.15-7.88 (m, 4H), 7.75-7.64 (m, 2H), 5.70-5.50 (m, 3H), 3.81-3.60 (m, 3H), 3.23 (s, 3H), 1.55 (s, 6H)

Example 96. (Z)-3-fluoro-4-(2-isopropyl-4-(4-(methylsulfonyl)phenyl)-1H-benzo[d]imidazol-1-yl) but-2-en-1-amine hydrochloride The titled compound (9.1 mg) was prepared in accordance with the same procedures as in Example 1, except for using tert-butyl N—[(Z)-4-(4-bromo-2-isopropyl-benzimidazol-1-yl)-3-fluoro-but-2-enyl]carbamate prepared in Preparation 10 (20 mg) instead of tert-butyl N—[(Z)-4-(4-bromo-6-fluoro-benzimidazol-1-yl)-3-fluoro-but-2-enyl]carbamate; and 4-(methanesulfonyl)phenylboronic acid (9.4 mg) instead of 3-fluorophenylboronic acid. (Yield: 44.3%)

$^1$H-NMR (MeOD, 400 MHz) δ 8.17-7.94 (m, 5H), 7.72-7.62 (m, 2H), 5.60-5.50 (m, 3H), 3.70-3.61 (m, 3H), 3.25 (s, 3H), 1.53 (s, 6H)

Example 97. (Z)-4-(1-(4-amino-2-fluorobut-2-en-1-yl)-2-isopropyl-1H-benzo[d]imidazol-4-yl)-N-cyclopropylbenzenesulfonamide hydrochloride The titled compound (9.4 mg) was prepared in accordance with the same procedures as in Example 1, except for using tert-butyl N—[(Z)-4-(4-bromo-2-isopropyl-benzimidazol-1-yl)-3-fluoro-but-2-enyl]carbamate prepared in Preparation 10 (20 mg) instead of tert-butyl N—[(Z)-4-(4-bromo-6-fluoro-benzimidazol-1-yl)-3-fluoro-but-2-enyl]carbamate; and N-cyclopropyl-4-(4,4,5,5-tetramethyl-1,3,2-dioxaborolan-2-yl)benzenesulfonamide (15.2 mg) instead of 3-fluorophenylboronic acid. (Yield: 41.8%)

$^1$H-NMR (MeOD, 400 MHz) δ 8.10-8.01 (m, 4H), 7.74-7.55 (m, 1H), 7.51-7.48 (m, 2H), 5.37-5.34 (m, 3H), 3.68-3.61 (m, 3H), 2.24-2.21 (m, 1H), 1.49 (s, 6H), 0.60-0.56 (m, 4H)

Example 98. (Z)-3-fluoro-4-(2-isopropyl-4-(3-(pyrrolidin-1-ylsulfonyl)phenyl)-1H-benzo[d]imidazol-1-yl) but-2-en-1-amine hydrochloride The titled compound (13.5 mg) was prepared in accordance with the same procedures as in Example 1, except for using tert-butyl N—[(Z)-4-(4-bromo-2-isopropyl-benzimidazol-1-yl)-3-fluoro-but-2-enyl]carbamate prepared in Preparation 10 (20 mg) instead of tert-butyl N—[(Z)-4-(4-bromo-6-fluoro-benzimidazol-1-yl)-3-fluoro-but-2-enyl] carbamate; and (3-pyrrolidin-1-ylsulfonylphenyl)boronic acid (12.0 mg) instead of 3-fluorophenylboronic acid. (Yield: 58.4%)

$^1$H-NMR (MeOD, 400 MHz) δ 8.14-7.98 (m, 4H), 7.84-7.62 (m, 3H), 5.68-5.49 (m, 3H), 3.79-3.61 (m, 3H), 3.32-3.25 (m, 4H), 1.79-1.73 (m, 4H), 1.54 (s, 6H)

Example 99. (Z)-4-(1-(4-amino-2-fluorobut-2-en-1-yl)-2-isopropyl-1H-benzo[d]imidazol-4-yl)-N-(tert-butyl)benzenesulfonamide hydrochloride The titled compound (2.2 mg) was prepared in accordance with the same procedures as in Example 1, except for using tert-butyl N—[(Z)-4-(4-bromo-2-isopropyl-benzimidazol-1-yl)-3-fluoro-but-2-enyl]carbamate prepared in Preparation 10 (20 mg) instead of tert-butyl N—[(Z)-4-(4-bromo-6-fluoro-benzimidazol-1-yl)-3-fluoro-but-2-enyl]carbamate; and N-tert-butyl-4-(4,4,5,5-tetramethyl-1,3,2-dioxaborolan-2-yl)benzenesulfonamide (15.9 mg) instead of 3-fluorophenylboronic acid. (Yield: 9.5%)

$^1$H-NMR (MeOD, 400 MHz) δ 8.12 (d, 2H), 8.01 (d, 2H), 7.57-7.37 (m, 3H), 5.20-5.04 (m, 3H), 3.63-3.42 (m, 3H), 1.44 (s, 6H)

Example 100. (Z)-3-(1-(4-amino-2-fluorobut-2-en-1-yl)-2-isopropyl-1H-benzo[d]imidazol-4-yl)-N-cyclopropylbenzenesulfonamide hydrochloride The titled compound (17.2 mg) was prepared in accordance with the same procedures as in Example 1, except for using tert-butyl N—[(Z)-4-(4-bromo-2-isopropyl-benzimidazol-1-yl)-3-fluoro-but-2-enyl]carbamate prepared in Preparation 10 (20 mg) instead of tert-butyl N—[(Z)-4-(4-bromo-6-fluoro-benzimidazol-1-yl)-3-fluoro-but-2-enyl] carbamate; and N-cyclopropyl-3-(4,4,5,5-tetramethyl-1,3,2-dioxaborolan-2-yl)benzenesulfonamide (15.2 mg) instead of 3-fluorophenylboronic acid. (Yield: 76.5%)

$^1$H-NMR (MeOD, 400 MHz) δ 8.30 (s, 1H), 8.10-8.00 (m, 2H), 7.96-7.75 (m, 2H), 7.60-7.54 (m, 2H), 5.44-5.41 (m, 3H), 3.67-3.61 (m, 3H), 2.28-2.21 (m, 1H), 1.51 (s, 6H), 0.58-0.54 (m, 4H)

Example 101. (Z)-3-(1-(4-amino-2-fluorobut-2-en-1-yl)-2-isopropyl-1H-benzo[d]imidazol-4-yl)-N-methyl benzenesulfonamide hydrochloride The titled compound (8.2 mg) was prepared in accordance with the same procedures as in Example 1, except for using tert-butyl N—[(Z)-4-(4-bromo-2-isopropyl-benzimidazol-1-yl)-3-fluoro-but-2-enyl]carbamate prepared in Preparation 10 (20 mg) instead of tert-butyl N—[(Z)-4-(4-bromo-6-fluoro-benzimidazol-1-yl)-3-fluoro-but-2-enyl]carbamate; and N-methyl-3-(4,4,5,5-tetramethyl-1,3,2-dioxaborolan-2-yl)benzenesulfonamide (13.9 mg) instead of 3-fluorophenylboronic acid. (Yield: 38.6%)

$^1$H-NMR (MeOD, 400 MHz) δ 8.14 (s, 1H), 8.00-7.96 (m, 4H), 7.82-7.75 (m, 2H), 5.65-5.50 (m, 3H), 3.78-3.66 (m, 3H), 2.60 (s, 3H), 1.55 (s, 6H)

Example 102. (Z)-5-(1-(4-amino-2-fluorobut-2-en-1-yl)-1H-benzo[d][1,2,3]triazol-4-yl)-2-methoxy-N,N-dimethylbenzenesulfonamide hydrochloride The titled compound (11.1 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and (3-(N,N-dim ethylsulfamoyl)-4-methoxyphenyl)boronic acid (13.5 mg) instead of 3-fluorophenylboronic acid. (Yield: 46.9%)

$^1$H-NMR (MeOD, 400 MHz) δ 8.61 (s, 1H), 8.36 (d, 1H), 7.80 (d, 1H), 7.69-7.65 (m, 2H), 7.40 (d, 1H), 5.66 (d, 2H), 5.30 (dt, 1H), 4.04 (s, 3H), 3.66 (d, 2H), 3.30 (s, 6H)

Example 103. (Z)-4-(4-(3-((3,3-difluoropyrrolidin-1-yl)sulfonyl)phenyl)-1H-benzo[d][1,2,3]triazol-1-yl)-3-fluorobut-2-en-1-amine hydrochloride The titled compound (10.1 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and 3,3-difluoro-1-((3-(4,4,5,5-tetramethyl-1,3,2-dioxaborolan-2-yl)phenyl)sulfonyl)pyrrolidine (19.4 mg) instead of 3-fluorophenylboronic acid. (Yield: 39.9%)

$^1$H-NMR (MeOD, 400 MHz) δ 8.67 (s, 1H), 8.39 (d, 1H), 7.96-7.72 (m, 5H), 5.68 (d, 2H), 5.35 (dt, 1H), 3.68-3.58 (m, 4H), 3.56 (d, 2H), 2.41-2.30 (m, 2H)

Example 104. (Z)-3-fluoro-4-(4-(3-(pyrrolidin-1-ylsulfonyl)phenyl)-1H-benzo[d][1,2,3]triazol-1-yl)but-2-en-1-amine hydrochloride The titled compound (9.3 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and (3-pyrrolidin-1-ylsulfonylphenyl)boronic acid (13.2 mg) instead of 3-fluorophenylboronic acid. (Yield: 39.6%)

$^1$H-NMR (MeOD, 400 MHz) δ 8.64 (s, 1H), 8.35 (d, 1H), 7.89-7.72 (m, 5H), 5.68 (d, 2H), 5.38 (dt, 1H), 3.64 (d, 2H), 3.31-3.27 (m, 4H), 1.81-1.78 (m, 4H)

Example 105. (Z)-3-(1-(4-amino-2-fluorobut-2-en-1-yl)-1H-benzo[d][1,2,3]triazol-4-yl)-4-methoxy-N-methylbenzenesulfonamide hydrochloride The titled compound (10 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and [2-methoxy-5-(methylsulfamoyl)phenyl]boronic acid (12.7 mg) instead of 3-fluorophenylboronic acid. (Yield: 43.6%)

$^1$H-NMR (MeOD, 400 MHz) δ 7.97 (s, 1H), 7.94 (d, 1H), 7.92 (d, 1H), 7.70 (dd, 1H), 7.53 (d, 1H), 7.35 (d, 1H), 5.70 (d, 2H), 5.36 (dt, 1H), 3.87 (s, 3H), 3.67 (d, 2H), 2.59 (s, 3H)

Example 106. (Z)-3-fluoro-4-(4-(3-(methylsulfonyl)phenyl)-1H-benzo[d][1,2,3]triazol-1-yl)but-2-en-1-amine hydrochloride The titled compound (14.3 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and 3-(methanesulfonyl)phenylboronic acid (10.4 mg) instead of 3-fluorophenylboronic acid. (Yield: 69.4%)

$^1$H-NMR (MeOD, 400 MHz) δ 8.68 (s, 1H), 8.41 (d, 1H), 8.05 (d, 1H), 7.91 (d, 1H), 7.89-7.71 (m, 3H), 5.70 (d, 2H), 5.41 (dt, 1H), 3.69 (d, 2H), 3.31 (s, 3H)

Example 107. (Z)-3-(1-(4-amino-2-fluorobut-2-en-1-yl)-1H-benzo[d][1,2,3]triazol-4-yl)-N,N-diethyl-4-methoxybenzenesulfonamide hydrochloride The titled compound (15.7 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and (5-(N,N-diethylsulfamoyl)-2-methoxyphenyl)boronic acid (14.9 mg) instead of 3-fluorophenylboronic acid. (Yield: 62.5%)

$^1$H-NMR (MeOD, 400 MHz) δ 7.94 (s, 1H), 7.90 (d, 1H), 7.87 (d, 1H), 7.69 (dd, 1H), 7.52 (d, 1H), 7.35 (d, 1H), 5.67 (d, 2H), 5.41 (dt, 1H), 3.87 (s, 3H), 3.61 (d, 2H), 3.27 (q, 4H), 1.16 (t, 6H)

Example 108. (Z)-3-(1-(4-amino-2-fluorobut-2-en-1-yl)-1H-benzo[d][1,2,3]triazol-4-yl)-N-cyclopropyl-4-methoxybenzenesulfonamide hydrochloride The titled compound (16.0 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and (5-(N-cyclopropylsulfamoyl)-2-methoxyphenyl)boronic acid (14.1 mg) instead of 3-fluorophenylboronic acid. (Yield: 65.9%)

$^1$H-NMR (MeOD, 400 MHz) δ 8.03 (s, 1H), 8.00 (d, 1H), 7.96 (d, 1H), 7.69 (dd, 1H), 7.54 (d, 1H), 7.37 (d, 1H), 5.67 (d, 2H), 5.43 (dt, 1H), 3.89 (s, 3H), 3.69 (d, 2H), 2.27-2.23 (m, 1H), 0.58-0.54 (m, 4H)

Example 109. (Z)-5-(1-(4-amino-2-fluorobut-2-en-1-yl)-1H-benzo[d][1,2,3]triazol-4-yl)-N-isopropyl-2-methoxybenzenesulfonamide hydrochloride The titled compound (13.8 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and [3-(isopropylsulfamoyl)-4-methoxyphenyl]boronic acid (14.2 mg) instead of 3-fluorophenylboronic acid. (Yield: 56.6%)

$^1$H-NMR (MeOD, 400 MHz) δ 8.60 (s, 1H), 8.36 (d, 1H), 7.78 (d, 1H), 7.69 (d, 1H), 7.67 (d, 1H), 7.40 (d, 1H), 5.68 (d, 2H), 5.37 (dt, 1H), 4.07 (s, 3H), 3.64 (d, 2H), 3.45-3.43 (m, 1H), 1.09 (s, 6H)

Example 110. (Z)-3-(1-(4-amino-2-fluorobut-2-en-1-yl)-1H-benzo[d][1,2,3]triazol-4-yl)-N-cyclopropylbenzenesulfonamide hydrochloride The titled compound (9.7 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and (3-(N-cyclopropylsulfamoyl)phenylboronic acid (12.5 mg) instead of 3-fluorophenylboronic acid. (Yield: 42.7%)

$^1$H-NMR (MeOD, 400 MHz) δ 8.63 (s, 1H), 8.35 (d, 1H), 7.98 (d, 1H), 7.88-7.73 (m, 4H), 5.68 (d, 2H), 5.40 (dt, 1H), 3.66 (d, 2H), 2.29-2.26 (m, 1H), 0.61-0.57 (m, 4H)

Example 111. (Z)-3-(1-(4-amino-2-fluorobut-2-en-1-yl)-1H-benzo[d][1,2,3]triazol-4-yl)-N-methylbenzenesulfonamide hydrochloride The titled compound (12.2 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and 3-(N-methylsulfamoyl)phenylboronic acid (11.2 mg) instead of 3-fluorophenylboronic acid. (Yield: 57.1%)

$^1$H-NMR (MeOD, 400 MHz) δ 8.58 (s, 1H), 8.32 (d, 1H), 7.94-7.89 (m, 2H), 7.78-7.72 (m, 3H), 5.69 (d, 2H), 5.38 (dt, 1H), 3.67 (d, 2H), 2.62 (s, 3H)

Example 112. (Z)-3-(1-(4-amino-2-fluorobut-2-en-1-yl)-1H-benzo[d][1,2,3]triazol-4-yl)-N,N-dimethylbenzenesulfonamide hydrochloride The titled compound (10.8 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and [3-(dimethylsulfamoyl)phenyl]boronic acid (11.9 mg) instead of 3-fluorophenylboronic acid. (Yield: 48.8%)

$^1$H-NMR (MeOD, 400 MHz) δ 8.57 (s, 1H), 8.35 (d, 1H), 7.89-7.72 (m, 5H), 5.67 (d, 2H), 5.41 (dt, 1H), 3.64 (d, 2H), 2.79 (s, 6H)

Example 113. (Z)-3-fluoro-4-(4-(2-methoxy-5-((4-methyl piperazin-1-yl)sulfonyl)phenyl)-1H-benzo[d][1,2,3]triazol-1-yl)but-2-en-1-amine hydrochloride The titled compound (11.1 mg) was prepared in accordance with the same procedures as in Example 1, except for using tert-butyl N—[(Z)-4-(4-bromobenzotriazol-1-yl)-3-fluoro-but-2-enyl]carbamate prepared in Preparation 11 (20 mg) instead of tert-butyl N—[(Z)-4-(4-bromo-6-fluoro-benzimidazol-1-yl)-3-fluoro-but-2-enyl]carbamate; and (2-methoxy-5-((4-m ethylpiperazin-1-yl)sulfonyl)phenyl)boronic acid (13.9 mg) instead of 3-fluorophenylboronic acid. (Yield: 48.4%)

$^1$H-NMR (MeOD, 400 MHz) δ 7.99 (s, 1H), 7.95 (d, 1H), 7.94 (d, 1H), 7.92 (d, 1H), 7.70 (dd, 1H), 7.64 (d, 1H), 7.45 (d, 1H), 5.67 (d, 2H), 5.39 (dt, 1H), 3.98-3.94 (m, 2H), 3.90 (s, 3H), 3.61 (d, 2H), 3.60-3.58 (m, 2H), 3.30-3.28 (m, 2H), 2.91 (s, 3H), 2.89-2.87 (m, 2H)

Example 114. methyl (Z)-1-(4-amino-2-fluorobut-2-en-1-yl)-4-(3-(N,N-dimethylsulfamoyl)-4-methoxyphenyl)-1H-benzo[d][1,2,3]triazol-6-carboxylate hydrochloride The titled compound (5.1 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl]carbamate; and (3-(N,N-dimethylsulfamoyl)-4-methoxyphenyl)boronic acid (11.7 mg) instead of 3-fluorophenylboronic acid. (Yield: 22.0%)

$^1$H-NMR (MeOD, 400 MHz) δ 8.66 (s, 1H), 8.65 (s, 1H), 8.41 (d, 1H), 8.21 (s, 1H), 7.43 (d, 1H), 5.67 (d, 2H), 5.41 (dt, 1H), 4.05 (s, 3H), 4.02 (s, 3H), 3.52 (d, 2H), 2.90 (s, 6H)

Example 115. methyl (Z)-1-(4-amino-2-fluorobut-2-en-1-yl)-4-(3-((3,3-difluoropyrrolidin-1-yl)sulfonyl)phenyl)-1H-benzo[d][1,2,3]triazol-6-carboxylate hydrochloride The titled compound (4.4 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl]carbamate; and 3,3-difluoro-1-((3-(4,4,5,5-tetramethyl-1,3,2-dioxaborolan-2-yl)phenyl)sulfonyl)pyrrolidine (16.8 mg) instead of 3-fluorophenylboronic acid. (Yield: 17.9%)

$^1$H-NMR (MeOD, 400 MHz) δ 8.71 (s, 1H), 8.70 (s, 1H), 8.56 (d, 1H), 8.42 (s, 1H), 7.99 (d, 1H), 7.87 (dd, 1H), 5.69 (d, 2H), 5.35 (dt, 1H), 4.03 (s. 3H), 3.69 (d, 2H), 3.57 (t, 2H), 3.47 (d, 2H), 2.41-2.31 (m, 2H)

Example 116. methyl (Z)-1-(4-amino-2-fluorobut-2-en-1-yl)-4-(3-(pyrrolidin-1-ylsulfonyl)phenyl)-1H-benzo[d][1,2,3]triazol-6-carboxylate hydrochloride The titled compound (5.6 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and (3-pyrrolidin-1-ylsulfonylphenyl)boronic acid (11.5 mg) instead of 3-fluorophenylboronic acid. (Yield: 24.3%)

$^1$H-NMR (MeOD, 400 MHz) δ 8.68 (s, 1H), 8.56 (s, 1H), 8.36 (d, 1H), 8.29 (s, 1H), 7.96 (d, 1H), 7.82 (dd, 1H), 5.69 (d, 2H), 5.42 (dt, 1H), 4.03 (s, 3H), 3.49 (d, 2H), 3.38-3.35 (m, 4H), 1.82-1.79 (m, 4H)

Example 117. methyl (Z)-1-(4-amino-2-fluorobut-2-en-1-yl)-4-(2-methoxy-5-(N-m ethylsulfamoyl)phenyl)-1H-benzo[d][1,2,3]triazol-6-carboxylate hydrochloride The titled compound (6.1 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and [2-methoxy-5-(methylsulfamoyl)phenyl]boronic acid (11.1 mg) instead of 3-fluorophenylboronic acid. (Yield: 27.0%)

$^1$H-NMR (MeOD, 400 MHz) δ 8.56 (s, 1H), 8.14 (s, 1H), 8.00-7.96 (m, 2H), 7.38 (d, 1H), 5.71 (d, 2H), 5.40 (dt, 1H), 4.00 (s, 3H), 3.89 (s, 3H), 3.61 (d, 2H), 2.60 (s, 3H)

Example 118. methyl (Z)-1-(4-amino-2-fluorobut-2-en-1-yl)-4-(3-(methylsulfonyl)phenyl)-1H-benzo[d][1,2,3]triazol-6-carboxylate hydrochloride The titled compound (7.1 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and 3-(methanesulfonyl)phenylboronic acid (9.0 mg) instead of 3-fluorophenylboronic acid. (Yield: 34.6%)

$^1$H-NMR (MeOD, 400 MHz) δ 8.71 (s, 1H), 8.70 (s, 1H), 8.56 (d, 1H), 8.46 (s, 1H), 8.07 (d, 1H), 7.84 (dd, 1H), 5.71 (d, 2H), 5.39 (dt, 1H), 4.03 (s, 3H), 3.53 (d, 2H), 3.26 (s, 3H)

Example 119. methyl (Z)-1-(4-amino-2-fluorobut-2-en-1-yl)-4-(5-(N,N-diethylsulfamoyl)-2-methoxyphenyl)-1H-benzo[d][1,2,3]triazol-6-carboxylate hydrochloride The titled compound (9.9 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and (5-(N,N-diethylsulfamoyl)-2-methoxyphenyl)boronic acid (13.0 mg) instead of 3-fluorophenylboronic acid. (Yield: 40.5%)

$^1$H-NMR (MeOD, 400 MHz) δ 8.54 (s, 1H), 8.50 (s, 1H), 8.12 (s, 1H), 7.96 (d, 1H), 7.37 (d, 1H), 5.70 (d, 2H), 5.43 (dt, 1H), 4.00 (s, 3H), 3.89 (s, 3H), 3.56 (d, 2H), 3.27 (q, 4H), 1.17 (t, 6H)

Example 120. methyl (Z)-1-(4-amino-2-fluorobut-2-en-1-yl)-4-(5-(N-cyclopropylsulfamoyl)-2-methoxyphenyl)-1H-benzo[d][1,2,3]triazol-6-carboxylate hydrochloride The titled compound (6.7 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and (5-(N-cyclopropylsulfamoyl)-2-methoxyphenyl)boronic acid (14.2 mg) instead of 3-fluorophenylboronic acid. (Yield: 28.2%)

$^1$H-NMR (MeOD, 400 MHz) δ 8.55 (s, 1H), 8.13 (s, 1H), 8.05 (s, 1H), 8.03-8.00 (m, 1H), 7.38 (d, 1H), 5.70 (d, 1H), 5.44 (dt, 1H), 4.00 (s, 3H), 3.90 (s, 3H), 3.56 (d, 2H), 2.30-2.25 (m, 1H), 0.60-0.57 (m, 4H)

Example 121. methyl (Z)-1-(4-amino-2-fluorobut-2-en-1-yl)-4-(3-(N-isopropylsulfamoyl)-4-methoxyphenyl)-1H-benzo[d][1,2,3]triazol-6-carboxylate hydrochloride The titled compound (7.2 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and [3-(isopropylsulfamoyl)-4-methoxyphenyl] boronic acid (12.3 mg) instead of 3-fluorophenylboronic acid. (Yield: 30.2%)

$^1$H-NMR (MeOD, 400 MHz) δ 8.64 (s, 1H), 8.47 (s, 1H), 8.40 (d, 1H), 8.19 (s, 1H), 7.41 (d, 1H), 5.70 (d, 2H), 5.41 (dt, 1H), 4.08 (s, 3H), 4.01 (s, 3H), 3.53 (d, 2H), 3.45 (m, 1H), 1.10 (s, 3H), 1.09 (s, 3H)

Example 122. methyl (Z)-1-(4-amino-2-fluorobut-2-en-1-yl)-4-(3-(N-cyclopropylsulfamoyl)phenyl)-1H-benzo[d][1,2,3]triazol-6-carboxylate hydrochloride The titled compound (5.3 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and (3-(N-cyclopropylsulfamoyl)phenylboronic acid (10.9 mg) instead of 3-fluorophenylboronic acid. (Yield: 23.7%)

$^1$H-NMR (MeOD, 400 MHz) δ 8.65 (s, 1H), 8.64 (s, 1H), 8.56 (d, 1H), 8.40 (s, 1H), 8.00 (d, 1H), 7.80 (dd, 1H), 5.70 (d, 2H), 5.41 (dt, 1H), 4.03 (s. 3H), 3.54 (d, 2H), 2.32-2.27 (m, 1H), 0.62-0.57 (m, 4H)

Example 123. methyl (Z)-1-(4-amino-2-fluorobut-2-en-1-yl)-4-(3-(N-m ethylsulfamoyl)phenyl)-1H-benzo[d][1,2,3]triazol-6-carboxylate hydrochloride The titled compound (7.0 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and 3-(N-methylsulfamoyl)phenylboronic acid (9.7 mg) instead of 3-fluorophenylboronic acid. (Yield: 33.0%)

$^1$H-NMR (MeOD, 400 MHz) δ 8.60 (s, 1H), 8.59 (s, 1H), 8.55 (d, 1H), 8.38 (s, 1H), 7.97 (d, 1H), 7.79 (dd, 1H), 5.74 (d, 2H), 5.42 (d, 1H), 4.03 (s, 3H), 3.57 (d, 2H), 2.63 (s, 3H)

Example 124. methyl (Z)-1-(4-amino-2-fluorobut-2-en-1-yl)-4-(3-(N,N-dimethylsulfamoyl)phenyl)-1H-benzo[d][1,2,3]triazol-6-carboxylate hydrochloride The titled compound (4.9 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and [3-(dimethylsulfamoyl)phenyl]boronic acid (10.3 mg) instead of 3-fluorophenylboronic acid. (Yield: 22.4%)

$^{1}$H-NMR (MeOD, 400 MHz) δ 8.61 (s, 1H), 8.60 (s, 1H), 8.41 (d, 1H), 8.31 (s, 1H), 7.91 (d, 1H), 7.84 (dd, 1H), 5.70 (d, 2H), 5.42 (dt, 1H), 4.03 (s, 3H), 3.46 (d, 2H), 2.80 (s, 6H)

Example 125. methyl (Z)-1-(4-amino-2-fluorobut-2-en-1-yl)-4-(3-(N-(4-methoxybenzyl)sulfamoyl)phenyl)-1H-benzo[d][1,2,3]triazol-6-carboxylate hydrochloride The titled compound (5.8 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and [3[(4-methoxyphenyl)methylsulfamoyl]phenyl]boronic acid (14.5 mg) instead of 3-fluorophenylboronic acid. (Yield: 22.3%)

$^{1}$H-NMR (MeOD, 400 MHz) δ 8.55 (s, 1H), 8.44 (s, 1H), 8.31 (d, 1H), 8.22 (s, 1H), 7.91 (d, 1H), 7.71 (dd, 1H), 7.11 (d, 2H), 6.69 (d, 2H), 5.70 (d, 2H), 5.45 (dt, 1H), 4.12 (s, 2H), 4.03 (s, 3H), 3.62 (s, 3H), 3.46 (d, 2H)

Example 126. methyl (Z)-1-(4-amino-2-fluorobut-2-en-1-yl)-4-(3-(piperidin-1-ylsulfonyl)phenyl)-1H-benzo[d][1,2,3]triazol-6-carboxylate hydrochloride The titled compound (4.5 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and [3-(1-piperidylsulfonyl)phenyl]boronic acid (12.1 mg) instead of 3-fluorophenylboronic acid. (Yield: 19.0%)

$^{1}$H-NMR (MeOD, 400 MHz) δ 8.57 (s, 1H), 8.56 (s, 1H), 8.37 (d, 1H), 8.28 (s, 1H), 7.90 (d, 1H), 7.81 (dd, 1H), 5.67 (d, 2H), 5.43 (dt, 1H), 4.02 (s, 3H), 3.43 (d, 2H), 3.31-3.09 (m, 4H), 1.70-1.64 (m, 4H), 1.49-1.46 (m, 2H)

Example 127. methyl (Z)-1-(4-amino-2-fluorobut-2-en-1-yl)-4-(3-(ethylsulfonyl)phenyl)-1H-benzo[d][1,2,3]triazol-6-carboxylate hydrochloride The titled compound (5.4 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and (3-ethylsulfonylphenyl)boronic acid (9.7 mg) instead of 3-fluorophenylboronic acid. (Yield: 25.5%)

$^{1}$H-NMR (MeOD, 400 MHz) δ 8.69 (s, 1H), 8.68 (s, 1H), 8.59 (d, 1H), 8.31 (s, 1H), 8.04 (d, 1H), 7.86 (dd, 1H), 5.72 (d, 2H), 5.43 (dt, 1H), 4.03 (s, 3H), 3.52 (d, 2H), 3.35 (q, 2H), 1.32 (t, 3H)

Example 128. methyl (Z)-1-(4-amino-2-fluorobut-2-en-1-yl)-4-(2-methyl-5-((trifluoromethyl)sulfonyl)phenyl)-1H-benzo[d][1,2,3]triazol-6-carboxylate hydrochloride The titled compound (2.3 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and 4,4,5,5-tetramethyl-2-[2-methyl-5-(trifluoromethylsulfonyl)phenyl]-1,3,2-dioxaborolane (15.8 mg) instead of 3-fluorophenylboronic acid. (Yield: 9.8%)

$^{1}$H-NMR (MeOD, 400 MHz) δ 8.65 (s, 1H), 8.13 (d, 1H), 8.11 (s, 1H), 8.04 (s, 1H), 7.84 (d, 1H), 5.68 (d, 2H), 5.44 (dt, 1H), 4.01 (s, 3H), 3.41 (d, 2H), 2.38 (s, 3H)

Example 129. methyl (Z)-1-(4-amino-2-fluorobut-2-en-1-yl)-4-(3-(N-(tert-butyl)sulfamoyl)phenyl)-1H-benzo[d][1,2,3]triazol-6-carboxylate hydrochloride The titled compound (5.3 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and [3-(tert-butylsulfamoyl)phenyl]boronic acid (11.6 mg) instead of 3-fluorophenylboronic acid. (Yield: 22.9%)

$^{1}$H-NMR (MeOD, 400 MHz) δ 8.69 (s, 1H), 8.55 (s, 1H), 8.33 (d, 1H), 8.29 (s, 1H), 8.01 (d, 1H), 7.75 (dd, 1H), 5.71 (d, 2H), 5.43 (dt, 1H), 4.03 (s, 3H), 3.51 (d, 2H), 1.26 (s, 9H)

Example 130. methyl (Z)-1-(4-amino-2-fluorobut-2-en-1-yl)-4-(3-(N,N-diethylsulfamoyl)phenyl)-1H-benzo[d][1,2,3]triazol-6-carboxylate hydrochloride The titled compound (4 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4-bromo-6-fluoro-benzimidazol-1-yl)-3-fluoro-but-2-enyl] carbamate; and [3-(diethylsulfamoyl)phenyl]boronic acid (9.7 mg) instead of 3-fluorophenylboronic acid. (Yield: 17.3%)

$^{1}$H-NMR (MeOD, 400 MHz) δ 8.67 (s, 1H), 8.66 (s, 1H), 8.34 (d, 1H), 8.29 (s, 1H), 7.94 (d, 1H), 7.74 (dd, 1H), 5.71 (d, 2H), 5.41 (dt, 1H), 4.03 (s, 3H), 3.43 (d, 2H), 3.31 (q, 4H), 1.18 (t, 6H)

Example 131. methyl (Z)-1-(4-amino-2-fluorobut-2-en-1-yl)-4-(3-(diethoxyphosphoryl)phenyl)-1H-benzo[d][1,2,3]triazol-6-carboxylate hydrochloride The titled compound (5.7 mg) was prepared in accordance with the same procedures as in Example 1, except for using methyl 7-bromo-3-[(Z)-4-(tert-butoxycarbonylamino)-2-fluoro-but-2-enyl]benzotriazol-5-carboxylate prepared in Preparation 12 (20 mg) instead of tert-butyl N—[(Z)-4-(4- bromo-6-fluoro-benzimidazol-1-yl)-3-fluoro-but-2-enyl] carbamate; and 2-(3-diethoxyphosphorylphenyl)-4,4,5,5-tetramethyl-1,3,2-dioxaborolane (15.4 mg) instead of 3-fluorophenylboronic acid. (Yield: 24.6%)

$^1$H-NMR (MeOD, 400 MHz) δ 8.56-8.53 (m, 2H), 8.37 (d, 1H), 8.29 (s, 1H), 7.94-7.89 (m, 1H), 7.80-7.75 (m, 1H), 5.75 (d, 2H), 5.42 (dt, 1H), 4.20 (q, 4H), 4.03 (s, 3H), 3.63 (d, 2H), 1.38 (t, 6H)

Example 132. (Z)-1-(4-amino-2-fluorobut-2-en-1-yl)-4-(3-(N,N-dimethylsulfamoyl)-4-methoxyphenyl)-N-methoxy-1H-benzo[d][1,2,3]triazol-6-carboxamide hydrochloride The titled compound (2.9 mg) was prepared in accordance with the same procedures as in Example 1, except for using tert-butyl N—[(Z)-4-[4-bromo-6-(methoxycarbamoyl)benzotriazol-1-yl]-3-fluoro-but-2-enyl]carbamat e prepared in Preparation 13 (20 mg) instead of tert-butyl N—[(Z)-4-(4-bromo-6-fluoro-benzimidazol-1-yl)-3-fluoro-but-2-enyl] carbamate; and (3-(N,N-dim ethylsulfamoyl)-4-methoxyphenyl)boronic acid (12.1 mg) instead of 3-fluorophenylboronic acid. (Yield: 12.6%)

$^1$H-NMR (MeOD, 400 MHz) δ 8.69 (s, 1H), 8.44 (d, 1H), 8.23 (s, 1H), 7.98 (s, 1H), 7.43 (d, 1H), 5.70 (d, 2H), 5.37 (dt, 1H), 4.05 (s, 3H), 3.89 (s, 3H), 3.57 (d, 2H), 2.90 (s, 6H)

Example 133. (Z)-1-(4-amino-2-fluorobut-2-en-1-yl)-N-methoxy-4-(3-(pyrrolidin-1-ylsulfonyl)phenyl)-1H-benzo[d][1,2,3]triazol-6-carboxamide hydrochloride The titled compound (7.1 mg) was prepared in accordance with the same procedures as in Example 1, except for using tert-butyl N—[(Z)-4-[4-bromo-6-(methoxycarbamoyl)benzotriazol-1-yl]-3-fluoro-but-2-enyl]carbamat e prepared in Preparation 13 (20 mg) instead of tert-butyl N—[(Z)-4-(4-bromo-6-fluoro-benzimidazol-1-yl)-3-fluoro-but-2-enyl] carbamate; and (3-pyrrolidin-1-ylsulfonylphenyl)boronic acid (11.9 mg) instead of 3-fluorophenylboronic acid. (Yield: 31.0%)

$^1$H-NMR (MeOD, 400 MHz) δ 8.70 (s, 1H), 8.39 (d, 1H), 8.31 (s, 1H), 8.06 (s, 1H), 7.95 (d, 1H), 7.82 (dd, 1H), 5.72 (d, 2H), 5.44 (dt, 1H), 3.90 (s, 3H), 3.61 (d, 2H), 3.36-3.33 (m, 4H), 1.82-1.78 (m, 4H)

Example 134. (Z)-1-(4-amino-2-fluorobut-2-en-1-yl)-N-methoxy-4-(2-methoxy-5-(N-methylsulfamoyl)phenyl)-1H-benzo[d][1,2,3]triazol-6-carboxamide hydrochloride The titled compound (2 mg) was prepared in accordance with the same procedures as in Example 1, except for using tert-butyl N—[(Z)-4-[4-bromo-6-(methoxycarbamoyl)benzotriazol-1-yl]-3-fluoro-but-2-enyl]carbamat e prepared in Preparation 13 (20 mg) instead of tert-butyl N—[(Z)-4-(4-bromo-6-fluoro-benzimidazol-1-yl)-3-fluoro-but-2-enyl] carbamate; and [2-methoxy-5-(methylsulfamoyl)phenyl]boronic acid (11.4 mg) instead of 3-fluorophenylboronic acid. (Yield: 8.9%)

$^1$H-NMR (MeOD, 400 MHz) δ 8.30 (s, 1H), 8.00 (s, 1H), 7.97 (d, 1H), 7.86 (s, 1H), 7.38 (d, 1H), 5.71 (d, 2H), 5.39 (dt, 1H), 3.89 (s, 3H), 3.87 (s, 3H), 3.60 (d, 2H), 2.60 (s, 3H)

Example 135. (Z)-1-(4-amino-2-fluorobut-2-en-1-yl)-4-(5-(N,N-diethylsulfamoyl)-2-methoxyphenyl)-N-m ethoxy-1H-benzo[d][1,2,3]triazol-6-carboxamide hydrochloride The titled compound (4.5 mg) was prepared in accordance with the same procedures as in Example 1, except for using tert-butyl N—[(Z)-4-[4-bromo-6-(methoxycarbamoyl)benzotriazol-1-yl]-3-fluoro-but-2-enyl]carbamat e prepared in Preparation 13 (20 mg) instead of tert-butyl N—[(Z)-4-(4-bromo-6-fluoro-benzimidazol-1-yl)-3-fluoro-but-2-enyl] carbamate; and (5-(N,N-diethylsulfamoyl)-2-methoxyphenyl)boronic acid (13.4 mg) instead of 3-fluorophenylboronic acid. (Yield: 18.5%)

$^1$H-NMR (MeOD, 400 MHz) δ 8.29 (s, 1H), 8.00 (s, 1H), 7.96 (d, 1H), 7.86 (s, 1H), 7.37 (d, 1H), 5.69 (d, 1H), 5.40 (dt, 1H), 3.89 (s, 3H), 3.87 (s, 3H), 3.58 (d, 2H), 3.28 (q, 4H), 1.17 (t, 6H)

Example 136. (Z)-1-(4-amino-2-fluorobut-2-en-1-yl)-4-(5-(N-cyclopropylsulfamoyl)-2-methoxyphenyl)-N-methoxy-1H-benzo[d][1,2,3]triazol-6-carboxamide hydrochloride The titled compound (1.3 mg) was prepared in accordance with the same procedures as in Example 1, except for using tert-butyl N—[(Z)-4-[4-bromo-6-(methoxycarbamoyl)benzotriazol-1-yl]-3-fluoro-but-2-enyl]carbamat e prepared in Preparation 13 (20 mg) instead of tert-butyl N—[(Z)-4-(4-bromo-6-fluoro-benzimidazol-1-yl)-3-fluoro-but-2-enyl] carbamate; and (5-(N-cyclopropylsulfamoyl)-2-methoxyphenyl)boronic acid (12.6 mg) instead of 3-fluorophenylboronic acid. (Yield: 5.5%)

$^1$H-NMR (MeOD, 400 MHz) δ 8.30 (s, 1H), 8.04 (s, 1H), 8.04-8.03 (m, 1H), 7.87 (s, 1H), 7.39 (d, 1H), 5.70 (d, 2H), 5.42 (dt, 1H), 3.90 (s, 3H), 3.87 (s, 3H), 3.56 (d, 2H), 2.33-2.30 (m, 1H), 0.59-0.55 (m, 4H)

Example 137. (Z)-1-(4-amino-2-fluorobut-2-en-1-yl)-N-methoxy-N-methyl-4-(3-(pyrrolidin-1-ylsulfonyl)phenyl)-1H-benzo[d][1,2,3]triazol-6-carboxamide hydrochloride The titled compound (2.1 mg) was prepared in accordance with the same procedures as in Example 1, except for using tert-butyl N—[(Z)-4-[4-bromo-6-[methoxy(methyl)carbamoyl]benzotriazol-1-yl]-3-fluoro-but-2-enyl]c arbamate prepared in Preparation 14 (20 mg) instead of tert-butyl N—[(Z)-4-(4-bromo-6-fluoro-benzimidazol-1-yl)-3-fluoro-but-2-enyl]carbamate; and (3-pyrrolidin-1-ylsulfonylphenyl)boronic acid (10.8 mg) instead of 3-fluorophenylboronic acid. (Yield: 9.2%)

$^1$H-NMR (MeOD, 400 MHz) δ 8.68 (s, 1H), 8.37 (d, 1H), 8.18 (s, 1H), 7.95 (s, 1H), 7.80 (dd, 2H), 5.68 (d, 2H), 5.42 (dt, 1H), 3.65 (s, 3H), 3.41-3.36 (m, 9H), 1.82-1.79 (m, 4H)

Example 138. (Z)-1-(4-amino-2-fluorobut-2-en-1-yl)-4-(5-(N,N-diethylsulfamoyl)-2-methoxyphenyl)-N-m ethoxy-N-methyl-1H-benzo[d][1,2,3]triazol-6-carboxamide hydrochloride The titled compound (1.0 mg) was prepared in accordance with the same procedures as in Example 1, except for using tert-butyl N—[(Z)-4-[4-bromo-6-[methoxy(methyl)carbamoyl]benzotriazol-1-yl]-3-fluoro-but-2-enyl]c arbamate prepared in Preparation 14 (20 mg) instead of tert-butyl N—[(Z)-4-(4-bromo-6-fluoro-benzimidazol-1-yl)-3-fluoro-but-2-enyl]carbamate; and (5-(N,N-diethylsulfamoyl)-2-methoxyphenyl)boronic acid (12.2 mg) instead of 3-fluorophenylboronic acid. (Yield: 4.1%)

$^1$H-NMR (MeOD, 400 MHz) δ 8.14 (s, 1H), 8.02 (s, 1H), 7.96 (d, 1H), 7.75 (s, 1H), 7.37 (d, 1H), 5.63 (d, 2H), 5.40

(dt, 1H), 3.89 (s, 3H), 3.65 (s, 3H), 3.44 (d, 2H), 3.39 (s, 3H), 3.36-3.31 (q, 4H), 1.30-1.18 (t, 6H)

Example 139. (Z)-1-(4-amino-2-fluorobut-2-en-1-yl)-4-(3-(N,N-dimethylsulfamoyl)phenyl)-N-methoxy-N-methyl-1H-benzo[d][1,2,3]triazol-6-carboxamide The titled compound (1.0 mg) was prepared in accordance with the same procedures as in Example 1, except for using tert-butyl N—[(Z)-4-[4-bromo-6-[methoxy(methyl)carbamoyl]benzotriazol-1-yl]-3-fluoro-but-2-enyl]c arbamate prepared in Preparation 14 (20 mg) instead of tert-butyl N—[(Z)-4-(4-bromo-6-fluoro-benzimidazol-1-yl)-3-fluoro-but-2-enyl]carbamate; and [3-(dimethylsulfamoyl)phenyl] boronic acid (9.7 mg) instead of 3-fluorophenylboronic acid. (Yield: 4.2%)

$^1$H-NMR (MeOD, 400 MHz) δ 8.06 (s, 1H), 8.40 (d, 1H), 8.18 (s, 1H), 7.94-7.90 (m, 2H), 7.82 (dd, 1H), 5.67 (d, 2H), 5.51 (dt, 1H), 3.65 (s, 3H), 3.49 (d, 2H), 3.30 (s, 3H), 2.80 (s, 6H)

Example 140. (Z)-9-(4-amino-2-fluorobut-2-en-1-yl)-7-methyl-6-(3-(pyrrolidin-1-ylsulfonyl)phenyl)-7,9-di hydro-8H-purin-8-one hydrochloride The titled compound (24.5 mg) was prepared in accordance with the same procedures as in Example 1, except for using tert-butyl N—[(Z)-4-(6-chloro-7-methyl-8-oxo-purin-9-yl)-3-fluoro-but-2-enyl]carbamate prepared in Preparation 15 (20 mg) instead of tert-butyl N—[(Z)-4-(4-bromo-6-fluoro-benzimidazol-1-yl)-3-fluoro-but-2-enyl]carbamate; and (3-pyrrolidin-1-ylsulfonylphenyl)boronic acid (16.5 mg) instead of 3-fluorophenylboronic acid. (Yield: 93.9%)

$^1$H-NMR (MeOD, 400 MHz) δ 8.86 (s, 1H), 8.19-8.03 (m, 3H), 7.88 (s, 1H), 5.37 (d, 1H), 4.89-4.92 (m, 2H), 3.66 (s, 2H), 3.31-3.35 (m, 4H), 3.17 (s, 3H), 1.79-1.80 (m, 4H)

Example 141. (Z)-3-(9-(4-amino-2-fluorobut-2-en-1-yl)-7-methyl-8-oxo-8,9-dihydro-7H-purin-6-yl)-N-cy clopropylbenzenesulfonamide hydrochloride The titled compound (14.1 mg) was prepared in accordance with the same procedures as in Example 1, except for using tert-butyl N—[(Z)-4-(6-chloro-7-methyl-8-oxo-purin-9-yl)-3-fluoro-but-2-enyl]carbamate prepared in Preparation 15 (20 mg) instead of tert-butyl N—[(Z)-4-(4-bromo-6-fluoro-benzimidazol-1-yl)-3-fluoro-but-2-enyl]carbamate; and (3-(N-cyclopropylsulfamoyl)phenylboronic acid (15.6 mg) instead of 3-fluorophenylboronic acid. (Yield: 55.7%)

$^1$H-NMR (MeOD, 400 MHz) δ 8.70 (s, 1H), 8.14 (s, 1H), 8.07 (d, 1H), 7.94 (s, 1H), 7.81 (s, 1H), 5.31 (d, 1H), 4.88-4.84 (m, 2H), 3.65 (s, 2H), 3.16 (s, 3H), 2.22 (s, 1H), 0.57-0.52 (m, 4H)

Example 142. (Z)-3-(9-(4-amino-2-fluorobut-2-en-1-yl)-7-methyl-8-oxo-8,9-dihydro-7H-purin-6-yl)-N-methylbenzenesulfonamide hydrochloride The titled compound (22.6 mg) was prepared in accordance with the same procedures as in Example 1, except for using tert-butyl N—[(Z)-4-(6-chloro-7-methyl-8-oxo-purin-9-yl)-3-fluoro-but-2-enyl]carbamate prepared in Preparation 15 (20 mg) instead of tert-butyl N—[(Z)-4-(4-bromo-6-fluoro-benzimidazol-1-yl)-3-fluoro-but-2-enyl]carbamate; and 3-(N-methylsulfamoyl)phenylboronic acid (13.9 mg) instead of 3-fluorophenylboronic acid. (Yield: 94.5%)

$^1$H-NMR (MeOD, 400 MHz) δ 9.05 (s, 1H), 8.26 (s, 1H), 8.16 (d, 1H), 8.05 (d, 1H), 7.91 (t, 1H), 5.44 (dt, 1H), 4.96 (d, 2H), 3.67 (d, 2H), 3.17 (s, 3H), 2.60 (s, 3H)

Example 143. (Z)-9-(4-amino-2-fluorobut-2-en-1-yl)-7-methyl-6-(3-(methylsulfonyl)phenyl)-7,9-dihydro-8H-purin-8-one hydrochloride The titled compound (18.3 mg) was prepared in accordance with the same procedures as in Example 1, except for using tert-butyl N—[(Z)-4-(6-chloro-7-methyl-8-oxo-purin-9-yl)-3-fluoro-but-2-enyl]carbamate prepared in Preparation 15 (20 mg) instead of tert-butyl N—[(Z)-4-(4-bromo-6-fluoro-benzimidazol-1-yl)-3-fluoro-but-2-enyl]carbamate; and [3-(methanesulfonyl)phenylboronic acid (12.9 mg) instead of 3-fluorophenylboronic acid. (Yield: 79.2%)

$^1$H-NMR (MeOD, 400 MHz) δ 9.06 (s, 1H), 8.41 (s, 1H), 8.30 (d, 1H), 8.15 (d, 1H), 7.96 (t, 1H), 5.44 (dt, 1H), 4.96 (d, 2H), 3.67 (d, 2H), 3.25 (s, 3H), 3.18 (s, 3H)

Example 144. (Z)-3-(9-(4-amino-2-fluorobut-2-en-1-yl)-7-methyl-8-oxo-8,9-dihydro-7H-purin-6-yl)-N,N-dimethylbenzenesulfonamide hydrochloride The titled compound (22.3 mg) was prepared in accordance with the same procedures as in Example 1, except for using tert-butyl N—[(Z)-4-(6-chloro-7-methyl-8-oxo-purin-9-yl)-3-fluoro-but-2-enyl]carbamate prepared in Preparation 15 (20 mg) instead of tert-butyl N—[(Z)-4-(4-bromo-6-fluoro-benzimidazol-1-yl)-3-fluoro-but-2-enyl]carbamate; and 3-(N,N-dimethylaminosulfonyl)phenylboronic acid pinacol ester (20.1 mg) instead of 3-fluorophenylboronic acid. (Yield: 90.4%)

$^1$H-NMR (MeOD, 400 MHz) δ 8.91 (s, 1H), 8.16 (s, 1H), 8.06 (t, 2H), 7.90 (t, 1H), 5.39 (dt, 1H), 4.92 (d, 2H), 3.66 (d, 2H), 3.16 (s, 3H), 2.77 (s, 6H)

Example 145. (Z)-1-(4-amino-2-fluorobut-2-en-1-yl)-4-(3-(N,N-dimethylsulfamoyl)-4-methoxyphenyl)-N-methyl-1H-benzo[d][1,2,3]triazol-6-carboxamide hydrochloride The titled compound (5.2 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and (3-(N,N-dimethylsulfamoyl)-4-methoxyphenyl)boronic acid (11.7 mg) instead of 3-fluorophenylboronic acid. (Yield: 22.4%)

$^1$H-NMR (MeOD, 400 MHz) δ 8.69 (s, 1H), 8.44 (d, 1H), 8.26 (s, 1H), 8.05 (s, 1H), 7.43 (d, 1H), 5.71 (d, 1H), 5.43 (dt, 1H), 4.05 (s, 3H), 3.63 (d, 2H), 3.02 (s, 3H), 2.90 (s, 6H)

Example 146. (Z)-1-(4-amino-2-fluorobut-2-en-1-yl)-4-(3-((3,3-difluoropyrrolidin-1-yl)sulfonyl)phenyl)-N-methyl-1H-benzo[d][1,2,3]triazol-6-carboxamide hydrochloride The titled compound (5.8 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and 3,3-difluoro-1-((3-(4,4,5,5-tetramethyl-1,3,2-dioxaborolan-2-yl)phenyl)sulfonyl)pyrrolidine (16.9 mg) instead of 3-fluorophenylboronic acid. (Yield: 23.5%)

$^1$H-NMR (MeOD, 400 MHz) δ 8.73 (s, 1H), 8.46 (d, 1H), 8.35 (s, 1H), 8.16 (s, 1H), 7.92 (d, 1H), 7.84 (dd, 1H), 5.72 (d, 2H), 5.40 (dt, 1H), 3.69 (t, 2H), 3.60-3.57 (m, 4H), 3.03 (s, 3H), 2.41-2.30 (m, 2H)

Example 147. (Z)-1-(4-amino-2-fluorobut-2-en-1-yl)-N-methyl-4-(3-(pyrrolidin-1-ylsulfonyl)phenyl)-1H-benzo[d][1,2,3]triazol-6-carboxamide hydrochloride The titled compound (5.2 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and (3-pyrrolidin-1-ylsulfonylphenyl)boronic acid (11.7 mg) instead of 3-fluorophenylboronic acid. (Yield: 22.4%)

$^1$H-NMR (MeOD, 400 MHz) δ 8.71 (s, 1H), 8.41 (d, 1H), 8.34 (s, 1H), 8.14 (s, 1H), 7.95 (d, 1H), 7.82 (dd, 1H), 5.72 (d, 2H), 5.45 (dt, 1H), 3.62 (d, 2H), 3.38-3.36 (m, 4H), 3.02 (s, 3H), 1.82-1.78 (m, 4H)

Example 148. (Z)-1-(4-amino-2-fluorobut-2-en-1-yl)-4-(2-methoxy-5-(N-m ethylsulfamoyl)phenyl)-N-methyl-1H-benzo[d][1,2,3]triazol-6-carboxamide hydrochloride The titled compound (6.2 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and [2-methoxy-5-(methylsulfamoyl)phenyl]boronic acid (11.5 mg) instead of 3-fluorophenylboronic acid. (Yield: 26.9%)

$^1$H-NMR (MeOD, 400 MHz) δ 8.34 (s, 1H), 8.00-7.98 (m, 2H), 7.96 (s, 1H), 7.38 (d, 1H), 5.71 (d, 2H), 5.43 (dt, 1H), 3.88 (s, 3H), 3.62 (d, 2H), 2.99 (s, 3H), 2.59 (s, 3H)

Example 149. (Z)-1-(4-amino-2-fluorobut-2-en-1-yl)-N-methyl-4-(3-(methylsulfonyl)phenyl)-1H-benzo[d][1,2,3]triazol-6-carboxamide hydrochloride The titled compound (6.2 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and 3-(methanesulfonyl)phenylboronic acid (9.0 mg) instead of 3-fluorophenylboronic acid. (Yield: 26.9%)

$^1$H-NMR (MeOD, 400 MHz) δ 8.75 (s, 1H), 8.51 (d, 1H), 8.36 (s, 1H), 8.17 (s, 1H), 8.08 (d, 1H), 7.86 (dd, 1H), 5.74 (d, 2H), 5.44 (dt, 1H), 3.63 (d, 2H), 3.30 (s. 3H), 3.03 (s, 3H)

Example 150. (Z)-1-(4-amino-2-fluorobut-2-en-1-yl)-4-(5-(N,N-diethylsulfamoyl)-2-methoxyphenyl)-N-m ethyl-1H-benzo[d][1,2,3]triazol-6-carboxamide hydrochloride The titled compound (3.9 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and (5-(N,N-diethylsulfamoyl)-2-methoxyphenyl)boronic acid (13.0 mg) instead of 3-fluorophenylboronic acid. (Yield: 15.9%)

$^1$H-NMR (MeOD, 400 MHz) δ 8.32 (s, 1H), 7.99 (s, 1H), 7.97 (d, 1H), 7.96 (s, 1H), 7.37 (d, 1H), 5.68 (d, 2H), 5.44 (dt, 1H), 3.88 (s, 3H), 3.59 (d, 2H), 3.31-3.29 (q, 4H), 3.26 (s, 3H), 1.18-1.15 (t, 6H)

Example 151. (Z)-1-(4-amino-2-fluorobut-2-en-1-yl)-4-(3-(N-cyclopropylsulfamoyl)-4-methoxyphenyl)-N-methyl-1H-benzo[d][1,2,3]triazol-6-carboxamide hydrochloride The titled compound (2.3 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and (3-(N-cyclopropylsulfamoyl)-4-methoxyphenyl)boronic acid (12.3 mg) instead of 3-fluorophenylboronic acid. (Yield: 9.7%)

$^1$H-NMR (MeOD, 400 MHz) δ 8.33 (s, 1H), 8.04 (s, 1H), 8.03 (d, 1H), 8.00 (s, 1H), 7.38 (d, 1H), 5.71 (d, 2H), 5.43 (dt, 1H), 3.88 (s, 3H), 3.62 (d, 2H), 2.99 (s, 3H), 2.30-2.27 (m, 1H), 0.59-0.56 (m, 4H)

Example 152. (Z)-1-(4-amino-2-fluorobut-2-en-1-yl)-4-(3-(N-isopropylsulfamoyl)-4-methoxyphenyl)-N-methyl-1H-benzo[d][1,2,3]triazol-6-carboxamide hydrochloride The titled compound (4.8 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and [3-(isopropylsulfamoyl)-4-methoxyphenyl] boronic acid (12.4 mg) instead of 3-fluorophenylboronic acid. (Yield: 20.1%)

$^1$H-NMR (MeOD, 400 MHz) δ 8.68 (s, 1H), 8.46 (d, 1H), 8.26 (s, 1H), 8.05 (s, 1H), 7.41 (d, 1H), 5.70 (d, 2H), 5.42 (dt, 1H), 4.08 (s, 3H), 3.53 (d, 2H), 3.45-3.42 (m, 1H), 3.02 (s, 3H), 1.09 (s, 6H)

Example 153. (Z)-1-(4-amino-2-fluorobut-2-en-1-yl)-4-(3-(N-cyclopropylsulfamoyl)phenyl)-N-methyl-1H-benzo[d][1,2,3]triazol-6-carboxamide hydrochloride The titled compound (4.3 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and (3-(N-cyclopropylsulfamoyl)phenylboronic acid (10.9 mg) instead of 3-fluorophenylboronic acid. (Yield: 19.2%)

$^1$H-NMR (MeOD, 400 MHz) δ 8.70 (s, 1H), 8.40 (d, 1H), 8.34 (s, 1H), 8.14 (s, 1H), 8.05 (d, 1H), 7.79 (dd, 1H), 5.74 (d, 2H), 5.41 (dt, 1H), 3.62 (d, 2H), 3.02 (s, 3H), 2.32-2.27 (m, 1H), 0.61-0.58 (m, 4H)

Example 154. (Z)-1-(4-amino-2-fluorobut-2-en-1-yl)-N-methyl-4-(3-(N-methylsulfamoyl)phenyl)-1H-benzo[d][1,2,3]triazol-6-carboxamide hydrochloride The titled compound (3.2 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and 3-(N-methylsulfamoyl)phenylboronic acid (9.7 mg) instead of 3-fluorophenylboronic acid. (Yield: 15.1%)

$^1$H-NMR (MeOD, 400 MHz) δ 8.65 (s, 1H), 8.44 (d, 1H), 8.28 (s, 1H), 8.14 (s, 1H), 7.85 (d, 1H), 7.80 (dd, 1H), 5.73 (d, 2H), 5.40 (dt, 1H), 3.61 (d, 2H), 3.02 (s, 3H), 2.63 (s, 3H)

Example 155. (Z)-1-(4-amino-2-fluorobut-2-en-1-yl)-4-(3-(N,N-dimethylsulfamoyl)phenyl)-N-methyl-1H-benzo[d][1,2,3]triazol-6-carboxamide hydrochloride The titled compound (3.1 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and [3-(dimethylsulfamoyl)phenyl]boronic acid (10.4 mg) instead of 3-fluorophenylboronic acid. (Yield: 14.2%)

$^1$H-NMR (MeOD, 400 MHz) δ 8.64 (s, 1H), 8.44 (d, 1H), 8.34 (s, 1H), 8.14 (s, 1H), 7.87 (d, 1H), 7.84 (dd, 1H), 5.72 (d, 2H), 5.38 (dt, 1H), 3.61 (d, 2H), 3.02 (s, 3H), 2.79 (s, 6H)

Example 156. (Z)-1-(4-amino-2-fluorobut-2-en-1-yl)-4-(3-(ethylsulfonyl)phenyl)-N-methyl-1H-benzo[d][1,2,3]triazol-6-carboxamide hydrochloride The titled compound (4.6 mg) was prepared in accordance with the same procedures as in Example 1, except for using tert-butyl N—[(Z)-4-[4-bromo-6-(methylcarbamoyl)benzotriazol-1-yl]-3-fluoro-but-2-enyl]carbamate prepared in Preparation 16 (20 mg) instead of tert-butyl N—[(Z)-4-(4-bromo-6-fluoro-benzimidazol-1-yl)-3-fluoro-but-2-enyl] carbamate; and (3-ethylsulfonylphenyl)boronic acid (9.7 mg) instead of 3-fluorophenylboronic acid. (Yield: 21.7%)

$^1$H-NMR (MeOD, 400 MHz) δ 8.73 (s, 1H), 8.52 (d, 1H), 8.36 (s, 1H), 8.16 (s, 1H), 8.04 (d, 1H), 7.86 (dd, 1H), 5.73 (d, 2H), 5.40 (dt, 1H), 3.62 (d, 2H), 3.36 (q, 2H), 3.03 (s, 3H), 1.32 (t, 3H)

Example 157. (Z)-5-(1-(4-amino-2-fluorobut-2-en-1-yl)-6-(pyrrolidin-1-carbonyl)-1H-benzo[d][1,2,3]triazol-4-yl)-2-methoxy-N,N-dimethylbenzenesulfonamide hydrochloride The titled compound (1.9 mg) was prepared in accordance with the same procedures as in Example 1, except for using tert-butyl N—[(Z)-4-[4-bromo-6-(pyrrolidin-1-carbonyl)benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and (3-(N,N-dim ethylsulfamoyl)-4-methoxyphenyl)boronic acid (10.7 mg) instead of 3-fluorophenylboronic acid. (Yield: 8.3%)

$^1$H-NMR (MeOD, 400 MHz) δ 8.67 (s, 1H), 8.41 (d, 1H), 7.96 (s, 1H), 7.76 (s, 1H), 7.42 (d, 1H), 5.70 (d, 2H), 5.35 (dt, 1H), 4.05 (s, 3H), 3.68 (t, 2H), 3.63 (d, 2H), 3.58 (t, 2H), 2.89 (s, 6H), 2.08-1.94 (m, 4H)

Example 158. (Z)-(1-(4-amino-2-fluorobut-2-en-1-yl)-4-(3-((3,3-difluoropyrrolidin-1-yl)sulfonyl)phenyl)-1H-benzo[d][1,2,3]triazol-6-yl)(pyrrolidin-1-yl) methanone hydrochloride The titled compound (1.0 mg) was prepared in accordance with the same procedures as in Example 1, except for using tert-butyl N—[(Z)-4-[4-bromo-6-(pyrrolidin-1-carbonyl)benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and 3,3-difluoro-1-((3-(4,4,5,5-tetramethyl-1,3,2-dioxaborolan-2-yl)phenyl)sulfonyl)pyrrolidine (15.5 mg) instead of 3-fluorophenylboronic acid. (Yield: 4.1%)

$^1$H-NMR (MeOD, 400 MHz) δ 8.72 (s, 1H), 8.42 (d, 1H), 8.05 (s, 1H), 7.98 (d, 1H), 7.89-7.83 (m, 2H), 5.73 (d, 2H), 5.32 (dt, 1H), 3.73-3.55 (m, 10H), 2.41-2.34 (m, 2H), 2.30-1.93 (m, 4H)

Example 159. (Z)-(1-(4-amino-2-fluorobut-2-en-1-yl)-4-(3-(pyrrolidin-1-ylsulfonyl)phenyl)-1H-benzo[d][1,2,3]triazol-6-yl)(pyrrolidin-1-yl)methanone hydrochloride The titled compound (1.6 mg) was prepared in accordance with the same procedures as in Example 1, except for using tert-butyl N—[(Z)-4-[4-bromo-6-(pyrrolidin-1-carbonyl)benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and (3-pyrrolidin-1-ylsulfonylphenyl)boronic acid (10.6 mg) instead of 3-fluorophenylboronic acid. (Yield: 7.0%)

$^1$H-NMR (MeOD, 400 MHz) δ 8.69 (s, 1H), 8.37 (d, 1H), 8.04 (s, 1H), 7.95 (d, 1H), 7.83 (s, 1H), 7.80 (dd, 1H), 5.70 (d, 2H), 5.34 (dt, 1H), 3.69 (t, 2H), 3.59-3.56 (m, 4H), 3.35-3.30 (m, 4H), 2.09-1.92 (m, 4H), 1.90-1.77 (m, 4H)

Example 160. (Z)-3-(1-(4-amino-2-fluorobut-2-en-1-yl)-6-(pyrrolidin-1-carbonyl)-1H-benzo[d][1,2,3]triazol-4-yl)-4-methoxy-N-methylbenzenesulfonamide hydrochloride The titled compound (2.0 mg) was prepared in accordance with the same procedures as in Example 1, except for using tert-butyl N—[(Z)-4-[4-bromo-6-(pyrrolidin-1-carbonyl) benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and [2-methoxy-5-(methylsulfamoyl)phenyl]boronic acid (10.2 mg) instead of 3-fluorophenylboronic acid. (Yield: 9.0%)

$^1$H-NMR (MeOD, 400 MHz) δ 8.05 (s, 1H), 8.04 (s, 1H), 7.98 (d, 1H), 7.70 (s, 1H), 7.38 (d, 1H), 5.72 (d, 2H), 5.37 (dt, 1H), 3.90 (s, 3H), 3.69-3.63 (m, 4H), 3.57-3.54 (m, 2H), 2.59 (s, 3H), 2.07-1.95 (m, 4H)

Example 161. (Z)-(1-(4-amino-2-fluorobut-2-en-1-yl)-4-(3-(methylsulfonyl)phenyl)-1H-benzo[d][1,2,3]triazol-6-yl)(pyrrolidin-1-yl)methanone hydrochloride The titled compound (1.0 mg) was prepared in accordance with the same procedures as in Example 1, except for using tert-butyl N—[(Z)-4-[4-bromo-6-(pyrrolidin-1-carbonyl) benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and 3-(methanesulfonyl)phenylboronic acid (8.3 mg) instead of 3-fluorophenylboronic acid. (Yield: 4.9%)

$^1$H-NMR (MeOD, 400 MHz) δ 8.72 (s, 1H), 8.46 (d, 1H), 8.08 (d, 1H), 8.05 (s, 1H), 7.89-7.83 (m, 2H), 5.73 (d, 2H), 5.39 (dt, 1H), 3.69 (t, 2H), 3.58 (d, 2H), 3.54 (t, 2H), 2.08-1.93 (m, 4H)

Example 162. (Z)-3-(1-(4-amino-2-fluorobut-2-en-1-yl)-6-(pyrrolidin-1-carbonyl)-1H-benzo[d][1,2,3]triazol-4-yl)-N,N-diethyl-4-methoxybenzenesulfonamide hydrochloride The titled compound (2.2 mg) was prepared in accordance with the same procedures as in Example 1, except for using tert-butyl N—[(Z)-4-[4-bromo-6-(pyrrolidin-1-carbonyl) benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and (5-(N,N-diethylsulfamoyl)-2-methoxyphenyl)boronic acid (11.9 mg) instead of 3-fluorophenylboronic acid. (Yield: 9.1%)

$^1$H-NMR (MeOD, 400 MHz) δ 8.05 (s, 1H), 8.04 (s, 1H), 7.95 (d, 1H), 7.70 (s, 1H), 7.37 (d, 1H), 5.72 (d, 2H), 5.36 (dt, 1H), 3.90 (s. 3H), 3.69-3.56 (m, 6H), 3.35-3.32 (m, 4H), 2.07-1.95 (m, 4H), 1.15 (t, 6H)

Example 163. (Z)-5-(1-(4-amino-2-fluorobut-2-en-1-yl)-6-(pyrrolidin-1-carbonyl)-1H-benzo[d][1,2,3]triazol-4-yl)-N-cyclopropyl-2-methoxybenzenesulfonamide hydrochloride The titled compound (1.6 mg) was prepared in accordance with the same procedures as in Example 1, except for using tert-butyl N—[(Z)-4-[4-bromo-6-(pyrrolidin-1-carbonyl) benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and (3-(N-cyclopropylsulfamoyl)-4-methoxyphenyl)boronic acid (11.2 mg) instead of 3-fluorophenylboronic acid. (Yield: 6.8%)

$^1$H-NMR (MeOD, 400 MHz) δ 8.09 (s, 1H), 8.08 (s, 1H), 8.03 (d, 1H), 7.70 (s, 1H), 7.38 (d, 1H), 5.45 (d, 2H), 5.37 (dt, 1H), 3.90 (s, 3H), 3.68-3.56 (m, 6H), 2.29-2.27 (m, 1H), 2.24-1.93 (m, 4H), 0.59-0.56 (m, 4H)

Example 164. (Z)-5-(1-(4-amino-2-fluorobut-2-en-1-yl)-6-(pyrrolidin-1-carbonyl)-1H-benzo[d][1,2,3]triazol-4-yl)-N-isopropyl-2-methoxybenzenesulfonamide hydrochloride The titled compound (2.1 mg) was prepared in accordance with the same procedures as in Example 1, except for using tert-butyl N—[(Z)-4-[4-bromo-6-(pyrrolidin-1-carbonyl) benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and [3-(isopropylsulfamoyl)-4-methoxyphenyl] boronic acid (11.3 mg) instead of 3-fluorophenylboronic acid. (Yield: 8.9%)

$^1$H-NMR (MeOD, 400 MHz) δ 8.66 (s, 1H), 8.42 (d, 1H), 7.96 (s, 1H), 7.76 (s, 1H), 7.40 (d, 1H), 5.70 (d, 1H), 5.35 (dt, 1H), 4.07 (s, 3H), 3.69-3.66 (m, 2H), 3.61-3.53 (m, 4H), 3.45-3.31 (m, 1H), 2.07-1.94 (m, 4H), 1.09 (s, 6H)

Example 165. (Z)-3-(1-(4-amino-2-fluorobut-2-en-1-yl)-6-(pyrrolidin-1-carbonyl)-1H-benzo[d][1,2,3]triazol-4-yl)-N-cyclopropylbenzenesulfonamide hydrochloride The titled compound (2.6 mg) was prepared in accordance with the same procedures as in Example 1, except for using tert-butyl N—[(Z)-4-[4-bromo-6-(pyrrolidin-1-carbonyl) benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and (3-(N-cyclopropylsulfamoyl)phenylboronic acid (10 mg) instead of 3-fluorophenylboronic acid. (Yield: 11.7%)

$^1$H-NMR (MeOD, 400 MHz) δ 8.67 (s, 1H), 8.38 (d, 1H), 8.05 (s, 1H), 8.01 (d, 1H), 7.85-7.76 (m, 2H), 5.71 (d, 2H), 5.35 (dt, 1H), 3.71-3.60 (m, 2H), 3.59-3.54 (m, 4H), 2.30-2.27 (m, 1H), 2.02-1.93 (m, 4H), 0.60-0.57 (m, 4H)

Example 166. (Z)-3-(1-(4-amino-2-fluorobut-2-en-1-yl)-6-(pyrrolidin-1-carbonyl)-1H-benzo[d][1,2,3]triazol-4-yl)-N-methylbenzenesulfonamide hydrochloride The titled compound (2.6 mg) was prepared in accordance with the same procedures as in Example 1, except for using tert-butyl N—[(Z)-4-[4-bromo-6-(pyrrolidin-1-carbonyl) benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and 3-(N-methylsulfamoyl)phenylboronic acid (8.9 mg) instead of 3-fluorophenylboronic acid. (Yield: 11.7%)

$^1$H-NMR (MeOD, 400 MHz) δ 8.62 (s, 1H), 8.37 (d, 1H), 8.05 (s, 1H), 7.95 (d, 1H), 7.85 (s, 1H), 7.79 (dd, 1H), 5.73 (d, 2H), 5.44 (dt, 1H), 3.71-3.63 (m, 4H), 3.58 (t, 2H), 2.62 (s, 3H), 2.08-1.94 (m, 4H)

Example 167. (Z)-3-(1-(4-amino-2-fluorobut-2-en-1-yl)-6-(pyrrolidin-1-carbonyl)-1H-benzo[d][1,2,3]triazol-4-yl)-N,N-dimethylbenzenesulfonamide hydrochloride The titled compound (1.7 mg) was prepared in accordance with the same procedures as in Example 1, except for using tert-butyl N—[(Z)-4-[4-bromo-6-(pyrrolidin-1-carbonyl) benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and [3-(dimethylsulfamoyl)phenyl]boronic acid (9.5 mg) instead of 3-fluorophenylboronic acid. (Yield: 7.8%)

$^1$H-NMR (MeOD, 400 MHz) δ 8.62 (s, 1H), 8.39 (d, 1H), 8.05 (s, 1H), 7.91 (d, 1H), 7.85-7.81 (m, 2H), 5.70 (d, 2H), 5.42 (dt, 1H), 3.68 (t, 2H), 3.57-3.53 (m, 4H), 2.79 (s, 6H), 2.08-1.94 (m, 4H)

Example 168. (Z)-(1-(4-amino-2-fluorobut-2-en-1-yl)-4-(3-(ethylsulfonyl)phenyl)-1H-benzo[d][1,2,3]triazol-6-yl)(pyrrolidin-1-yl)methanone hydrochloride The titled compound (1.3 mg) was prepared in accordance with the same procedures as in Example 1, except for using tert-butyl N—[(Z)-4-[4-bromo-6-(pyrrolidin-1-carbonyl) benzotriazol-1-yl]-3-fluoro-but-2-enyl]carbamate prepared in Preparation 17 (20 mg) instead of tert-butyl N—[(Z)-4-(4-bromo-6-fluoro-benzimidazol-1-yl)-3-fluoro-but-2-enyl] carbamate; and (3-ethylsulfonylphenyl)boronic acid (8.9 mg) instead of 3-fluorophenylboronic acid. (Yield: 6.2%)

$^1$H-NMR (MeOD, 400 MHz) δ 8.70 (s, 1H), 8.46 (d, 1H), 8.06-8.03 (m, 2H), 7.88-7.83 (m, 2H), 5.76 (d, 2H), 5.38 (dt, 1H), 3.71-3.63 (m, 4H), 3.56 (t, 2H), 3.37 (q, 2H), 2.08-1.96 (m, 4H), 1.32 (t, 3H)

Example 169. (Z)-1-(3-(1-(4-amino-2-fluorobut-2-en-1-yl)-6-(trifluoromethyl)-1H-benzo[d]imidazol-4-yl)-4-fluorophenyl)ethan-1-one hydrochloride The titled compound (11.1 mg) was prepared in accordance with the same procedures as in Example 1, except for using tert-butyl N—[(Z)-4-[4-bromo-6-(trifluoromethyl) benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (5-acetyl-2-fluorophenyl)boronic acid (8.1 mg) instead of 3-fluorophenylboronic acid. (Yield: 56.3%)

$^1$H-NMR (MeOD, 400 MHz) δ 8.49 (s, 1H), 8.33 (d, 1H), 8.18-8.14 (m, 2H), 7.68 (s, 1H), 7.42 (t, 1H), 5.44-5.32 (m, 3H), 3.63 (d, 2H), 2.64 (s, 3H)

Example 170. (Z)-(3-(1-(4-amino-2-fluorobut-2-en-1-yl)-6-(trifluoromethyl)-1H-benzo[d]imidazol-4-yl)-4-fluorophenyl)methanol hydrochloride The titled compound (5.9 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (2-fluoro-5(hydroxymethyl)phenyl)boronic acid (7.5 mg) instead of 3-fluorophenylboronic acid. (Yield: 30.8%)

$^1$H-NMR (MeOD, 400 MHz) δ 8.46 (s, 1H), 8.08 (s, 1H), 7.66-7.62 (m, 2H), 7.48 (d, 1H), 7.26 (t, 1H), 5.39-5.27 (m, 3H), 4.68 (s, 2H), 3.60 (d, 2H)

Example 171. (Z)-(3-(1-(4-amino-2-fluorobut-2-en-1-yl)-6-(trifluoromethyl)-1H-benzo[d]imidazol-4-yl)-2-chlorophenyl)methanol hydrochloride The titled compound (3.1 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (2-chloro-3-(hydroxymethyl)phenyl)boronic acid (8.3 mg) instead of 3-fluorophenylboronic acid. (Yield: 15.5%)

$^1$H-NMR (MeOD, 400 MHz) δ 8.40 (s, 1H), 8.09 (s, 1H), 7.69 (t, 1H), 7.51-7.46 (m, 2H), 7.37 (d, 1H), 5.49-5.31 (m, 3H), 3.61 (d, 2H)

Example 172. (Z)-3-fluoro-4-(4-(pyridin-3-yl)-6-(trifluoromethyl)-1H-benzo[d]imidazol-1-yl)but-2-en-1-amine hydrochloride The titled compound (4.1 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and pyridin-3-ylboronic acid (5.4 mg) instead of 3-fluorophenylboronic acid. (Yield: 23.9%)

$^1$H-NMR (MeOD, 400 MHz) δ 9.15 (s, 1H), 8.62 (d, 1H), 8.49 (s, 1H), 8.40 (d, 1H), 8.10 (s, 1H), 7.79 (s, 1H), 7.62 (t, 1H), 5.42-5.31 (m, 3H), 3.66 (d, 2H)

Example 173. (Z)-3-fluoro-4-(4-(5-fluoropyridin-3-yl)-6-(trifluoromethyl)-1H-benzo[d]imidazol-1-yl)but-2-en-1-amine hydrochloride The titled compound (5.7 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (5-fluoropyridin-3-yl)boronic acid (6.2 mg) instead of 3-fluorophenylboronic acid. (Yield: 31.8%)

$^1$H-NMR (MeOD, 400 MHz) δ 9.03 (s, 1H), 8.55 (s, 1H), 8.51 (s, 1H), 8.33 (s, 1H), 8.30 (s, 1H), 8.13 (s, 1H), 7.86 (s, 1H), 5.43-5.33 (m, 3H), 3.67 (d, 2H)

Example 174. (Z)-4-(4-(5-chloropyridin-3-yl)-6-(trifluoromethyl)-1H-benzo[d]imidazol-1-yl)-3-fluoro-but-2-en-1-amine hydrochloride iii The titled compound (7.2 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (5-chloropyridin-3-yl)boronic acid (7.0 mg) instead of 3-fluorophenylboronic acid. (Yield: 38.7%)

$^1$H-NMR (MeOD, 400 MHz) δ 9.26 (s, 1H), 8.83 (s, 1H), 8.82 (s, 1H), 8.78 (s, 1H), 8.25 (s, 1H), 7.98 (s, 1H), 5.53-5.41 (m, 3H), 3.68 (d, 2H)

Example 175. (Z)-3-fluoro-4-(4-(pyrimidin-5-yl)-6-(trifluoromethyl)-1H-benzo[d]imidazol-1-yl)but-2-en-1-amine hydrochloride The titled compound (1.0 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and pyrimidin-5-ylboronic acid (5.5 mg) instead of 3-fluorophenylboronic acid. (Yield: 5.8%)

$^1$H-NMR (MeOD, 400 MHz) δ 9.43 (s, 2H), 9.22 (s, 1H), 8.51 (s, 1H), 8.15 (s, 1H), 7.89 (s, 1H), 5.39-5.22 (m, 3H), 3.50 (d, 2H)

Example 176. (Z)-3-fluoro-4-(4-(1-methyl-1H-pyrazol-5-yl)-6-(trifluoromethyl)-1H-benzo[d]imidazol-1-yl) but-2-en-1-yl-amine hydrochloride The titled compound (3.9 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (1-methyl-1H-pyrazol-5-yl)boronic acid (5.6 mg) instead of 3-fluorophenylboronic acid. (Yield: 22.7%)

$^1$H-NMR (MeOD, 400 MHz) δ 8.49 (s, 1H), 8.16 (s, 1H), 7.63 (d, 1H), 7.61 (d, 1H), 6.55 (s, 1H), 5.43-5.31 (m, 3H), 3.84 (s, 3H), 3.57 (d, 2H)

Example 177. (Z)-4-(4-(1-ethyl-1H-pyrazol-5-yl)-6-(trifluoromethyl)-1H-benzo[d]imidazol-1-yl]-3-fluoro-but-2-en-1-amine hydrochloride The titled compound (6.6 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (1-ethyl-1H-pyrazol-5-yl)boronic acid (6.2 mg) instead of 3-fluorophenylboronic acid. (Yield: 36.8%)

$^1$H-NMR (MeOD, 400 MHz) δ 8.80 (s, 1H), 8.75 (s, 1H), 7.73 (d, 1H), 7.66 (d, 1H), 6.59 (s, 1H), 5.54-5.41 (m, 3H), 4.18 (q, 2H), 3.68 (d, 2H), 1.29 (t, 3H)

Example 178. (Z)-3-fluoro-4-(4-(1-isopropyl-1H-pyrazol-5-yl)-6-(trifluoromethyl)-1H-benzo[d]imidazol-1-yl)but-2-en-1-amine hydrochloride The titled compound (6.1 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (1-isopropyl-1H-pyrazol-5-yl)boronic acid (6.8 mg) instead of 3-fluorophenylboronic acid. (Yield: 33.0%)

$^1$H-NMR (MeOD, 400 MHz) δ 8.96 (s, 1H), 8.33 (s, 1H), 7.79 (s, 1H), 7.72 (s, 1H), 6.57 (s, 1H), 5.59-5.44 (m, 3H), 4.44-4.41 (m, 1H), 3.68 (d, 2H), 1.46 (s, 3H), 1.44 (s, 3H)

Example 179. (Z)-3-fluoro-4-(4-[1-methyl-3-(trifluoromethyl)-1H-pyrazol-5-yl]-6-(trifluoromethyl)-1H-benzo[d]imidazol-1-yl)but-2-en-1-amine hydrochloride The titled compound (4.8 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (1-methyl-3-(trifluoromethyl)-1H-pyrazol-5-yl)boronic acid (8.6 mg) instead of 3-fluorophenylboronic acid. (Yield: 23.7%)

$^1$H-NMR (MeOD, 400 MHz) δ 8.89 (s, 1H), 8.33 (s, 1H), 7.80 (s, 1H), 6.91 (s, 1H), 5.57-5.43 (m, 3H), 3.89 (s, 3H), 3.67 (d, 2H)

Example 180. (Z)-2-(4-(1-(4-amino-2-fluorobut-2-en-1-yl)-6-(trifluoromethyl)-1H-benzo[d]imidazol-4-yl)-1H-pyrazol-1-yl)ethan-1-ol hydrochloride The titled compound (6.0 mg) was prepared in accordance with the same procedures as in Example 1, except for using tert-butyl N—[(Z)-4-[4-bromo-6-(trifluoromethyl)benzimidazol-1-yl]-3-fluoro-but-2-enyl]carbamate prepared in Preparation 2 (20 mg) instead of tert-butyl N—[(Z)-4-(4-bromo-6-fluoro-benzimidazol-1-yl)-3-fluoro-but-2-enyl] carbamate; and (1-(2-hydroxyethyl)-1H-pyrazol-4-yl)boronic acid (6.9 mg) instead of 3-fluorophenylboronic acid. (Yield: 32.4%)

$^1$H-NMR (MeOD, 400 MHz) δ 8.56 (s, 1H), 8.43 (s, 1H), 8.29 (s, 1H), 7.84 (s, 1H), 7.78 (s, 1H), 5.37-5.28 (m, 3H), 4.34 (t, 2H), 3.97 (t, 2H), 3.62 (d, 2H), 2.76 (s, 6H)

Example 181. (Z)-1-(4-amino-2-fluorobut-2-en-1-yl)-4-(3-(pyrrolidin-1-ylsulfonyl)phenyl)-1H-benzo[d]imidazol-6-carbonitrile hydrochloride The titled compound (2.9 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and (3-(pyrrolidin-1-ylsulfonyl)phenyl)boronic acid (12.5 mg) instead of 3-fluorophenylboronic acid. (Yield: 12.4%)

$^1$H-NMR (MeOD, 400 MHz) δ 8.52-8.50 (m, 2H), 8.22-8.16 (m, 2H), 7.92 (d, 1H), 7.87 (s, 1H), 7.74 (t, 1H), 5.41-5.22 (m, 3H), 3.65 (d, 2H), 3.34-3.32 (m, 4H), 1.81-1.75 (m, 4H)

Example 182. (Z)-3-(1-(4-amino-2-fluorobut-2-en-1-yl)-6-cyano-1H-benzo[d]imidazol-4-yl)-N,N-dimethylbenzenesulfonamide hydrochloride The titled compound (10.7 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl] carbamate; and (3-(N,N-dimethylsulfamoyl)phenyl)boronic acid (11.2 mg) instead of 3-fluorophenylboronic acid. (Yield: 48.7%)

$^1$H-NMR (MeOD, 400 MHz) δ 8.52 (s, 1H), 8.44 (s, 1H), 8.22 (d, 1H), 8.18 (s, 1H), 7.88-7.85 (m, 2H), 7.78 (t, 1H), 5.46-5.34 (m, 3H), 3.67 (d, 2H), 2.77 (s, 6H)

Example 183. (Z)-3-(1-(4-amino-2-fluorobut-2-en-1-yl)-6-cyano-1H-benzo[d]imidazol-4-yl)-4-methoxy-N-methylbenzenesulfonamide hydrochloride The titled compound (6.8 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and (2-methoxy-5-(N-methylsulfamoyl)phenyl)boronic acid (12.0 mg) instead of 3-fluorophenylboronic acid. (Yield: 29.9%)

$^1$H-NMR (MeOD, 400 MHz) δ 8.50 (s, 1H), 8.17 (s, 1H), 7.94 (d, 1H), 7.89 (s, 1H), 7.67 (s, 1H), 7.34 (d, 1H), 5.49-5.37 (m, 3H), 3.87 (s, 3H), 3.67 (d, 2H), 2.58 (s, 3H)

Example 184. (Z)-4-(5-acetyl-2-fluorophenyl)-1-(4-amino-2-fluorobut-2-en-1-yl)-1H-benzo[d]imidazol-6-carbonitrile hydrochloride The titled compound (13.2 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl] carbamate; and (5-acetyl-2-fluorophenyl)boronic acid (8.9 mg) instead of 3-fluorophenylboronic acid. (Yield: 67.1%)

$^1$H-NMR (MeOD, 400 MHz) δ 9.25 (s, 1H), 8.45 (d, 1H), 8.25 (d, 1H), 7.89 (d, 1H), 7.69 (s, 1H), 7.47-7.32 (m, 1H), 5.64-5.46 (m, 3H), 3.72 (d, 2H), 2.66 (s, 3H)

Example 185. (Z)-1-(4-amino-2-fluorobut-2-en-1-yl)-4-(2-fluoro-5-(hydroxymethyl)phenyl)-1H-benzo[d]imidazol-6-carbonitrile hydrochloride The titled compound (4.5 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and (2-fluoro-5(hydroxymethyl)phenyl)boronic acid (8.3 mg) instead of 3-fluorophenylboronic acid. (Yield: 23.6%)

$^1$H-NMR (MeOD, 400 MHz) δ 8.85 (s, 1H), 8.17 (s, 1H), 7.79 (d, 1H), 7.64-7.53 (m, 2H), 7.34-7.31 (m, 1H), 5.56-5.39 (m, 3H), 4.68 (s, 2H), 3.68 (d, 2H)

Example 186. (Z)-1-(4-amino-2-fluoro-2-but-1-yl)-4-(2-chloro-3-(hydroxymethyl)phenyl)-1H-benzo[d]imidazol-6-carbonitrile hydrochloride The titled compound (6.5 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and (2-chloro-3-(hydroxymethyl)phenyl)boronic acid (9.1 mg) instead of 3-fluorophenylboronic acid. (Yield: 32.7%)

$^1$H-NMR (MeOD, 400 MHz) δ 8.70 (s, 1H), 8.27 (s, 1H), 7.72 (d, 1H), 7.64 (s, 1H), 7.49 (t, 1H), 7.37 (d, 1H), 5.40-5.36 (m, 3H), 4.61 (s, 2H), 3.68 (d, 2H)

Example 187. (Z)-1-(4-amino-2-fluorobut-2-en-1-yl)-4-(pyridin-3-yl)-1H-benzo[d]imidazol-6-carbonitrile hydrochloride The titled compound (1.0 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and pyridin-3-ylboronic acid (6.0 mg) instead of 3-fluorophenylboronic acid. (Yield: 6.0%)

$^1$H-NMR (MeOD, 400 MHz) δ 9.73 (s, 1H), 9.28 (d, 1H), 8.92 (d, 1H), 8.63 (s, 1H), 8.33 (s, 1H), 8.24 (d, 1H), 8.17 (s, 1H), 5.53-5.40 (m, 3H), 3.68 (d, 2H)

Example 188. (Z)-1-(4-amino-2-fluorobut-2-en-1-yl)-4-(5-fluoropyridin-3-yl)-1H-benzo[d]imidazol-6-carbonitrile hydrochloride The titled compound (5.7 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and (5-fluoropyridin-3-yl)boronic acid (6.9 mg) instead of 3-fluorophenylboronic acid. (Yield: 32.2%)

$^1$H-NMR (MeOD, 400 MHz) δ 9.56 (s, 1H), 9.11 (d, 1H), 9.05 (d, 1H), 8.87 (s, 1H), 8.41 (s, 1H), 8.21 (s, 1H), 5.61-5.41 (m, 3H), 3.69 (d, 2H)

Example 189. (Z)-1-(4-amino-2-fluorobut-2-en-1-yl)-4-(5-chloropyridin-3-yl)-1H-benzo[d]imidazol-6-carbonitrile hydrochloride The titled compound (1.4 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and (5-chloropyridin-3-yl)boronic acid (7.7 mg) instead of 3-fluorophenylboronic acid. (Yield: 7.6%)

$^1$H-NMR (MeOD, 400 MHz) δ 9.49 (s, 1H), 9.14 (s, 1H), 9.00 (s, 1H), 8.81 (s, 1H), 8.37 (s, 1H), 8.15 (s, 1H), 5.58-5.43 (m, 3H), 3.69 (d, 2H)

Example 190. (Z)-1-(4-amino-2-fluorobut-2-en-1-yl)-4-(pyrimidin-5-yl)-1H-benzo[d]imidazol-6-carbonitrile hydrochloride The titled compound (1.0 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and pyrimidin-5-ylboronic acid (6.1 mg) instead of 3-fluorophenylboronic acid. (Yield: 5.9%)

$^1$H-NMR (MeOD, 400 MHz) δ 9.48 (s, 2H), 9.27 (s, 1H), 8.66 (s, 1H), 8.28 (s, 1H), 8.04 (s, 1H), 5.49-5.35 (m, 3H), 3.68 (d, 2H)

Example 191. (Z)-1-(4-amino-2-fluorobut-2-en-1-yl)-4-(1-methyl-1H-pyrazol-5-yl)-1H-benzo[d]imidazol-6-carbonitrile hydrochloride The titled compound (1.6 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate;

and (1-methyl-1H-pyrazol-5-yl)boronic acid (6.2 mg) instead of 3-fluorophenylboronic acid. (Yield: 9.4%)

$^1$H-NMR (MeOD, 400 MHz) δ 8.90 (s, 1H), 8.38 (s, 1H), 7.86 (s, 1H), 7.79 (s, 1H), 6.68 (s, 1H), 5.58-5.43 (m, 3H), 3.89 (s, 3H), 3.69 (d, 2H)

Example 192. (Z)-1-(4-amino-2-fluorobut-2-en-1-yl)-4-(1-ethyl-1H-pyrazol-5-yl)-1H-benzo[d]imidazol-6-carbonitrile hydrochloride The titled compound (6.3 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and (1-ethyl-1H-pyrazol-5-yl)boronic acid (6.9 mg) instead of 3-fluorophenylboronic acid. (Yield: 35.2%)

$^1$H-NMR (MeOD, 400 MHz) δ 8.94 (s, 1H), 8.41 (s, 1H), 7.83 (s, 1H), 7.79 (s, 1H), 6.62 (s, 1H), 5.61-5.41 (m, 3H), 4.20 (q, 2H), 3.69 (d, 2H), 1.31 (t, 3H)

Example 193. (Z)-1-(4-amino-2-fluorobut-2-en-1-yl)-4-(1-methyl-3-(trifluoromethyl)-1H-pyrazol-5-yl)-1H-benzo[d]imidazol-6-carbonitrile hydrochloride The titled compound (7.4 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and (1-methyl-3-(trifluoromethyl)-1H-pyrazol-5-yl)boronic acid (9.6 mg) instead of 3-fluorophenylboronic acid. (Yield: 36.0%)

$^1$H-NMR (MeOD, 400 MHz) δ 8.68 (s, 1H), 8.35 (s, 1H), 7.81 (s, 1H), 6.89 (s, 1H), 5.52-5.36 (m, 3H), 3.93 (s, 3H), 3.68 (d, 2H)

Example 194. (Z)-1-(4-amino-2-fluorobut-2-en-1-yl)-4-(1,3-dimethyl-1H-pyrazol-5-yl)-1H-benzo[d]imidazol-6-carbonitrile hydrochloride The titled compound (4.3 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and (1,3-dimethyl-1H-pyrazol-5-yl)boronic acid (6.9 mg) instead of 3-fluorophenylboronic acid. (Yield: 24.1%)

$^1$H-NMR (MeOD, 400 MHz) δ 8.71 (s, 1H), 8.35 (s, 1H), 7.81 (s, 1H), 6.57 (s, 1H), 5.55-5.40 (m, 3H), 3.85 (s, 3H), 3.68 (d, 2H), 2.42 (s, 3H)

Example 195. (Z)—1-(4-amino-2-fluorobut-2-en-1-yl)-4-(1-(2-hydroxyethyl)-1H-pyrazol-3-yl)-1H-benzo[d]imidazol-6-carbonitrile hydrochloride The titled compound (5.5 mg) was prepared in accordance with the same procedures as in Example 1, except for using tert-butyl (Z)-(4-(4-bromo-6-cyano-1H-benzo[d]imidazol-1-yl)-3-fluorobut-2-en-1-yl)carbamate prepared in Preparation 18 (20 mg) instead of tert-butyl N—[(Z)-4-(4-bromo-6-fluoro-benzimidazol-1-yl)-3-fluoro-but-2-enyl]carbamate; and (1-(2-hydroxyethyl)-1H-pyrazol-3-yl)boronic acid (7.7 mg) instead of 3-fluorophenylboronic acid. (Yield: 29.5%)

$^1$H-NMR (MeOD, 400 MHz) δ 8.81 (s, 1H), 8.56 (s, 1H), 8.29 (s, 1H), 8.05 (s, 1H), 7.93 (s, 1H), 5.54-5.34 (m, 3H), 4.36 (t, 2H), 3.97 (t, 2H), 3.68 (d, 2H)

Example 196. (Z)-3-(1-(4-amino-2-fluorobut-2-en-1-yl)-6-(trifluoromethyl)-1H-benzo[d][1,2,3]triazol-4-yl)—N,N-dimethylbenzenesulfonamide hydrochloride The titled compound (5.8 mg) was prepared in accordance with the same procedures as in Example 1, except for using tert-butyl (Z)-(4-(4-bromo-6-(trifluoromethyl)-1H-benzo[d][1,2,3]triazol-1-yl)-3-fluorobut-2-en-1-yl)carbamate prepared in Preparation 19 (20 mg) instead of tert-butyl N—[(Z)-4-(4-bromo-6-fluoro-benzimidazol-1-yl)-3-fluoro-but-2-enyl]carbamate; and (3-(N,N-dimethylsulfamoyl)phenyl)boronic acid (10.1 mg) instead of 3-fluorophenylboronic acid. (Yield: 26.6%)

$^1$H-NMR (MeOD, 400 MHz) δ 8.65 (s, 1H), 8.39-8.35 (m, 2H), 7.96 (d, 1H), 7.94 (d, 1H), 7.85 (t, 1H), 5.80 (d, 2H), 5.49-5.35 (m, 1H), 3.68 (d, 2H), 2.80 (s, 6H)

Example 197. (Z)-1-(3-(1-(4-amino-2-fluorobut-2-en-1-yl)-6-(trifluoromethyl)-1H-benzo[d][1,2,3]triazol-4-yl)-4-fluorophenyl)ethan-1-one hydrochloride The titled compound (7.3 mg) was prepared in accordance with the same procedures as in Example 1, except for using tert-butyl (Z)-(4-(4-bromo-6-(trifluoromethyl)-1H-benzo[d][1,2,3]triazol-1-yl)-3-fluorobut-2-en-1-yl)carbamate prepared in Preparation 19 (20 mg) instead of tert-butyl N—[(Z)-4-(4-bromo-6-fluoro-benzimidazol-1-yl)-3-fluoro-but-2-enyl]carbamate; and (5-acetyl-2-fluorophenyl)boronic acid (8.0 mg) instead of 3-fluorophenylboronic acid. (Yield: 37.1%)

$^1$H-NMR (MeOD, 400 MHz) δ 8.52 (d, 2H), 8.40 (s, 1H), 8.23 (d, 1H), 7.87 (s, 1H), 7.49 (t, 1H), 5.80 (d, 2H), 5.51-5.41 (m, 1H), 3.69 (d, 2H), 2.68 (s, 3H)

Example 198. (Z)-(3-(1-(4-amino-2-fluorobut-2-en-1-yl)-6-(trifluoromethyl)-1H-benzo[d][1,2,3]triazol-4-yl)-4-fluorophenyl)methanol hydrochloride The titled compound (5.2 mg) was prepared in accordance with the same procedures as in Example 1, except for using tert-butyl (Z)-(4-(4-bromo-6-(trifluoromethyl)-1H-benzo[d][1,2,3]triazol-1-yl)-3-fluorobut-2-en-1-yl)carbamate prepared in Preparation 19 (20 mg) instead of tert-butyl N—[(Z)-4-(4-bromo-6-fluoro-benzimidazol-1-yl)-3-fluoro-but-2-enyl]carbamate; and (2-fluoro-5(hydroxymethyl)phenyl)boronic acid (7.5 mg) instead of 3-fluorophenylboronic acid. (Yield: 27.1%)

$^1$H-NMR (MeOD, 400 MHz) δ 8.34 (s, 1H), 7.83-7.80 (m, 2H), 7.56 (d, 1H), 7.32 (t, 1H), 5.78 (d, 2H), 5.50-5.40 (m, 1H), 4.71 (s, 2H), 3.68 (d, 2H)

Example 199. (Z)-(3-(1-(4-amino-2-fluoro-2-en-1-yl)-6-(trifluoromethyl)-1H-benzo[d][1,2,3]triazol-4-yl)-2-chlorophenyl)methanol hydrochloride The titled compound (8.4 mg) was prepared in accordance with the same procedures as in Example 1, except for using tert-butyl (Z)-(4-(4-bromo-6-(trifluoromethyl)-1H-benzo[d][1,2,3]triazol-1-yl)-3-fluorobut-2-en-1-yl)carbamate prepared in Preparation 19 (20 mg) instead of tert-butyl N—[(Z)-4-(4-bromo-6-fluoro-benzimidazol-1-yl)-3-fluoro-but-2-enyl]carbamate; and (2-chloro-3-(hydroxymethyl)phenyl)boronic acid (8.2 mg) instead of 3-fluorophenylboronic acid. (Yield: 42.2%)

$^1$H-NMR (MeOD, 400 MHz) δ 8.37 (s, 1H), 7.76 (d, 1H), 7.67 (s, 1H), 7.51 (t, 1H), 7.46 (t, 1H), 5.78 (d, 2H), 5.51-5.42 (m, 1H), 4.69 (s, 2H), 3.69 (d, 2H)

Example 200. (Z)-3-fluoro-4-(4-(5-fluoropyridin-3-yl)-6-(trifluoromethyl)-1H-benzo[d][1,2,3]triazol-1-yl)but-2-en-1-amine hydrochloride The titled compound (7.6 mg) was prepared in accordance with the same procedures as in Example 1, except for using tert-butyl (Z)-(4-(4-bromo-6-(trifluoromethyl)-1H-benzo[d][1,2,3]triazol-1-yl)-3-fluorobut-2-en-1-yl)carbamate prepared in Preparation 19 (20 mg) instead of tert-butyl N—[(Z)-4-(4-bromo-6-fluoro-benzimidazol-1-yl)-3-fluoro-but-2-enyl]carbamate; and (5-fluoropyridin-3-yl)boronic acid (6.2 mg) instead of 3-fluorophenylboronic acid. (Yield: 42.5%)

$^1$H-NMR (MeOD, 400 MHz) δ 9.55 (s, 1H), 9.03 (d, 1H), 8.93 (s, 1H), 8.49 (s, 1H), 8.22 (s, 1H), 5.83 (d, 2H), 5.56-5.46 (m, 1H), 3.69 (d, 2H)

Example 201. (Z)-4-(4-(5-chloropyridin-3-yl)-6-(trifluoromethyl)-1H-benzo[d][1,2,3]triazol-1-yl)-3-fluorobut-2-en-1-amine hydrochloride The titled compound (4.9 mg) was prepared in accordance with the same procedures as in Example 1, except for using tert-butyl (Z)-(4-(4-bromo-6-(trifluoromethyl)-1H-benzo[d][1,2,3]triazol-1-yl)-3-fluorobut-2-en-1-yl)carbamate prepared in Preparation 19 (20 mg) instead of tert-butyl N—[(Z)-4-(4-bromo-6-fluoro-benzimidazol-1-yl)-3-fluoro-but-2-enyl]carbamate; and (5-chloropyridin-3-yl)boronic acid (7.0 mg) instead of 3-fluorophenylboronic acid. (Yield: 26.3%)

$^1$H-NMR (MeOD, 400 MHz) δ 9.56 (s, 1H), 9.16 (s, 1H), 8.97 (s, 1H), 8.49 (s, 1H), 8.19 (s, 1H), 5.83 (d, 2H), 5.58-5.46 (m, 1H), 3.69 (d, 2H)

Example 202. (Z)-3-fluoro-4-(4-(pyrimidin-5-yl)-6-(trifluoromethyl)-1H-benzo[d][1,2,3]triazol-1-yl)but-2-en-1-amine hydrochloride The titled compound (5.3 mg) was prepared in accordance with the same procedures as in Example 1, except for using tert-butyl (Z)-(4-(4-bromo-6-(trifluoromethyl)-1H-benzo[d][1,2,3]triazol-1-yl)-3-fluorobut-2-en-1-yl)carbamate prepared in Preparation 19 (20 mg) instead of tert-butyl N—[(Z)-4-(4-bromo-6-fluoro-benzimidazol-1-yl)-3-fluoro-but-2-enyl]carbamate; and pyrimidin-5-ylboronic acid (5.5 mg) instead of 3-fluorophenylboronic acid. (Yield: 30.9%)

$^1$H-NMR (MeOD, 400 MHz) δ 9.63 (s, 2H), 9.32 (s, 1H), 8.43 (s, 1H), 8.19 (s, 1H), 5.82 (d, 2H), 5.53-5.45 (m, 1H), 3.68 (d, 2H)

Example 203. (Z)-4-(4-(1-ethyl-1H-pyrazol-5-yl)-6-(trifluoromethyl)-1H-benzo[d][1,2,3]triazol-1-yl)-3-fluorobut-2-en-1-amine hydrochloride The titled compound (8.0 mg) was prepared in accordance with the same procedures as in Example 1, except for using tert-butyl (Z)-(4-(4-bromo-6-(trifluoromethyl)-1H-benzo[d][1,2,3]triazol-1-yl)-3-fluorobut-2-en-1-yl)carbamate prepared in Preparation 19 (20 mg) instead of tert-butyl N—[(Z)-4-(4-bromo-6-fluoro-benzimidazol-1-yl)-3-fluoro-but-2-enyl]carbamate; and (1-ethyl-1H-pyrazol-5-yl)boronic acid (6.2 mg) instead of 3-fluorophenylboronic acid. (Yield: 44.8%)

$^1$H-NMR (MeOD, 400 MHz) δ 8.46 (s, 1H), 7.81 (d, 1H), 7.79 (d, 1H), 6.73 (s, 1H), 5.82 (d, 2H), 5.56-5.49 (m, 1H), 4.27 (q, 2H), 3.69 (d, 2H), 1.37 (t, 3H)

Example 204. (Z)-4-[4-(1,3-dimethyl-1H-pyrazol-5-yl)-6-(trifluoromethyl)-1H-benzo[d][1,2,3]triazol-1-yl]-3-fluorobut-2-en-1-amine hydrochloride The titled compound (1.0 mg) was prepared in accordance with the same procedures as in Example 1, except for using tert-butyl (Z)-(4-(4-bromo-6-(trifluoromethyl)-1H-benzo[d][1,2,3]triazol-1-yl)-3-fluorobut-2-en-1-yl)carbamate prepared in Preparation 19 (20 mg) instead of tert-butyl N—[(Z)-4-(4-bromo-6-fluoro-benzimidazol-1-yl)-3-fluoro-but-2-enyl]carbamate; and (1,3-dimethyl-1H-pyrazol-5-yl)boronic acid (6.2 mg) instead of 3-fluorophenylboronic acid. (Yield: 5.6%)

$^1$H-NMR (MeOD, 400 MHz) δ 8.42 (s, 1H), 7.81 (s, 1H), 6.58 (s, 1H), 5.80 (d, 2H), 5.51-5.42 (m, 1H), 3.88 (s, 3H), 3.68 (d, 2H), 2.37 (s, 3H)

Example 205. (Z)-2-(4-(1-(4-amino-2-fluorobut-2-en-1-yl)-6-(trifluoromethyl)-1H-benzo[d][1,2,3]triazol-4-yl]-1H-pyrazol-1-yl)ethan-1-ol hydrochloride The titled compound (1.0 mg) was prepared in accordance with the same procedures as in Example 1, except for using tert-butyl (Z)-(4-(4-bromo-6-(trifluoromethyl)-1H-benzo[d][1,2,3]triazol-1-yl)-3-fluorobut-2-en-1-yl)carbamate prepared in Preparation 19 (20 mg) instead of tert-butyl N—[(Z)-4-(4-bromo-6-fluoro-benzimidazol-1-yl)-3-fluoro-but-2-enyl]carbamate; and (1-(2-hydroxyethyl)-1H-pyrazol-4-yl)boronic acid (6.9 mg) instead of 3-fluorophenylboronic acid. (Yield: 5.4%)

$^1$H-NMR (MeOD, 400 MHz) δ 8.79 (s, 1H), 8.50 (s, 1H), 8.11 (s, 1H), 7.92 (s, 1H), 5.75 (d, 2H), 5.45-5.36 (m, 1H), 4.38 (t, 2H), 3.90 (t, 2H), 3.69 (d, 2H)

Example 206. (Z)-1-(4-amino-2-fluorobut-2-en-1-yl)-4-[2-fluoro-5-(hydroxymethyl)phenyl]-1H-benzo[d][1,2,3]triazol-6-carbonitrile hydrochloride The titled compound (1.0 mg) was prepared in accordance with the same procedures as in Example 1, except for using tert-butyl (Z)-(4-(4-bromo-6-cyano-1H-benzo[d][1,2,3]triazol-1-yl)-3-fluorobut-2-en-1-yl)carbamate prepared in Preparation 20 (20 mg) instead of tert-butyl N—[(Z)-4-(4-bromo-6-fluoro-benzimidazol-1-yl)-3-fluoro-but-2-enyl]carbamate; and (2-fluoro-5(hydroxymethyl)phenyl)boronic acid (8.3 mg) instead of 3-fluorophenylboronic acid. (Yield: 5.2%)

$^1$H-NMR (MeOD, 400 MHz) δ 8.44 (s, 1H), 7.85-7.79 (m, 2H), 7.56 (d, 1H), 7.32 (t, 1H), 5.76 (d, 2H), 5.51-5.41 (m, 1H), 4.70 (s, 2H), 3.68 (d, 2H)

Example 207. (Z)-1-(4-amino-2-fluorobut-2-en-1-yl)-4-[2-chloro-3-(hydroxymethyl)phenyl-1H-benzo[d][1,2,3]triazol-6-carbonitrile hydrochloride The titled compound (2.7 mg) was prepared in accordance with the same procedures as in Example 1, except for using tert-butyl (Z)-(4-(4-bromo-6-cyano-1H-benzo[d][1,2,3]triazol-1-yl)-3-fluorobut-2-en-1-yl)carbamate prepared in Preparation 20 (20 mg) instead of tert-butyl N—[(Z)-4-(4-bromo-6-fluoro-benzimidazol-1-yl)-3-fluoro-but-2-enyl] carbamate; and (2-chloro-3-(hydroxymethyl)phenyl)boronic acid (9.1 mg) instead of 3-fluorophenylboronic acid. (Yield: 13.6%)

$^1$H-NMR (MeOD, 400 MHz) δ 8.44 (s, 1H), 7.77-7.69 (m, 2H), 7.54-7.51 (m, 1H), 7.45 (d, 1H), 5.76 (d, 2H), 5.53-5.45 (m, 1H), 4.79 (d, 2H), 3.70 (d, 2H)

Example 208. (Z)-1-(4-amino-2-fluorobut-2-en-1-yl)-4-(5-fluoropyridin-3-yl)-1H-benzo[d][1,2,3]triazol-6-carbonitrile hydrochloride The titled compound (2.5 mg) was prepared in accordance with the same procedures as in Example 1, except for using tert-butyl (Z)-(4-(4-bromo-6-cyano-1H-benzo[d][1,2,3]triazol-1-yl)-3-fluorobut-2-en-1-yl)carbamate prepared in Preparation 20 (20 mg) instead of tert-butyl N—[(Z)-4-(4-bromo-6-fluoro-benzimidazol-1-yl)-3-fluoro-but-2-enyl] carbamate; and (5-fluoropyridin-3-yl)boronic acid (6.9 mg) instead of 3-fluorophenylboronic acid. (Yield: 14.1%)

$^1$H-NMR (MeOD, 400 MHz) δ 9.15 (s, 1H), 8.81 (s, 1H), 8.77 (s, 1H), 8.55 (s, 1H), 8.21 (s, 1H), 5.80 (d, 2H), 5.58-5.48 (m, 1H), 3.70 (d, 2H)

Example 209. (Z)-1-(4-amino-2-fluorobut-2-en-1-yl)-4-(5-chloropyridin-3-yl)-1H-benzo[d][1,2,3]triazol-6-carbonitrile hydrochloride The titled compound (1.2 mg) was prepared in accordance with the same procedures as in Example 1, except for using tert-butyl (Z)-(4-(4-bromo-6-cyano-1H-benzo[d][1,2,3]triazol-1-yl)-3-fluorobut-2-en-1-yl)carbamate prepared in Preparation 20 (20 mg) instead of tert-butyl N—[(Z)-4-(4-bromo-6-fluoro-benzimidazol-1-yl)-3-fluoro-but-2-enyl] carbamate; and (5-chloropyridin-3-yl)boronic acid (7.7 mg) instead of 3-fluorophenylboronic acid. (Yield: 6.5%)

$^1$H-NMR (MeOD, 400 MHz) δ 9.43 (s, 1H), 8.94 (s, 1H), 8.83 (s, 1H), 8.51 (s, 1H), 8.19 (s, 1H), 5.79 (d, 2H), 5.56-5.46 (m, 1H), 3.69 (d, 2H)

Example 210. (Z)-1-(4-amino-2-fluorobut-2-en-1-yl)-4-(pyrimidin-5-yl)-1H-benzo[d][1,2,3]triazol-6-carbo nitrile hydrochloride The titled compound (2.8 mg) was prepared in accordance with the same procedures as in Example 1, except for using tert-butyl (Z)-(4-(4-bromo-6-cyano-1H-benzo[d][1,2,3]triazol-1-yl)-3-fluorobut-2-en-1-yl)carbamate prepared in Preparation 20 (20 mg) instead of tert-butyl N—[(Z)-4-(4-bromo-6-fluoro-benzimidazol-1-yl)-3-fluoro-but-2-enyl] carbamate; and pyrimidin-5-ylboronic acid (6.1 mg) instead of 3-fluorophenylboronic acid. (Yield: 16.6%)

$^1$H-NMR (MeOD, 400 MHz) δ 9.60 (s, 2H), 9.30 (s, 1H), 8.52 (s, 1H), 8.17 (s, 1H), 5.79 (d, 2H), 5.58-5.47 (m, 1H), 3.69 (d, 2H)

Example 211. (Z)-1-(4-amino-2-fluorobut-2-en-1-yl)-4-(1-methyl-1H-pyrazol-5-yl)-1H-benzo[d][1,2,3]triazol-6-carbonitrile hydrochloride The titled compound (1.0 mg) was prepared in accordance with the same procedures as in Example 1, except for using tert-butyl (Z)-(4-(4-bromo-6-cyano-1H-benzo[d][1,2,3]triazol-1-yl)-3-fluorobut-2-en-1-yl)carbamate prepared in Preparation 20 (20 mg) instead of tert-butyl N—[(Z)-4-(4-bromo-6-fluoro-benzimidazol-1-yl)-3-fluoro-but-2-enyl] carbamate; and (1-methyl-1H-pyrazol-5-yl)boronic acid (6.1 mg) instead of 3-fluorophenylboronic acid. (Yield: 5.9%)

$^1$H-NMR (MeOD, 400 MHz) δ 8.33 (s, 1H), 8.24 (s, 1H), 7.92 (s, 1H), 7.53 (s, 1H), 5.76 (d, 2H), 5.51-5.42 (m, 1H), 3.69 (d, 2H)

Test Example 1: Evaluation of Activities Against Amine Oxidases

The activities of the compounds according to the present invention against recombinant human Lysyl Oxidase-Like 2 (recombinant human LOXL2, R&D systems) were evaluated by measuring the levels of hydrogen peroxide in the HRP (horseradish peroxidase) coupled reactions, with the Amplex Red Hydrogen Peroxide Assay Kit (Molecular Probes, Invitrogen, USA). The tests were carried out at 37° C., and putrescine was used as a substrate. In the HRP coupling reaction, the oxidation of 10-acetyl-3,7-dihydroxyphenoxazine (Amplex Red reagent) by hydrogen peroxide generates a fluorescent product, i.e., resorufin. Briefly, the test compounds were dissolved in dimethyl sulfoxide (DMSO) at a concentration of 20 mM. Dose-response measurements were carried out by serial dilutions in DMSO to generate a six-point curve. The upper concentration was adjusted according to the potency of the compound, and then diluted with the reaction buffer to obtain a final DMSO concentration of 1%. Purified human LOXL2 in 50 mM sodium phosphate buffer (pH7.4) was added to each well of a 96 well black plate. The test compounds dissolved in DMSO were incubated with the human LOXL2 enzyme at 37° C. for 60 minutes. After the incubation for 60 minutes, a reaction mixture containing 400 μM Amplex Red reagent, 30 mM putrescine, and 2 U/mL HRP in 50 mM sodium phosphate buffer (pH 7.4) was added to each well. Fluorescence was measured with a microplate reader (Flexstation3, Molecular Devices), under the conditions of excitation at 530 nm and emission at 590 nm, 1 hour after the addition of the mixture. Inhibition by each compound was measured as % reduction in signal, compared to the control without an inhibitor (diluted DMSO only). The data were fixed to a four-variable logistic model, and 1050 values were calculated using the GraphPad Prism program.

And, the activities of the compounds according to the present invention against recombinant human MAO-A (monoamine oxidase-A, Sigma-Aldrich) and recombinant human MAO-B (monoamine oxidase-B, Sigma-Aldrich) were evaluated in a similar manner to the activity evaluation method for recombinant human LOXL2, using 0.5 mM tyramine and 1 mM benzylamine as a substrate, respectively. In addition, the activities of the compounds according to the present invention against recombinant human DAO (diamine oxidase, R&D systems) were evaluated in a similar manner to the activity evaluation method for recombinant human LOXL2, using 1 mM putrescine as a substrate.

The results obtained by evaluating the activities against each enzyme as described above are shown in Tables 1 to 3 below.

TABLE 1

| Example | Inhibitory activity ($IC_{50}$, nM) human LOXL2 | MAO-A | MAO-B | DAO |
|---|---|---|---|---|
| 3 | 54 | >100,000 | 71,200 | 2,938 |
| 7 | 35 | 26,460 | >100,000 | 2,410 |
| 9 | 39 | 48,640 | >100,000 | 3,103 |
| 10 | 22 | 65,480 | >100,000 | 3,920 |
| 13 | 104 | >100,000 | >100,000 | >100,000 |
| 20 | 77 | >100,000 | >100,000 | >100,000 |
| 21 | 22.7 | 12,160 | >100,000 | 380.4 |
| 22 | 19.9 | 53,320 | >100,000 | 5,068 |
| 23 | 16.7 | >100,000 | >100,000 | 985.7 |
| 24 | 15.9 | >100,000 | >100,000 | 21,770 |
| 25 | 22.7 | >100,000 | >100,000 | 1,230 |
| 26 | 62.5 | — | — | — |
| 27 | 31.3 | 45,690 | >100,000 | 16,080 |
| 28 | 54.2 | — | — | — |
| 29 | 34.9 | >100,000 | >100,000 | 1,368 |
| 30 | 29.7 | >100,000 | >100,000 | 3,459 |
| 31 | 19.4 | 24,560 | >100,000 | 139.5 |
| 32 | 60.1 | — | — | — |
| 33 | 55.6 | — | — | — |
| 34 | 37.6 | >100,000 | >100,000 | 495 |
| 35 | 67.6 | >100,000 | >100,000 | 47,720 |
| 37 | 70.3 | — | — | — |
| 38 | 82.3 | >100,000 | >100,000 | 44,480 |
| 53 | 68 | >100,000 | >100,000 | >100,000 |
| 56 | 74 | 6,535 | >100,000 | 227 |
| 60 | 92 | 64,240 | >100,000 | 636 |
| 66 | 28 | 7,892 | >100,000 | 1,608 |
| 67 | 83 | >100,000 | >100,000 | 646 |
| 70 | 60 | 10,330 | >100,000 | 2,498 |
| 73 | 58 | 47,860 | >100,000 | 1,807 |
| 76 | 58 | 12,400 | >100,000 | 24,570 |
| 84 | 65 | 65,000 | >100,000 | 6,694 |
| 102 | 17 | 86,600 | 12,360 | 37,380 |
| 103 | 25 | 9,056 | 23,460 | 27,860 |
| 104 | 51 | — | — | — |
| 105 | 26 | 55,130 | >100,000 | 35,990 |
| 106 | 94 | — | — | — |
| 108 | 42 | >100,000 | >100,000 | >100,000 |
| 109 | 72 | — | — | — |
| 110 | 60 | — | — | — |
| 111 | 35 | >100,000 | >100,000 | 30,660 |

TABLE 2

| Example | Inhibitory activity ($IC_{50}$, nM) human LOXL2 | MAO-A | MAO-B | DAO |
|---|---|---|---|---|
| 112 | 15 | >100,000 | 26,540 | 32,100 |
| 113 | 65 | — | — | — |
| 114 | 18.6 | — | — | — |
| 115 | 58.7 | — | — | — |
| 116 | 52.4 | — | — | — |
| 117 | 11.9 | >100,000 | 46,640 | 4,440 |
| 118 | 34.0 | — | — | — |
| 119 | 47.3 | >100,000 | >100,000 | 14,490 |
| 120 | 17.1 | — | 96,980 | 2,828 |
| 121 | 42.9 | — | — | — |
| 122 | 32.2 | — | — | — |
| 123 | 12.6 | — | — | — |
| 124 | 14.2 | — | — | — |
| 125 | 70.6 | — | — | — |
| 127 | 19.0 | — | — | — |
| 128 | 94.2 | — | — | — |
| 132 | 18.7 | — | — | — |
| 133 | 24.4 | — | — | — |
| 134 | 8 | — | — | — |
| 135 | 35.6 | — | — | — |
| 136 | 6.4 | — | — | — |
| 137 | 37 | — | — | — |
| 138 | 54.3 | — | — | — |

TABLE 2-continued

| Example | Inhibitory activity ($IC_{50}$, nM) human LOXL2 | MAO-A | MAO-B | DAO |
|---|---|---|---|---|
| 139 | 69.6 | — | — | — |
| 169 | 273.4 | 26,890 | >100,000 | 5,396 |
| 172 | 311.1 | 17,780 | 51,590 | 3,524 |
| 173 | 269.4 | 15,370 | >100,000 | 3,729 |
| 174 | 303.9 | 81,240 | >100,000 | 2,214 |
| 175 | 259.3 | >100,000 | >100,000 | 2,577 |
| 176 | 92.4 | >100,000 | >100,000 | 26,690 |
| 177 | 419 | — | — | — |
| 178 | 463.1 | — | — | — |
| 179 | 505.9 | — | — | — |
| 180 | 323.4 | — | — | — |
| 181 | 43.1 | >100,000 | >100,000 | — |
| 182 | 28.7 | >100,000 | >100,000 | — |
| 183 | 35.1 | >100,000 | >100,000 | 1,820 |
| 184 | 99.0 | >100,000 | >100,000 | — |
| 185 | 104.8 | — | — | — |
| 186 | 108.7 | — | — | — |
| 187 | 463.8 | — | — | — |

TABLE 3

| Example | Inhibitory activity ($IC_{50}$, nM) human LOXL2 | MAO-A | MAO-B | DAO |
|---|---|---|---|---|
| 188 | 131.4 | — | — | — |
| 189 | 92.8 | — | — | — |
| 190 | 117.2 | — | — | — |
| 191 | 95.5 | >100,000 | >100,000 | — |
| 192 | 136.9 | >100,000 | >100,000 | — |
| 193 | 204 | — | — | — |
| 194 | 104.6 | 36,820 | >100,000 | 7,590 |
| 195 | 158.6 | >100,000 | >100,000 | 5,563 |
| 196 | 34.0 | — | — | 3,153 |
| 197 | 308.4 | — | — | — |
| 198 | 226.1 | — | — | — |
| 199 | 305.3 | — | — | — |
| 200 | 330.3 | — | — | — |
| 201 | 142.3 | — | — | — |
| 202 | 189.6 | — | — | — |
| 203 | 351.5 | — | — | — |
| 204 | 496.7 | — | — | — |
| 205 | 181.6 | — | — | — |
| 206 | 200.2 | — | — | 1,957 |
| 207 | 281.4 | — | — | 7,444 |
| 208 | 269.9 | — | — | — |
| 209 | 86.8 | — | — | — |
| 210 | 264.2 | — | — | 432.2 |
| 211 | 350.2 | — | — | 1,728 |

From the results in Tables 1 to 3, it can be seen that the compounds according to the present invention have excellent inhibitory activity against LOXL2 in various amine oxidases.

What is claimed is:

1. A compound of Formula 1 or pharmaceutically acceptable salt thereof:

<Formula 1>

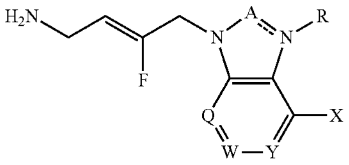

wherein,

A is —$CR_1$═, —N═, or —C(O)—,

R is absent where A is —$CR_1$═ or —N═, and R is $C_{1-6}$ alkyl where A is —C(O)—, Q is N or $CR_2$, W is N or $CR_3$, Y is N or $CR_4$, X is a heterocyclic ring or a benzene ring, the heterocyclic ring or the benzene ring is optionally substituted with 1 or 2 substituents selected from the group consisting of $C_{1-6}$ alkyl, hydroxy-$C_{1-6}$ alkyl, halogen, trifluoromethyl, $C_{1-6}$ alkoxy, $C_{1-6}$ alkylcarbonyl, $C_{1-6}$ alkoxybenzylaminosulfonyl, $C_{1-6}$ alkylsulfonyl, di-$C_{1-6}$ alkylphosphoryl, di-$C_{1-6}$ alkoxyphosphoryl, mono- or di-$C_{1-6}$ alkylaminosulfonyl, cyclopropylaminosulfonyl, pyrrolidinylsulfonyl, morpholinylsulfonyl, piperidinylsulfonyl, 3,3-difluoropyrrolidinylsulfonyl, $C_{1-3}$ alkyl-piperazinylsulfonyl, and trifluoromethylsulfonyl, $R_1$ is hydrogen, trifluoromethyl, or $C_{1-6}$ alkyl, $R_2$, $R_3$, and $R_4$ are, independently each other, selected from the group consisting of hydrogen, halogen, trifluoromethyl, cyano, nitro, hydroxycarbonyl, $C_{1-6}$ alkoxycarbonyl and —C(O)$NR_5R_6$, and $R_5$ and $R_6$ are, independently each other, hydrogen, $C_{1-6}$ alkyl, or $C_{1-6}$ alkoxy; or form a 3- to 7-membered N-containing cyclic ring together with the nitrogen atom to which they are bonded.

2. The compound or pharmaceutically acceptable salt thereof as claimed in claim 1, wherein A is —$CR_1$═ or —N═, R is absent, compound or pharmaceutically Q and Y are —CH═, and W is $CR_3$.

3. The compound or pharmaceutically acceptable salt thereof as claimed in claim 1, wherein A is —C(O)—, R is $C_{1-6}$ alkyl, Q and Y are —N═, and W is —CH═.

4. The compound or pharmaceutically acceptable salt thereof as claimed in claim 1, wherein X is a benzene ring, a pyridine ring, a pyrimidine ring, or a pyrazole ring.

5. The compound or pharmaceutically acceptable salt thereof as claimed in claim 4, wherein A is —$CR_1$═ or —N═, R is absent, Q and Y are —CH═, and W is $CR_3$, X is a benzene ring, a pyridine ring, a pyrimidine ring, or a pyrazole ring, the benzene ring, the pyridine ring, the pyrimidine ring, or the pyrazole ring is optionally substituted with 1 or 2 substituents selected from the group consisting of $C_{1-6}$ alkyl, hydroxy-$C_{1-6}$ alkyl, halogen, trifluoromethyl, $C_{1-6}$ alkoxy, $C_{1-6}$ alkylcarbonyl, $C_{1-6}$ alkoxybenzylaminosulfonyl, $C_{1-6}$ alkylsulfonyl, di-$C_{1-6}$ alkylphosphoryl, di-$C_{1-6}$ alkoxyphosphoryl, mono- or di-$C_{1-6}$ alkylaminosulfonyl, cyclopropylaminosulfonyl, pyrrolidinylsulfonyl, morpholinylsulfonyl, piperidinylsulfonyl, 3,3-difluoropyrrolidinylsulfonyl, $C_{1-3}$ alkyl-piperazinylsulfonyl, and trifluoromethylsulfonyl, $R_1$ is hydrogen, trifluoromethyl or $C_{1-6}$ alkyl, $R_3$ is selected from the group consisting of hydrogen, halogen, trifluoromethyl, cyano, hydroxycarbonyl, $C_{1-6}$ alkoxycarbonyl and —C(O)$NR_5R_6$, $R_5$ and $R_6$ are, independently each other, hydrogen, $C_{1-6}$ alkyl, or $C_{1-6}$ alkoxy; or form a 3- to 7-membered N-containing cyclic ring together with the nitrogen atom to which they are bonded.

6. The compound or pharmaceutically acceptable salt thereof as claimed in claim 1, which is selected from the group consisting of:

(Z)-3-fluoro-4-(6-fluoro-4-(3-fluorophenyl)-1H-benzo[d]imidazol-1-yl)but-2-en-1-amine;

(Z)-3-fluoro-4-(6-fluoro-4-(3-(trifluoromethyl)phenyl)-1H-benzo[d]imidazol-1-yl)but-2-en-1-amine;

(Z)-3-fluoro-4-(6-fluoro-4-(3-(methylsulfonyl)phenyl)-1H-benzo[d]imidazol-1-yl)but-2-en-1-amine;

(Z)-4-(1-(4-amino-2-fluorobut-2-en-1-yl)-6-fluoro-1H-benzo[d]imidazol-4-yl)-N,N-dimethylbenzenesulfonamide;

(Z)-4-(1-(4-amino-2-fluorobut-2-en-1-yl)-6-fluoro-1H-benzo[d]imidazol-4-yl)-N-cyclopropylbenzenesulfonamide;

(Z)-3-fluoro-4-(6-fluoro-4-(4-(methylsulfonyl)phenyl)-1H-benzo[d]imidazol-1-yl)but-2-en-1-amine;

(Z)-3-fluoro-4-(6-fluoro-4-(3-(pyrrolidin-1-ylsulfonyl)phenyl)-1H-benzo[d]imidazol-1-yl)but-2-en-1-amine;

(Z)-3-fluoro-4-(6-fluoro-4-(4-(morpholinosulfonyl)phenyl)-1H-benzo[d]imidazol-1-yl)but-2-en-1-amine;

(Z)-3-(1-(4-amino-2-fluorobut-2-en-1-yl)-6-fluoro-1H-benzo[d]imidazol-4-yl)-N-cyclopropylbenzenesulfonamide;

(Z)-3-(1-(4-amino-2-fluorobut-2-en-1-yl)-6-fluoro-1H-benzo[d]imidazol-4-yl)-N-methylbenzenesulfonamide;

(Z)-3-fluoro-4-(4-(3-fluorophenyl)-6-(trifluoromethyl)-1H-benzo[d]imidazol-1-yl)but-2-en-1-amine;

(Z)-3-fluoro-4-(6-(trifluoromethyl)-4-(3-(trifluoromethyl)phenyl)-1H-benzo[d]imidazol-1-yl)but-2-en-1-amine;

(Z)-3-fluoro-4-(4-(3-(methylsulfonyl)phenyl)-6-(trifluoromethyl)-1H-benzo[d]imidazol-1-yl)but-2-en-1-amine;

(Z)-4-(1-(4-amino-2-fluorobut-2-en-1-yl)-6-(trifluoromethyl)-1H-benzo[d]imidazol-4-yl)-N,N-dimethylbenzenesulfonamide;

(Z)-4-(1-(4-amino-2-fluorobut-2-en-1-yl)-6-(trifluoromethyl)-1H-benzo[d]imidazol-4-yl)-N-cyclopropylbenzenesulfonamide;

(Z)-3-fluoro-4-(4-(4-(methylsulfonyl)phenyl)-6-(trifluoromethyl)-1H-benzo[d]imidazol-1-yl)but-2-en-1-amine;

(Z)-3-fluoro-4-(4-(3-(pyrrolidin-1-ylsulfonyl)phenyl)-6-(trifluoromethyl)-1H-benzo[d]imidazol-1-yl)but-2-en-1-amine;

(Z)-3-fluoro-4-(4-(4-(morpholinosulfonyl)phenyl)-6-(trifluoromethyl)-1H-benzo[d]imidazol-1-yl)but-2-en-1-amine;

(Z)-3-(1-(4-amino-2-fluorobut-2-en-1-yl)-6-(trifluoromethyl)-1H-benzo[d]imidazol-4-yl)-N-cyclopropylbenzenesulfonamide;

(Z)-3-(1-(4-amino-2-fluorobut-2-en-1-yl)-6-(trifluoromethyl)-1H-benzo[d]imidazol-4-yl)-N-methylbenzenesulfonamide;

methyl (Z)-1-(4-amino-2-fluorobut-2-en-1-yl)-4-(3-(N,N-dimethylsulfamoyl)-4-methoxyphenyl)-1H-benzo[d]imidazol-6-carboxylate;

methyl (Z)-1-(4-amino-2-fluorobut-2-en-1-yl)-4-(3-((3,3-difluoropyrrolidin-1-yl)sulfonyl)phenyl)-1H-benzo[d]imidazol-6-carboxylate;

methyl (Z)-1-(4-amino-2-fluorobut-2-en-1-yl)-4-(3-(pyrrolidin-1-ylsulfonyl)phenyl)-1H-benzo[d]imidazol-6-carboxylate;

methyl (Z)-1-(4-amino-2-fluorobut-2-en-1-yl)-4-(2-methoxy-5-(N-methylsulfamoyl)phenyl)-1H-benzo[d]imidazol-6-carboxylate;

methyl (Z)-1-(4-amino-2-fluorobut-2-en-1-yl)-4-(3-(methylsulfonyl)phenyl)-1H-benzo[d]imidazol-6-carboxylate;

methyl (Z)-1-(4-amino-2-fluorobut-2-en-1-yl)-4-(5-(N,N-diethylsulfamoyl)-2-methoxyphenyl)-1H-benzo[d]imidazol-6-carboxylate;

methyl (Z)-1-(4-amino-2-fluorobut-2-en-1-yl)-4-(5-(N-cyclopropylsulfamoyl)-2-methoxyphenyl)-1H-benzo[d]imidazol-6-carboxylate;

methyl (Z)-1-(4-amino-2-fluorobut-2-en-1-yl)-4-(3-(N-isopropylsulfamoyl)-4-methoxyphenyl)-1H-benzo[d]imidazol-6-carboxylate;

methyl (Z)-1-(4-amino-2-fluorobut-2-en-1-yl)-4-(3-(N-cyclopropylsulfamoyl)phenyl)-1H-benzo[d]imidazol-6-carboxylate;

methyl (Z)-1-(4-amino-2-fluorobut-2-en-1-yl)-4-(3-(N-methylsulfamoyl)phenyl)-1H-benzo[d]imidazol-6-carboxylate;

methyl (Z)-1-(4-amino-2-fluorobut-2-en-1-yl)-4-(3-(N,N-dimethylsulfamoyl)phenyl)-1H-benzo[d]imidazol-6-carboxylate;

methyl (Z)-1-(4-amino-2-fluorobut-2-en-1-yl)-4-(3-(N-(4-methoxybenzyl)sulfamoyl)phenyl)-1H-benzo[d]imidazol-6-carboxylate;

methyl (Z)-1-(4-amino-2-fluorobut-2-en-1-yl)-4-(3-(piperidin-1-ylsulfonyl)phenyl)-1H-benzo[d]imidazol-6-carboxylate;

methyl (Z)-1-(4-amino-2-fluorobut-2-en-1-yl)-4-(3-(ethylsulfonyl)phenyl)-1H-benzo[d]imidazol-6-carboxylate;

methyl (Z)-1-(4-amino-2-fluorobut-2-en-1-yl)-4-(2-methyl-5-((trifluoromethyl)sulfonyl)phenyl)-1H-benzo[d]imidazol-6-carboxylate;

methyl (Z)-1-(4-amino-2-fluorobut-2-en-1-yl)-4-(3-(N-(tert-butyl)sulfamoyl)phenyl)-1H-benzo[d]imidazol-6-carboxylate;

methyl (Z)-1-(4-amino-2-fluorobut-2-en-1-yl)-4-(3-(N,N-diethylsulfamoyl)phenyl)-1H-benzo[d]imidazol-6-carboxylate;

methyl (Z)-1-(4-amino-2-fluorobut-2-en-1-yl)-4-(3-(dimethylphosphoryl)phenyl)-1H-benzo[d]imidazol-6-carboxylate;

methyl (Z)-1-(4-amino-2-fluorobut-2-en-1-yl)-4-(4-(dimethylphosphoryl)phenyl)-1H-benzo[d]imidazol-6-carboxylate;

methyl (Z)-1-(4-amino-2-fluorobut-2-en-1-yl)-4-(3-(diethoxyphosphoryl)phenyl)-1H-benzo[d]imidazol-6-carboxylate;

(Z)-1-(4-amino-2-fluorobut-2-en-1-yl)-4-(3-((3,3-difluoropyrrolidin-1-yl)sulfonyl)phenyl)-1H-benzo[d]imidazole-6-carboxylic acid;

(Z)-1-(4-amino-2-fluorobut-2-en-1-yl)-4-(3-(pyrrolidin-1-ylsulfonyl)phenyl)-1H-benzo[d]imidazol-6-carboxylic acid;

(Z)-3-fluoro-4-(4-(3-fluorophenyl)-2-(trifluoromethyl)-1H-benzo[d]imidazol-1-yl)but-2-en-1-amine;

(Z)-3-fluoro-4-(2-(trifluoromethyl)-4-(3-(trifluoromethyl)phenyl)-1H-benzo[d]imidazol-1-yl)but-2-en-1-amine;

(Z)-3-(1-(4-amino-2-fluorobut-2-en-1-yl)-2-(trifluoromethyl)-1H-benzo[d]imidazol-4-yl)-N,N-dimethylbenzenesulfonamide;

(Z)-3-fluoro-4-(4-(3-(methylsulfonyl)phenyl)-2-(trifluoromethyl)-1H-benzo[d]imidazol-1-yl)but-2-en-1-amine;

(Z)-4-(1-(4-amino-2-fluorobut-2-en-1-yl)-2-(trifluoromethyl)-1H-benzo[d]imidazol-4-yl)-N,N-dimethylbenzenesulfonamide;

(Z)-4-(1-(4-amino-2-fluorobut-2-en-1-yl)-2-(trifluoromethyl)-1H-benzo[d]imidazol-4-yl)-N-cyclopropylbenzenesulfonamide;

(Z)-3-fluoro-4-(4-(4-(methylsulfonyl)phenyl)-2-(trifluoromethyl)-1H-benzo[d]imidazol-1-yl)but-2-en-1-amine;

(Z)-3-fluoro-4-(4-(3-(pyrrolidin-1-ylsulfonyl)phenyl)-2-(trifluoromethyl)-1H-benzo[d]imidazol-1-yl)but-2-en-1-amine;

(Z)-4-(1-(4-amino-2-fluorobut-2-en-1-yl)-2-(trifluoromethyl)-1H-benzo[d]imidazol-4-yl)-N-(tert-butyl)benzenesulfonamide;

(Z)-3-(1-(4-amino-2-fluorobut-2-en-1-yl)-2-(trifluoromethyl)-1H-benzo[d]imidazol-4-yl)-N-cyclopropylbenzenesulfonamide;

(Z)-3-(1-(4-amino-2-fluorobut-2-en-1-yl)-2-(trifluoromethyl)-1H-benzo[d]imidazol-4-yl)-N-methylbenzenesulfonamide;

(Z)-4-(1-(4-amino-2-fluorobut-2-en-1-yl)-2-methyl-1H-benzo[d]imidazol-4-yl)-N,N-dimethylbenzenesulfonamide;

(Z)-3-fluoro-4-(2-methyl-4-(4-(morpholinosulfonyl)phenyl)-1H-benzo[d]imidazol-1-yl)but-2-en-1-amine;

(Z)-3-(1-(4-amino-2-fluorobut-2-en-1-yl)-2-methyl-1H-benzo[d]imidazol-4-yl)-N,N-dimethylbenzenesulfonamide;

(Z)-3-fluoro-4-(2-methyl-4-(3-(methylsulfonyl)phenyl)-1H-benzo[d]imidazol-1-yl)but-2-en-1-amine;

(Z)-3-fluoro-4-(2-methyl-4-(4-(methylsulfonyl)phenyl)-1H-benzo[d]imidazol-1-yl)but-2-en-1-amine;

(Z)-4-(1-(4-amino-2-fluorobut-2-en-1-yl)-2-methyl-1H-benzo[d]imidazol-4-yl)-N-cyclopropylbenzenesulfonamide;

(Z)-3-fluoro-4-(2-methyl-4-(3-(pyrrolidin-1-ylsulfonyl)phenyl)-1H-benzo[d]imidazol-1-yl)but-2-en-1-amine;

(Z)-4-(1-(4-amino-2-fluorobut-2-en-1-yl)-2-methyl-1H-benzo[d]imidazol-4-yl)-N-(tert-butyl)benzenesulfonamide;

(Z)-3-(1-(4-amino-2-fluorobut-2-en-1-yl)-2-methyl-1H-benzo[d]imidazol-4-yl)-N-cyclopropylbenzenesulfonamide;

(Z)-3-(1-(4-amino-2-fluorobut-2-en-1-yl)-2-methyl-1H-benzo[d]imidazol-4-yl)-N-methylbenzenesulfonamide;

methyl (Z)-1-(4-amino-2-fluorobut-2-en-1-yl)-4-(4-(N,N-dimethylsulfamoyl)phenyl)-2-methyl-1H-benzo[d]imidazol-6-carboxylate;

methyl (Z)-1-(4-amino-2-fluorobut-2-en-1-yl)-2-methyl-4-(4-(morpholinosulfonyl)phenyl)-1H-benzo[d]imidazol-6-carboxylate;

methyl (Z)-1-(4-amino-2-fluorobut-2-en-1-yl)-4-(3-(N,N-dimethylsulfamoyl)phenyl)-2-methyl-1H-benzo[d]imidazol-6-carboxylate;

methyl (Z)-1-(4-amino-2-fluorobut-2-en-1-yl)-2-methyl-4-(3-(methylsulfonyl)phenyl)-1H-benzo[d]imidazol-6-carboxylate;

methyl (Z)-1-(4-amino-2-fluorobut-2-en-1-yl)-2-methyl-4-(4-(methylsulfonyl)phenyl)-1H-benzo[d]imidazol-6-carboxylate;

methyl (Z)-1-(4-amino-2-fluorobut-2-en-1-yl)-4-(4-(N-cyclopropylsulfamoyl)phenyl)-2-methyl-1H-benzo[d]imidazol-6-carboxylate;

methyl (Z)-1-(4-amino-2-fluorobut-2-en-1-yl)-2-methyl-4-(3-(pyrrolidin-1-ylsulfonyl)phenyl)-1H-benzo[d]imidazol-6-carboxylate;

methyl (Z)-1-(4-amino-2-fluorobut-2-en-1-yl)-4-(4-(N-(tert-butyl)sulfamoyl)phenyl)-2-methyl-1H-benzo[d]imidazol-6-carboxylate;

methyl (Z)-1-(4-amino-2-fluorobut-2-en-1-yl)-4-(3-(N-cyclopropylsulfamoyl)phenyl)-2-methyl-1H-benzo[d]imidazol-6-carboxylate;

methyl (Z)-1-(4-amino-2-fluorobut-2-en-1-yl)-2-methyl-4-(3-(N-methylsulfamoyl)phenyl)-1H-benzo[d]imidazol-6-carboxylate;

(Z)-1-(4-amino-2-fluorobut-2-en-1-yl)-4-(4-(N,N-dimethylsulfamoyl)phenyl)-N,N,2-trimethyl-1H-benzo[d]imidazol-6-carboxamide;

(Z)-1-(4-amino-2-fluorobut-2-en-1-yl)-N,N,2-trimethyl-4-(4-(morpholinosulfonyl)phenyl)-1H-benzo[d]imidazol-6-carboxamide;

(Z)-1-(4-amino-2-fluorobut-2-en-1-yl)-4-(3-(N,N-dimethylsulfamoyl)phenyl)-N,N,2-trimethyl-1H-benzo[d]imidazol-6-carboxamide;

(Z)-1-(4-amino-2-fluorobut-2-en-1-yl)-N,N,2-trimethyl-4-(3-(methylsulfonyl)phenyl)-1H-benzo[d]imidazol-6-carboxamide;

(Z)-1-(4-amino-2-fluorobut-2-en-1-yl)-N,N,2-trimethyl-4-(4-(methylsulfonyl)phenyl)-1H-benzo[d]imidazol-6-carboxamide;

(Z)-1-(4-amino-2-fluorobut-2-en-1-yl)-4-(4-(N-cyclopropylsulfamoyl)phenyl)-N,N,2-trimethyl-1H-benzo[d]imidazol-6-carboxamide;

(Z)-1-(4-amino-2-fluorobut-2-en-1-yl)-4-(3-(N-cyclopropylsulfamoyl)phenyl)-N,N,2-trimethyl-1H-benzo[d]imidazol-6-carboxamide;

(Z)-1-(4-amino-2-fluorobut-2-en-1-yl)-N,N,2-trimethyl-4-(3-(N-methylsulfamoyl)phenyl)-1H-benzo[d]imidazol-6-carboxamide;

(Z)-4-(1-(4-amino-2-fluorobut-2-en-1-yl)-2-ethyl-1H-benzo[d]imidazol-4-yl)-N,N-dimethylbenzenesulfonamide;

(Z)-4-(2-ethyl-4-(4-(morpholinosulfonyl)phenyl)-1H-benzo[d]imidazol-1-yl)-3-fluorobut-2-en-1-amine;

(Z)-3-(1-(4-amino-2-fluorobut-2-en-1-yl)-2-ethyl-1H-benzo[d]imidazol-4-yl)-N,N-dimethylbenzenesulfonamide;

(Z)-4-(2-ethyl-4-(3-(methylsulfonyl)phenyl)-1H-benzo[d]imidazol-1-yl)-3-fluorobut-2-en-1-amine;

(Z)-4-(2-ethyl-4-(4-(methylsulfonyl)phenyl)-1H-benzo[d]imidazol-1-yl)-3-fluorobut-2-en-1-amine;

(Z)-4-(1-(4-amino-2-fluorobut-2-en-1-yl)-2-ethyl-1H-benzo[d]imidazol-4-yl)-N-cyclopropylbenzenesulfonamide;

(Z)-4-(2-ethyl-4-(3-(pyrrolidin-1-ylsulfonyl)phenyl)-1H-benzo[d]imidazol-1-yl)-3-fluorobut-2-en-1-amine;

(Z)-4-(1-(4-amino-2-fluorobut-2-en-1-yl)-2-ethyl-1H-benzo[d]imidazol-4-yl)-N-(tert-butyl)benzenesulfonamide;

(Z)-3-(1-(4-amino-2-fluorobut-2-en-1-yl)-2-ethyl-1H-benzo[d]imidazol-4-yl)-N-cyclopropylbenzenesulfonamide;

(Z)-3-(1-(4-amino-2-fluorobut-2-en-1-yl)-2-ethyl-1H-benzo[d]imidazol-4-yl)-N-methylbenzenesulfonamide;

(Z)-4-(1-(4-amino-2-fluorobut-2-en-1-yl)-2-isopropyl-1H-benzo[d]imidazol-4-yl)-N,N-dimethylbenzenesulfonamide;

(Z)-3-fluoro-4-(2-isopropyl-4-(4-(morpholinosulfonyl)phenyl)-1H-benzo[d]imidazol-1-yl)but-2-en-1-amine;

(Z)-3-(1-(4-amino-2-fluorobut-2-en-1-yl)-2-isopropyl-1H-benzo[d]imidazol-4-yl)-N,N-dimethylbenzenesulfonamide;

(Z)-3-fluoro-4-(2-isopropyl-4-(3-(methylsulfonyl)phenyl)-1H-benzo[d]imidazol-1-yl)but-2-en-1-amine;

(Z)-3-fluoro-4-(2-isopropyl-4-(4-(methylsulfonyl)phenyl)-1H-benzo[d]imidazol-1-yl)but-2-en-1-amine;

(Z)-4-(1-(4-amino-2-fluorobut-2-en-1-yl)-2-isopropyl-1H-benzo[d]imidazol-4-yl)-N-cyclopropylbenzenesulfonamide;

(Z)-3-fluoro-4-(2-isopropyl-4-(3-(pyrrolidin-1-ylsulfonyl)phenyl)-1H-benzo[d]imidazol-1-yl)but-2-en-1-amine;

(Z)-4-(1-(4-amino-2-fluorobut-2-en-1-yl)-2-isopropyl-1H-benzo[d]imidazol-4-yl)-N-(tert-butyl)benzenesulfonamide;

(Z)-3-(1-(4-amino-2-fluorobut-2-en-1-yl)-2-isopropyl-1H-benzo[d]imidazol-4-yl)-N-cyclopropylbenzenesulfonamide;

(Z)-3-(1-(4-amino-2-fluorobut-2-en-1-yl)-2-isopropyl-1H-benzo[d]imidazol-4-yl)-N-methylbenzenesulfonamide;

(Z)-5-(1-(4-amino-2-fluorobut-2-en-1-yl)-1H-benzo[d][1,2,3]triazol-4-yl)-2-methoxy-N,N-dimethylbenzenesulfonamide;

(Z)-4-(4-(3-((3,3-difluoropyrrolidin-1-yl)sulfonyl)phenyl)-1H-benzo[d][1,2,3]triazol-1-yl)-3-fluorobut-2-en-1-amine;

(Z)-3-fluoro-4-(4-(3-(pyrrolidin-1-ylsulfonyl)phenyl)-1H-benzo[d][1,2,3]triazol-1-yl)but-2-en-1-amine;

(Z)-3-(1-(4-amino-2-fluorobut-2-en-1-yl)-1H-benzo[d][1,2,3]triazol-4-yl)-4-methoxy-N-methylbenzenesulfonamide;

(Z)-3-fluoro-4-(4-(3-(methylsulfonyl)phenyl)-1H-benzo[d][1,2,3]triazol-1-yl)but-2-en-1-amine;

(Z)-3-(1-(4-amino-2-fluorobut-2-en-1-yl)-1H-benzo[d][1,2,3]triazol-4-yl)-N,N-diethyl-4-methoxybenzenesulfonamide;

(Z)-3-(1-(4-amino-2-fluorobut-2-en-1-yl)-1H-benzo[d][1,2,3]triazol-4-yl)-N-cyclopropyl-4-methoxybenzenesulfonamide;

(Z)-5-(1-(4-amino-2-fluorobut-2-en-1-yl)-1H-benzo[d][1,2,3]triazol-4-yl)-N-isopropyl-2-methoxybenzenesulfonamide;

(Z)-3-(1-(4-amino-2-fluorobut-2-en-1-yl)-1H-benzo[d][1,2,3]triazol-4-yl)-N-cyclopropylbenzenesulfonamide;

(Z)-3-(1-(4-amino-2-fluorobut-2-en-1-yl)-1H-benzo[d][1,2,3]triazol-4-yl)-N-methylbenzenesulfonamide;

(Z)-3-(1-(4-amino-2-fluorobut-2-en-1-yl)-1H-benzo[d][1,2,3]triazol-4-yl)-N,N-dimethylbenzenesulfonamide;

(Z)-3-fluoro-4-(4-(2-methoxy-5-((4-methylpiperazin-1-yl)sulfonyl)phenyl)-1H-benzo[d][1,2,3]triazol-1-yl)but-2-en-1-amine;

methyl (Z)-1-(4-amino-2-fluorobut-2-en-1-yl)-4-(3-(N,N-dimethylsulfamoyl)-4-methoxyphenyl)-1H-benzo[d][1,2,3]triazol-6-carboxylate;

methyl (Z)-1-(4-amino-2-fluorobut-2-en-1-yl)-4-(3-((3,3-difluoropyrrolidin-1-yl)sulfonyl)phenyl)-1H-benzo[d][1,2,3]triazol-6-carboxylate;

methyl (Z)-1-(4-amino-2-fluorobut-2-en-1-yl)-4-(3-(pyrrolidin-1-ylsulfonyl)phenyl)-1H-benzo[d][1,2,3]triazol-6-carboxylate;

methyl (Z)-1-(4-amino-2-fluorobut-2-en-1-yl)-4-(2-methoxy-5-(N-methylsulfamoyl)phenyl)-1H-benzo[d][1,2,3]triazol-6-carboxylate;

methyl (Z)-1-(4-amino-2-fluorobut-2-en-1-yl)-4-(3-(methylsulfonyl)phenyl)-1H-benzo[d][1,2,3]triazol-6-carboxylate;

methyl (Z)-1-(4-amino-2-fluorobut-2-en-1-yl)-4-(5-(N,N-diethylsulfamoyl)-2-methoxyphenyl)-1H-benzo[d][1,2,3]triazol-6-carboxylate;

methyl (Z)-1-(4-amino-2-fluorobut-2-en-1-yl)-4-(5-(N-cyclopropylsulfamoyl)-2-methoxyphenyl)-1H-benzo[d][1,2,3]triazol-6-carboxylate;

methyl (Z)-1-(4-amino-2-fluorobut-2-en-1-yl)-4-(3-(N-isopropylsulfamoyl)-4-methoxyphenyl)-1H-benzo[d][1,2,3]triazol-6-carboxylate;

methyl (Z)-1-(4-amino-2-fluorobut-2-en-1-yl)-4-(3-(N-cyclopropylsulfamoyl)phenyl)-1H-benzo[d][1,2,3]triazol-6-carboxylate;

methyl (Z)-1-(4-amino-2-fluorobut-2-en-1-yl)-4-(3-(N-methylsulfamoyl)phenyl)-1H-benzo[d][1,2,3]triazol-6-carboxylate;

methyl (Z)-1-(4-amino-2-fluorobut-2-en-1-yl)-4-(3-(N,N-dimethylsulfamoyl)phenyl)-1H-benzo[d][1,2,3]triazol-6-carboxylate;

methyl (Z)-1-(4-amino-2-fluorobut-2-en-1-yl)-4-(3-(N-(4-methoxybenzyl)sulfamoyl)phenyl)-1H-benzo[d][1,2,3]triazol-6-carboxylate;

methyl (Z)-1-(4-amino-2-fluorobut-2-en-1-yl)-4-(3-(piperidin-1-ylsulfonyl)phenyl)-1H-benzo[d][1,2,3]triazol-6-carboxylate;

methyl (Z)-1-(4-amino-2-fluorobut-2-en-1-yl)-4-(3-(ethylsulfonyl)phenyl)-1H-benzo[d][1,2,3]triazol-6-carboxylate;

methyl (Z)-1-(4-amino-2-fluorobut-2-en-1-yl)-4-(2-methyl-5-((trifluoromethyl)sulfonyl)phenyl)-1H-benzo[d][1,2,3]triazol-6-carboxylate;

methyl (Z)-1-(4-amino-2-fluorobut-2-en-1-yl)-4-(3-(N-(tert-butyl)sulfamoyl)phenyl)-1H-benzo[d][1,2,3]triazol-6-carboxylate;

methyl (Z)-1-(4-amino-2-fluorobut-2-en-1-yl)-4-(3-(N,N-diethylsulfamoyl)phenyl)-1H-benzo[d][1,2,3]triazol-6-carboxylate;

methyl (Z)-1-(4-amino-2-fluorobut-2-en-1-yl)-4-(3-(diethoxyphosphoryl)phenyl)-1H-benzo[d][1,2,3]triazol-6-carboxylate;

(Z)-1-(4-amino-2-fluorobut-2-en-1-yl)-4-(3-(N,N-dimethylsulfamoyl)-4-methoxyphenyl)-N-methoxy-1H-benzo[d][1,2,3]triazol-6-carboxamide;

(Z)-1-(4-amino-2-fluorobut-2-en-1-yl)-N-methoxy-4-(3-(pyrrolidin-1-ylsulfonyl)phenyl)-1H-benzo[d][1,2,3]triazol-6-carboxamide;

(Z)-1-(4-amino-2-fluorobut-2-en-1-yl)-N-methoxy-4-(2-methoxy-5-(N-methylsulfamoyl)phenyl)-1H-benzo[d][1,2,3]triazol-6-carboxamide;

(Z)-1-(4-amino-2-fluorobut-2-en-1-yl)-4-(5-(N,N-diethylsulfamoyl)-2-methoxyphenyl)-N-methoxy-1H-benzo[d][1,2,3]triazol-6-carboxamide;

(Z)-1-(4-amino-2-fluorobut-2-en-1-yl)-4-(5-(N-cyclopropylsulfamoyl)-2-methoxyphenyl)-N-methoxy-1H-benzo[d][1,2,3]triazol-6-carboxamide;

(Z)-1-(4-amino-2-fluorobut-2-en-1-yl)-N-methoxy-N-methyl-4-(3-(pyrrolidin-1-ylsulfonyl)phenyl)-1H-benzo[d][1,2,3]triazol-6-carboxamide;

(Z)-1-(4-amino-2-fluorobut-2-en-1-yl)-4-(5-(N,N-diethylsulfamoyl)-2-methoxyphenyl)-N-methoxy-N-methyl-1H-benzo[d][1,2,3]triazol-6-carboxamide;

(Z)-1-(4-amino-2-fluorobut-2-en-1-yl)-4-(3-(N,N-dimethylsulfamoyl)phenyl)-N-methoxy-N-methyl-1H-benzo[d][1,2,3]triazol-6-carboxamide;

(Z)-9-(4-amino-2-fluorobut-2-en-1-yl)-7-methyl-6-(3-(pyrrolidin-1-ylsulfonyl)phenyl)-7,9-dihydro-8H-purin-8-one;

(Z)-3-(9-(4-amino-2-fluorobut-2-en-1-yl)-7-methyl-8-oxo-8,9-dihydro-7H-purin-6-yl)-N-cyclopropylbenzenesulfonamide;

(Z)-3-(9-(4-amino-2-fluorobut-2-en-1-yl)-7-methyl-8-oxo-8,9-dihydro-7H-purin-6-yl)-N-methylbenzenesulfonamide;

(Z)-9-(4-amino-2-fluorobut-2-en-1-yl)-7-methyl-6-(3-(methylsulfonyl)phenyl)-7,9-dihydro-8H-purin-8-one;

(Z)-3-(9-(4-amino-2-fluorobut-2-en-1-yl)-7-methyl-8-oxo-8,9-dihydro-7H-purin-6-yl)-N,N-dimethylbenzenesulfonamide;

(Z)-1-(4-amino-2-fluorobut-2-en-1-yl)-4-(3-(N,N-dimethylsulfamoyl)-4-methoxyphenyl)-N-methyl-1H-benzo[d][1,2,3]triazol-6-carboxamide;

(Z)-1-(4-amino-2-fluorobut-2-en-1-yl)-4-(3-((3,3-difluoropyrrolidin-1-yl)sulfonyl)phenyl)-N-methyl-1H-benzo[d][1,2,3]triazol-6-carboxamide;

(Z)-1-(4-amino-2-fluorobut-2-en-1-yl)-N-methyl-4-(3-(pyrrolidin-1-ylsulfonyl)phenyl)-1H-benzo[d][1,2,3]triazol-6-carboxamide;

(Z)-1-(4-amino-2-fluorobut-2-en-1-yl)-4-(2-methoxy-5-(N-methylsulfamoyl)phenyl)-N-methyl-1H-benzo[d][1,2,3]triazol-6-carboxamide;

(Z)-1-(4-amino-2-fluorobut-2-en-1-yl)-N-methyl-4-(3-(methylsulfonyl)phenyl)-1H-benzo[d][1,2,3]triazol-6-carboxamide;

(Z)-1-(4-amino-2-fluorobut-2-en-1-yl)-4-(5-(N,N-diethylsulfamoyl)-2-methoxyphenyl)-N-methyl-1H-benzo[d][1,2,3]triazol-6-carboxamide;

(Z)-1-(4-amino-2-fluorobut-2-en-1-yl)-4-(3-(N-cyclopropylsulfamoyl)-4-methoxyphenyl)-N-methyl-1H-benzo[d][1,2,3]triazol-6-carboxamide;

(Z)-1-(4-amino-2-fluorobut-2-en-1-yl)-4-(3-(N-isopropylsulfamoyl)-4-methoxyphenyl)-N-methyl-1H-benzo[d][1,2,3]triazol-6-carboxamide;

(Z)-1-(4-amino-2-fluorobut-2-en-1-yl)-4-(3-(N-cyclopropylsulfamoyl)phenyl)-N-methyl-1H-benzo[d][1,2,3]triazol-6-carboxamide;

(Z)-1-(4-amino-2-fluorobut-2-en-1-yl)-N-methyl-4-(3-(N-methylsulfamoyl)phenyl)-1H-benzo[d][1,2,3]triazol-6-carboxamide;

(Z)-1-(4-amino-2-fluorobut-2-en-1-yl)-4-(3-(N,N-dimethylsulfamoyl)phenyl)-N-methyl-1H-benzo[d][1,2,3]triazol-6-carboxamide;

(Z)-1-(4-amino-2-fluorobut-2-en-1-yl)-4-(3-(ethylsulfonyl)phenyl)-N-methyl-1H-benzo[d][1,2,3]triazol-6-carboxamide;

(Z)-5-(1-(4-amino-2-fluorobut-2-en-1-yl)-6-(pyrrolidin-1-carbonyl)-1H-benzo[d][1,2,3]triazol-4-yl)-2-methoxy-N,N-dimethylbenzenesulfonamide;

(Z)-(1-(4-amino-2-fluorobut-2-en-1-yl)-4-(3-((3,3-difluoropyrrolidin-1-yl)sulfonyl)phenyl)-1H-benzo[d][1,2,3]triazol-6-yl)(pyrrolidin-1-yl)methanone;

(Z)-(1-(4-amino-2-fluorobut-2-en-1-yl)-4-(3-(pyrrolidin-1-ylsulfonyl)phenyl)-1H-benzo[d][1,2,3]triazol-6-yl)(pyrrolidin-1-yl)methanone;

(Z)-3-(1-(4-amino-2-fluorobut-2-en-1-yl)-6-(pyrrolidin-1-carbonyl)-1H-benzo[d][1,2,3]triazol-4-yl)-4-methoxy-N-methylbenzenesulfonamide;

(Z)-(1-(4-amino-2-fluorobut-2-en-1-yl)-4-(3-(methylsulfonyl)phenyl)-1H-benzo[d][1,2,3]triazol-6-yl)(pyrrolidin-1-yl)methanone;

(Z)-3-(1-(4-amino-2-fluorobut-2-en-1-yl)-6-(pyrrolidin-1-carbonyl)-1H-benzo[d][1,2,3]triazol-4-yl)-N,N-diethyl-4-methoxybenzenesulfonamide;

(Z)-5-(1-(4-amino-2-fluorobut-2-en-1-yl)-6-(pyrrolidin-1-carbonyl)-1H-benzo[d][1,2,3]triazol-4-yl)-N-cyclopropyl-2-methoxybenzenesulfonamide;

(Z)-5-(1-(4-amino-2-fluorobut-2-en-1-yl)-6-(pyrrolidin-1-carbonyl)-1H-benzo[d][1,2,3]triazol-4-yl)-N-isopropyl-2-methoxybenzenesulfonamide;

(Z)-3-(1-(4-amino-2-fluorobut-2-en-1-yl)-6-(pyrrolidin-1-carbonyl)-1H-benzo[d][1,2,3]triazol-4-yl)-N-cyclopropylbenzenesulfonamide;

(Z)-3-(1-(4-amino-2-fluorobut-2-en-1-yl)-6-(pyrrolidin-1-carbonyl)-1H-benzo[d][1,2,3]triazol-4-yl)-N-methylbenzenesulfonamide;

(Z)-3-(1-(4-amino-2-fluorobut-2-en-1-yl)-6-(pyrrolidin-1-carbonyl)-1H-benzo[d][1,2,3]triazol-4-yl)-N,N-dimethylbenzenesulfonamide;

(Z)-(1-(4-amino-2-fluorobut-2-en-1-yl)-4-(3-(ethylsulfonyl)phenyl)-1H-benzo[d][1,2,3]triazol-6-yl)(pyrrolidin-1-yl)methanone;

(Z)-1-(3-(1-(4-amino-2-fluorobut-2-en-1-yl)-6-(trifluoromethyl)-1H-benzo[d]imidazol-4-yl)-4-fluorophenyl) ethan-1-one;

(Z)-(3-(1-(4-amino-2-fluorobut-2-en-1-yl)-6-(trifluoromethyl)-1H-benzo[d]imidazol-4-yl)-4-fluorophenyl) methanol;

(Z)-(3-(1-(4-amino-2-fluorobut-2-en-1-yl)-6-(trifluoromethyl)-1H-benzo[d]imidazol-4-yl)-2-chlorophenyl) methanol;

(Z)-3-fluoro-4-(4-(pyridin-3-yl)-6-(trifluoromethyl)-1H-benzo[d]imidazol-1-yl)but-2-en-1-amine;

(Z)-3-fluoro-4-(4-(5-fluoropyridin-3-yl)-6-(trifluoromethyl)-1H-benzo[d]imidazol-1-yl)but-2-en-1-amine;

(Z)-4-(4-(5-chloropyridin-3-yl)-6-(trifluoromethyl)-1H-benzo[d]imidazol-1-yl)-3-fluoro-but-2-en-1-amine;

(Z)-3-fluoro-4-(4-(pyrimidin-5-yl)-6-(trifluoromethyl)-1H-benzo[d]imidazol-1-yl)but-2-en-1-amine;

(Z)-3-fluoro-4-(4-(1-methyl-1H-pyrazol-5-yl)-6-(trifluoromethyl)-1H-benzo[d]imidazol-1-yl)but-2-en-1-yl-amine;

(Z)-4-(4-(1-ethyl-1H-pyrazol-5-yl)-6-(trifluoromethyl)-1H-benzo[d]imidazol-1-yl]-3-fluoro-but-2-en-1-amine;

(Z)-3-fluoro-4-(4-(1-isopropyl-1H-pyrazol-5-yl)-6-(trifluoromethyl)-1H-benzo[d]imidazol-1-yl)but-2-en-1-amine;

(Z)-3-fluoro-4-(4-[1-methyl-3-(trifluoromethyl)-1H-pyrazol-5-yl]-6-(trifluoromethyl)-1H-benzo[d]imidazol-1-yl)but-2-en-1-amine;

(Z)-2-(4-(1-(4-amino-2-fluorobut-2-en-1-yl)-6-(trifluoromethyl)-1H-benzo[d]imidazol-4-yl)-1H-pyrazol-1-yl)ethan-1-ol;

(Z)-1-(4-amino-2-fluorobut-2-en-1-yl)-4-(3-(pyrrolidin-1-ylsulfonyl)phenyl)-1H-benzo[d]imidazol-6-carbonitrile;

(Z)-3-(1-(4-amino-2-fluorobut-2-en-1-yl)-6-cyano-1H-benzo[d]imidazol-4-yl)-N,N-dimethylbenzenesulfonamide;

(Z)-3-(1-(4-amino-2-fluorobut-2-en-1-yl)-6-cyano-1H-benzo[d]imidazol-4-yl)-4-methoxy-N-methylbenzenesulfonamide;

(Z)-4-(5-acetyl-2-fluorophenyl)-1-(4-amino-2-fluorobut-2-en-1-yl)-1H-benzo[d]imidazol-6-carbonitrile;

(Z)-1-(4-amino-2-fluorobut-2-en-1-yl)-4-(2-fluoro-5-(hydroxymethyl)phenyl)-1H-benzo[d]imidazol-6-carbonitrile;

(Z)-1-(4-amino-2-fluoro-2-but-1-yl)-4-(2-chloro-3-(hydroxymethyl)phenyl)-1H-benzo[d]imidazol-6-carbonitrile;

(Z)-1-(4-amino-2-fluorobut-2-en-1-yl)-4-(pyridin-3-yl)-1H-benzo[d]imidazol-6-carbonitrile;

(Z)-1-(4-amino-2-fluorobut-2-en-1-yl)-4-(5-fluoropyridin-3-yl)-1H-benzo[d]imidazol-6-carbonitrile;

(Z)-1-(4-amino-2-fluorobut-2-en-1-yl)-4-(5-chloropyridin-3-yl)-1H-benzo[d]imidazol-6-carbonitrile;

(Z)-1-(4-amino-2-fluorobut-2-en-1-yl)-4-(pyrimidin-5-yl)-1H-benzo[d]imidazol-6-carbonitrile;

(Z)-1-(4-amino-2-fluorobut-2-en-1-yl)-4-(1-methyl-1H-pyrazol-5-yl)-1H-benzo[d]imidazol-6-carbonitrile;

(Z)-1-(4-amino-2-fluorobut-2-en-1-yl)-4-(1-ethyl-1H-pyrazol-5-yl)-1H-benzo[d]imidazol-6-carbonitrile;

(Z)-1-(4-amino-2-fluorobut-2-en-1-yl)-4-(1-methyl-3-(trifluoromethyl)-1H-pyrazol-5-yl)-1H-benzo[d]imidazol-6-carbonitrile;

(Z)-1-(4-amino-2-fluorobut-2-en-1-yl)-4-(1,3-dimethyl-1H-pyrazol-5-yl)-1H-benzo[d]imidazol-6-carbonitrile;

(Z)-1-(4-amino-2-fluorobut-2-en-1-yl)-4-(1-(2-hydroxyethyl)-1H-pyrazol-3-yl)-1H-benzo[d]imidazol-6-carbonitrile;

(Z)-3-(1-(4-amino-2-fluorobut-2-en-1-yl)-6-(trifluoromethyl)-1H-benzo[d][1,2,3]triazol-4-yl)-N,N-dimethylbenzenesulfonamide;

(Z)-1-(3-(1-(4-amino-2-fluorobut-2-en-1-yl)-6-(trifluoromethyl)-1H-benzo[d][1,2,3]triazol-4-yl)-4-fluorophenyl)ethan-1-one;

(Z)-(3-(1-(4-amino-2-fluorobut-2-en-1-yl)-6-(trifluoromethyl)-1H-benzo[d][1,2,3]triazol-4-yl)-4-fluorophenyl) methanol;

(Z)-(3-(1-(4-amino-2-fluoro-2-en-1-yl)-6-(trifluoromethyl)-1H-benzo[d][1,2,3]triazol-4-yl)-2-chlorophenyl)methanol;

(Z)-3-fluoro-4-(4-(5-fluoropyridin-3-yl)-6-(trifluoromethyl)-1H-benzo[d][1,2,3]triazol-1-yl)but-2-en-1-amine;

(Z)-4-(4-(5-chloropyridin-3-yl)-6-(trifluoromethyl)-1H-benzo[d][1,2,3]triazol-1-yl)-3-fluorobut-2-en-1-amine;

(Z)-3-fluoro-4-(4-(pyrimidin-5-yl)-6-(trifluoromethyl)-1H-benzo[d][1,2,3]triazol-1-yl)but-2-en-1-amine;

(Z)-4-(4-(1-ethyl-1H-pyrazol-5-yl)-6-(trifluoromethyl)-1H-benzo[d][1,2,3]triazol-1-yl)-3-fluorobut-2-en-1-amine;

(Z)-4-[4-(1,3-dimethyl-1H-pyrazol-5-yl)-6-(trifluoromethyl)-1H-benzo[d][1,2,3]triazol-1-yl]-3-fluorobut-2-en-1-amine;

(Z)-2-(4-(1-(4-amino-2-fluorobut-2-en-1-yl)-6-(trifluoromethyl)-1H-benzo[d][1,2,3]triazol-4-yl]-1H-pyrazol-1-yl)ethan-1-ol;

(Z)-1-(4-amino-2-fluorobut-2-en-1-yl)-4-[2-fluoro-5-(hydroxymethyl)phenyl]-1H-benzo[d][1,2,3]triazol-6-carbonitrile;

(Z)-1-(4-amino-2-fluorobut-2-en-1-yl)-4-[2-chloro-3-(hydroxymethyl)phenyl-1H-benzo[d][1,2,3]triazol-6-carbonitrile;

(Z)-1-(4-amino-2-fluorobut-2-en-1-yl)-4-(5-fluoropyridin-3-yl)-1H-benzo[d][1,2,3]triazol-6-carbonitrile;

(Z)-1-(4-amino-2-fluorobut-2-en-1-yl)-4-(5-chloropyridin-3-yl)-1H-benzo[d][1,2,3]triazol-6-carbonitrile;

(Z)-1-(4-amino-2-fluorobut-2-en-1-yl)-4-(pyrimidin-5-yl)-1H-benzo[d][1,2,3]triazol-6-carbonitrile; and (Z)-1-(4-amino-2-fluorobut-2-en-1-yl)-4-(1-methyl-1H-pyrazol-5-yl)-1H-benzo[d][1,2,3]triazol-6-carbonitrile.

7. The compound or pharmaceutically acceptable salt thereof as claimed in claim 1, which is selected from the group consisting of:

(Z)-3-fluoro-4-(6-fluoro-4-(3-(methylsulfonyl)phenyl)-1H-benzo[d]imidazol-1-yl)but-2-en-1-amine;
(Z)-3-fluoro-4-(6-fluoro-4-(3-(pyrrolidin-1-ylsulfonyl)phenyl)-1H-benzo[d]imidazol-1-yl)but-2-en-1-amine;
(Z)-3-(1-(4-amino-2-fluorobut-2-en-1-yl)-6-fluoro-1H-benzo[d]imidazol-4-yl)-N-cyclopropylbenzenesulfonamide;
(Z)-3-(1-(4-amino-2-fluorobut-2-en-1-yl)-6-fluoro-1H-benzo[d]imidazol-4-yl)-N-methylbenzenesulfonamide;
(Z)-3-fluoro-4-(4-(3-(methylsulfonyl)phenyl)-6-(trifluoromethyl)-1H-benzo[d]imidazol-1-yl)but-2-en-1-amine;
(Z)-3-(1-(4-amino-2-fluorobut-2-en-1-yl)-6-(trifluoromethyl)-1H-benzo[d]imidazol-4-yl)-N-methylbenzenesulfonamide;
methyl (Z)-1-(4-amino-2-fluorobut-2-en-1-yl)-4-(3-(N,N-dimethylsulfamoyl)-4-methoxyphenyl)-1H-benzo[d]imidazol-6-carboxylate;
methyl (Z)-1-(4-amino-2-fluorobut-2-en-1-yl)-4-(3-((3,3-difluoropyrrolidin-1-yl)sulfonyl)phenyl)-1H-benzo[d]imidazol-6-carboxylate;
methyl (Z)-1-(4-amino-2-fluorobut-2-en-1-yl)-4-(3-(pyrrolidin-1-ylsulfonyl)phenyl)-1H-benzo[d]imidazol-6-carboxylate;
methyl (Z)-1-(4-amino-2-fluorobut-2-en-1-yl)-4-(2-methoxy-5-(N-methylsulfamoyl)phenyl)-1H-benzo[d]imidazol-6-carboxylate;
methyl (Z)-1-(4-amino-2-fluorobut-2-en-1-yl)-4-(3-(methylsulfonyl)phenyl)-1H-benzo[d]imidazol-6-carboxylate;
methyl (Z)-1-(4-amino-2-fluorobut-2-en-1-yl)-4-(5-(N,N-diethylsulfamoyl)-2-methoxyphenyl)-1H-benzo[d]imidazol-6-carboxylate;
methyl (Z)-1-(4-amino-2-fluorobut-2-en-1-yl)-4-(5-(N-cyclopropylsulfamoyl)-2-methoxyphenyl)-1H-benzo[d]imidazol-6-carboxylate;
methyl (Z)-1-(4-amino-2-fluorobut-2-en-1-yl)-4-(3-(N-isopropylsulfamoyl)-4-methoxyphenyl)-1H-benzo[d]imidazol-6-carboxylate;
methyl (Z)-1-(4-amino-2-fluorobut-2-en-1-yl)-4-(3-(N-cyclopropylsulfamoyl)phenyl)-1H-benzo[d]imidazol-6-carboxylate;
methyl (Z)-1-(4-amino-2-fluorobut-2-en-1-yl)-4-(3-(N-methylsulfamoyl)phenyl)-1H-benzo[d]imidazol-6-carboxylate;
methyl (Z)-1-(4-amino-2-fluorobut-2-en-1-yl)-4-(3-(N,N-dimethylsulfamoyl)phenyl)-1H-benzo[d]imidazol-6-carboxylate;
methyl (Z)-1-(4-amino-2-fluorobut-2-en-1-yl)-4-(3-(N-(4-methoxybenzyl)sulfamoyl)phenyl)-1H-benzo[d]imidazol-6-carboxylate;
methyl (Z)-1-(4-amino-2-fluorobut-2-en-1-yl)-4-(3-(piperidin-1-ylsulfonyl)phenyl)-1H-benzo[d]imidazol-6-carboxylate;
methyl (Z)-1-(4-amino-2-fluorobut-2-en-1-yl)-4-(3-(ethylsulfonyl)phenyl)-1H-benzo[d]imidazol-6-carboxylate;
methyl (Z)-1-(4-amino-2-fluorobut-2-en-1-yl)-4-(2-methyl-5-((trifluoromethyl)sulfonyl)phenyl)-1H-benzo[d]imidazol-6-carboxylate;
methyl (Z)-1-(4-amino-2-fluorobut-2-en-1-yl)-4-(3-(N,N-diethylsulfamoyl)phenyl)-1H-benzo[d]imidazol-6-carboxylate;
methyl (Z)-1-(4-amino-2-fluorobut-2-en-1-yl)-4-(3-(dimethylphosphoryl)phenyl)-1H-benzo[d]imidazol-6-carboxylate;
(Z)-3-(1-(4-amino-2-fluorobut-2-en-1-yl)-2-(trifluoromethyl)-1H-benzo[d]imidazol-4-yl)-N-methylbenzenesulfonamide;
(Z)-3-(1-(4-amino-2-fluorobut-2-en-1-yl)-2-methyl-1H-benzo[d]imidazol-4-yl)-N,N-dimethylbenzenesulfonamide;
(Z)-3-fluoro-4-(2-methyl-4-(3-(pyrrolidin-1-ylsulfonyl)phenyl)-1H-benzo[d]imidazol-1-yl)but-2-en-1-amine;
methyl (Z)-1-(4-amino-2-fluorobut-2-en-1-yl)-4-(3-(N,N-dimethylsulfamoyl)phenyl)-2-methyl-1H-benzo[d]imidazol-6-carboxylate;
methyl (Z)-1-(4-amino-2-fluorobut-2-en-1-yl)-2-methyl-4-(3-(methylsulfonyl)phenyl)-1H-benzo[d]imidazol-6-carboxylate;
methyl (Z)-1-(4-amino-2-fluorobut-2-en-1-yl)-2-methyl-4-(3-(pyrrolidin-1-ylsulfonyl)phenyl)-1H-benzo[d]imidazol-6-carboxylate;
methyl (Z)-1-(4-amino-2-fluorobut-2-en-1-yl)-2-methyl-4-(3-(N-methylsulfamoyl)phenyl)-1H-benzo[d]imidazol-6-carboxylate;
(Z)-1-(4-amino-2-fluorobut-2-en-1-yl)-4-(3-(N,N-dimethylsulfamoyl)phenyl)-N,N,2-trimethyl-1H-benzo[d]imidazol-6-carboxamide;
(Z)-3-(1-(4-amino-2-fluorobut-2-en-1-yl)-2-ethyl-1H-benzo[d]imidazol-4-yl)-N,N-dimethylbenzenesulfonamide;
(Z)-5-(1-(4-amino-2-fluorobut-2-en-1-yl)-1H-benzo[d][1,2,3]triazol-4-yl)-2-methoxy-N,N-dimethylbenzenesulfonamide;
(Z)-4-(4-(3-((3,3-difluoropyrrolidin-1-yl)sulfonyl)phenyl)-1H-benzo[d][1,2,3]triazol-1-yl)-3-fluorobut-2-en-1-amine;
(Z)-3-fluoro-4-(4-(3-(pyrrolidin-1-ylsulfonyl)phenyl)-1H-benzo[d][1,2,3]triazol-1-yl)but-2-en-1-amine;
(Z)-3-(1-(4-amino-2-fluorobut-2-en-1-yl)-1H-benzo[d][1,2,3]triazol-4-yl)-4-methoxy-N-methylbenzenesulfonamide;
(Z)-3-fluoro-4-(4-(3-(methylsulfonyl)phenyl)-1H-benzo[d][1,2,3]triazol-1-yl)but-2-en-1-amine;
(Z)-3-(1-(4-amino-2-fluorobut-2-en-1-yl)-1H-benzo[d][1,2,3]triazol-4-yl)-N-cyclopropyl-4-methoxybenzenesulfonamide;
(Z)-5-(1-(4-amino-2-fluorobut-2-en-1-yl)-1H-benzo[d][1,2,3]triazol-4-yl)-N-isopropyl-2-methoxybenzenesulfonamide;
(Z)-3-(1-(4-amino-2-fluorobut-2-en-1-yl)-1H-benzo[d][1,2,3]triazol-4-yl)-N-cyclopropylbenzenesulfonamide;
(Z)-3-(1-(4-amino-2-fluorobut-2-en-1-yl)-1H-benzo[d][1,2,3]triazol-4-yl)-N-methylbenzenesulfonamide;
(Z)-3-(1-(4-amino-2-fluorobut-2-en-1-yl)-1H-benzo[d][1,2,3]triazol-4-yl)-N,N-dimethylbenzenesulfonamide;
(Z)-3-fluoro-4-(4-(2-methoxy-5-((4-methylpiperazin-1-yl)sulfonyl)phenyl)-1H-benzo[d][1,2,3]triazol-1-yl)but-2-en-1-amine;
methyl (Z)-1-(4-amino-2-fluorobut-2-en-1-yl)-4-(3-(N,N-dimethylsulfamoyl)-4-methoxyphenyl)-1H-benzo[d][1,2,3]triazol-6-carboxylate;
methyl (Z)-1-(4-amino-2-fluorobut-2-en-1-yl)-4-(3-((3,3-difluoropyrrolidin-1-yl)sulfonyl)phenyl)-1H-benzo[d][1,2,3]triazol-6-carboxylate;

methyl (Z)-1-(4-amino-2-fluorobut-2-en-1-yl)-4-(3-(pyrrolidin-1-ylsulfonyl)phenyl)-1H-benzo[d][1,2,3]triazol-6-carboxylate;

methyl (Z)-1-(4-amino-2-fluorobut-2-en-1-yl)-4-(2-methoxy-5-(N-methylsulfamoyl)phenyl)-1H-benzo[d][1,2,3]triazol-6-carboxylate;

methyl (Z)-1-(4-amino-2-fluorobut-2-en-1-yl)-4-(3-(methylsulfonyl)phenyl)-1H-benzo[d][1,2,3]triazol-6-carboxylate;

methyl (Z)-1-(4-amino-2-fluorobut-2-en-1-yl)-4-(5-(N,N-diethylsulfamoyl)-2-methoxyphenyl)-1H-benzo[d][1,2,3]triazol-6-carboxylate;

methyl (Z)-1-(4-amino-2-fluorobut-2-en-1-yl)-4-(5-(N-cyclopropylsulfamoyl)-2-methoxyphenyl)-1H-benzo[d][1,2,3]triazol-6-carboxylate;

methyl (Z)-1-(4-amino-2-fluorobut-2-en-1-yl)-4-(3-(N-isopropylsulfamoyl)-4-methoxyphenyl)-1H-benzo[d][1,2,3]triazol-6-carboxylate;

methyl (Z)-1-(4-amino-2-fluorobut-2-en-1-yl)-4-(3-(N-cyclopropylsulfamoyl)phenyl)-1H-benzo[d][1,2,3]triazol-6-carboxylate;

methyl (Z)-1-(4-amino-2-fluorobut-2-en-1-yl)-4-(3-(N-methylsulfamoyl)phenyl)-1H-benzo[d][1,2,3]triazol-6-carboxylate;

methyl (Z)-1-(4-amino-2-fluorobut-2-en-1-yl)-4-(3-(N,N-dimethylsulfamoyl)phenyl)-1H-benzo[d][1,2,3]triazol-6-carboxylate;

methyl (Z)-1-(4-amino-2-fluorobut-2-en-1-yl)-4-(3-(N-(4-methoxybenzyl)sulfamoyl)phenyl)-1H-benzo[d][1,2,3]triazol-6-carboxylate;

methyl (Z)-1-(4-amino-2-fluorobut-2-en-1-yl)-4-(3-(ethylsulfonyl)phenyl)-1H-benzo[d][1,2,3]triazol-6-carboxylate;

methyl (Z)-1-(4-amino-2-fluorobut-2-en-1-yl)-4-(2-methyl-5-((trifluoromethyl)sulfonyl)phenyl)-1H-benzo[d][1,2,3]triazol-6-carboxylate;

(Z)-1-(4-amino-2-fluorobut-2-en-1-yl)-4-(3-(N,N-dimethylsulfamoyl)-4-methoxyphenyl)-N-methoxy-1H-benzo[d][1,2,3]triazol-6-carboxamide;

(Z)-1-(4-amino-2-fluorobut-2-en-1-yl)-N-methoxy-4-(3-(pyrrolidin-1-ylsulfonyl)phenyl)-1H-benzo[d][1,2,3]triazol-6-carboxamide;

(Z)-1-(4-amino-2-fluorobut-2-en-1-yl)-N-methoxy-4-(2-methoxy-5-(N-methylsulfamoyl)phenyl)-1H-benzo[d][1,2,3]triazol-6-carboxamide;

(Z)-1-(4-amino-2-fluorobut-2-en-1-yl)-4-(5-(N,N-diethylsulfamoyl)-2-methoxyphenyl)-N-methoxy-1H-benzo[d][1,2,3]triazol-6-carboxamide;

(Z)-1-(4-amino-2-fluorobut-2-en-1-yl)-4-(5-(N-cyclopropylsulfamoyl)-2-methoxyphenyl)-N-methoxy-1H-benzo[d][1,2,3]triazol-6-carboxamide;

(Z)-1-(4-amino-2-fluorobut-2-en-1-yl)-N-methoxy-N-methyl-4-(3-(pyrrolidin-1-ylsulfonyl)phenyl)-1H-benzo[d][1,2,3]triazol-6-carboxamide;

(Z)-1-(4-amino-2-fluorobut-2-en-1-yl)-4-(5-(N,N-diethylsulfamoyl)-2-methoxyphenyl)-N-methoxy-N-methyl-1H-benzo[d][1,2,3]triazol-6-carboxamide;

(Z)-1-(4-amino-2-fluorobut-2-en-1-yl)-4-(3-(N,N-dimethylsulfamoyl)phenyl)-N-methoxy-N-methyl-1H-benzo[d][1,2,3]triazol-6-carboxamide;

(Z)-1-(3-(1-(4-amino-2-fluorobut-2-en-1-yl)-6-(trifluoromethyl)-1H-benzo[d]imidazol-4-yl)-4-fluorophenyl)ethan-1-one;

(Z)-3-fluoro-4-(4-(pyridin-3-yl)-6-(trifluoromethyl)-1H-benzo[d]imidazol-1-yl)but-2-en-1-amine;

(Z)-3-fluoro-4-(4-(5-fluoropyridin-3-yl)-6-(trifluoromethyl)-1H-benzo[d]imidazol-1-yl)but-2-en-1-amine;

(Z)-4-(4-(5-chloropyridin-3-yl)-6-(trifluoromethyl)-1H-benzo[d]imidazol-1-yl)-3-fluoro-but-2-en-1-amine;

(Z)-3-fluoro-4-(4-(pyrimidin-5-yl)-6-(trifluoromethyl)-1H-benzo[d]imidazol-1-yl)but-2-en-1-amine;

(Z)-3-fluoro-4-(4-(1-methyl-1H-pyrazol-5-yl)-6-(trifluoromethyl)-1H-benzo[d]imidazol-1-yl)but-2-en-1-ylamine;

(Z)-4-(4-(1-ethyl-1H-pyrazol-5-yl)-6-(trifluoromethyl)-1H-benzo[d]imidazol-1-yl]-3-fluoro-but-2-en-1-amine;

(Z)-3-fluoro-4-(4-(1-isopropyl-1H-pyrazol-5-yl)-6-(trifluoromethyl)-1H-benzo[d]imidazol-1-yl)but-2-en-1-amine;

(Z)-3-fluoro-4-(4-[1-methyl-3-(trifluoromethyl)-1H-pyrazol-5-yl]-6-(trifluoromethyl)-1H-benzo[d]imidazol-1-yl)but-2-en-1-amine;

(Z)-2-(4-(1-(4-amino-2-fluorobut-2-en-1-yl)-6-(trifluoromethyl)-1H-benzo[d]imidazol-4-yl)-1H-pyrazol-1-yl)ethan-1-ol;

(Z)-1-(4-amino-2-fluorobut-2-en-1-yl)-4-(3-(pyrrolidin-1-ylsulfonyl)phenyl)-1H-benzo[d]imidazol-6-carbonitrile;

(Z)-3-(1-(4-amino-2-fluorobut-2-en-1-yl)-6-cyano-1H-benzo[d]imidazol-4-yl)-N,N-dimethylbenzenesulfonamide;

(Z)-3-(1-(4-amino-2-fluorobut-2-en-1-yl)-6-cyano-1H-benzo[d]imidazol-4-yl)-4-methoxy-N-methylbenzenesulfonamide;

(Z)-4-(5-acetyl-2-fluorophenyl)-1-(4-amino-2-fluorobut-2-en-1-yl)-1H-benzo[d]imidazol-6-carbonitrile;

(Z)-1-(4-amino-2-fluorobut-2-en-1-yl)-4-(2-fluoro-5-(hydroxymethyl)phenyl)-1H-benzo[d]imidazol-6-carbonitrile;

(Z)-1-(4-amino-2-fluoro-2-but-1-yl)-4-(2-chloro-3-(hydroxymethyl)phenyl)-1H-benzo[d]imidazol-6-carbonitrile;

(Z)-1-(4-amino-2-fluorobut-2-en-1-yl)-4-(pyridin-3-yl)-1H-benzo[d]imidazol-6-carbonitrile;

(Z)-1-(4-amino-2-fluorobut-2-en-1-yl)-4-(5-fluoropyridin-3-yl)-1H-benzo[d]imidazol-6-carbonitrile;

(Z)-1-(4-amino-2-fluorobut-2-en-1-yl)-4-(5-chloropyridin-3-yl)-1H-benzo[d]imidazol-6-carbonitrile;

(Z)-1-(4-amino-2-fluorobut-2-en-1-yl)-4-(pyrimidin-5-yl)-1H-benzo[d]imidazol-6-carbonitrile;

(Z)-1-(4-amino-2-fluorobut-2-en-1-yl)-4-(1-methyl-1H-pyrazol-5-yl)-1H-benzo[d]imidazol-6-carbonitrile;

(Z)-1-(4-amino-2-fluorobut-2-en-1-yl)-4-(1-ethyl-1H-pyrazol-5-yl)-1H-benzo[d]imidazol-6-carbonitrile;

(Z)-1-(4-amino-2-fluorobut-2-en-1-yl)-4-(1-methyl-3-(trifluoromethyl)-1H-pyrazol-5-yl)-1H-benzo[d]imidazol-6-carbonitrile;

(Z)-1-(4-amino-2-fluorobut-2-en-1-yl)-4-(1,3-dimethyl-1H-pyrazol-5-yl)-1H-benzo[d]imidazol-6-carbonitrile;

(Z)-1-(4-amino-2-fluorobut-2-en-1-yl)-4-(1-(2-hydroxyethyl)-1H-pyrazol-3-yl)-1H-benzo[d]imidazol-6-carbonitrile;

(Z)-3-(1-(4-amino-2-fluorobut-2-en-1-yl)-6-(trifluoromethyl)-1H-benzo[d][1,2,3]triazol-4-yl)-N,N-dimethylbenzenesulfonamide;

(Z)-1-(3-(1-(4-amino-2-fluorobut-2-en-1-yl)-6-(trifluoromethyl)-1H-benzo[d][1,2,3]triazol-4-yl)-4-fluorophenyl)ethan-1-one;

(Z)-(3-(1-(4-amino-2-fluorobut-2-en-1-yl)-6-(trifluoromethyl)-1H-benzo[d][1,2,3]triazol-4-yl)-4-fluorophenyl)methanol;

(Z)-(3-(1-(4-amino-2-fluoro-2-en-1-yl)-6-(trifluoromethyl)-1H-benzo[d][1,2,3]triazol-4-yl)-2-chlorophenyl)methanol;

(Z)-3-fluoro-4-(4-(5-fluoropyridin-3-yl)-6-(trifluoromethyl)-1H-benzo[d][1,2,3]triazol-1-yl)but-2-en-1-amine;

(Z)-4-(4-(5-chloropyridin-3-yl)-6-(trifluoromethyl)-1H-benzo[d][1,2,3]triazol-1-yl)-3-fluorobut-2-en-1-amine;

(Z)-3-fluoro-4-(4-(pyrimidin-5-yl)-6-(trifluoromethyl)-1H-benzo[d][1,2,3]triazol-1-yl)but-2-en-1-amine;

(Z)-4-(4-(1-ethyl-1H-pyrazol-5-yl)-6-(trifluoromethyl)-1H-benzo[d][1,2,3]triazol-1-yl)-3-fluorobut-2-en-1-amine;

(Z)-4-[4-(1,3-dimethyl-1H-pyrazol-5-yl)-6-(trifluoromethyl)-1H-benzo[d][1,2,3]triazol-1-yl]-3-fluorobut-2-en-1-amine;

(Z)-2-(4-(1-(4-amino-2-fluorobut-2-en-1-yl)-6-(trifluoromethyl)-1H-benzo[d][1,2,3]triazol-4-yl]-1H-pyrazol-1-yl)ethan-1-ol;

(Z)-1-(4-amino-2-fluorobut-2-en-1-yl)-4-[2-fluoro-5-(hydroxymethyl)phenyl]-1H-benzo[d][1,2,3]triazol-6-carbonitrile;

(Z)-1-(4-amino-2-fluorobut-2-en-1-yl)-4-[2-chloro-3-(hydroxymethyl)phenyl-1H-benzo[d][1,2,3]triazol-6-carbonitrile;

(Z)-1-(4-amino-2-fluorobut-2-en-1-yl)-4-(5-fluoropyridin-3-yl)-1H-benzo[d][1,2,3]triazol-6-carbonitrile;

(Z)-1-(4-amino-2-fluorobut-2-en-1-yl)-4-(5-chloropyridin-3-yl)-1H-benzo[d][1,2,3]triazol-6-carbonitrile;

(Z)-1-(4-amino-2-fluorobut-2-en-1-yl)-4-(pyrimidin-5-yl)-1H-benzo[d][1,2,3]triazol-6-carbonitrile; and (Z)-1-(4-amino-2-fluorobut-2-en-1-yl)-4-(1-methyl-1H-pyrazol-5-yl)-1H-benzo[d][1,2,3]triazol-6-carbonitrile.

8. A process for preparing a compound of Formula 1 or pharmaceutically acceptable salt thereof, the process of which comprises reacting a compound of Formula 2 with a compound of Formula 3 to obtain a compound of Formula 1a; deprotecting the compound of Formula 1a to obtain a compound of Formula 1; and optionally converting the compound of Formula 1 to a pharmaceutically acceptable salt thereof:

<Formula 1>

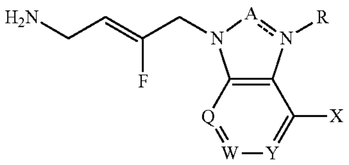

<Formula 1a>

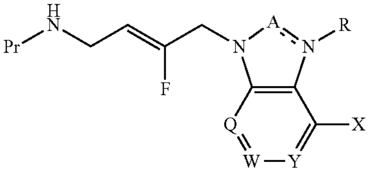

<Formula 2>

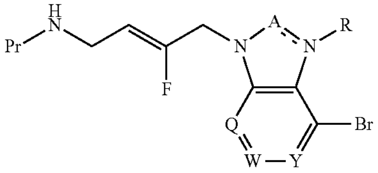

<Formula 3>

B—X wherein, A, R, Q, W, Y, and X are the same as defined in claim 1; Pr is an amine protecting group; and B is boronic acid ($B(OH)_2$) or boronic acid pinacol ester.

9. A pharmaceutical composition for inhibiting lysyl oxidase family comprising the compound or pharmaceutically acceptable salt thereof as claimed in claim 1 as an active ingredient.

10. A method for inhibiting lysyl oxidase family in a mammal, which comprises administering a therapeutically effective amount of the compound or pharmaceutically acceptable salt thereof as claimed in claim 1 to the mammal in need thereof.

* * * * *